US012723078B2

(12) United States Patent
An et al.

(10) Patent No.: US 12,723,078 B2
(45) Date of Patent: Sep. 1, 2026

(54) MONOCLONAL ANTIBODIES AGAINST LILRB1 FOR DIAGNOSTIC AND THERAPEUTIC USE

(71) Applicant: THE BOARD OF REGENTS OF THE UNIVERSITY OF TEXAS SYSTEM, Austin, TX (US)

(72) Inventors: Zhiqiang An, Houston, TX (US); Chengcheng Zhang, Southlake, TX (US); Ningyan Zhang, Houston, TX (US); Yuanzhi Chen, Houston, TX (US); Heyu Chen, Dallas, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 860 days.

(21) Appl. No.: 18/007,185

(22) PCT Filed: Jul. 26, 2021

(86) PCT No.: PCT/US2021/043128

§ 371 (c)(1),
(2) Date: Jan. 27, 2023

(87) PCT Pub. No.: WO2022/026360

PCT Pub. Date: Feb. 3, 2022

(65) Prior Publication Data

US 2023/0235055 A1 Jul. 27, 2023

Related U.S. Application Data

(60) Provisional application No. 63/124,516, filed on Dec. 11, 2020, provisional application No. 63/057,601, filed on Jul. 28, 2020.

(51) Int. Cl.

| | |
|---|---|
| ***C07K 16/28*** | (2006.01) |
| ***A61K 39/00*** | (2006.01) |
| ***A61K 39/395*** | (2006.01) |
| ***A61K 45/06*** | (2006.01) |
| ***A61P 35/00*** | (2006.01) |
| ***G01N 33/575*** | (2026.01) |

(52) U.S. Cl.

CPC ...... *C07K 16/2803* (2013.01); *A61K 39/3955* (2013.01); *A61K 45/06* (2013.01); *A61P 35/00* (2018.01); *G01N 33/5758* (2026.01); *A61K 2039/505* (2013.01); *C07K 2317/21* (2013.01); *C07K 2317/24* (2013.01); *C07K 2317/73* (2013.01); *C07K 2317/75* (2013.01); *C07K 2317/76* (2013.01); *C07K 2317/92* (2013.01)

(58) Field of Classification Search

None

See application file for complete search history.

(56) References Cited

U.S. PATENT DOCUMENTS

| | | | | |
|---|---|---|---|---|
| 2018/0086829 A1 | 3/2018 | Zhang et al. | | |
| 2018/0251558 A1* | 9/2018 | Maute | ................ | A61K 38/1774 |

FOREIGN PATENT DOCUMENTS

| | | |
|---|---|---|
| CN | 110381998 | 10/2019 |
| WO | WO 2018/126259 A1 | 7/2018 |
| WO | WO 2018/162724 | 9/2018 |
| WO | WO 2019/005638 | 1/2019 |
| WO | WO 2019/069993 | 4/2019 |
| WO | WO 2019/131988 | 7/2019 |
| WO | WO 2019/144052 A1 | 7/2019 |
| WO | WO 2020/136145 | 7/2020 |
| WO | WO 2020/136147 | 7/2020 |
| WO | WO 2021/028921 | 2/2021 |
| WO | WO 2022/187968 | 9/2022 |

OTHER PUBLICATIONS

Kussie "A Single Engineered Amino Acid Substitution Changes Antibody Fine Specificity" J immunol 152(1):146-52 (Year: 1994).*

Björkström, Niklas K., et al. "Expression patterns of NKG2A, KIR, and CD57 define a process of CD56dim NK-cell differentiation uncoupled from NK-cell education." *Blood, The Journal of the American Society of Hematology* 116.19 (2010): 3853-3864.

Chen et al. "Antagonistic anti-LILRB1 monoclonal antibody regulates antitumor functions of natural killer cells." *Journal for ImmunoTherapy of Cancer* 8.2 (2020).

Desgrandchamps, Francois, et al. "Prediction of non-muscle-invasive bladder cancer recurrence by measurement of checkpoint HLAG's receptor ILT2 on peripheral CD8+ T cells." *Oncotarget* 9.69 (2018): 33160.

European Search Report issued in European Application No. 21850504.8, dated Jul. 15, 2024.

Freed, Daniel C., et al. "Pentameric complex of viral glycoprotein H is the primary target for potent neutralization by a human cytomegalovirus vaccine." *Proceedings of the National Academy of Sciences* 110.51 (2013): E4997-E5005.

Godal, Robert, et al. "Natural killer cell killing of acute myelogenous leukemia and acute lymphoblastic leukemia blasts by killer cell immunoglobulin-like receptor-negative natural killer cells after NKG2A and LIR-1 blockade." *Biology of Blood and Marrow Transplantation* 16.5 (2010): 612-621. Guillerey, Camille, Nicholas D. Huntington, and Mark J. Smyth. "Targeting natural killer cells in cancer immunotherapy." *Nature immunology* 17.9 (2016): 1025-1036.

Ha, Sha, et al. "Isolation and characterization of IgG1 with asymmetrical Fc glycosylation." *Glycobiology* 21.8 (2011): 1087-1096.

Harly, Christelle, et al. "Up-regulation of cytolytic functions of human Vδ2-γδ T lymphocytes through engagement of ILT2 expressed by tumor target cells." *Blood, The Journal of the American Society of Hematology* 117.10 (2011): 2864-2873.

Heidenreich, Silke, et al. "Impact of the NK Cell Receptor LIR-1 (ILT-2/CD85j/LILRB1) on Cytotoxicity against Multiple Myeloma." *Journal of Immunology Research* 2012.1 (2012): 652130.

(Continued)

*Primary Examiner* — Adam Weidner

(74) *Attorney, Agent, or Firm* — pH IP Law

(57) ABSTRACT

Provided herein are antibodies binding to LILRB1 and the uses of the antibodies in detecting and treating cancer and autoimmune diseases.

36 Claims, 21 Drawing Sheets
(10 of 21 Drawing Sheet(s) Filed in Color)

Specification includes a Sequence Listing.

(56) References Cited

OTHER PUBLICATIONS

International Search Report and Written Opinion issued in International Application No. PCT/US2021/043128, dated Feb. 7, 2022.
Invitation to Pay Additional Fees issued in International Application No. PCT/US2021/043128, dated Oct. 18, 2021.
Kim, Aeryon, et al. "LILRB1 blockade enhances bispecific T cell engager antibody-induced tumor cell killing by effector CD8+ T cells." *The Journal of Immunology* 203.4 (2019): 1076-1087.
LeMaoult, Joël, et al. "HLA-G up-regulates ILT2, ILT3, ILT4, and KIR2DL4 in antigen presenting cells, NK cells, and T cells." *The FASEB journal* 19.6 (2005): 1-23.
Lo, Megan, et al. "Effector-attenuating substitutions that maintain antibody stability and reduce toxicity in mice." *Journal of Biological Chemistry* 292.9 (2017): 3900-3908.
Lozano, Ester, et al. "Loss of the immune checkpoint CD85j/LILRB1 on malignant plasma cells contributes to immune escape in multiple myeloma." *The Journal of Immunology* 200.8 (2018): 2581-2591.
Menier, Catherine, et al. "MICA triggering signal for NK cell tumor lysis is counteracted by HLA-G1-mediated inhibitory signal." *International journal of cancer* 100.1 (2002): 63-70.
Miller, Jeffrey S., et al. "Successful adoptive transfer and in vivo expansion of human haploidentical NK cells in patients with cancer." *Blood* 105.8 (2005): 3051-3057.
Morandi, Fabio, et al. "Soluble HLA-G dampens CD94/NKG2A expression and function and differentially modulates chemotaxis and cytokine and chemokine secretion in CD56bright and CD56dim NK cells." *Blood, The Journal of the American Society of Hematology* 118.22 (2011): 5840-5850.
Pasero, Christine, et al. "Inherent and tumor-driven immune tolerance in the prostate microenvironment impairs natural killer cell antitumor activity." *Cancer research* 76.8 (2016): 2153-2165.
R&D Systems: "Human LILRB1/CD85j/ILT2 Antibody", dated Jul. 7, 2018 (Jul. 7, 2018), XP093177312, Retrieved from the Internet: URL:https://www.rndsystems.com/products/hu man-lilrbl-cd85j-ilt2-antibody-292319_mab2 0172.
Roberti, María P., et al. "Overexpression of CD85j in TNBC patients inhibits Cetuximab-mediated NK-cell ADCC but can be restored with CD85j functional blockade." *European journal of immunology* 45.5 (2015): 1560-1569.
Seeber, Stefan, et al. "A robust high throughput platform to generate functional recombinant monoclonal antibodies using rabbit B cells from peripheral blood." *PloS one* 9.2 (2014): e86184.
Shiroishi, Mitsunori, et al. "Efficient leukocyte Ig-like receptor signaling and crystal structure of disulfide-linked HLA-G dimer." *Journal of Biological Chemistry* 281.15 (2006): 10439-10447.
Shiroishi, Mitsunori, et al. "Human inhibitory receptors Ig-like transcript 2 (ILT2) and ILT4 compete with CD8 for MHC class I binding and bind preferentially to HLA-G." *Proceedings of the National Academy of Sciences* 100.15 (2003): 8856-8861.
Suck, Garnet, et al. "NK-92: an 'off-the-shelf therapeutic' for adoptive natural killer cell-based cancer immunotherapy." *Cancer immunology, immunotherapy* 65 (2016): 485-492.
Yu, Kang, Chelsea E. Davidson, and Deborah N. Burshtyn. "LILRB1 intron 1 has a polymorphic regulatory region that enhances transcription in NK cells and recruits YY1." *The Journal of Immunology* 204.11 (2020): 3030-3041.
Yu, Yanlan, et al. "A humanized anti-VEGF rabbit monoclonal antibody inhibits angiogenesis and blocks tumor growth in xenograft models." *PloS one* 5.2 (2010): e9072.
Search Report issued in European Application No. 202180066081.3, dated Jun. 25, 2026. Machine Translation.

* cited by examiner

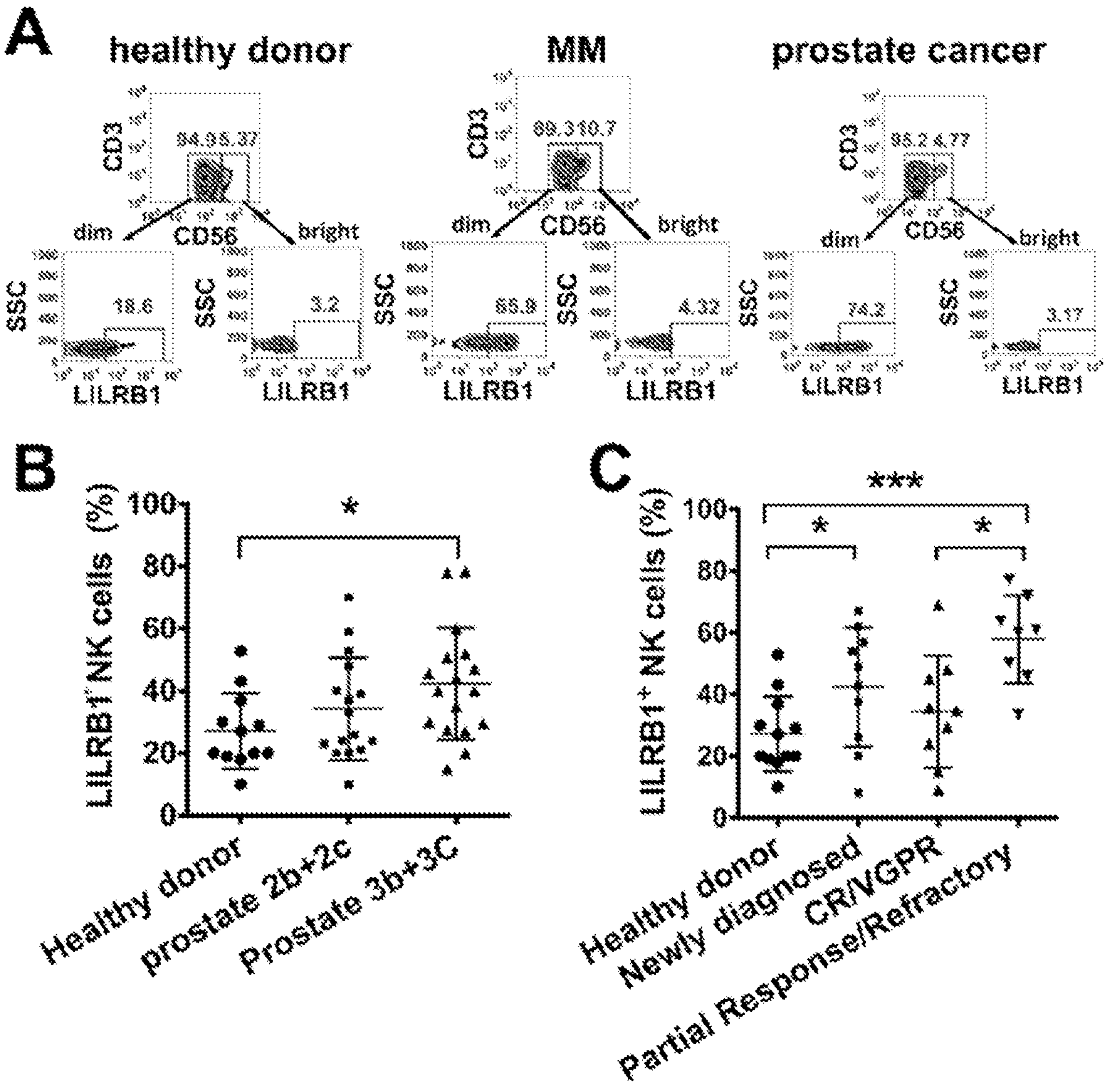
FIGS. 1A-C

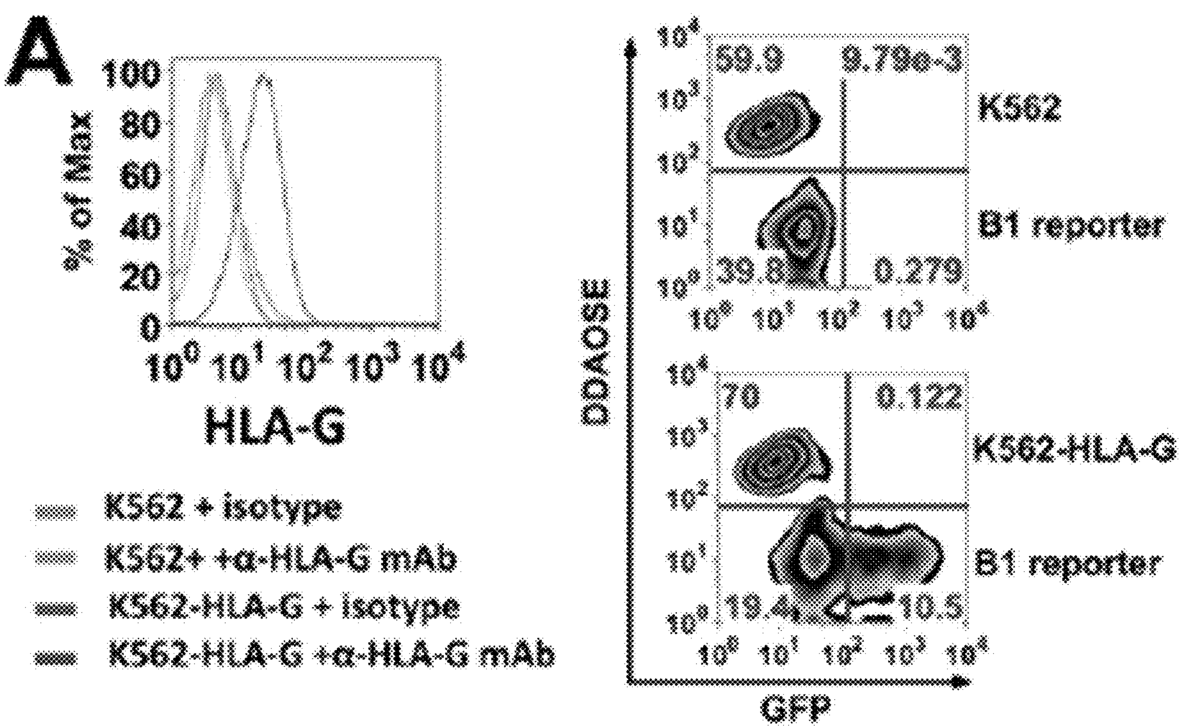
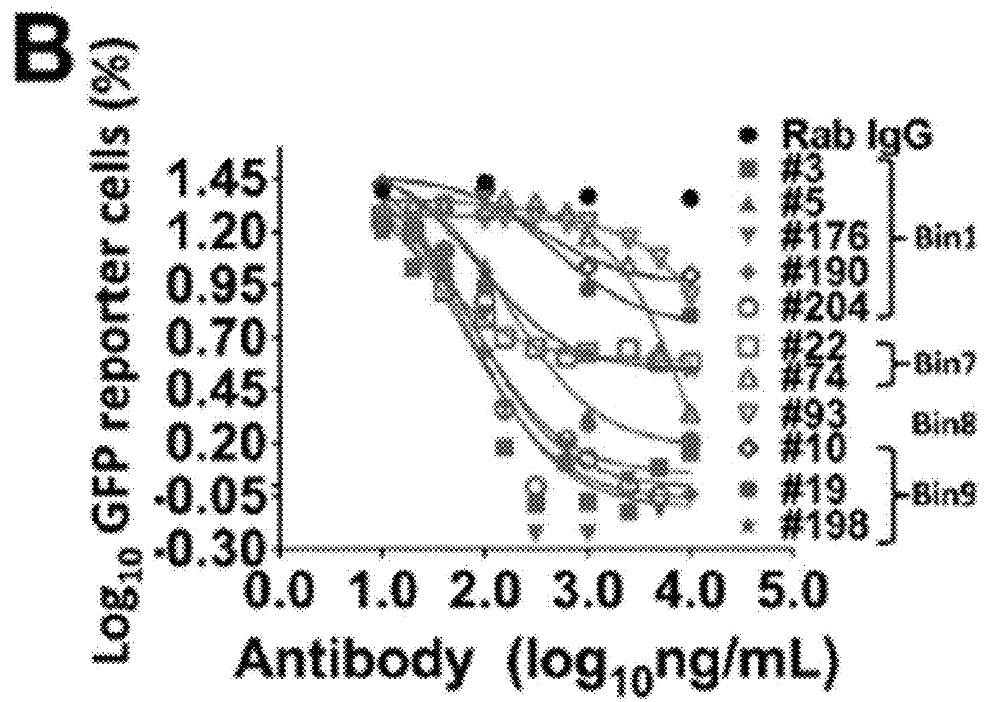
FIGS. 2A-B

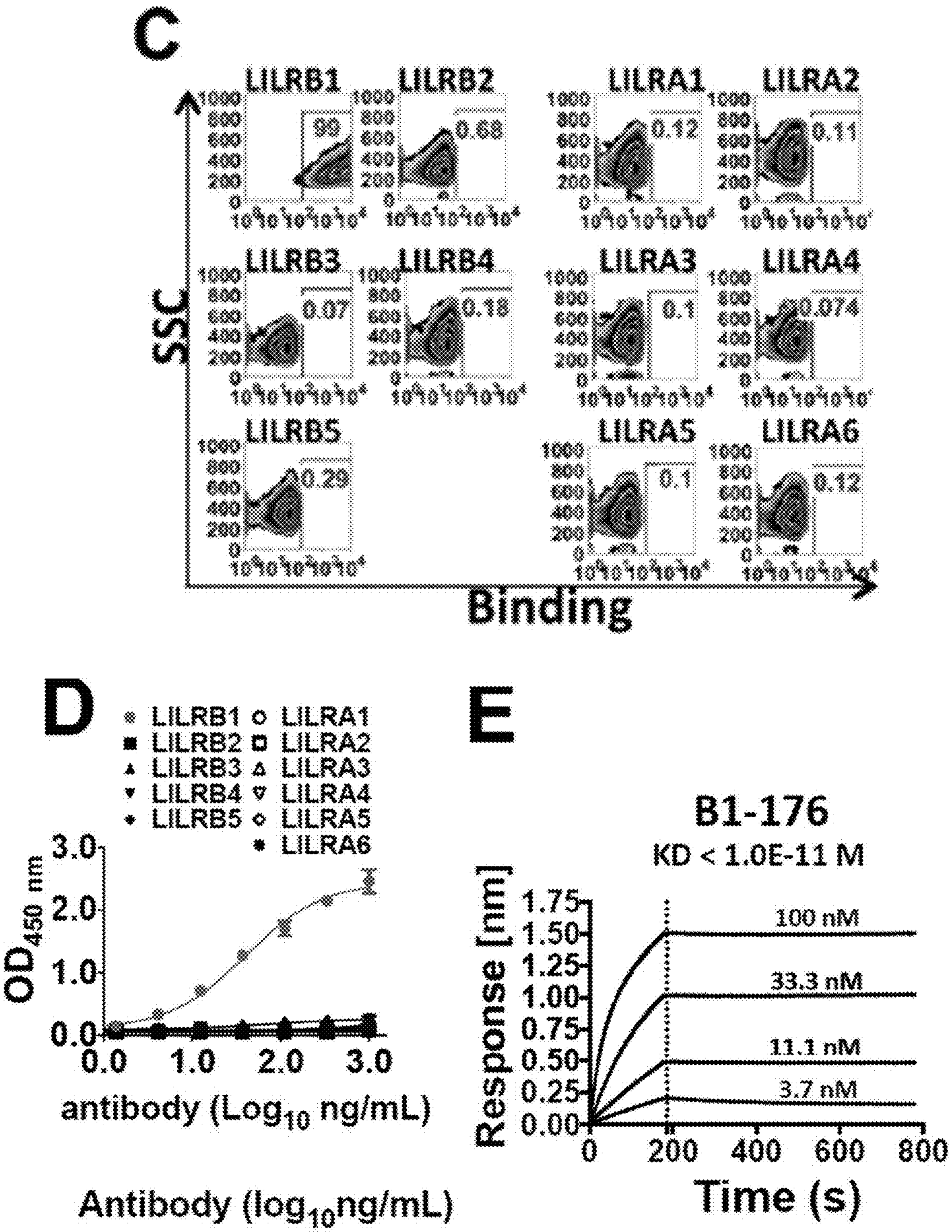
FIGS. 2C-E

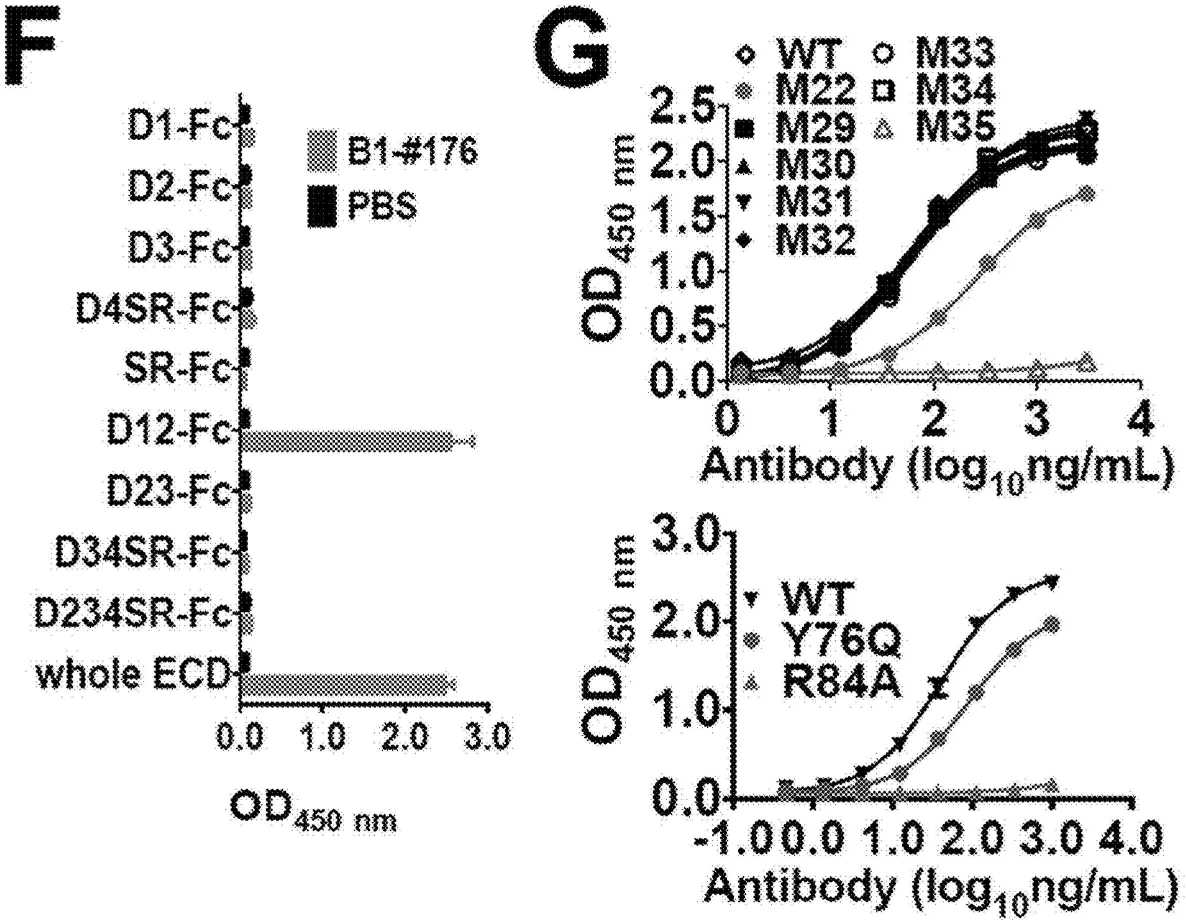
FIGS. 2F-G

PE

| | * | |
|---|---|---|
| Rab-176 VH | QSLEESEGGLVKPGGTLTLTCTAS HCDR1 WVRQAPGKGLELIA HCDR2 RFTISK.SSSTTITLQMTSLTAADTATYFC HCDR3 WGPGTLVTVSS | |
| Hu IGHV3-53*04 | EVQLVESGGGLVQPGGSLRLSCAAS ——— WVRQAPGKGLEWVS ——— RFTISRHNSKNTLYLQMNSLRAEDTAVYYC ——— WGRGTLVTVSS | |
| Hu-176 VH-1 | EVQLVESGGGLVQPGGSLRLSCAAS HCDR1 WVRQAPGKGLEWVS HCDR2 RFTISRHNSKNTLYLQMNSLRAEDTAVYYC HCDR3 WGRGTLVTVSS | |
| Hu-176 VH-2(W48L) | EVQLVESGGGLVQPGGSLRLSCAAS HCDR1 WVRQAPGKGLELVS HCDR2 RFTISRHNSKNTLYLQMNSLRAEDTAVYYC HCDR3 WGRGTLVTVSS | |

| | |
|---|---|
| Rab-176 VL | ELDLTQTPSSVEAAV GGTVTIKC LCDR1 WYQQKP GQPPNLLIY LCDR2 GVSS RFKGSGSGTEFTLTISDLEC ADAATYYC LCDR3 FGGGTEVEIK |
| Hu IGKV1-9*01 | DIQLTQSPSFLSASV GDRVTITC ——— WYQQKP GKAPKLLIY ——— GVPS RFSGSGSGTEFTLTISSLQP EDFATYYC ——— FGGGTKVEIK |
| Hu-176 VL | DIQLTQSPSFLSASV GDRVTITC LCDR1 WYQQKP GKAPKLLIY LCDR2 GVPS RFSGSGSGTEFTLTISSLQP EDFATYYC LCDR3 FGGGTKVEIK |

FIG. 3A

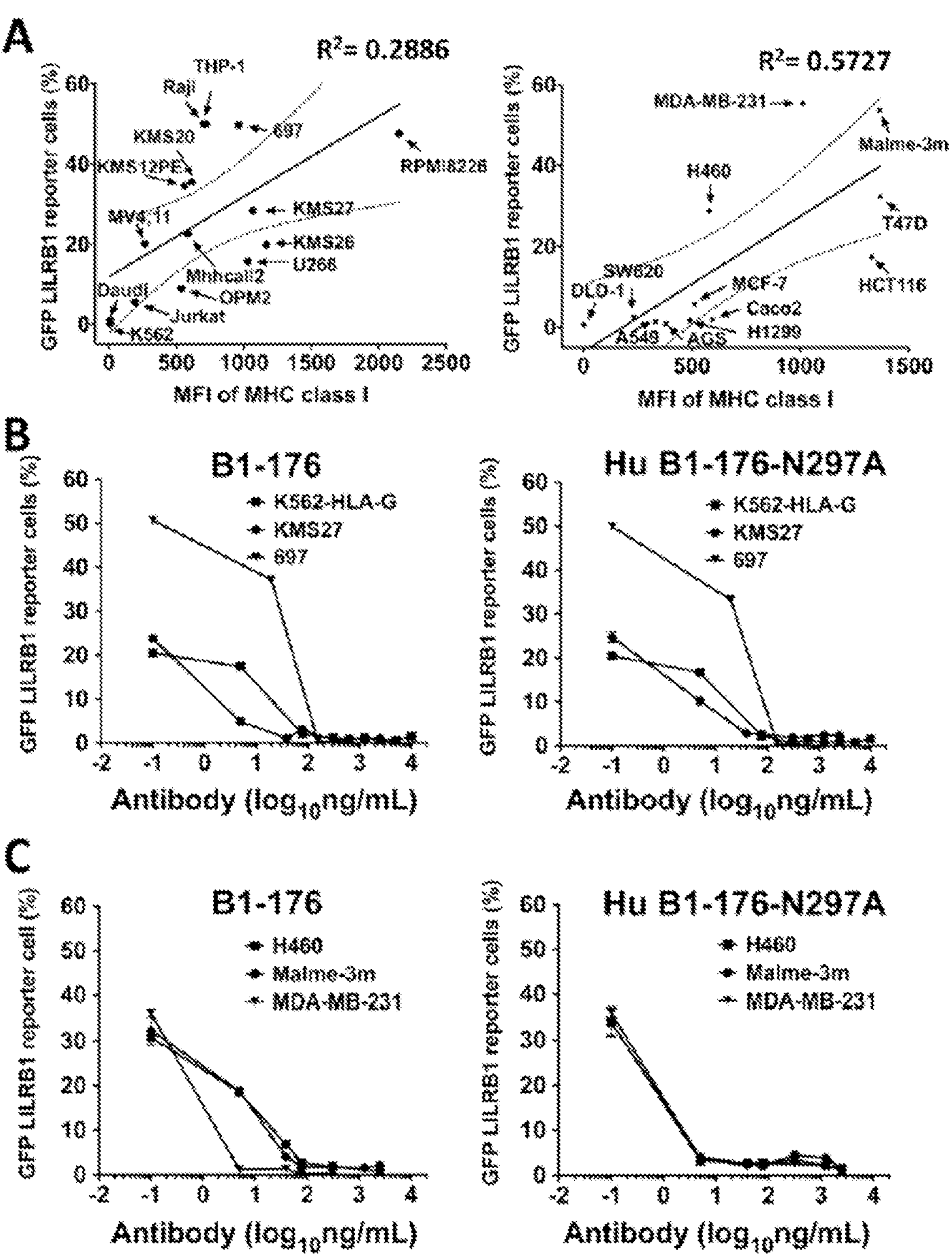
FIGS. 4A-C

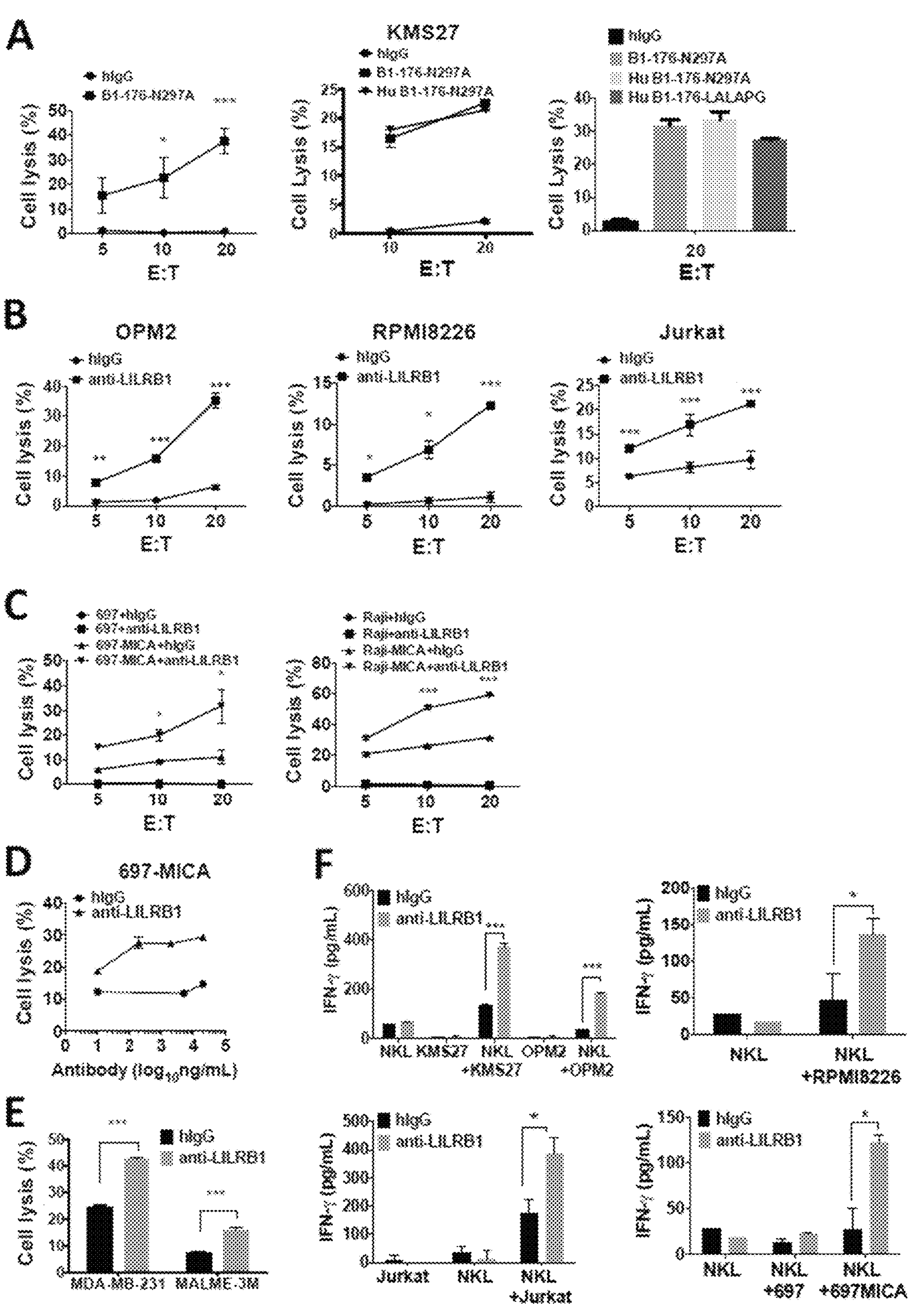
FIGS. 5A-F

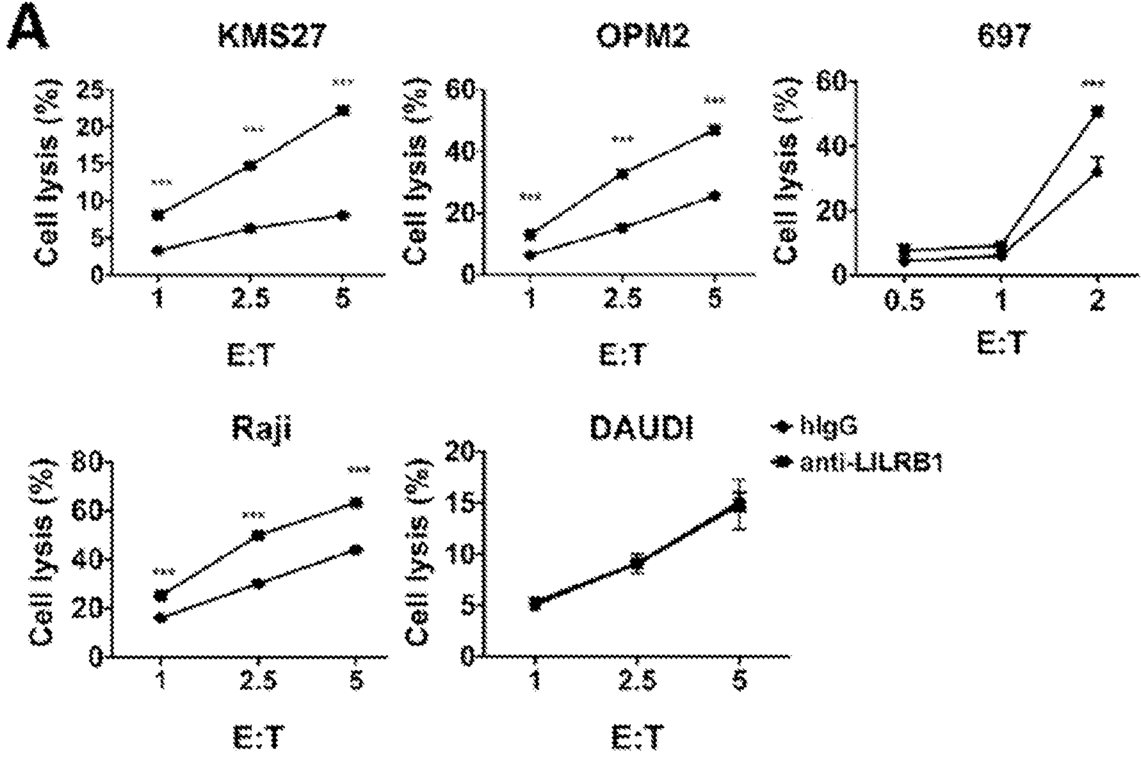
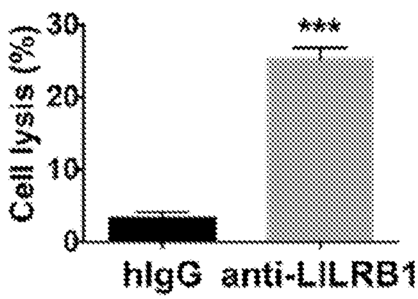
FIGS. 6A-B

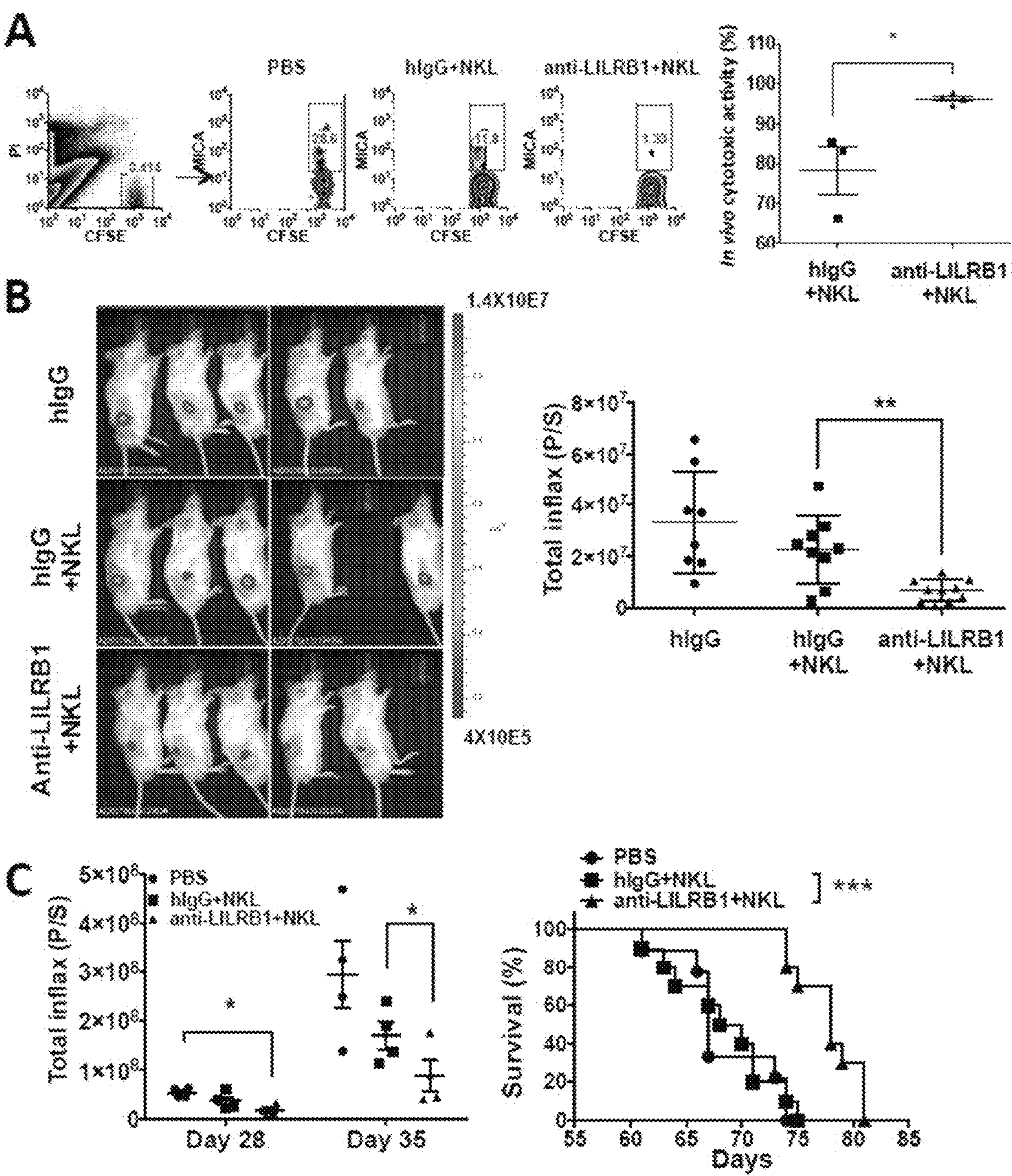
FIGS. 7A-C

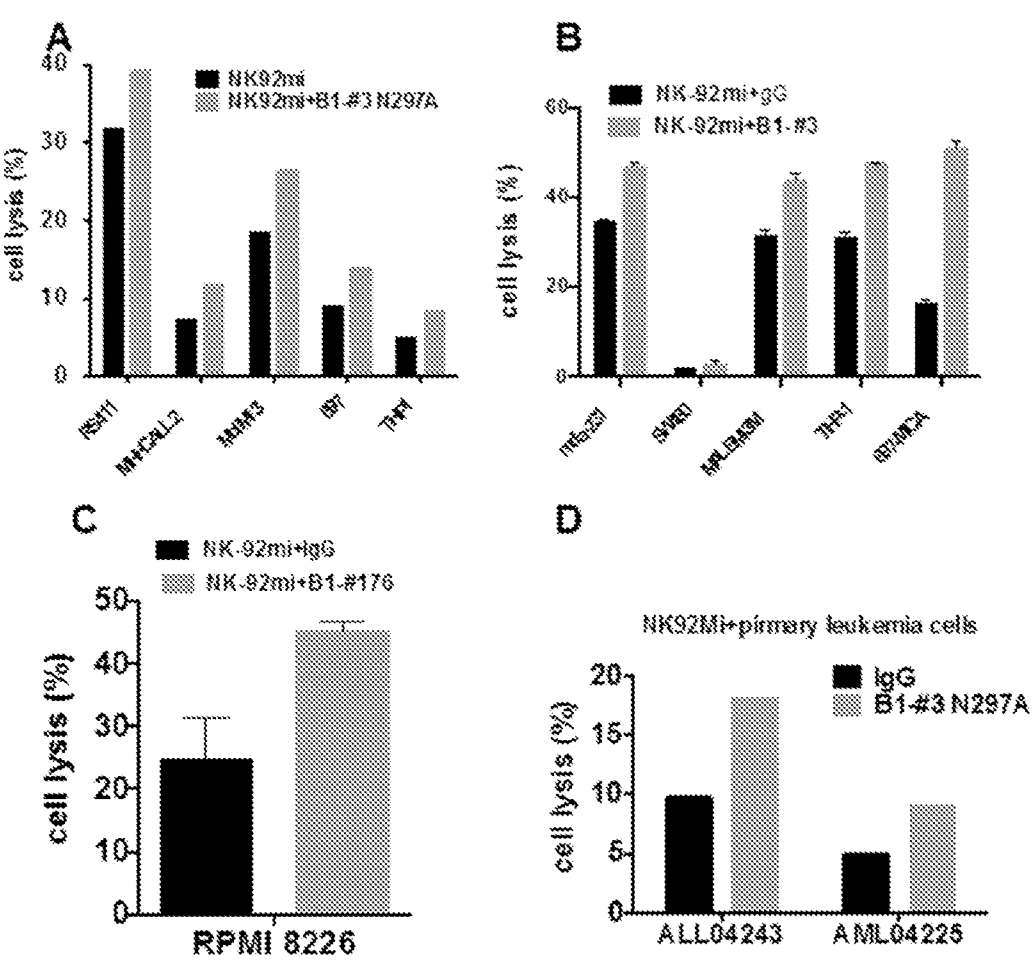
FIGS. 8A-D
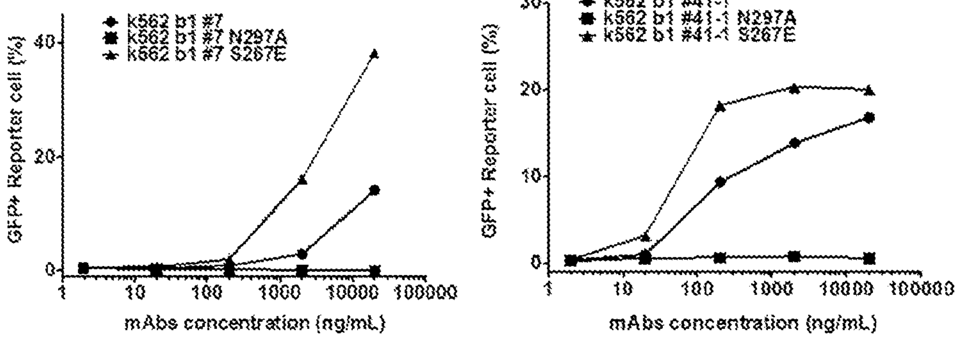
FIG. 9

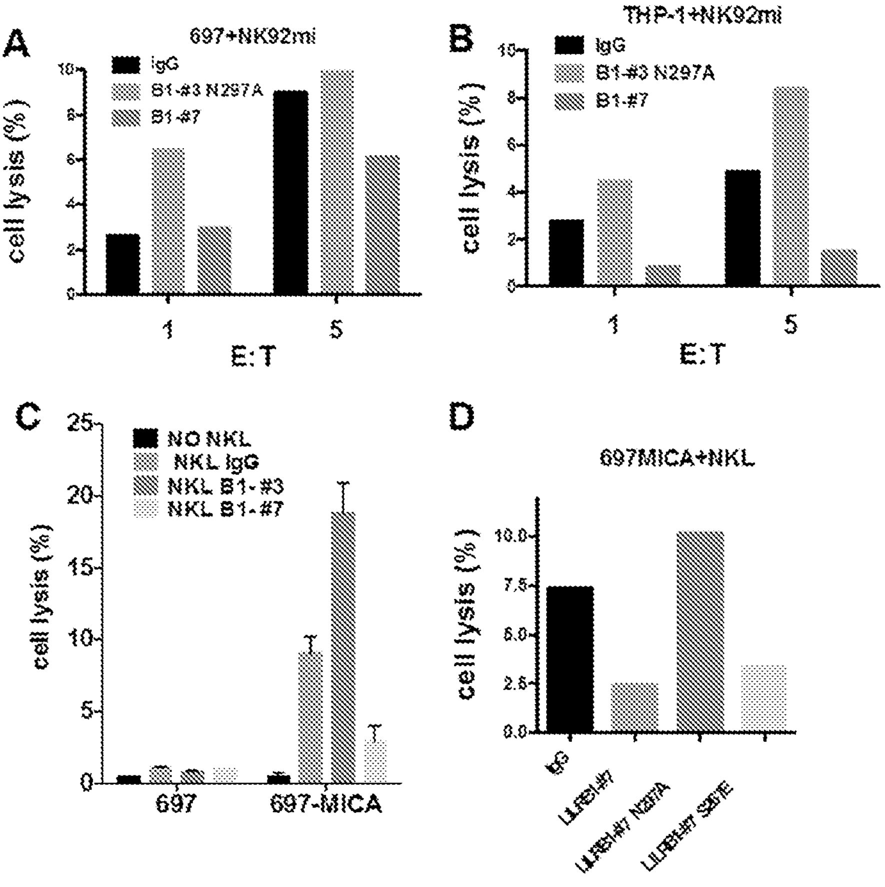
FIGS. 10A-D
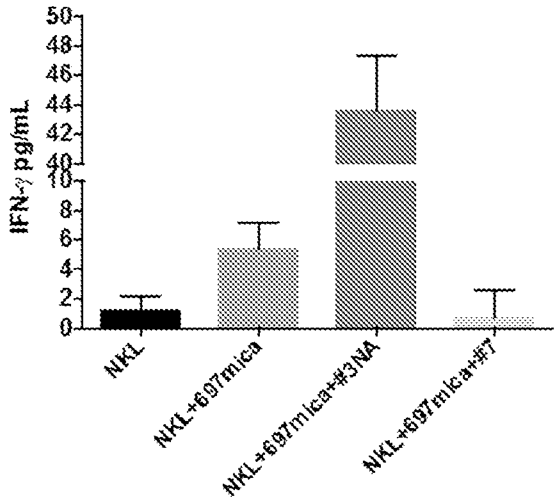
FIG. 11

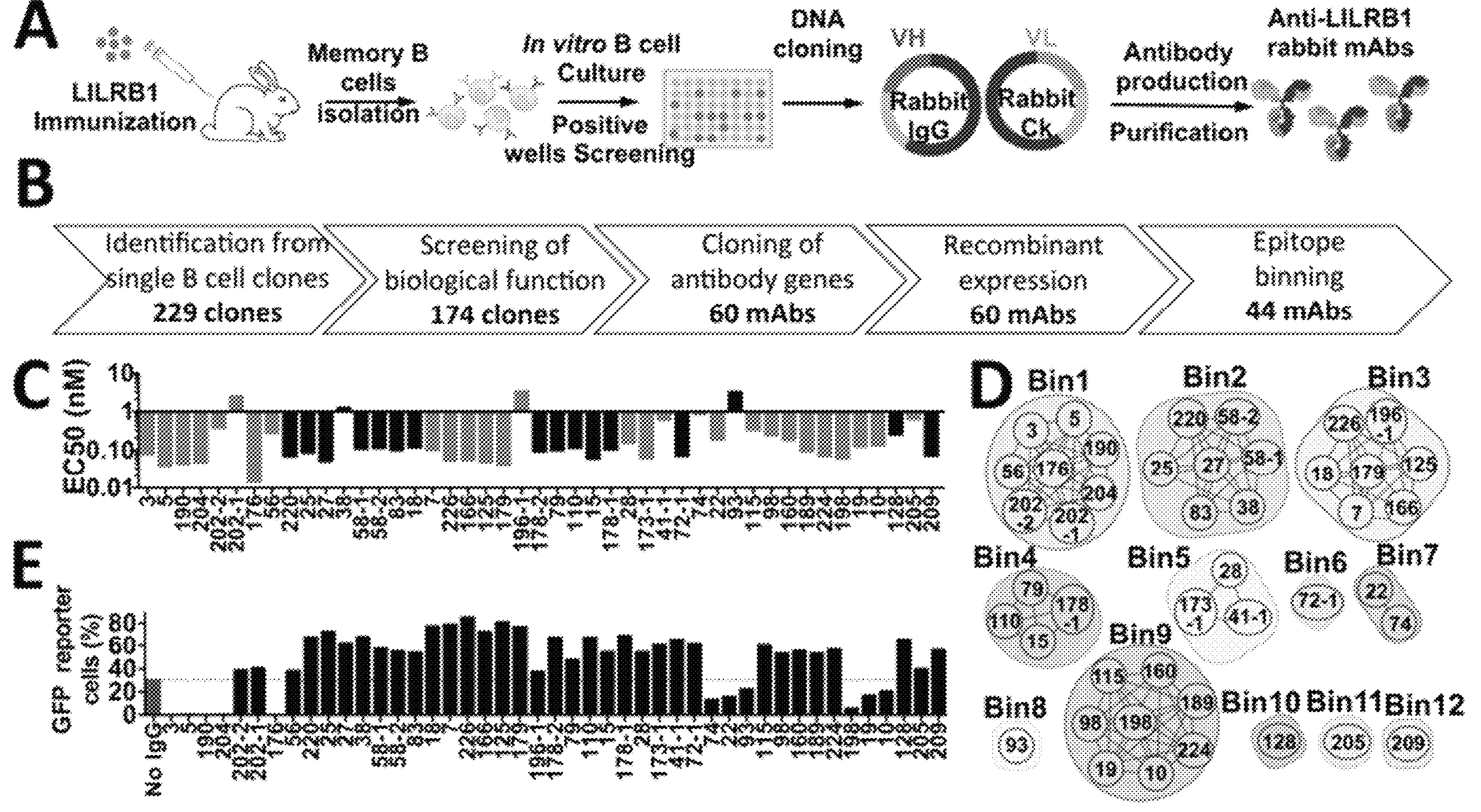
FIGS. 12A-E

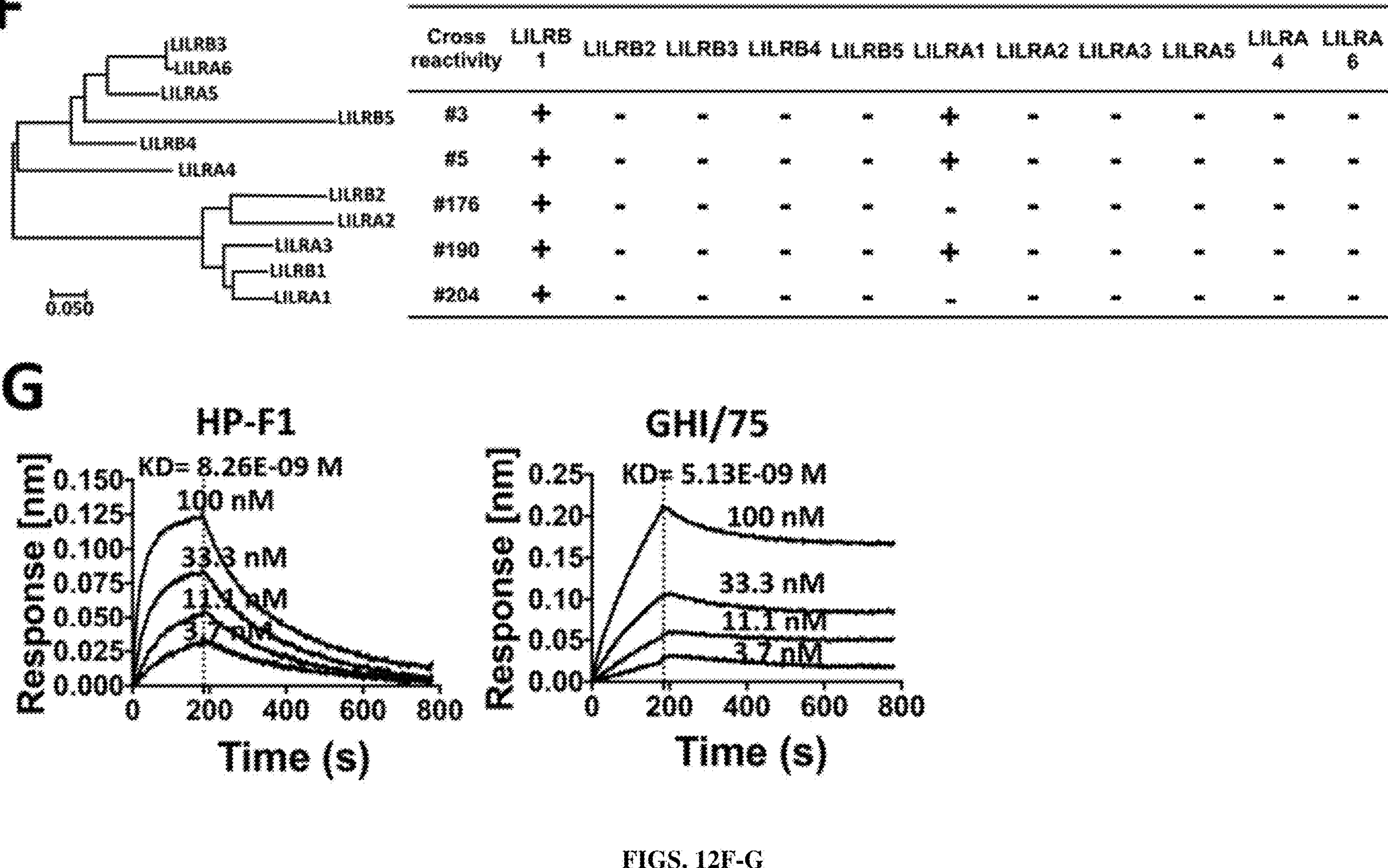
| Cross reactivity | LILRB 1 | LILRB2 | LILRB3 | LILRB4 | LILRB5 | LILRA1 | LILRA2 | LILRA3 | LILRA5 | LILRA 4 | LILRA 6 |
|---|---|---|---|---|---|---|---|---|---|---|---|
| #3 | + | - | - | - | - | + | - | - | - | - | - |
| #5 | + | - | - | - | - | + | - | - | - | - | - |
| #176 | + | - | - | - | - | - | - | - | - | - | - |
| #190 | + | - | - | - | - | + | - | - | - | - | - |
| #204 | + | - | - | - | - | - | - | - | - | - | - |
FIGS. 12F-G

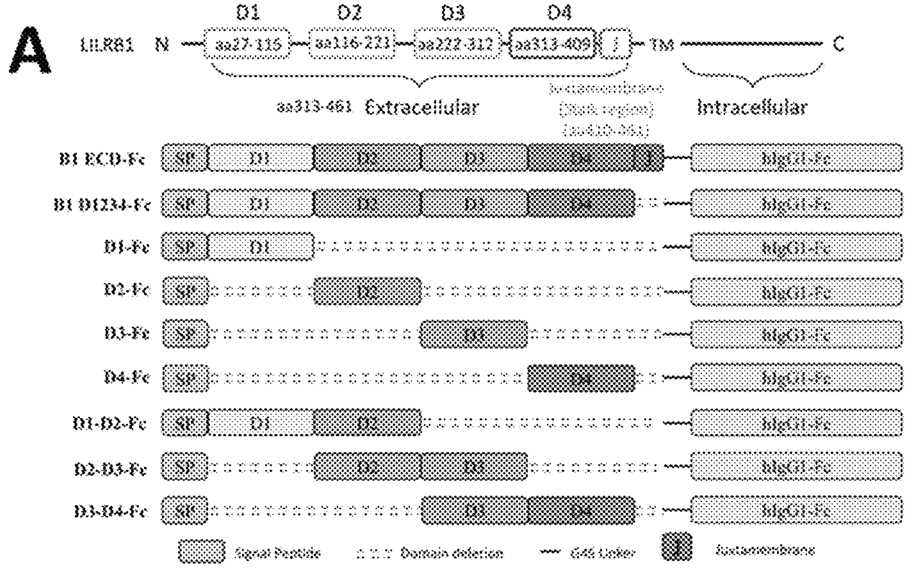
B
| Mutant NO. | Ig Domain | Mutation | Mutant NO. | Ig Domain | Mutation |
|---|---|---|---|---|---|
| M1 | D1 | R25S | M18 | D2 | A176G, S179L |
| M2 | D1 | G29S, Q30L, T31A | M19 | D2 | E184V, L187S |
| M3 | D1 | R36A, Y38A | M20 | D1 | R74G |
| M4 | D1 | T43S, L45S | M21 | D1 | Y76Q |
| M5 | D1 | I47A, T48A | M22 | D1 | G78Y |
| M6 | D1 | P51R, Q52P | M23 | D2 | Y99A |
| M7 | D1 | K57N | M24 | D2 | I100P |
| M8 | D1 | P61H | M25 | D2 | N117R |
| M9 | D1 | W67A | M26 | D2 | D129G |
| M10 | D1 | R74G, Y76Q, G78Y | M27 | D2 | W171S |
| M11 | D1 | aa80-84, DTAGR-RABW | M28 | D2 | Y172H |
| M12 | D1 | S87L | M29 | D1 | Q33A |
| M13 | D1 | E92V | M30 | D1 | E34A |
| M14 | D2 | Y99A, I100P | M31 | D1 | Q52A |
| M15 | D2 | N117R | M32 | D1 | S79A |
| M16 | D2 | D129G | M33 | D1 | D80A |
| M17 | D2 | W171S, Y172H | M34 | D1 | T81A |
| | | | M35 | D1 | R84A |
FIGS. 13A-B

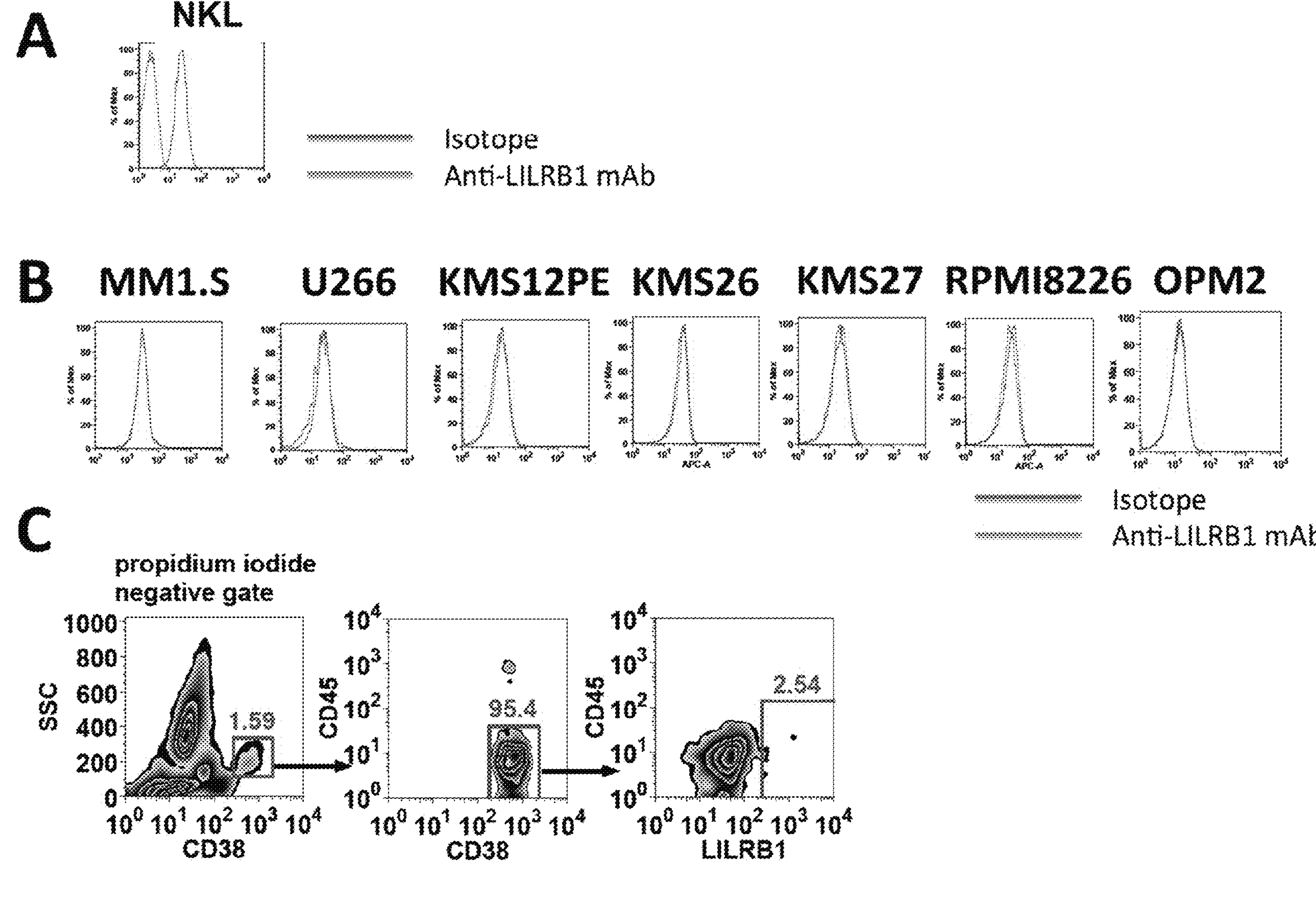
FIGS. 14A-C

```
                    SEQUENCE LISTING

<160> NUMBER OF SEQ ID NOS: 875

<210> SEQ ID NO 1
<211> LENGTH: 650
<212> TYPE: PRT
<213> ORGANISM: Homo sapiens

<400> SEQUENCE: 1

Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
            20                  25                  30

Ala Glu Pro Gly Ser Val Ile Thr Gln Gly Ser Pro Val Thr Leu Arg
        35                  40                  45

Cys Gln Gly Gly Gln Glu Thr Gln Glu Tyr Arg Leu Tyr Arg Glu Lys
    50                  55                  60

Lys Thr Ala Leu Trp Ile Thr Arg Ile Pro Gln Glu Leu Val Lys Lys
65                  70                  75                  80

Gly Gln Phe Pro Ile Pro Ser Ile Thr Trp Glu His Ala Gly Arg Tyr
                85                  90                  95

Arg Cys Tyr Tyr Gly Ser Asp Thr Ala Gly Arg Ser Glu Ser Ser Asp
            100                 105                 110

Pro Leu Glu Leu Val Val Thr Gly Ala Tyr Ile Lys Pro Thr Leu Ser
        115                 120                 125

Ala Gln Pro Ser Pro Val Val Asn Ser Gly Gly Asn Val Ile Leu Gln
    130                 135                 140
```

```
Cys Asp Ser Gln Val Ala Phe Asp Gly Phe Ser Leu Cys Lys Glu Gly
145                 150                 155                 160

Glu Asp Glu His Pro Gln Cys Leu Asn Ser Gln Pro His Ala Arg Gly
                165                 170                 175

Ser Ser Arg Ala Ile Phe Ser Val Gly Pro Val Ser Pro Ser Arg Arg
            180                 185                 190

Trp Trp Tyr Arg Cys Tyr Ala Tyr Asp Ser Asn Ser Pro Tyr Glu Trp
        195                 200                 205

Ser Leu Pro Ser Asp Leu Leu Glu Leu Leu Val Leu Gly Val Ser Lys
    210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255

Leu Tyr Lys Asp Gly Glu Arg Asp Phe Leu Gln Leu Ala Gly Ala Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Arg Cys Tyr Gly Ala His Asn Leu Ser
    290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
                325                 330                 335

Ala Ser Gly Glu Asn Val Thr Leu Leu Cys Gln Ser Gln Gly Trp Met
            340                 345                 350

Gln Thr Phe Leu Leu Thr Lys Glu Gly Ala Ala Asp Asp Pro Trp Arg
        355                 360                 365

Leu Arg Ser Thr Tyr Gln Ser Gln Lys Tyr Gln Ala Glu Phe Pro Met
    370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                405                 410                 415

Leu Val Val Ser Gly Pro Ser Gly Gly Pro Ser Ser Pro Thr Thr Gly
            420                 425                 430

Pro Thr Ser Thr Ser Gly Pro Glu Asp Gln Pro Leu Thr Pro Thr Gly
        435                 440                 445

Ser Asp Pro Gln Ser Gly Leu Gly Arg His Leu Gly Val Val Ile Gly
    450                 455                 460

Ile Leu Val Ala Val Ile Leu Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
            500                 505                 510

Thr Asp Arg Gly Leu Gln Trp Arg Ser Ser Pro Ala Ala Asp Ala Gln
        515                 520                 525

Glu Glu Asn Leu Tyr Ala Ala Val Lys His Thr Gln Pro Glu Asp Gly
    530                 535                 540

Val Glu Met Asp Thr Arg Ser Pro His Asp Glu Asp Pro Gln Ala Val
545                 550                 555                 560

Thr Tyr Ala Glu Val Lys His Ser Arg Pro Arg Arg Glu Met Ala Ser
```

```
                565                 570                 575

Pro Pro Ser Pro Leu Ser Gly Glu Phe Leu Asp Thr Lys Asp Arg Gln
            580                 585                 590

Ala Glu Glu Asp Arg Gln Met Asp Thr Glu Ala Ala Ala Ser Glu Ala
        595                 600                 605

Pro Gln Asp Val Thr Tyr Ala Gln Leu His Ser Leu Thr Leu Arg Arg
    610                 615                 620

Glu Ala Thr Glu Pro Pro Pro Ser Gln Glu Gly Pro Ser Pro Ala Val
625                 630                 635                 640

Pro Ser Ile Tyr Ala Thr Leu Ala Ile His
                645                 650


<210> SEQ ID NO 2
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 2

Gly Phe Asp Phe Ser Ser Asp Ala
1               5


<210> SEQ ID NO 3
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 3

Ile Tyr Asn Gly Asp Glu Ile
1               5


<210> SEQ ID NO 4
<211> LENGTH: 20
<212> TYPE: PRT
<213> ORGANISM: Artificial sequence
<220> FEATURE:
<223> OTHER INFORMATION: Synthetic antibody sequence

<400> SEQUENCE: 4

Ala Arg Ala Val Tyr Ser Asp Gly Gly Ala Gly Tyr Pro Tyr Met Tyr
1               5                   10                  15

Gly Met Asp Leu
            20


<210> SEQ ID NO 5
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 5

Gly Phe Asp Phe Ser Gly Ile Tyr Trp
1               5


<210> SEQ ID NO 6
<211> LENGTH: 9
<212> TYPE: PRT
<213> ORGANISM: Artificial sequence
<220> FEATURE:
<223> OTHER INFORMATION: Synthetic antibody sequence
```

<400> SEQUENCE: 6

Phe Asp Ala Glu Arg Thr Gly Asn Thr
1 5

<210> SEQ ID NO 7
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 7

Ala Arg Ser Tyr Tyr Met
1 5

<210> SEQ ID NO 8
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 8

Glu Leu Ser Phe Ser Ser Ala Tyr Tyr
1 5

<210> SEQ ID NO 9
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 9

Ile Tyr Ser Gly Asp Gly Asp
1 5

<210> SEQ ID NO 10
<211> LENGTH: 13
<212> TYPE: PRT
<213> ORGANISM: Artificial sequence
<220> FEATURE:
<223> OTHER INFORMATION: Synthetic antibody sequence

<400> SEQUENCE: 10

Ala Arg Ala Leu Asp Ser His Tyr Ser Ser Phe Asp Leu
1 5 10

<210> SEQ ID NO 11
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 11

Gly Phe Ser Leu Asn Ser Tyr Ala
1 5

<210> SEQ ID NO 12
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 12

Ile Asp Thr Gly Ala Ser Ile
1 5

<210> SEQ ID NO 13
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 13

Ala Arg Gly Phe Ser Met Phe Lys Leu
1 5

<210> SEQ ID NO 14
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 14

Gly Leu Asp Phe Ser Ser Ser Tyr Trp
1 5

<210> SEQ ID NO 15
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 15

Ile Asp Thr Gly Ser Ser Gly Ser Thr
1 5

<210> SEQ ID NO 16
<211> LENGTH: 11
<212> TYPE: PRT
<213> ORGANISM: Artificial sequence
<220> FEATURE:
<223> OTHER INFORMATION: Synthetic antibody sequence

<400> SEQUENCE: 16

Ala Ser Thr Pro Asn Ser Leu Gly Tyr Asp Leu
1 5 10

<210> SEQ ID NO 17
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 17

Gly Phe Ser Ser Ser Ser Ser Ala Tyr
1 5

<210> SEQ ID NO 18
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 18

Ile Phe Ile Gly Ser Gly Ser Asp Ser
1 5

<210> SEQ ID NO 19
<211> LENGTH: 19
<212> TYPE: PRT
<213> ORGANISM: Artificial sequence
<220> FEATURE:
<223> OTHER INFORMATION: Synthetic antibody sequence

<400> SEQUENCE: 19

Ala Arg Asn Thr Tyr Asp Trp Asn Gly Tyr Ile Tyr Gly Pro Cys Tyr
1 5 10 15

Phe Gly Leu

<210> SEQ ID NO 20
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 20

Gly Phe Ser Leu Ser Arg Tyr Ala
1 5

<210> SEQ ID NO 21
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 21

Ile Asp Thr Ser Ser Gly Asn
1 5

<210> SEQ ID NO 22
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 22

Ala Arg Gly Phe Ser Met Phe Lys Leu
1 5

<210> SEQ ID NO 23
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 23

Gly Leu Asp Phe Ser Ser Ser Tyr Trp
1 5

<210> SEQ ID NO 24
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 24

Ile Asp Val Gly Ser Ser Gly Gly Ser
1 5

<210> SEQ ID NO 25
<211> LENGTH: 12
<212> TYPE: PRT
<213> ORGANISM: Artificial sequence
<220> FEATURE:
<223> OTHER INFORMATION: Synthetic antibody sequence

<400> SEQUENCE: 25

Ala Ser Thr Thr Thr Asn Val Phe Gly Tyr Asp Leu
1 5 10

<210> SEQ ID NO 26
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 26

Gly Phe Asp Phe Ser Ser Asn Asp Tyr
1 5

<210> SEQ ID NO 27
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 27

Ile Tyr Gly Gly Asp Gly His Thr
1 5

<210> SEQ ID NO 28
<211> LENGTH: 19
<212> TYPE: PRT
<213> ORGANISM: Artificial sequence
<220> FEATURE:
<223> OTHER INFORMATION: Synthetic antibody sequence

<400> SEQUENCE: 28

Arg Gly Tyr Ser Tyr Gly Asp Thr Gly Tyr Ala Asp Ala Ile Leu Thr
1 5 10 15

Leu Asp Leu

<210> SEQ ID NO 29
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 29

Phe Asn Tyr Tyr Asn Tyr Tyr Tyr
1 5

<210> SEQ ID NO 30
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 30

```
Met Ser Thr Ala Ser Ala Asn
1               5
```

<210> SEQ ID NO 31
<211> LENGTH: 14
<212> TYPE: PRT
<213> ORGANISM: Artificial sequence
<220> FEATURE:
<223> OTHER INFORMATION: Synthetic antibody sequence

<400> SEQUENCE: 31

```
Ala Lys Ser His Gly Gly Asp Gly Gly Tyr Gly Val Val Leu
1               5                   10
```

<210> SEQ ID NO 32
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 32

```
Gly Phe Ser Phe Ser Gly Ser Tyr Trp
1               5
```

<210> SEQ ID NO 33
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 33

```
Ile Tyr Gly Asp Ser Ile Ala
1               5
```

<210> SEQ ID NO 34
<211> LENGTH: 15
<212> TYPE: PRT
<213> ORGANISM: Artificial sequence
<220> FEATURE:
<223> OTHER INFORMATION: Synthetic antibody sequence

<400> SEQUENCE: 34

```
Ala Arg Asp Arg Asn Gly Gly Ser Gly Ala Tyr Gly Trp Asp Leu
1               5                   10                  15
```

<210> SEQ ID NO 35
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 35

```
Gly Phe Ser Phe Ser Ser Asp Tyr Asp
1               5
```

<210> SEQ ID NO 36
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 36

Ile Val Thr Gly Phe Ser Gly Arg Ile
1               5

<210> SEQ ID NO 37
<211> LENGTH: 11
<212> TYPE: PRT
<213> ORGANISM: Artificial sequence
<220> FEATURE:
<223> OTHER INFORMATION: Synthetic antibody sequence

<400> SEQUENCE: 37

Ala Arg Asp Ser Gly Asn Tyr Asn Trp Asp Leu
1               5                   10

<210> SEQ ID NO 38
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 38

Gly Phe Ser Phe Ser Asn Asp Tyr Trp
1               5

<210> SEQ ID NO 39
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 39

Gly His Ile Gly Ser Phe Arg Thr Thr
1               5

<210> SEQ ID NO 40
<211> LENGTH: 16
<212> TYPE: PRT
<213> ORGANISM: Artificial sequence
<220> FEATURE:
<223> OTHER INFORMATION: Synthetic antibody sequence

<400> SEQUENCE: 40

Ala Arg Ser Pro Tyr Asp Asp Gly Tyr Gly Gly Phe Thr Phe Asn Leu
1               5                   10                  15

<210> SEQ ID NO 41
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 41

Gly Phe Ser Phe Ser Ser Ser Tyr Trp
1               5

<210> SEQ ID NO 42
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 42

```
Ile Tyr Ala Gly Ser Ser Gly Ser Thr
1               5


<210> SEQ ID NO 43
<211> LENGTH: 14
<212> TYPE: PRT
<213> ORGANISM: Artificial sequence
<220> FEATURE:
<223> OTHER INFORMATION: Synthetic antibody sequence

<400> SEQUENCE: 43

Ala Arg Ser Thr Ser Gly Ser Tyr Gly Ala Gly Leu Gly Leu
1               5                   10


<210> SEQ ID NO 44
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 44

Gly Phe Ser Phe Ser Ile Asn Leu Tyr
1               5


<210> SEQ ID NO 45
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 45

Ile Tyr Gly Asn Asn Asn Ala Asn Thr
1               5


<210> SEQ ID NO 46
<211> LENGTH: 12
<212> TYPE: PRT
<213> ORGANISM: Artificial sequence
<220> FEATURE:
<223> OTHER INFORMATION: Synthetic antibody sequence

<400> SEQUENCE: 46

Ala Arg Asp Thr Ala Ala Tyr Tyr Ala Phe Ser Leu
1               5                   10


<210> SEQ ID NO 47
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 47

Ser Gly Phe Thr Phe Ser Gly Tyr Tyr
1               5


<210> SEQ ID NO 48
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 48
```

```
Ile Tyr Val Gly Ser Gly Gly Ser Thr
1               5


<210> SEQ ID NO 49
<211> LENGTH: 13
<212> TYPE: PRT
<213> ORGANISM: Artificial sequence
<220> FEATURE:
<223> OTHER INFORMATION: Synthetic antibody sequence

<400> SEQUENCE: 49

Ala Arg Gly Val Asn Asp Tyr Gly Trp Ala Leu Lys Leu
1               5                   10


<210> SEQ ID NO 50
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 50

Ala Phe Ser Phe Ser Ser Ser Ser Trp
1               5


<210> SEQ ID NO 51
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 51

Ile Tyr Gly Gly Ser Val Gly Thr Thr
1               5


<210> SEQ ID NO 52
<211> LENGTH: 13
<212> TYPE: PRT
<213> ORGANISM: Artificial sequence
<220> FEATURE:
<223> OTHER INFORMATION: Synthetic antibody sequence

<400> SEQUENCE: 52

Ala Thr Asn Thr Asp Ser Ser Arg Ser Tyr Tyr Asn Leu
1               5                   10


<210> SEQ ID NO 53
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 53

Gly Ile Asp Leu Ser Asn Tyr Trp Tyr
1               5


<210> SEQ ID NO 54
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 54

Val Ala Thr Asp Ser Ser Arg Thr
```

1 5

<210> SEQ ID NO 55
<211> LENGTH: 20
<212> TYPE: PRT
<213> ORGANISM: Artificial sequence
<220> FEATURE:
<223> OTHER INFORMATION: Synthetic antibody sequence

<400> SEQUENCE: 55

Arg Gly Ser Gly Ala Ser Thr Asn Gly Val Trp Trp Val Met Gly Asp
1 5 10 15

Gly Met Asp Leu
20

<210> SEQ ID NO 56
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 56

Gly Phe Ser Leu Asn Arg Tyr Tyr
1 5

<210> SEQ ID NO 57
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 57

Ile Tyr Ser Gly Ser Gly Ser
1 5

<210> SEQ ID NO 58
<211> LENGTH: 13
<212> TYPE: PRT
<213> ORGANISM: Artificial sequence
<220> FEATURE:
<223> OTHER INFORMATION: Synthetic antibody sequence

<400> SEQUENCE: 58

Gly Arg Leu Asp Tyr Arg Val Ile Tyr Ala Phe Asn Leu
1 5 10

<210> SEQ ID NO 59
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 59

Gly Phe Ser Phe Ser Gly Ser Cys Asp
1 5

<210> SEQ ID NO 60
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 60

Ile Val Leu Ser Asn Gly Asn
1               5

<210> SEQ ID NO 61
<211> LENGTH: 15
<212> TYPE: PRT
<213> ORGANISM: Artificial sequence
<220> FEATURE:
<223> OTHER INFORMATION: Synthetic antibody sequence

<400> SEQUENCE: 61

Ala Arg Glu Arg Tyr Pro Gly Ala Phe Ser Ser Gly Leu Asp Leu
1               5                   10                  15

<210> SEQ ID NO 62
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 62

Gly Phe Ser Phe Ser Ser Ser Trp Tyr
1               5

<210> SEQ ID NO 63
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 63

Ile Tyr Thr Leu Arg Ser Gly Ala Ala
1               5

<210> SEQ ID NO 64
<211> LENGTH: 13
<212> TYPE: PRT
<213> ORGANISM: Artificial sequence
<220> FEATURE:
<223> OTHER INFORMATION: Synthetic antibody sequence

<400> SEQUENCE: 64

Ala Arg Ala Thr Tyr Ala Tyr Ala Gly Ala Gly Asp Leu
1               5                   10

<210> SEQ ID NO 65
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 65

Ala Phe Ser Phe Ser Ser Ser Ser Trp
1               5

<210> SEQ ID NO 66
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 66

```
Ile Tyr Gly Gly Ser Val Ala Thr Thr
1               5


<210> SEQ ID NO 67
<211> LENGTH: 13
<212> TYPE: PRT
<213> ORGANISM: Artificial sequence
<220> FEATURE:
<223> OTHER INFORMATION: Synthetic antibody sequence

<400> SEQUENCE: 67

Ala Thr Asn Thr Asp Ser Ser Arg Ser Tyr Tyr Asn Leu
1               5                   10


<210> SEQ ID NO 68
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 68

Gly Phe Ser Phe Ser Gly Asn Thr
1               5


<210> SEQ ID NO 69
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 69

Ile Tyr Pro Ser Ser Thr Ser Ile
1               5


<210> SEQ ID NO 70
<211> LENGTH: 17
<212> TYPE: PRT
<213> ORGANISM: Artificial sequence
<220> FEATURE:
<223> OTHER INFORMATION: Synthetic antibody sequence

<400> SEQUENCE: 70

Ala Arg Arg Tyr Ala Ala Phe Leu Thr Tyr Gly Ser Gly Ala Phe Asp
1               5                   10                  15

Pro


<210> SEQ ID NO 71
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 71

Gly Phe Ser Phe Ser Ser Ser Tyr Trp
1               5


<210> SEQ ID NO 72
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 72
```

Val Ala Thr Gly Ser Gly Thr
1 5

<210> SEQ ID NO 73
<211> LENGTH: 11
<212> TYPE: PRT
<213> ORGANISM: Artificial sequence
<220> FEATURE:
<223> OTHER INFORMATION: Synthetic antibody sequence

<400> SEQUENCE: 73

Ala Arg Ile Gly Ala Phe Tyr Ser Phe Arg Leu
1 5 10

<210> SEQ ID NO 74
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 74

Gly Phe Ser Phe Ser Ser Ser Tyr Trp
1 5

<210> SEQ ID NO 75
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 75

Ile Tyr Ala Gly Asn Ser Ala Asn Thr
1 5

<210> SEQ ID NO 76
<211> LENGTH: 13
<212> TYPE: PRT
<213> ORGANISM: Artificial sequence
<220> FEATURE:
<223> OTHER INFORMATION: Synthetic antibody sequence

<400> SEQUENCE: 76

Ala Ser Arg Asn Gly Gly Ala Pro Asp Gly Leu Asn Leu
1 5 10

<210> SEQ ID NO 77
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 77

Gly Phe Ser Phe Ser Ser Ser Tyr Trp
1 5

<210> SEQ ID NO 78
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 78

```
Ile Ala Thr Gly Thr Gly Ser
1               5


<210> SEQ ID NO 79
<211> LENGTH: 11
<212> TYPE: PRT
<213> ORGANISM: Artificial sequence
<220> FEATURE:
<223> OTHER INFORMATION: Synthetic antibody sequence

<400> SEQUENCE: 79

Ala Arg Gly Gly Gly Tyr Trp Ser Phe Ser Leu
1               5                   10


<210> SEQ ID NO 80
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 80

Gly Phe Ser Phe Ser Ser Ser Tyr Tyr
1               5


<210> SEQ ID NO 81
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 81

Ile Tyr Thr Gly Ser Asp Ser Thr
1               5


<210> SEQ ID NO 82
<211> LENGTH: 19
<212> TYPE: PRT
<213> ORGANISM: Artificial sequence
<220> FEATURE:
<223> OTHER INFORMATION: Synthetic antibody sequence

<400> SEQUENCE: 82

Gly Asp Trp Asp Tyr Ala Asp Ala Ala Gly Tyr Tyr Val Ala Arg Gly
1               5                   10                  15

Phe Asn Leu


<210> SEQ ID NO 83
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 83

Gly Phe Ser Phe Thr Lys Asn Tyr Tyr
1               5


<210> SEQ ID NO 84
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 84
```

```
Ile Tyr Ala Gly Ser Thr Asn Thr
1               5


<210> SEQ ID NO 85
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 85

Arg Asp Phe Val Ser Tyr Leu Asn Leu
1               5


<210> SEQ ID NO 86
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 86

Gly Ile Asp Leu Ser Asn Phe Tyr Tyr
1               5


<210> SEQ ID NO 87
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 87

Val Ala Ser Asp Ser Ser Arg
1               5


<210> SEQ ID NO 88
<211> LENGTH: 21
<212> TYPE: PRT
<213> ORGANISM: Artificial sequence
<220> FEATURE:
<223> OTHER INFORMATION: Synthetic antibody sequence

<400> SEQUENCE: 88

Ala Arg Gly Ser Gly Ala Ser Thr Asn Gly Val Trp Trp Val Met Gly
1               5                   10                  15

Asp Gly Met Asp Leu
            20


<210> SEQ ID NO 89
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 89

Gly Phe Ser Phe Ser Ser Gly His Tyr
1               5


<210> SEQ ID NO 90
<211> LENGTH: 9
<212> TYPE: PRT
<213> ORGANISM: Artificial sequence
<220> FEATURE:
<223> OTHER INFORMATION: Synthetic antibody sequence
```

<400> SEQUENCE: 90

Ile Tyr Ala Gly Ser Asp Thr Gly Ser
1 5

<210> SEQ ID NO 91
<211> LENGTH: 16
<212> TYPE: PRT
<213> ORGANISM: Artificial sequence
<220> FEATURE:
<223> OTHER INFORMATION: Synthetic antibody sequence

<400> SEQUENCE: 91

Cys Ala Arg Ser Ser Asn Ser Tyr Gly Asn Tyr Gly Val Ser Asn Leu
1 5 10 15

<210> SEQ ID NO 92
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 92

Gly Ile Asp Phe Ser Ser Gly Tyr Trp
1 5

<210> SEQ ID NO 93
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 93

Ile Phe Thr Ser Ser Gly Thr Thr
1 5

<210> SEQ ID NO 94
<211> LENGTH: 10
<212> TYPE: PRT
<213> ORGANISM: Artificial sequence
<220> FEATURE:
<223> OTHER INFORMATION: Synthetic antibody sequence

<400> SEQUENCE: 94

Arg Asp Ile Tyr Ser Tyr Gly Met Asp Leu
1 5 10

<210> SEQ ID NO 95
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 95

Gly Ile Asp Phe Ser Ser Ala Tyr
1 5

<210> SEQ ID NO 96
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 96

Met Arg Ile Asn Asp Arg Ser
1               5

<210> SEQ ID NO 97
<211> LENGTH: 12
<212> TYPE: PRT
<213> ORGANISM: Artificial sequence
<220> FEATURE:
<223> OTHER INFORMATION: Synthetic antibody sequence

<400> SEQUENCE: 97

Ala Arg Ile Ala Thr Gly Thr Asn Val Asp Asp Phe
1               5                   10

<210> SEQ ID NO 98
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 98

Gly Phe Ser Phe Ser Ser Lys Gln Tyr
1               5

<210> SEQ ID NO 99
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 99

Ile Val Thr Val Asn Asn Lys
1               5

<210> SEQ ID NO 100
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 100

Ala Arg Trp Arg Thr Phe Gly Leu
1               5

<210> SEQ ID NO 101
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 101

Arg Phe Ser Leu Ser Asn Met Asn Val
1               5

<210> SEQ ID NO 102
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 102

```
Ile Asn Ile Gly Gly Thr Asn
1               5


<210> SEQ ID NO 103
<211> LENGTH: 14
<212> TYPE: PRT
<213> ORGANISM: Artificial sequence
<220> FEATURE:
<223> OTHER INFORMATION: Synthetic antibody sequence

<400> SEQUENCE: 103

Ala Arg Ser Tyr Ile Thr Asp Arg Ile Tyr Asp Tyr Asp Phe
1               5                   10


<210> SEQ ID NO 104
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 104

Gly Phe Asp Phe Ser Ser Lys Tyr Tyr
1               5


<210> SEQ ID NO 105
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 105

Ile Tyr Gly Gly Ser Ser Asp Ser Thr
1               5


<210> SEQ ID NO 106
<211> LENGTH: 12
<212> TYPE: PRT
<213> ORGANISM: Artificial sequence
<220> FEATURE:
<223> OTHER INFORMATION: Synthetic antibody sequence

<400> SEQUENCE: 106

Gly Arg Val Ile Asp Gly Ala Cys Gly Tyr Asp Leu
1               5                   10


<210> SEQ ID NO 107
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 107

Gly Phe Asp Phe Ser Ser Asn Ala Tyr
1               5


<210> SEQ ID NO 108
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 108
```

Ile Tyr Asp Gly Thr Ser Gly Asp Thr
1 5

<210> SEQ ID NO 109
<211> LENGTH: 13
<212> TYPE: PRT
<213> ORGANISM: Artificial sequence
<220> FEATURE:
<223> OTHER INFORMATION: Synthetic antibody sequence

<400> SEQUENCE: 109

Ala Arg Asp Thr Arg Ser Ser Asn Tyr Tyr Phe Asn Leu
1 5 10

<210> SEQ ID NO 110
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 110

Asn Ser Tyr Lys Tyr Tyr Tyr Met
1 5

<210> SEQ ID NO 111
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 111

Ser Thr Ala Ser Arg Asn Ile
1 5

<210> SEQ ID NO 112
<211> LENGTH: 14
<212> TYPE: PRT
<213> ORGANISM: Artificial sequence
<220> FEATURE:
<223> OTHER INFORMATION: Synthetic antibody sequence

<400> SEQUENCE: 112

Ala Lys Ser His Gly Gly Asp Gly Gly Tyr Gly Val Val Leu
1 5 10

<210> SEQ ID NO 113
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 113

Gly Phe Ser Phe Ser Ser Ser Tyr Cys
1 5

<210> SEQ ID NO 114
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 114

Ile Tyr Thr Asp Ser Ser Gly Ala Thr 1 5

<210> SEQ ID NO 115
<211> LENGTH: 19
<212> TYPE: PRT
<213> ORGANISM: Artificial sequence
<220> FEATURE:
<223> OTHER INFORMATION: Synthetic antibody sequence

<400> SEQUENCE: 115

Ala Arg Gly Trp Asp Tyr Glu Asp Pro Gly Tyr Thr Asp Thr Thr Tyr
1 5 10 15

Phe Ser Leu

<210> SEQ ID NO 116
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 116

Gly Phe Ser Phe Ser Ser Ser Tyr Trp
1 5

<210> SEQ ID NO 117
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 117

Ile Tyr Ala Gly Ser Ser Gly Ser Thr
1 5

<210> SEQ ID NO 118
<211> LENGTH: 11
<212> TYPE: PRT
<213> ORGANISM: Artificial sequence
<220> FEATURE:
<223> OTHER INFORMATION: Synthetic antibody sequence

<400> SEQUENCE: 118

Ala Arg Gly Gly Thr Ser Tyr Arg Leu Asp Leu
1 5 10

<210> SEQ ID NO 119
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 119

Gly Phe Ser Phe Ser Ser Lys Gln Tyr
1 5

<210> SEQ ID NO 120
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 120

Ile Val Thr Val Asn Asn Lys
1 5

<210> SEQ ID NO 121
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 121

Thr Arg Trp Arg Thr Phe Gly Leu
1 5

<210> SEQ ID NO 122
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 122

Gly Ile Asp Phe Asn Asn Asp Tyr Asn
1 5

<210> SEQ ID NO 123
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 123

Ile Tyr Thr Gly Ser Asp Ser Thr
1 5

<210> SEQ ID NO 124
<211> LENGTH: 17
<212> TYPE: PRT
<213> ORGANISM: Artificial sequence
<220> FEATURE:
<223> OTHER INFORMATION: Synthetic antibody sequence

<400> SEQUENCE: 124

Ala Arg Asp Leu Val Thr Gly Tyr Ala Thr Tyr Gly Tyr Gly Phe Ile
1 5 10 15

Leu

<210> SEQ ID NO 125
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 125

Ser Ser Ser Tyr Trp Ile Cys Trp
1 5

<210> SEQ ID NO 126
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 126

```
Gly Ile Gly Ser Ser Gly Thr Thr
1               5


<210> SEQ ID NO 127
<211> LENGTH: 11
<212> TYPE: PRT
<213> ORGANISM: Artificial sequence
<220> FEATURE:
<223> OTHER INFORMATION: Synthetic antibody sequence

<400> SEQUENCE: 127

Ala Arg Val Gly Gly Tyr Trp Thr Phe Asp Leu
1               5                   10


<210> SEQ ID NO 128
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 128

Gly Phe Ser Phe Ser Ser Asp Tyr Trp
1               5


<210> SEQ ID NO 129
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 129

Ile Tyr Thr Gly Asp Asp Asp
1               5


<210> SEQ ID NO 130
<211> LENGTH: 13
<212> TYPE: PRT
<213> ORGANISM: Artificial sequence
<220> FEATURE:
<223> OTHER INFORMATION: Synthetic antibody sequence

<400> SEQUENCE: 130

Ala Arg Gly Leu Thr Ile Gly Thr Ala Glu Leu Tyr Phe
1               5                   10


<210> SEQ ID NO 131
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 131

Gly Phe Ser Phe Thr Lys Asn Tyr Tyr
1               5


<210> SEQ ID NO 132
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 132
```

```
Ile Tyr Ala Gly Ser Thr Asn
1               5


<210> SEQ ID NO 133
<211> LENGTH: 10
<212> TYPE: PRT
<213> ORGANISM: Artificial sequence
<220> FEATURE:
<223> OTHER INFORMATION: Synthetic antibody sequence

<400> SEQUENCE: 133

Ala Arg Asp Phe Val Ser Tyr Leu Asn Leu
1               5                   10


<210> SEQ ID NO 134
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 134

Gly Phe Asp Leu Ser Asn Asn Tyr Tyr
1               5


<210> SEQ ID NO 135
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 135

Val Asp Ser Asp Leu Thr Asp Ser Ala
1               5


<210> SEQ ID NO 136
<211> LENGTH: 15
<212> TYPE: PRT
<213> ORGANISM: Artificial sequence
<220> FEATURE:
<223> OTHER INFORMATION: Synthetic antibody sequence

<400> SEQUENCE: 136

Ala Gly Ser Gly Ser Gly Tyr Tyr Tyr Tyr Tyr Gly Met Asp Leu
1               5                   10                  15


<210> SEQ ID NO 137
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 137

Gly Phe Ser Phe Asn Gly Asp Tyr Tyr
1               5


<210> SEQ ID NO 138
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 138

Ile Tyr Ala Ala Gly Asp Asp
```

```
1               5


<210> SEQ ID NO 139
<211> LENGTH: 12
<212> TYPE: PRT
<213> ORGANISM: Artificial sequence
<220> FEATURE:
<223> OTHER INFORMATION: Synthetic antibody sequence

<400> SEQUENCE: 139

Ala Arg Asp Gln Ala Asp Ser Tyr Ala Phe Gly Leu
1               5                   10


<210> SEQ ID NO 140
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 140

Gly Phe Ser Phe Ser Ser Ser Tyr Trp
1               5


<210> SEQ ID NO 141
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 141

Ile Tyr Ala Gly Ser Ser Gly Ser Thr
1               5


<210> SEQ ID NO 142
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 142

Ala Arg Gly Phe Ser Met Phe Lys Leu
1               5


<210> SEQ ID NO 143
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 143

Gly Phe Ser Phe Ser Ser Ser Tyr Cys
1               5


<210> SEQ ID NO 144
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 144

Ile Tyr Thr Asp Ser Ser Gly Ala Thr
1               5
```

<210> SEQ ID NO 145
<211> LENGTH: 19
<212> TYPE: PRT
<213> ORGANISM: Artificial sequence
<220> FEATURE:
<223> OTHER INFORMATION: Synthetic antibody sequence

<400> SEQUENCE: 145

Ala Arg Gly Trp Asp Tyr Glu Asp Pro Gly Tyr Thr Asp Thr Thr Tyr
1 5 10 15

Phe Ser Leu

<210> SEQ ID NO 146
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 146

Arg Ile Asp Leu Asn Asn Tyr Tyr Tyr
1 5

<210> SEQ ID NO 147
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 147

Val Ala Thr Asp Ser Ser Val Thr
1 5

<210> SEQ ID NO 148
<211> LENGTH: 20
<212> TYPE: PRT
<213> ORGANISM: Artificial sequence
<220> FEATURE:
<223> OTHER INFORMATION: Synthetic antibody sequence

<400> SEQUENCE: 148

Arg Gly Ser Gly Ala Ala Thr Asn Gly Val Trp Trp Val Met Gly Asp
1 5 10 15

Gly Met Asp Leu
20

<210> SEQ ID NO 149
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 149

Gly Ile Asp Leu Ser Ser Tyr Ala
1 5

<210> SEQ ID NO 150
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 150

Ile Gly Lys Ser Gly Thr Thr
1 5

<210> SEQ ID NO 151
<211> LENGTH: 13
<212> TYPE: PRT
<213> ORGANISM: Artificial sequence
<220> FEATURE:
<223> OTHER INFORMATION: Synthetic antibody sequence

<400> SEQUENCE: 151

Ala Arg Ala Gly Ala Ser Arg Ser Ile Tyr Tyr Asp Leu
1 5 10

<210> SEQ ID NO 152
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 152

Gly Phe Ser Phe Ser Gly Ile Val Tyr
1 5

<210> SEQ ID NO 153
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 153

Ala Phe Val Gly Ser Gly Gly Ser Thr
1 5

<210> SEQ ID NO 154
<211> LENGTH: 11
<212> TYPE: PRT
<213> ORGANISM: Artificial sequence
<220> FEATURE:
<223> OTHER INFORMATION: Synthetic antibody sequence

<400> SEQUENCE: 154

Ala Lys Ser Tyr Asn Tyr Asn Gly Leu Gly Leu
1 5 10

<210> SEQ ID NO 155
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 155

Gly Phe Ser Phe Ser Ser Ser Tyr Tyr
1 5

<210> SEQ ID NO 156
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 156

Ile Tyr Gly Gly Ser Thr Gly Thr Thr
1 5

<210> SEQ ID NO 157
<211> LENGTH: 15
<212> TYPE: PRT
<213> ORGANISM: Artificial sequence
<220> FEATURE:
<223> OTHER INFORMATION: Synthetic antibody sequence

<400> SEQUENCE: 157

Ala Arg Ser Tyr Asn Ser Ala Ser Ser Gly Tyr Tyr Trp Asp Leu
1 5 10 15

<210> SEQ ID NO 158
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 158

Gly Ile Asp Phe Ser Ser Gly Ala Trp
1 5

<210> SEQ ID NO 159
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 159

Ile Phe Thr Thr Ser Gly Phe Thr
1 5

<210> SEQ ID NO 160
<211> LENGTH: 10
<212> TYPE: PRT
<213> ORGANISM: Artificial sequence
<220> FEATURE:
<223> OTHER INFORMATION: Synthetic antibody sequence

<400> SEQUENCE: 160

Arg Asp Ile Tyr Ser Tyr Gly Met Asp Leu
1 5 10

<210> SEQ ID NO 161
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 161

Gly Phe Ser Phe Ser Ser Arg Gln Tyr
1 5

<210> SEQ ID NO 162
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 162

Ile Val Thr Val Asn Asn Lys
1 5

<210> SEQ ID NO 163
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 163

Ala Arg Trp Arg Thr Phe Gly Leu
1 5

<210> SEQ ID NO 164
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 164

Gly Phe Ser Phe Ser Ser Ser Tyr Cys
1 5

<210> SEQ ID NO 165
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 165

Ile Tyr Thr Asp Ser Ser Gly Ala Thr
1 5

<210> SEQ ID NO 166
<211> LENGTH: 19
<212> TYPE: PRT
<213> ORGANISM: Artificial sequence
<220> FEATURE:
<223> OTHER INFORMATION: Synthetic antibody sequence

<400> SEQUENCE: 166

Ala Arg Gly Trp Asp Tyr Glu Asp Pro Gly Tyr Thr Asp Thr Thr Tyr
1 5 10 15

Phe Ser Leu

<210> SEQ ID NO 167
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 167
cagaacattt acagctac 18

<210> SEQ ID NO 168
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 168 aaggcatcc 9

<210> SEQ ID NO 169
<211> LENGTH: 60
<212> TYPE: DNA
<213> ORGANISM: Artificial sequence
<220> FEATURE:
<223> OTHER INFORMATION: Synthetic antibody sequence

<400> SEQUENCE: 169
gcgagagctg tctatagtga tggtggtgct ggttatcctt atatgtatgg catggacctc 60

<210> SEQ ID NO 170
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 170
cagagtcttt ataatgcgaa cgac 24

<210> SEQ ID NO 171
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 171 tgggcatcc 9

<210> SEQ ID NO 172
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 172
gcgagatcat attatatg 18

<210> SEQ ID NO 173
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 173
cagagcattt acaggtac 18

<210> SEQ ID NO 174
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 174 tatggatcc 9

<210> SEQ ID NO 175
<211> LENGTH: 39
<212> TYPE: DNA
<213> ORGANISM: Artificial sequence
<220> FEATURE:
<223> OTHER INFORMATION: Synthetic antibody sequence

<400> SEQUENCE: 175
gcgagggctc tggatagtca ttattcttcc tttgacttg 39

<210> SEQ ID NO 176
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 176
cagagtgttt atggtaacaa ccgc 24

<210> SEQ ID NO 177
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 177 ctggcatcc 9

<210> SEQ ID NO 178
<211> LENGTH: 27
<212> TYPE: DNA
<213> ORGANISM: Artificial sequence
<220> FEATURE:
<223> OTHER INFORMATION: Synthetic antibody sequence

<400> SEQUENCE: 178
gcgaggggtt tttcgatgtt taagttg 27

<210> SEQ ID NO 179
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 179
cagaacattg tcagtaat 18

<210> SEQ ID NO 180
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 180 tatgcatcc 9

<210> SEQ ID NO 181
<211> LENGTH: 33
<212> TYPE: DNA
<213> ORGANISM: Artificial sequence
<220> FEATURE:
<223> OTHER INFORMATION: Synthetic antibody sequence

<400> SEQUENCE: 181
gcgagtactc ctaatagtct aggttacgac tta 33

<210> SEQ ID NO 182
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 182
cagagcattt acaactac 18

<210> SEQ ID NO 183
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 183 gatgtatcc 9

<210> SEQ ID NO 184
<211> LENGTH: 57
<212> TYPE: DNA
<213> ORGANISM: Artificial sequence
<220> FEATURE:
<223> OTHER INFORMATION: Synthetic antibody sequence

<400> SEQUENCE: 184
gcgagaaata cttatgattg gaatggttat atttatggcc cgtgttattt tggcttg 57

<210> SEQ ID NO 185
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 185
cagagtgttt ataataacaa caac 24

<210> SEQ ID NO 186
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 186 tctgcatcc 9

<210> SEQ ID NO 187
<211> LENGTH: 27
<212> TYPE: DNA
<213> ORGANISM: Artificial sequence
<220> FEATURE:
<223> OTHER INFORMATION: Synthetic antibody sequence

<400> SEQUENCE: 187
gcgagaggtt tttctatgtt taagttg 27

<210> SEQ ID NO 188
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 188
cagaacattt acaacaat 18

<210> SEQ ID NO 189
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 189 tatgcatcc 9

<210> SEQ ID NO 190
<211> LENGTH: 36
<212> TYPE: DNA
<213> ORGANISM: Artificial sequence
<220> FEATURE:
<223> OTHER INFORMATION: Synthetic antibody sequence

<400> SEQUENCE: 190
gcgagcacta cgactaatgt tttcggttac gactta 36

<210> SEQ ID NO 191
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 191
cagactattg gtagctac 18

<210> SEQ ID NO 192
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 192 gaagcatcc 9

<210> SEQ ID NO 193
<211> LENGTH: 57
<212> TYPE: DNA
<213> ORGANISM: Artificial sequence
<220> FEATURE:
<223> OTHER INFORMATION: Synthetic antibody sequence

<400> SEQUENCE: 193
aggggatata gttatggtga tactggatat gctgatgcta ttcttacctt ggacttg 57

<210> SEQ ID NO 194
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 194
gagaccatta gtaataga 18

<210> SEQ ID NO 195

<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 195 tctgcatcc 9

<210> SEQ ID NO 196
<211> LENGTH: 42
<212> TYPE: DNA
<213> ORGANISM: Artificial sequence
<220> FEATURE:
<223> OTHER INFORMATION: Synthetic antibody sequence

<400> SEQUENCE: 196
gcgaaatccc atggtggtga tggtggttat ggggttgtat ta 42

<210> SEQ ID NO 197
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 197
cagagcatta gtagttac 18

<210> SEQ ID NO 198
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 198 aaggcatcc 9

<210> SEQ ID NO 199
<211> LENGTH: 45
<212> TYPE: DNA
<213> ORGANISM: Artificial sequence
<220> FEATURE:
<223> OTHER INFORMATION: Synthetic antibody sequence

<400> SEQUENCE: 199
gcgagagatc gaaatggtgg ttctggtgct tatggttggg acttg 45

<210> SEQ ID NO 200
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 200
cagagcatta gtgattac 18

<210> SEQ ID NO 201
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 201 agggcatcc 9

<210> SEQ ID NO 202
<211> LENGTH: 33
<212> TYPE: DNA
<213> ORGANISM: Artificial sequence
<220> FEATURE:
<223> OTHER INFORMATION: Synthetic antibody sequence

<400> SEQUENCE: 202
gcgagagata gtggtaatta taattgggac ttg 33

<210> SEQ ID NO 203
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 203
cagagcattg gcaatgca 18

<210> SEQ ID NO 204
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 204 aaggcatcc 9

<210> SEQ ID NO 205
<211> LENGTH: 48
<212> TYPE: DNA
<213> ORGANISM: Artificial sequence
<220> FEATURE:
<223> OTHER INFORMATION: Synthetic antibody sequence

<400> SEQUENCE: 205
gcgaggtccc catatgatga tggttatggt ggtttcactt ttaattta 48

<210> SEQ ID NO 206
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 206
cagaacattt ataataac 18

<210> SEQ ID NO 207
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 207 ggtccatcc 9

<210> SEQ ID NO 208
<211> LENGTH: 42
<212> TYPE: DNA

<213> ORGANISM: Artificial sequence
<220> FEATURE:
<223> OTHER INFORMATION: Synthetic antibody sequence

<400> SEQUENCE: 208
gcgagatcga ctagtggtag ttatggtgcg ggtttgggct tg 42

<210> SEQ ID NO 209
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 209
cagagtattg gtagtaga 18

<210> SEQ ID NO 210
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 210 gaagcatcc 9

<210> SEQ ID NO 211
<211> LENGTH: 36
<212> TYPE: DNA
<213> ORGANISM: Artificial sequence
<220> FEATURE:
<223> OTHER INFORMATION: Synthetic antibody sequence

<400> SEQUENCE: 211
gcgagagata ctgctgctta ttacgccttt agctta 36

<210> SEQ ID NO 212
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 212
catatcatta ctaactac 18

<210> SEQ ID NO 213
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 213 gatgcatcg 9

<210> SEQ ID NO 214
<211> LENGTH: 39
<212> TYPE: DNA
<213> ORGANISM: Artificial sequence
<220> FEATURE:
<223> OTHER INFORMATION: Synthetic antibody sequence

<400> SEQUENCE: 214
gcgaggggtg ttaatgatta tggttgggcc cttaagttg 39

<210> SEQ ID NO 215
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 215
ccgagcatta gtacttac 18

<210> SEQ ID NO 216
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 216 agggcatcc 9

<210> SEQ ID NO 217
<211> LENGTH: 39
<212> TYPE: DNA
<213> ORGANISM: Artificial sequence
<220> FEATURE:
<223> OTHER INFORMATION: Synthetic antibody sequence

<400> SEQUENCE: 217
gcgaccaata cggatagtag taggtcttat tataatttg 39

<210> SEQ ID NO 218
<211> LENGTH: 21
<212> TYPE: DNA
<213> ORGANISM: Artificial sequence
<220> FEATURE:
<223> OTHER INFORMATION: Synthetic antibody sequence

<400> SEQUENCE: 218
cagagtattg gtagtggtaa t 21

<210> SEQ ID NO 219
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 219 ctggcatcc 9

<210> SEQ ID NO 220
<211> LENGTH: 60
<212> TYPE: DNA
<213> ORGANISM: Artificial sequence
<220> FEATURE:
<223> OTHER INFORMATION: Synthetic antibody sequence

<400> SEQUENCE: 220
agaggatccg gtgctagcac caatggtgtt tggtgggtaa tgggagacgg catggacctc 60

<210> SEQ ID NO 221
<211> LENGTH: 21
<212> TYPE: DNA
<213> ORGANISM: Artificial sequence
<220> FEATURE:

<223> OTHER INFORMATION: Synthetic antibody sequence

<400> SEQUENCE: 221
cagattgttg ctaacggccg c 21

<210> SEQ ID NO 222
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 222 gctacatcc 9

<210> SEQ ID NO 223
<211> LENGTH: 39
<212> TYPE: DNA
<213> ORGANISM: Artificial sequence
<220> FEATURE:
<223> OTHER INFORMATION: Synthetic antibody sequence

<400> SEQUENCE: 223
gggagattgg attatcgtgt tatttatgcc tttaatttg 39

<210> SEQ ID NO 224
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 224
gaggacattg ataggtat 18

<210> SEQ ID NO 225
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 225 gatgcatcc 9

<210> SEQ ID NO 226
<211> LENGTH: 45
<212> TYPE: DNA
<213> ORGANISM: Artificial sequence
<220> FEATURE:
<223> OTHER INFORMATION: Synthetic antibody sequence

<400> SEQUENCE: 226
gcgagagagc gctatcctgg tgctttttca agtggattgg atctc 45

<210> SEQ ID NO 227
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 227
catatcatta ctaactac 18

<210> SEQ ID NO 228
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 228 gatgcatcg 9

<210> SEQ ID NO 229
<211> LENGTH: 39
<212> TYPE: DNA
<213> ORGANISM: Artificial sequence
<220> FEATURE:
<223> OTHER INFORMATION: Synthetic antibody sequence

<400> SEQUENCE: 229
gcgagagcga cttatgctta tgctggtgct ggggacttg 39

<210> SEQ ID NO 230
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 230
gagagcattg gcagtgca 18

<210> SEQ ID NO 231
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 231 tctgcatcc 9

<210> SEQ ID NO 232
<211> LENGTH: 39
<212> TYPE: DNA
<213> ORGANISM: Artificial sequence
<220> FEATURE:
<223> OTHER INFORMATION: Synthetic antibody sequence

<400> SEQUENCE: 232
gcgaccaata cggatagtag taggtcttat tataatttg 39

<210> SEQ ID NO 233
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 233
cagagcattt acaactac 18

<210> SEQ ID NO 234
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 234 tctgcatcc 9

<210> SEQ ID NO 235
<211> LENGTH: 51
<212> TYPE: DNA
<213> ORGANISM: Artificial sequence
<220> FEATURE:
<223> OTHER INFORMATION: Synthetic antibody sequence

<400> SEQUENCE: 235
gcgcgaagat atgctgcttt tcttacttat ggtagtgggg cttttgatcc c 51

<210> SEQ ID NO 236
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 236
ctgaacatta atagttgg 18

<210> SEQ ID NO 237
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 237 tatacatcc 9

<210> SEQ ID NO 238
<211> LENGTH: 33
<212> TYPE: DNA
<213> ORGANISM: Artificial sequence
<220> FEATURE:
<223> OTHER INFORMATION: Synthetic antibody sequence

<400> SEQUENCE: 238
gcgagaattg gtgcttttta ttcctttaga tta 33

<210> SEQ ID NO 239
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 239
gaggacattt atagcaat 18

<210> SEQ ID NO 240
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 240 ggtgcaacc 9

<210> SEQ ID NO 241
<211> LENGTH: 39

<212> TYPE: DNA
<213> ORGANISM: Artificial sequence
<220> FEATURE:
<223> OTHER INFORMATION: Synthetic antibody sequence

<400> SEQUENCE: 241
gcgagccgaa atggtggtgc gcctgatggt ttgaacttg 39

<210> SEQ ID NO 242
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 242
gaggatattt atagtaat 18

<210> SEQ ID NO 243
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 243 aaggcatcc 9

<210> SEQ ID NO 244
<211> LENGTH: 33
<212> TYPE: DNA
<213> ORGANISM: Artificial sequence
<220> FEATURE:
<223> OTHER INFORMATION: Synthetic antibody sequence

<400> SEQUENCE: 244
gcgagaggtg gtggttattg gtcttttagt ttg 33

<210> SEQ ID NO 245
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 245
cagagtgttt ataataagaa ctac 24

<210> SEQ ID NO 246
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 246 tatgcttcc 9

<210> SEQ ID NO 247
<211> LENGTH: 57
<212> TYPE: DNA
<213> ORGANISM: Artificial sequence
<220> FEATURE:
<223> OTHER INFORMATION: Synthetic antibody sequence

<400> SEQUENCE: 247
ggagattggg attatgctga tgctgctggt tattatgttg cgagaggttt taacttg 57

<210> SEQ ID NO 248
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 248
cagagcatta gtagttac 18

<210> SEQ ID NO 249
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 249 aaggcatcc 9

<210> SEQ ID NO 250
<211> LENGTH: 27
<212> TYPE: DNA
<213> ORGANISM: Artificial sequence
<220> FEATURE:
<223> OTHER INFORMATION: Synthetic antibody sequence

<400> SEQUENCE: 250
agagatttcg ttagttattt gaatttg 27

<210> SEQ ID NO 251
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 251
cagagcatta gttactac 18

<210> SEQ ID NO 252
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 252 aaggcatcc 9

<210> SEQ ID NO 253
<211> LENGTH: 63
<212> TYPE: DNA
<213> ORGANISM: Artificial sequence
<220> FEATURE:
<223> OTHER INFORMATION: Synthetic antibody sequence

<400> SEQUENCE: 253
gcgagaggat ccggtgctag taccaatggt gtttggtggg taatgggaga cggcatggac 60
ctc 63

<210> SEQ ID NO 254
<211> LENGTH: 21

<212> TYPE: DNA
<213> ORGANISM: Artificial sequence
<220> FEATURE:
<223> OTHER INFORMATION: Synthetic antibody sequence

<400> SEQUENCE: 254
cagagtatta gtagtagcta c 21

<210> SEQ ID NO 255
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 255 tctgcgtcc 9

<210> SEQ ID NO 256
<211> LENGTH: 48
<212> TYPE: DNA
<213> ORGANISM: Artificial sequence
<220> FEATURE:
<223> OTHER INFORMATION: Synthetic antibody sequence

<400> SEQUENCE: 256
tgtgcgagat ctagtaatag ttatggtaat tatggtgttt ctaacttg 48

<210> SEQ ID NO 257
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 257
cagagtgttt atagtaacaa ctgg 24

<210> SEQ ID NO 258
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 258 aaggcatcc 9

<210> SEQ ID NO 259
<211> LENGTH: 30
<212> TYPE: DNA
<213> ORGANISM: Artificial sequence
<220> FEATURE:
<223> OTHER INFORMATION: Synthetic antibody sequence

<400> SEQUENCE: 259
agagatatct attcctacgg catggacctc 30

<210> SEQ ID NO 260
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 260
cagactattt ataataacaa aaat 24

<210> SEQ ID NO 261
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 261 caggcatcc 9

<210> SEQ ID NO 262
<211> LENGTH: 36
<212> TYPE: DNA
<213> ORGANISM: Artificial sequence
<220> FEATURE:
<223> OTHER INFORMATION: Synthetic antibody sequence

<400> SEQUENCE: 262
gcgagaatcg ctactggtac taatgttgat gacttc 36

<210> SEQ ID NO 263
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 263
gagaacattt atagctac 18

<210> SEQ ID NO 264
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 264 tctgcatcc 9

<210> SEQ ID NO 265
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 265
gcgagatggc ggacttttgg cttg 24

<210> SEQ ID NO 266
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 266
cagaccgttc ataataatca atgg 24

<210> SEQ ID NO 267
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 267 gatgcatcc 9

<210> SEQ ID NO 268
<211> LENGTH: 42
<212> TYPE: DNA
<213> ORGANISM: Artificial sequence
<220> FEATURE:
<223> OTHER INFORMATION: Synthetic antibody sequence

<400> SEQUENCE: 268
gcgagatcat atattactga tcgtatttat gattacgact tt 42

<210> SEQ ID NO 269
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 269
caaagtgttg ataacaacaa acaa 24

<210> SEQ ID NO 270
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 270 tctgcatcc 9

<210> SEQ ID NO 271
<211> LENGTH: 36
<212> TYPE: DNA
<213> ORGANISM: Artificial sequence
<220> FEATURE:
<223> OTHER INFORMATION: Synthetic antibody sequence

<400> SEQUENCE: 271
gggagagtaa ttgatggtgc ttgtggttat gacttg 36

<210> SEQ ID NO 272
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 272
gagaccatta gtaataga 18

<210> SEQ ID NO 273
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 273 tctgcatcc 9

<210> SEQ ID NO 274
<211> LENGTH: 39
<212> TYPE: DNA
<213> ORGANISM: Artificial sequence
<220> FEATURE:
<223> OTHER INFORMATION: Synthetic antibody sequence

<400> SEQUENCE: 274
gcgagggata ctcggagtag taattattat tttaatttg 39

<210> SEQ ID NO 275
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 275
cagaccattt ataccaat 18

<210> SEQ ID NO 276
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 276 gctgcatcc 9

<210> SEQ ID NO 277
<211> LENGTH: 42
<212> TYPE: DNA
<213> ORGANISM: Artificial sequence
<220> FEATURE:
<223> OTHER INFORMATION: Synthetic antibody sequence

<400> SEQUENCE: 277
gcgaaatccc atggtggtga tggtggttat ggggttgtgt ta 42

<210> SEQ ID NO 278
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 278
gataatgttt atagtaataa ctac 24

<210> SEQ ID NO 279
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 279 tatgcggcc 9

<210> SEQ ID NO 280
<211> LENGTH: 57
<212> TYPE: DNA
<213> ORGANISM: Artificial sequence
<220> FEATURE:
<223> OTHER INFORMATION: Synthetic antibody sequence

<400> SEQUENCE: 280
gcgagggggt gggattacga ggatcctggt tatactgata ctacctactt ttccttg 57

<210> SEQ ID NO 281
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 281
gataatgttt atagtaataa ctac 24

<210> SEQ ID NO 282
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 282 tatgcggcc 9

<210> SEQ ID NO 283
<211> LENGTH: 33
<212> TYPE: DNA
<213> ORGANISM: Artificial sequence
<220> FEATURE:
<223> OTHER INFORMATION: Synthetic antibody sequence

<400> SEQUENCE: 283
gcgagaggtg gtactagtta ccgccttgat ttg 33

<210> SEQ ID NO 284
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 284
gaggatatta gtagtaat 18

<210> SEQ ID NO 285
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 285 ggtgcatcc 9

<210> SEQ ID NO 286
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 286
acgagatggc ggacttttgg cttg 24

<210> SEQ ID NO 287

<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 287
cagagcatta gcaatgaa 18

<210> SEQ ID NO 288
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 288 ctggcatcc 9

<210> SEQ ID NO 289
<211> LENGTH: 51
<212> TYPE: DNA
<213> ORGANISM: Artificial sequence
<220> FEATURE:
<223> OTHER INFORMATION: Synthetic antibody sequence

<400> SEQUENCE: 289
gccagagatc ttgttactgg ttatgctact tatggttatg gatttatctt a 51

<210> SEQ ID NO 290
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 290
caaagtgttt acaataacaa ccaa 24

<210> SEQ ID NO 291
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 291 ggtgcatcc 9

<210> SEQ ID NO 292
<211> LENGTH: 33
<212> TYPE: DNA
<213> ORGANISM: Artificial sequence
<220> FEATURE:
<223> OTHER INFORMATION: Synthetic antibody sequence

<400> SEQUENCE: 292
gcgagagttg gtggttactg gacttttgac ttg 33

<210> SEQ ID NO 293
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 293
cagagtattg gtagctat 18

<210> SEQ ID NO 294
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 294 tatgcttcc 9

<210> SEQ ID NO 295
<211> LENGTH: 39
<212> TYPE: DNA
<213> ORGANISM: Artificial sequence
<220> FEATURE:
<223> OTHER INFORMATION: Synthetic antibody sequence

<400> SEQUENCE: 295
gcgagaggac tcactattgg tactgctgag ttgtacttc 39

<210> SEQ ID NO 296
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 296
cagaacattt acagcaat 18

<210> SEQ ID NO 297
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 297 tctgcatcc 9

<210> SEQ ID NO 298
<211> LENGTH: 30
<212> TYPE: DNA
<213> ORGANISM: Artificial sequence
<220> FEATURE:
<223> OTHER INFORMATION: Synthetic antibody sequence

<400> SEQUENCE: 298
gcgagagatt tcgttagtta tttgaatttg 30

<210> SEQ ID NO 299
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 299
cagagcattg gtagctac 18

<210> SEQ ID NO 300
<211> LENGTH: 9
<212> TYPE: DNA

<213> ORGANISM: Artificial sequence
<220> FEATURE:
<223> OTHER INFORMATION: Synthetic antibody sequence

<400> SEQUENCE: 300 aaggcatcc 9

<210> SEQ ID NO 301
<211> LENGTH: 45
<212> TYPE: DNA
<213> ORGANISM: Artificial sequence
<220> FEATURE:
<223> OTHER INFORMATION: Synthetic antibody sequence

<400> SEQUENCE: 301
gcgggaagtg ggagtggtta ttattattac tacggcatgg atctc 45

<210> SEQ ID NO 302
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 302
gaggacattg ataggtat 18

<210> SEQ ID NO 303
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 303 agggcatcc 9

<210> SEQ ID NO 304
<211> LENGTH: 36
<212> TYPE: DNA
<213> ORGANISM: Artificial sequence
<220> FEATURE:
<223> OTHER INFORMATION: Synthetic antibody sequence

<400> SEQUENCE: 304
gcgagagatc aggctgacag ttatgccttt ggtttg 36

<210> SEQ ID NO 305
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 305
cagagcatta gtagttac 18

<210> SEQ ID NO 306
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 306 aaggcttcc 9

<210> SEQ ID NO 307
<211> LENGTH: 27
<212> TYPE: DNA
<213> ORGANISM: Artificial sequence
<220> FEATURE:
<223> OTHER INFORMATION: Synthetic antibody sequence

<400> SEQUENCE: 307
gcgaggggtt tttcgatgtt taagttg 27

<210> SEQ ID NO 308
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 308
cagaccattt ataccaat 18

<210> SEQ ID NO 309
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 309 gctgcatcc 9

<210> SEQ ID NO 310
<211> LENGTH: 57
<212> TYPE: DNA
<213> ORGANISM: Artificial sequence
<220> FEATURE:
<223> OTHER INFORMATION: Synthetic antibody sequence

<400> SEQUENCE: 310
gcgagggggt gggattacga ggatcctggt tatactgata ctacctactt ttccttg 57

<210> SEQ ID NO 311
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 311
gagagtgttt atggtaacaa ccgt 24

<210> SEQ ID NO 312
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 312 caggcttcc 9

<210> SEQ ID NO 313
<211> LENGTH: 60
<212> TYPE: DNA
<213> ORGANISM: Artificial sequence
<220> FEATURE:

<223> OTHER INFORMATION: Synthetic antibody sequence

<400> SEQUENCE: 313
agaggatccg gtgctgctac taatggtgtt tggtgggtga tgggagacgg catggacctc 60

<210> SEQ ID NO 314
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 314
cagagcatta ccaatgca 18

<210> SEQ ID NO 315
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 315 agggcatcc 9

<210> SEQ ID NO 316
<211> LENGTH: 39
<212> TYPE: DNA
<213> ORGANISM: Artificial sequence
<220> FEATURE:
<223> OTHER INFORMATION: Synthetic antibody sequence

<400> SEQUENCE: 316
gccagggcag gtgctagtag gagtatttat tatgacttg 39

<210> SEQ ID NO 317
<211> LENGTH: 21
<212> TYPE: DNA
<213> ORGANISM: Artificial sequence
<220> FEATURE:
<223> OTHER INFORMATION: Synthetic antibody sequence

<400> SEQUENCE: 317
cagagcatta gtagtagcta c 21

<210> SEQ ID NO 318
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 318 tctgcatcc 9

<210> SEQ ID NO 319
<211> LENGTH: 33
<212> TYPE: DNA
<213> ORGANISM: Artificial sequence
<220> FEATURE:
<223> OTHER INFORMATION: Synthetic antibody sequence

<400> SEQUENCE: 319
gcgaaatctt ataattataa tggtttaggc ttg 33

<210> SEQ ID NO 320
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 320
cagagcattg gtagtaat 18

<210> SEQ ID NO 321
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 321 aaggcatcc 9

<210> SEQ ID NO 322
<211> LENGTH: 45
<212> TYPE: DNA
<213> ORGANISM: Artificial sequence
<220> FEATURE:
<223> OTHER INFORMATION: Synthetic antibody sequence

<400> SEQUENCE: 322
gcgagatcat ataatagtgc tagtagtggt tattattggg acttg 45

<210> SEQ ID NO 323
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 323
gagaatgttt atagtaataa ctac 24

<210> SEQ ID NO 324
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 324 tatgcggcc 9

<210> SEQ ID NO 325
<211> LENGTH: 30
<212> TYPE: DNA
<213> ORGANISM: Artificial sequence
<220> FEATURE:
<223> OTHER INFORMATION: Synthetic antibody sequence

<400> SEQUENCE: 325
agagatatct attcctacgg catggacctc 30

<210> SEQ ID NO 326
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 326
cagagcattg ctagcgac 18

<210> SEQ ID NO 327
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 327 gctgcatcc 9

<210> SEQ ID NO 328
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 328
gcgagatggc ggacttttgg cttg 24

<210> SEQ ID NO 329
<211> LENGTH: 27
<212> TYPE: DNA
<213> ORGANISM: Artificial sequence
<220> FEATURE:
<223> OTHER INFORMATION: Synthetic antibody sequence

<400> SEQUENCE: 329
ggattctcct tcagtagcag ctactgt 27

<210> SEQ ID NO 330
<211> LENGTH: 27
<212> TYPE: DNA
<213> ORGANISM: Artificial sequence
<220> FEATURE:
<223> OTHER INFORMATION: Synthetic antibody sequence

<400> SEQUENCE: 330
atttatactg atagtagtgg tgccact 27

<210> SEQ ID NO 331
<211> LENGTH: 57
<212> TYPE: DNA
<213> ORGANISM: Artificial sequence
<220> FEATURE:
<223> OTHER INFORMATION: Synthetic antibody sequence

<400> SEQUENCE: 331
gcgagggggt gggattacga ggatcctggt tatactgata ctacctactt ttccttg 57

<210> SEQ ID NO 332
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 332

Gln Asn Ile Tyr Ser Tyr
1               5

<210> SEQ ID NO 333

<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 333

Lys Ala Ser
1

<210> SEQ ID NO 334
<211> LENGTH: 15
<212> TYPE: PRT
<213> ORGANISM: Artificial sequence
<220> FEATURE:
<223> OTHER INFORMATION: Synthetic antibody sequence

<400> SEQUENCE: 334

Gln Thr Asn Tyr Phe Ser Ser Thr Ser His Phe Gly Val Phe Thr
1               5                   10                  15

<210> SEQ ID NO 335
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 335

Gln Ser Leu Tyr Asn Ala Asn Asp
1               5

<210> SEQ ID NO 336
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 336

Trp Ala Ser
1

<210> SEQ ID NO 337
<211> LENGTH: 13
<212> TYPE: PRT
<213> ORGANISM: Artificial sequence
<220> FEATURE:
<223> OTHER INFORMATION: Synthetic antibody sequence

<400> SEQUENCE: 337

Leu Gly Glu Phe Ser Cys Ser Ser Phe Asp Cys His Val
1               5                   10

<210> SEQ ID NO 338
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 338

Gln Ser Ile Tyr Arg Tyr
1               5

<210> SEQ ID NO 339
<211> LENGTH: 3

<212> TYPE: PRT
<213> ORGANISM: Artificial sequence
<220> FEATURE:
<223> OTHER INFORMATION: Synthetic antibody sequence

<400> SEQUENCE: 339

Tyr Gly Ser
1

<210> SEQ ID NO 340
<211> LENGTH: 12
<212> TYPE: PRT
<213> ORGANISM: Artificial sequence
<220> FEATURE:
<223> OTHER INFORMATION: Synthetic antibody sequence

<400> SEQUENCE: 340

Gln Thr Thr Tyr Asp Asp Tyr His Asn Gly Trp Ala
1               5                   10

<210> SEQ ID NO 341
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 341

Gln Ser Val Tyr Gly Asn Asn Arg
1               5

<210> SEQ ID NO 342
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 342

Leu Ala Ser
1

<210> SEQ ID NO 343
<211> LENGTH: 10
<212> TYPE: PRT
<213> ORGANISM: Artificial sequence
<220> FEATURE:
<223> OTHER INFORMATION: Synthetic antibody sequence

<400> SEQUENCE: 343

Ala Gly Gly Tyr Ala Gly Asn Phe Asn Ala
1               5                   10

<210> SEQ ID NO 344
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 344

Gln Asn Ile Val Ser Asn
1               5

<210> SEQ ID NO 345
<211> LENGTH: 3
<212> TYPE: PRT

<213> ORGANISM: Artificial sequence
<220> FEATURE:
<223> OTHER INFORMATION: Synthetic antibody sequence

<400> SEQUENCE: 345

Tyr Ala Ser
1

<210> SEQ ID NO 346
<211> LENGTH: 13
<212> TYPE: PRT
<213> ORGANISM: Artificial sequence
<220> FEATURE:
<223> OTHER INFORMATION: Synthetic antibody sequence

<400> SEQUENCE: 346

Gln Asn Asn Ala Gly Ile Tyr Gly Asn Tyr Gly His Gly
1 5 10

<210> SEQ ID NO 347
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 347

Gln Ser Ile Tyr Asn Tyr
1 5

<210> SEQ ID NO 348
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 348

Asp Val Ser
1

<210> SEQ ID NO 349
<211> LENGTH: 11
<212> TYPE: PRT
<213> ORGANISM: Artificial sequence
<220> FEATURE:
<223> OTHER INFORMATION: Synthetic antibody sequence

<400> SEQUENCE: 349

Gln Ser Tyr Tyr Gly Asn Thr Val Ser Phe Thr
1 5 10

<210> SEQ ID NO 350
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 350

Gln Ser Val Tyr Asn Asn Asn Asn
1 5

<210> SEQ ID NO 351
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 351

Ser Ala Ser
1

<210> SEQ ID NO 352
<211> LENGTH: 10
<212> TYPE: PRT
<213> ORGANISM: Artificial sequence
<220> FEATURE:
<223> OTHER INFORMATION: Synthetic antibody sequence

<400> SEQUENCE: 352

Ala Gly Gly Tyr Thr Tyr Asn Ile Asn Ile
1 5 10

<210> SEQ ID NO 353
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 353

Gln Asn Ile Tyr Asn Asn
1 5

<210> SEQ ID NO 354
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 354

Tyr Ala Ser
1

<210> SEQ ID NO 355
<211> LENGTH: 13
<212> TYPE: PRT
<213> ORGANISM: Artificial sequence
<220> FEATURE:
<223> OTHER INFORMATION: Synthetic antibody sequence

<400> SEQUENCE: 355

Gln Asn Asn Ala Gly Ile Tyr Gly Gly Tyr Gly His Gly
1 5 10

<210> SEQ ID NO 356
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 356

Gln Thr Ile Gly Ser Tyr
1 5

<210> SEQ ID NO 357
<211> LENGTH: 3
<212> TYPE: PRT
<213> ORGANISM: Artificial sequence
<220> FEATURE:

<223> OTHER INFORMATION: Synthetic antibody sequence

<400> SEQUENCE: 357

Glu Ala Ser
1

<210> SEQ ID NO 358
<211> LENGTH: 14
<212> TYPE: PRT
<213> ORGANISM: Artificial sequence
<220> FEATURE:
<223> OTHER INFORMATION: Synthetic antibody sequence

<400> SEQUENCE: 358

Gln Ser Asn Tyr Tyr Arg Ala Gly Gly Asn Tyr Gly Gly Ala
1 5 10

<210> SEQ ID NO 359
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 359

Glu Thr Ile Ser Asn Arg
1 5

<210> SEQ ID NO 360
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 360

Ser Ala Ser
1

<210> SEQ ID NO 361
<211> LENGTH: 14
<212> TYPE: PRT
<213> ORGANISM: Artificial sequence
<220> FEATURE:
<223> OTHER INFORMATION: Synthetic antibody sequence

<400> SEQUENCE: 361

Gln Ser Ile Arg Ser Ser Ser Gly Ile Val His Pro Asn Thr
1 5 10

<210> SEQ ID NO 362
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 362

Gln Ser Ile Ser Ser Tyr
1 5

<210> SEQ ID NO 363
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 363

Lys Ala Ser
1

<210> SEQ ID NO 364
<211> LENGTH: 13
<212> TYPE: PRT
<213> ORGANISM: Artificial sequence
<220> FEATURE:
<223> OTHER INFORMATION: Synthetic antibody sequence

<400> SEQUENCE: 364

Gln Ser Tyr Tyr Tyr Ile Ser Ala Thr Val Asp Asn Thr
1 5 10

<210> SEQ ID NO 365
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 365

Gln Ser Ile Ser Asp Tyr
1 5

<210> SEQ ID NO 366
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 366

Arg Ala Ser
1

<210> SEQ ID NO 367
<211> LENGTH: 11
<212> TYPE: PRT
<213> ORGANISM: Artificial sequence
<220> FEATURE:
<223> OTHER INFORMATION: Synthetic antibody sequence

<400> SEQUENCE: 367

Gln Ser Asn Tyr Tyr Gly Ser Gln Gly Cys Thr
1 5 10

<210> SEQ ID NO 368
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 368

Gln Ser Ile Gly Asn Ala
1 5

<210> SEQ ID NO 369
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 369

Lys Ala Ser
1

<210> SEQ ID NO 370
<211> LENGTH: 10
<212> TYPE: PRT
<213> ORGANISM: Artificial sequence
<220> FEATURE:
<223> OTHER INFORMATION: Synthetic antibody sequence

<400> SEQUENCE: 370

Gln Asn Tyr Tyr Tyr Ser Asn Thr Asn Ser
1               5                   10

<210> SEQ ID NO 371
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 371

Gln Asn Ile Tyr Asn Asn
1               5

<210> SEQ ID NO 372
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 372

Gly Pro Ser
1

<210> SEQ ID NO 373
<211> LENGTH: 13
<212> TYPE: PRT
<213> ORGANISM: Artificial sequence
<220> FEATURE:
<223> OTHER INFORMATION: Synthetic antibody sequence

<400> SEQUENCE: 373

Gln Ser Asp Asp Trp Met Ser Ile Ser Pro Asp Ile Val
1               5                   10

<210> SEQ ID NO 374
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 374

Gln Ser Ile Gly Ser Arg
1               5

<210> SEQ ID NO 375
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 375

Glu Ala Ser
1

<210> SEQ ID NO 376
<211> LENGTH: 12
<212> TYPE: PRT
<213> ORGANISM: Artificial sequence
<220> FEATURE:
<223> OTHER INFORMATION: Synthetic antibody sequence

<400> SEQUENCE: 376

Gln Cys Thr Tyr Tyr Glu Ser Ser Ser Gly Gly Gly
1               5                   10

<210> SEQ ID NO 377
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 377

Pro Ser Ile Ser Thr Tyr
1               5

<210> SEQ ID NO 378
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 378

Arg Ala Ser
1

<210> SEQ ID NO 379
<211> LENGTH: 15
<212> TYPE: PRT
<213> ORGANISM: Artificial sequence
<220> FEATURE:
<223> OTHER INFORMATION: Synthetic antibody sequence

<400> SEQUENCE: 379

Gln Asn Asn Tyr His Ser Gly Ser Ser Asn Gly Gly Gly Val Ala
1               5                   10                  15

<210> SEQ ID NO 380
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 380

Gln Ser Ile Gly Ser Gly Asn
1               5

<210> SEQ ID NO 381
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 381

Leu Ala Ser
1

<210> SEQ ID NO 382
<211> LENGTH: 12
<212> TYPE: PRT
<213> ORGANISM: Artificial sequence
<220> FEATURE:
<223> OTHER INFORMATION: Synthetic antibody sequence

<400> SEQUENCE: 382

Gln Tyr Thr Tyr Tyr Gly Thr Thr Tyr Asp Asn Ala
1               5                   10

<210> SEQ ID NO 383
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 383

Gln Ile Val Ala Asn Gly Arg
1               5

<210> SEQ ID NO 384
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 384

Ala Thr Ser
1

<210> SEQ ID NO 385
<211> LENGTH: 11
<212> TYPE: PRT
<213> ORGANISM: Artificial sequence
<220> FEATURE:
<223> OTHER INFORMATION: Synthetic antibody sequence

<400> SEQUENCE: 385

Gln Gly Ala Tyr Ser Ser Gly Asp Val Arg Thr
1               5                   10

<210> SEQ ID NO 386
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 386

Glu Asp Ile Asp Arg Tyr
1               5

<210> SEQ ID NO 387
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 387

Asp Ala Ser

1

<210> SEQ ID NO 388
<211> LENGTH: 10
<212> TYPE: PRT
<213> ORGANISM: Artificial sequence
<220> FEATURE:
<223> OTHER INFORMATION: Synthetic antibody sequence

<400> SEQUENCE: 388

Gln Ser Tyr Asp Asn Ser Asp Asn Asn Gly
1               5                   10

<210> SEQ ID NO 389
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 389

His Ile Ile Thr Asn Tyr
1               5

<210> SEQ ID NO 390
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 390

Asp Ala Ser
1

<210> SEQ ID NO 391
<211> LENGTH: 13
<212> TYPE: PRT
<213> ORGANISM: Artificial sequence
<220> FEATURE:
<223> OTHER INFORMATION: Synthetic antibody sequence

<400> SEQUENCE: 391

Gln Asn Tyr Leu Tyr Phe Ser Ser Gly Asp Trp Asn Val
1               5                   10

<210> SEQ ID NO 392
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 392

Glu Ser Ile Gly Ser Ala
1               5

<210> SEQ ID NO 393
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 393

Ser Ala Ser
1

<210> SEQ ID NO 394
<211> LENGTH: 13
<212> TYPE: PRT
<213> ORGANISM: Artificial sequence
<220> FEATURE:
<223> OTHER INFORMATION: Synthetic antibody sequence

<400> SEQUENCE: 394

Gln Ser Tyr Tyr Gly Ser Gly Thr Thr Ala Leu Asp Thr
1               5                   10

<210> SEQ ID NO 395
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 395

Gln Ser Ile Tyr Asn Tyr
1               5

<210> SEQ ID NO 396
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 396

Ser Ala Ser
1

<210> SEQ ID NO 397
<211> LENGTH: 13
<212> TYPE: PRT
<213> ORGANISM: Artificial sequence
<220> FEATURE:
<223> OTHER INFORMATION: Synthetic antibody sequence

<400> SEQUENCE: 397

Gln Asn Asn Tyr Gly Ile Gly Ser Asn Tyr Gly Pro Gly
1               5                   10

<210> SEQ ID NO 398
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 398

Leu Asn Ile Asn Ser Trp
1               5

<210> SEQ ID NO 399
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 399

Tyr Thr Ser
1

<210> SEQ ID NO 400
<211> LENGTH: 11
<212> TYPE: PRT
<213> ORGANISM: Artificial sequence
<220> FEATURE:
<223> OTHER INFORMATION: Synthetic antibody sequence

<400> SEQUENCE: 400

Gln Thr Thr Tyr Phe Gly Thr Asn Gly Gly Gly
1               5                   10

<210> SEQ ID NO 401
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 401

Glu Asp Ile Tyr Ser Asn
1               5

<210> SEQ ID NO 402
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 402

Gly Ala Thr
1

<210> SEQ ID NO 403
<211> LENGTH: 9
<212> TYPE: PRT
<213> ORGANISM: Artificial sequence
<220> FEATURE:
<223> OTHER INFORMATION: Synthetic antibody sequence

<400> SEQUENCE: 403

Gln Ala Glu Ser Asn Asp Val Trp Ala
1               5

<210> SEQ ID NO 404
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 404

Gln Ser Val Tyr Asn Lys Asn Tyr
1               5

<210> SEQ ID NO 405
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 405

Tyr Ala Ser
1

<210> SEQ ID NO 406
<211> LENGTH: 12
<212> TYPE: PRT
<213> ORGANISM: Artificial sequence
<220> FEATURE:
<223> OTHER INFORMATION: Synthetic antibody sequence

<400> SEQUENCE: 406

Ala Ala Tyr Lys Gly Val Ser Asp Asp Gly Ile Ser
1 5 10

<210> SEQ ID NO 407
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 407

Gln Ser Ile Ser Ser Tyr
1 5

<210> SEQ ID NO 408
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 408

Lys Ala Ser
1

<210> SEQ ID NO 409
<211> LENGTH: 15
<212> TYPE: PRT
<213> ORGANISM: Artificial sequence
<220> FEATURE:
<223> OTHER INFORMATION: Synthetic antibody sequence

<400> SEQUENCE: 409

Gln Asn Asn Tyr His Ser Gly Ser Ser Asn Gly Gly Gly Phe Ala
1 5 10 15

<210> SEQ ID NO 410
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 410

Gln Ser Ile Ser Tyr Tyr
1 5

<210> SEQ ID NO 411
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 411

Lys Ala Ser
1

<210> SEQ ID NO 412

<211> LENGTH: 14
<212> TYPE: PRT
<213> ORGANISM: Artificial sequence
<220> FEATURE:
<223> OTHER INFORMATION: Synthetic antibody sequence

<400> SEQUENCE: 412

Gln Ser Thr Tyr Gly Arg Asp Asn Asn Asp Leu Phe Phe Ala
1 5 10

<210> SEQ ID NO 413
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 413

Gln Ser Ile Ser Ser Ser Tyr
1 5

<210> SEQ ID NO 414
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 414

Ser Ala Ser
1

<210> SEQ ID NO 415
<211> LENGTH: 13
<212> TYPE: PRT
<213> ORGANISM: Artificial sequence
<220> FEATURE:
<223> OTHER INFORMATION: Synthetic antibody sequence

<400> SEQUENCE: 415

Gln Ser Thr Tyr Ile Ser Ser Ser Lys Tyr Gly Ala Val
1 5 10

<210> SEQ ID NO 416
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 416

Gln Ser Val Tyr Ser Asn Asn Trp
1 5

<210> SEQ ID NO 417
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 417

Lys Ala Ser
1

<210> SEQ ID NO 418
<211> LENGTH: 10

<212> TYPE: PRT
<213> ORGANISM: Artificial sequence
<220> FEATURE:
<223> OTHER INFORMATION: Synthetic antibody sequence

<400> SEQUENCE: 418

Ala Gly Gly Tyr Ser Gly Asp Leu Tyr Ala
1 5 10

<210> SEQ ID NO 419
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 419

Gln Thr Ile Tyr Asn Asn Lys Asn
1 5

<210> SEQ ID NO 420
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 420

Gln Ala Ser
1

<210> SEQ ID NO 421
<211> LENGTH: 13
<212> TYPE: PRT
<213> ORGANISM: Artificial sequence
<220> FEATURE:
<223> OTHER INFORMATION: Synthetic antibody sequence

<400> SEQUENCE: 421

Gln Gly Glu Phe Ser Cys Ser Ser Gly Asp Cys Thr Thr
1 5 10

<210> SEQ ID NO 422
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 422

Glu Asn Ile Tyr Ser Tyr
1 5

<210> SEQ ID NO 423
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 423

Ser Ala Ser
1

<210> SEQ ID NO 424
<211> LENGTH: 12
<212> TYPE: PRT

<213> ORGANISM: Artificial sequence
<220> FEATURE:
<223> OTHER INFORMATION: Synthetic antibody sequence

<400> SEQUENCE: 424

Gln Tyr Ser Asn Phe Arg Val Asn Asp Pro Ser Val
1 5 10

<210> SEQ ID NO 425
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 425

Gln Thr Val His Asn Asn Gln Trp
1 5

<210> SEQ ID NO 426
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 426

Asp Ala Ser
1

<210> SEQ ID NO 427
<211> LENGTH: 11
<212> TYPE: PRT
<213> ORGANISM: Artificial sequence
<220> FEATURE:
<223> OTHER INFORMATION: Synthetic antibody sequence

<400> SEQUENCE: 427

Gln Gly Gly Tyr Ser Tyr Gly Asp Val Tyr Gly
1 5 10

<210> SEQ ID NO 428
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 428

Gln Ser Val Asp Asn Asn Lys Gln
1 5

<210> SEQ ID NO 429
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 429

Ser Ala Ser
1

<210> SEQ ID NO 430
<211> LENGTH: 14
<212> TYPE: PRT
<213> ORGANISM: Artificial sequence
<220> FEATURE:
<223> OTHER INFORMATION: Synthetic antibody sequence

<400> SEQUENCE: 430

Ala Gly Tyr Tyr Tyr Ser Gly Ser Ala Thr Asp Ala Trp Ala
1 5 10

<210> SEQ ID NO 431
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 431

Glu Thr Ile Ser Asn Arg
1 5

<210> SEQ ID NO 432
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 432

Ser Ala Ser
1

<210> SEQ ID NO 433
<211> LENGTH: 14
<212> TYPE: PRT
<213> ORGANISM: Artificial sequence
<220> FEATURE:
<223> OTHER INFORMATION: Synthetic antibody sequence

<400> SEQUENCE: 433

Gln Ser Ile Arg Ser Ser Ser Gly Val Val His Pro Asn Thr
1 5 10

<210> SEQ ID NO 434
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 434

Gln Thr Ile Tyr Thr Asn
1 5

<210> SEQ ID NO 435
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 435

Ala Ala Ser
1

<210> SEQ ID NO 436
<211> LENGTH: 12
<212> TYPE: PRT
<213> ORGANISM: Artificial sequence
<220> FEATURE:

<223> OTHER INFORMATION: Synthetic antibody sequence

<400> SEQUENCE: 436

Gln Ser Tyr Tyr Gly Ser Ser Thr Thr Gly Asn Gly
1               5                   10

<210> SEQ ID NO 437
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 437

Asp Asn Val Tyr Ser Asn Asn Tyr
1               5

<210> SEQ ID NO 438
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 438

Tyr Ala Ala
1

<210> SEQ ID NO 439
<211> LENGTH: 12
<212> TYPE: PRT
<213> ORGANISM: Artificial sequence
<220> FEATURE:
<223> OTHER INFORMATION: Synthetic antibody sequence

<400> SEQUENCE: 439

Ser Gly His Lys Asp Tyr Ser Asp Asp Gly Ser Thr
1               5                   10

<210> SEQ ID NO 440
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 440

Asp Asn Val Tyr Ser Asn Asn Tyr
1               5

<210> SEQ ID NO 441
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 441

Tyr Ala Ala
1

<210> SEQ ID NO 442
<211> LENGTH: 12
<212> TYPE: PRT
<213> ORGANISM: Artificial sequence
<220> FEATURE:
<223> OTHER INFORMATION: Synthetic antibody sequence

<400> SEQUENCE: 442

Ser Gly His Lys Asp Tyr Ser Asp Asp Gly Ser Thr
1 5 10

<210> SEQ ID NO 443
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 443

Glu Asp Ile Ser Ser Asn
1 5

<210> SEQ ID NO 444
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 444

Gly Ala Ser
1

<210> SEQ ID NO 445
<211> LENGTH: 10
<212> TYPE: PRT
<213> ORGANISM: Artificial sequence
<220> FEATURE:
<223> OTHER INFORMATION: Synthetic antibody sequence

<400> SEQUENCE: 445

Gln Gly Ala Tyr Tyr Gly Ser Ser Tyr Gly
1 5 10

<210> SEQ ID NO 446
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 446

Gln Ser Ile Ser Asn Glu
1 5

<210> SEQ ID NO 447
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 447

Leu Ala Ser
1

<210> SEQ ID NO 448
<211> LENGTH: 14
<212> TYPE: PRT
<213> ORGANISM: Artificial sequence
<220> FEATURE:
<223> OTHER INFORMATION: Synthetic antibody sequence

<400> SEQUENCE: 448

Gln Ser His Tyr Tyr Gly Gly Ser Ser Asp Tyr Gly Trp Ala
1               5                   10

<210> SEQ ID NO 449
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 449

Gln Ser Val Tyr Asn Asn Asn Gln
1               5

<210> SEQ ID NO 450
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 450

Gly Ala Ser
1

<210> SEQ ID NO 451
<211> LENGTH: 10
<212> TYPE: PRT
<213> ORGANISM: Artificial sequence
<220> FEATURE:
<223> OTHER INFORMATION: Synthetic antibody sequence

<400> SEQUENCE: 451

Gln Gly Ala Val Ser Ser Asp Tyr Tyr Pro
1               5                   10

<210> SEQ ID NO 452
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 452

Gln Ser Ile Gly Ser Tyr
1               5

<210> SEQ ID NO 453
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 453

Tyr Ala Ser
1

<210> SEQ ID NO 454
<211> LENGTH: 12
<212> TYPE: PRT
<213> ORGANISM: Artificial sequence
<220> FEATURE:
<223> OTHER INFORMATION: Synthetic antibody sequence

<400> SEQUENCE: 454

Gln Ser Asn Arg Leu Ser Ser Ser Asp Val Asn Ala
1 5 10

<210> SEQ ID NO 455
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 455

Gln Asn Ile Tyr Ser Asn
1 5

<210> SEQ ID NO 456
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 456

Ser Ala Ser
1

<210> SEQ ID NO 457
<211> LENGTH: 12
<212> TYPE: PRT
<213> ORGANISM: Artificial sequence
<220> FEATURE:
<223> OTHER INFORMATION: Synthetic antibody sequence

<400> SEQUENCE: 457

Gln Ser Tyr Tyr Tyr Thr Ala Ser Ala Asp Thr Thr
1 5 10

<210> SEQ ID NO 458
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 458

Gln Ser Ile Gly Ser Tyr
1 5

<210> SEQ ID NO 459
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 459

Lys Ala Ser
1

<210> SEQ ID NO 460
<211> LENGTH: 10
<212> TYPE: PRT
<213> ORGANISM: Artificial sequence
<220> FEATURE:
<223> OTHER INFORMATION: Synthetic antibody sequence

<400> SEQUENCE: 460

Gln Tyr Thr Ser Tyr Ser Ser Gly Gly Ala
1 5 10

<210> SEQ ID NO 461
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 461

Glu Asp Ile Asp Arg Tyr
1 5

<210> SEQ ID NO 462
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 462

Arg Ala Ser
1

<210> SEQ ID NO 463
<211> LENGTH: 12
<212> TYPE: PRT
<213> ORGANISM: Artificial sequence
<220> FEATURE:
<223> OTHER INFORMATION: Synthetic antibody sequence

<400> SEQUENCE: 463

Gln Gly Asp Phe Ile Gly Ser Ser Tyr Gly Val Ala
1 5 10

<210> SEQ ID NO 464
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 464

Gln Ser Ile Ser Ser Tyr
1 5

<210> SEQ ID NO 465
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 465

Lys Ala Ser
1

<210> SEQ ID NO 466
<211> LENGTH: 15
<212> TYPE: PRT
<213> ORGANISM: Artificial sequence
<220> FEATURE:
<223> OTHER INFORMATION: Synthetic antibody sequence

<400> SEQUENCE: 466

Gln Asn Asn Tyr His Ser Gly Ser Ser Asn Gly Gly Gly Phe Ala 1 5 10 15

<210> SEQ ID NO 467
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 467

Gln Thr Ile Tyr Thr Asn
1 5

<210> SEQ ID NO 468
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 468

Ala Ala Ser
1

<210> SEQ ID NO 469
<211> LENGTH: 12
<212> TYPE: PRT
<213> ORGANISM: Artificial sequence
<220> FEATURE:
<223> OTHER INFORMATION: Synthetic antibody sequence

<400> SEQUENCE: 469

Gln Ser Tyr Tyr Gly Ser Ser Thr Thr Gly Asn Gly
1 5 10

<210> SEQ ID NO 470
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 470

Glu Ser Val Tyr Gly Asn Asn Arg
1 5

<210> SEQ ID NO 471
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 471

Gln Ala Ser
1

<210> SEQ ID NO 472
<211> LENGTH: 12
<212> TYPE: PRT
<213> ORGANISM: Artificial sequence
<220> FEATURE:
<223> OTHER INFORMATION: Synthetic antibody sequence

<400> SEQUENCE: 472

Ala Gly His Lys Gly Thr Thr Asn Asp Gly Asn Asp
1 5 10

<210> SEQ ID NO 473
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 473

Gln Ser Ile Thr Asn Ala
1               5

<210> SEQ ID NO 474
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 474

Arg Ala Ser
1

<210> SEQ ID NO 475
<211> LENGTH: 13
<212> TYPE: PRT
<213> ORGANISM: Artificial sequence
<220> FEATURE:
<223> OTHER INFORMATION: Synthetic antibody sequence

<400> SEQUENCE: 475

Gln Cys Ser Tyr Tyr Gly Ser Thr Tyr Phe Gly Ser Pro
1               5                   10

<210> SEQ ID NO 476
<211> LENGTH: 7
<212> TYPE: PRT
<213> ORGANISM: Artificial sequence
<220> FEATURE:
<223> OTHER INFORMATION: Synthetic antibody sequence

<400> SEQUENCE: 476

Gln Ser Ile Ser Ser Ser Tyr
1               5

<210> SEQ ID NO 477
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 477

Ser Ala Ser
1

<210> SEQ ID NO 478
<211> LENGTH: 13
<212> TYPE: PRT
<213> ORGANISM: Artificial sequence
<220> FEATURE:
<223> OTHER INFORMATION: Synthetic antibody sequence

<400> SEQUENCE: 478

Gln Ser Thr Tyr Ile Ser Ser Ser Asn Tyr Gly Ala Ala
1               5                   10

<210> SEQ ID NO 479
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 479

Gln Ser Ile Gly Ser Asn
1 5

<210> SEQ ID NO 480
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 480

Lys Ala Ser
1

<210> SEQ ID NO 481
<211> LENGTH: 11
<212> TYPE: PRT
<213> ORGANISM: Artificial sequence
<220> FEATURE:
<223> OTHER INFORMATION: Synthetic antibody sequence

<400> SEQUENCE: 481

Gln Asn Asn Asn Tyr Trp Ser Asn Gly Asn His
1 5 10

<210> SEQ ID NO 482
<211> LENGTH: 8
<212> TYPE: PRT
<213> ORGANISM: Artificial sequence
<220> FEATURE:
<223> OTHER INFORMATION: Synthetic antibody sequence

<400> SEQUENCE: 482

Glu Asn Val Tyr Ser Asn Asn Tyr
1 5

<210> SEQ ID NO 483
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 483

Tyr Ala Ala
1

<210> SEQ ID NO 484
<211> LENGTH: 12
<212> TYPE: PRT
<213> ORGANISM: Artificial sequence
<220> FEATURE:
<223> OTHER INFORMATION: Synthetic antibody sequence

<400> SEQUENCE: 484

Ser Gly His Lys Asp Tyr Ser Asp Asp Gly Ser Thr
1 5 10

<210> SEQ ID NO 485
<211> LENGTH: 6
<212> TYPE: PRT
<213> ORGANISM: Artificial sequence
<220> FEATURE:
<223> OTHER INFORMATION: Synthetic antibody sequence

<400> SEQUENCE: 485

Gln Ser Ile Ala Ser Asp
1 5

<210> SEQ ID NO 486
<211> LENGTH: 3
<212> TYPE: PRT
<213> ORGANISM: Artificial sequence
<220> FEATURE:
<223> OTHER INFORMATION: Synthetic antibody sequence

<400> SEQUENCE: 486

Ala Ala Ser
1

<210> SEQ ID NO 487
<211> LENGTH: 12
<212> TYPE: PRT
<213> ORGANISM: Artificial sequence
<220> FEATURE:
<223> OTHER INFORMATION: Synthetic antibody sequence

<400> SEQUENCE: 487

Gln Ser Tyr Tyr Gly Ser Ser Thr Thr Gly Asn Gly
1 5 10

<210> SEQ ID NO 488
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 488
cagaacattt acagctac 18

<210> SEQ ID NO 489
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 489 aaggcatcc 9

<210> SEQ ID NO 490
<211> LENGTH: 45
<212> TYPE: DNA
<213> ORGANISM: Artificial sequence
<220> FEATURE:
<223> OTHER INFORMATION: Synthetic antibody sequence

<400> SEQUENCE: 490
caaaccaatt attttagtag tactagtcat tttggtgttt ttact 45

<210> SEQ ID NO 491
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 491
cagagtcttt ataatgcgaa cgac 24

<210> SEQ ID NO 492
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 492 tgggcatcc 9

<210> SEQ ID NO 493
<211> LENGTH: 39
<212> TYPE: DNA
<213> ORGANISM: Artificial sequence
<220> FEATURE:
<223> OTHER INFORMATION: Synthetic antibody sequence

<400> SEQUENCE: 493
ctaggcgaat ttagttgcag tagttttgat tgtcatgtt 39

<210> SEQ ID NO 494
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 494
cagagcattt acaggtac 18

<210> SEQ ID NO 495
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 495 tatggatcc 9

<210> SEQ ID NO 496
<211> LENGTH: 36
<212> TYPE: DNA
<213> ORGANISM: Artificial sequence
<220> FEATURE:
<223> OTHER INFORMATION: Synthetic antibody sequence

<400> SEQUENCE: 496
caaaccactt atgatgatta tcataatggt tgggct 36

<210> SEQ ID NO 497
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 497
cagagtgttt atggtaacaa ccgc 24

<210> SEQ ID NO 498
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 498 ctggcatcc 9

<210> SEQ ID NO 499
<211> LENGTH: 30
<212> TYPE: DNA
<213> ORGANISM: Artificial sequence
<220> FEATURE:
<223> OTHER INFORMATION: Synthetic antibody sequence

<400> SEQUENCE: 499
gcaggcggtt atgctgggaa tttcaatgct 30

<210> SEQ ID NO 500
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 500
cagaacattg tcagtaat 18

<210> SEQ ID NO 501
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 501 tatgcatcc 9

<210> SEQ ID NO 502
<211> LENGTH: 39
<212> TYPE: DNA
<213> ORGANISM: Artificial sequence
<220> FEATURE:
<223> OTHER INFORMATION: Synthetic antibody sequence

<400> SEQUENCE: 502
caaaacaatg ctggtattta tggtaattat ggtcatggt 39

<210> SEQ ID NO 503
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 503
cagagcattt acaactac 18

<210> SEQ ID NO 504
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 504 gatgtatcc 9

<210> SEQ ID NO 505
<211> LENGTH: 33
<212> TYPE: DNA
<213> ORGANISM: Artificial sequence
<220> FEATURE:
<223> OTHER INFORMATION: Synthetic antibody sequence

<400> SEQUENCE: 505
caaagttatt atggtaatac tgtttctttt act 33

<210> SEQ ID NO 506
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 506
cagagtgttt ataataacaa caac 24

<210> SEQ ID NO 507
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 507 tctgcatcc 9

<210> SEQ ID NO 508
<211> LENGTH: 30
<212> TYPE: DNA
<213> ORGANISM: Artificial sequence
<220> FEATURE:
<223> OTHER INFORMATION: Synthetic antibody sequence

<400> SEQUENCE: 508
gcaggcggtt atacttacaa tatcaatatt 30

<210> SEQ ID NO 509
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 509
cagaacattt acaacaat 18

<210> SEQ ID NO 510
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 510 tatgcatcc 9

<210> SEQ ID NO 511

<211> LENGTH: 39
<212> TYPE: DNA
<213> ORGANISM: Artificial sequence
<220> FEATURE:
<223> OTHER INFORMATION: Synthetic antibody sequence

<400> SEQUENCE: 511
caaaacaatg ctggtattta tggtggttat ggtcatggt 39

<210> SEQ ID NO 512
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 512
cagactattg gtagctac 18

<210> SEQ ID NO 513
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 513 gaagcatcc 9

<210> SEQ ID NO 514
<211> LENGTH: 42
<212> TYPE: DNA
<213> ORGANISM: Artificial sequence
<220> FEATURE:
<223> OTHER INFORMATION: Synthetic antibody sequence

<400> SEQUENCE: 514
caaagcaatt attatcgtgc tggtggtaat tatggtggag ct 42

<210> SEQ ID NO 515
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 515
gagaccatta gtaataga 18

<210> SEQ ID NO 516
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 516 tctgcatcc 9

<210> SEQ ID NO 517
<211> LENGTH: 42
<212> TYPE: DNA
<213> ORGANISM: Artificial sequence
<220> FEATURE:
<223> OTHER INFORMATION: Synthetic antibody sequence

<400> SEQUENCE: 517
caaagtattc gtagtagtag tggtattgtt catccgaata ct 42

<210> SEQ ID NO 518
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 518
cagagcatta gtagttac 18

<210> SEQ ID NO 519
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 519 aaggcatcc 9

<210> SEQ ID NO 520
<211> LENGTH: 39
<212> TYPE: DNA
<213> ORGANISM: Artificial sequence
<220> FEATURE:
<223> OTHER INFORMATION: Synthetic antibody sequence

<400> SEQUENCE: 520
caaagctatt actatattag tgctactgtt gataatact 39

<210> SEQ ID NO 521
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 521
cagagcatta gtgattac 18

<210> SEQ ID NO 522
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 522 agggcatcc 9

<210> SEQ ID NO 523
<211> LENGTH: 33
<212> TYPE: DNA
<213> ORGANISM: Artificial sequence
<220> FEATURE:
<223> OTHER INFORMATION: Synthetic antibody sequence

<400> SEQUENCE: 523
caaagtaatt attatggtag tcagggttgt act 33

<210> SEQ ID NO 524
<211> LENGTH: 18
<212> TYPE: DNA

<213> ORGANISM: Artificial sequence
<220> FEATURE:
<223> OTHER INFORMATION: Synthetic antibody sequence

<400> SEQUENCE: 524
cagagcattg gcaatgca 18

<210> SEQ ID NO 525
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 525 aaggcatcc 9

<210> SEQ ID NO 526
<211> LENGTH: 30
<212> TYPE: DNA
<213> ORGANISM: Artificial sequence
<220> FEATURE:
<223> OTHER INFORMATION: Synthetic antibody sequence

<400> SEQUENCE: 526
caaaactatt attatagtaa tactaatagt 30

<210> SEQ ID NO 527
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 527
cagaacattt ataataac 18

<210> SEQ ID NO 528
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 528 ggtccatcc 9

<210> SEQ ID NO 529
<211> LENGTH: 39
<212> TYPE: DNA
<213> ORGANISM: Artificial sequence
<220> FEATURE:
<223> OTHER INFORMATION: Synthetic antibody sequence

<400> SEQUENCE: 529
caaagtgatg attggatgag tatcagtcct gatattgtt 39

<210> SEQ ID NO 530
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 530
cagagtattg gtagtaga 18

<210> SEQ ID NO 531
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 531 gaagcatcc 9

<210> SEQ ID NO 532
<211> LENGTH: 36
<212> TYPE: DNA
<213> ORGANISM: Artificial sequence
<220> FEATURE:
<223> OTHER INFORMATION: Synthetic antibody sequence

<400> SEQUENCE: 532
caatgtactt attatgaaag tagtagtggt ggtggt 36

<210> SEQ ID NO 533
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 533
catatcatta ctaactac 18

<210> SEQ ID NO 534
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 534 gatgcatcg 9

<210> SEQ ID NO 535
<211> LENGTH: 39
<212> TYPE: DNA
<213> ORGANISM: Artificial sequence
<220> FEATURE:
<223> OTHER INFORMATION: Synthetic antibody sequence

<400> SEQUENCE: 535
caaaactatc tttattttag tagtggtgat tggaatgtt 39

<210> SEQ ID NO 536
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 536
ccgagcatta gtacttac 18

<210> SEQ ID NO 537
<211> LENGTH: 9
<212> TYPE: DNA
<213> ORGANISM: Artificial sequence
<220> FEATURE:

<223> OTHER INFORMATION: Synthetic antibody sequence

<400> SEQUENCE: 537 agggcatcc 9

<210> SEQ ID NO 538
<211> LENGTH: 45
<212> TYPE: DNA
<213> ORGANISM: Artificial sequence
<220> FEATURE:
<223> OTHER INFORMATION: Synthetic antibody sequence

<400> SEQUENCE: 538
caaaacaatt accatagtgg tagtagtaat ggtggtggtg ttgct 45

<210> SEQ ID NO 539
<211> LENGTH: 21
<212> TYPE: DNA
<213> ORGANISM: Artificial sequence
<220> FEATURE:
<223> OTHER INFORMATION: Synthetic antibody sequence

<400> SEQUENCE: 539
cagagtattg gtagtggtaa t 21

<210> SEQ ID NO 540
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 540 ctggcatcc 9

<210> SEQ ID NO 541
<211> LENGTH: 36
<212> TYPE: DNA
<213> ORGANISM: Artificial sequence
<220> FEATURE:
<223> OTHER INFORMATION: Synthetic antibody sequence

<400> SEQUENCE: 541
caatatactt attatggtac tacttatgat aatgct 36

<210> SEQ ID NO 542
<211> LENGTH: 21
<212> TYPE: DNA
<213> ORGANISM: Artificial sequence
<220> FEATURE:
<223> OTHER INFORMATION: Synthetic antibody sequence

<400> SEQUENCE: 542
cagattgttg ctaacggccg c 21

<210> SEQ ID NO 543
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 543 gctacatcc 9

<210> SEQ ID NO 544
<211> LENGTH: 33
<212> TYPE: DNA
<213> ORGANISM: Artificial sequence
<220> FEATURE:
<223> OTHER INFORMATION: Synthetic antibody sequence

<400> SEQUENCE: 544
caaggcgctt atagtagtgg ggatgttcgg act 33

<210> SEQ ID NO 545
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 545
gaggacattg ataggtat 18

<210> SEQ ID NO 546
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 546 gatgcatcc 9

<210> SEQ ID NO 547
<211> LENGTH: 30
<212> TYPE: DNA
<213> ORGANISM: Artificial sequence
<220> FEATURE:
<223> OTHER INFORMATION: Synthetic antibody sequence

<400> SEQUENCE: 547
caaagctatg ataatagtga taataatggt 30

<210> SEQ ID NO 548
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 548
catatcatta ctaactac 18

<210> SEQ ID NO 549
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 549 gatgcatcg 9

<210> SEQ ID NO 550
<211> LENGTH: 39
<212> TYPE: DNA
<213> ORGANISM: Artificial sequence
<220> FEATURE:
<223> OTHER INFORMATION: Synthetic antibody sequence

<400> SEQUENCE: 550
caaaactatc tttattttag tagtggtgat tggaatgtt 39

<210> SEQ ID NO 551
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 551
gagagcattg gcagtgca 18

<210> SEQ ID NO 552
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 552 tctgcatcc 9

<210> SEQ ID NO 553
<211> LENGTH: 39
<212> TYPE: DNA
<213> ORGANISM: Artificial sequence
<220> FEATURE:
<223> OTHER INFORMATION: Synthetic antibody sequence

<400> SEQUENCE: 553
caaagttatt atggaagtgg tacgactgct ttagatact 39

<210> SEQ ID NO 554
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 554
cagagcattt acaactac 18

<210> SEQ ID NO 555
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 555 tctgcatcc 9

<210> SEQ ID NO 556
<211> LENGTH: 39
<212> TYPE: DNA
<213> ORGANISM: Artificial sequence
<220> FEATURE:
<223> OTHER INFORMATION: Synthetic antibody sequence

<400> SEQUENCE: 556
caaaacaatt atggtattgg tagtaattat ggtcctggt 39

<210> SEQ ID NO 557
<211> LENGTH: 18

<212> TYPE: DNA
<213> ORGANISM: Artificial sequence
<220> FEATURE:
<223> OTHER INFORMATION: Synthetic antibody sequence

<400> SEQUENCE: 557
ctgaacatta atagttgg 18

<210> SEQ ID NO 558
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 558 tatacatcc 9

<210> SEQ ID NO 559
<211> LENGTH: 33
<212> TYPE: DNA
<213> ORGANISM: Artificial sequence
<220> FEATURE:
<223> OTHER INFORMATION: Synthetic antibody sequence

<400> SEQUENCE: 559
caaaccacat attttggtac taatggtggt ggt 33

<210> SEQ ID NO 560
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 560
gaggacattt atagcaat 18

<210> SEQ ID NO 561
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 561 ggtgcaacc 9

<210> SEQ ID NO 562
<211> LENGTH: 27
<212> TYPE: DNA
<213> ORGANISM: Artificial sequence
<220> FEATURE:
<223> OTHER INFORMATION: Synthetic antibody sequence

<400> SEQUENCE: 562
caggccgaaa gtaatgatgt ttgggct 27

<210> SEQ ID NO 563
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 563

```
gaggatattt atagtaat                                                18


<210> SEQ ID NO 564
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 564

aaggcatcc                                                           9


<210> SEQ ID NO 565
<211> LENGTH: 36
<212> TYPE: DNA
<213> ORGANISM: Artificial sequence
<220> FEATURE:
<223> OTHER INFORMATION: Synthetic antibody sequence

<400> SEQUENCE: 565

cagactactt attggactac tactgatgat aatcct                            36


<210> SEQ ID NO 566
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 566

cagagtgttt ataataagaa ctac                                         24


<210> SEQ ID NO 567
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 567

tatgcttcc                                                           9


<210> SEQ ID NO 568
<211> LENGTH: 36
<212> TYPE: DNA
<213> ORGANISM: Artificial sequence
<220> FEATURE:
<223> OTHER INFORMATION: Synthetic antibody sequence

<400> SEQUENCE: 568

gcagcttata aaggtgttag tgatgatggt atttct                            36


<210> SEQ ID NO 569
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 569

cagagcatta gtagttac                                                18


<210> SEQ ID NO 570
<211> LENGTH: 9
<212> TYPE: DNA
<213> ORGANISM: Artificial sequence
```

<220> FEATURE:
<223> OTHER INFORMATION: Synthetic antibody sequence

<400> SEQUENCE: 570 aaggcatcc 9

<210> SEQ ID NO 571
<211> LENGTH: 45
<212> TYPE: DNA
<213> ORGANISM: Artificial sequence
<220> FEATURE:
<223> OTHER INFORMATION: Synthetic antibody sequence

<400> SEQUENCE: 571
caaaacaatt atcatagtgg tagtagtaat ggtggtggtt ttgct 45

<210> SEQ ID NO 572
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 572
cagagcatta gttactac 18

<210> SEQ ID NO 573
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 573 aaggcatcc 9

<210> SEQ ID NO 574
<211> LENGTH: 42
<212> TYPE: DNA
<213> ORGANISM: Artificial sequence
<220> FEATURE:
<223> OTHER INFORMATION: Synthetic antibody sequence

<400> SEQUENCE: 574
caaagcactt atggtaggga taataatgat cttttttcg ct 42

<210> SEQ ID NO 575
<211> LENGTH: 21
<212> TYPE: DNA
<213> ORGANISM: Artificial sequence
<220> FEATURE:
<223> OTHER INFORMATION: Synthetic antibody sequence

<400> SEQUENCE: 575
cagagtatta gtagtagcta c 21

<210> SEQ ID NO 576
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 576 tctgcgtcc 9

<210> SEQ ID NO 577
<211> LENGTH: 39
<212> TYPE: DNA
<213> ORGANISM: Artificial sequence
<220> FEATURE:
<223> OTHER INFORMATION: Synthetic antibody sequence

<400> SEQUENCE: 577
caaagcactt atattagtag tagtaagtat ggtgctgtt 39

<210> SEQ ID NO 578
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 578
cagagtgttt atagtaacaa ctgg 24

<210> SEQ ID NO 579
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 579 aaggcatcc 9

<210> SEQ ID NO 580
<211> LENGTH: 30
<212> TYPE: DNA
<213> ORGANISM: Artificial sequence
<220> FEATURE:
<223> OTHER INFORMATION: Synthetic antibody sequence

<400> SEQUENCE: 580
gcaggcgggt atagtggtga tctttatgct 30

<210> SEQ ID NO 581
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 581
cagactattt ataataacaa aaat 24

<210> SEQ ID NO 582
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 582 caggcatcc 9

<210> SEQ ID NO 583
<211> LENGTH: 39
<212> TYPE: DNA
<213> ORGANISM: Artificial sequence
<220> FEATURE:
<223> OTHER INFORMATION: Synthetic antibody sequence

<400> SEQUENCE: 583
caaggcgaat ttagttgtag tagtggtgat tgtactact 39

<210> SEQ ID NO 584
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 584
gagaacattt atagctac 18

<210> SEQ ID NO 585
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 585 tctgcatcc 9

<210> SEQ ID NO 586
<211> LENGTH: 36
<212> TYPE: DNA
<213> ORGANISM: Artificial sequence
<220> FEATURE:
<223> OTHER INFORMATION: Synthetic antibody sequence

<400> SEQUENCE: 586
caatatagta attttagggt gaatgatcct agtgtt 36

<210> SEQ ID NO 587
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 587
cagaccgttc ataataatca atgg 24

<210> SEQ ID NO 588
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 588 gatgcatcc 9

<210> SEQ ID NO 589
<211> LENGTH: 33
<212> TYPE: DNA
<213> ORGANISM: Artificial sequence
<220> FEATURE:
<223> OTHER INFORMATION: Synthetic antibody sequence

<400> SEQUENCE: 589
caaggcggtt atagttatgg tgatgtgtat ggt 33

<210> SEQ ID NO 590

<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 590
caaagtgttg ataacaacaa acaa 24

<210> SEQ ID NO 591
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 591 tctgcatcc 9

<210> SEQ ID NO 592
<211> LENGTH: 42
<212> TYPE: DNA
<213> ORGANISM: Artificial sequence
<220> FEATURE:
<223> OTHER INFORMATION: Synthetic antibody sequence

<400> SEQUENCE: 592
gcaggctatt attatagtgg tagtgccact gatgcgtggg ct 42

<210> SEQ ID NO 593
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 593
gagaccatta gtaataga 18

<210> SEQ ID NO 594
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 594 tctgcatcc 9

<210> SEQ ID NO 595
<211> LENGTH: 42
<212> TYPE: DNA
<213> ORGANISM: Artificial sequence
<220> FEATURE:
<223> OTHER INFORMATION: Synthetic antibody sequence

<400> SEQUENCE: 595
caaagtattc gtagtagtag tggtgttgtg catccaaata ct 42

<210> SEQ ID NO 596
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 596
cagaccattt ataccaat 18

<210> SEQ ID NO 597
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 597 gctgcatcc 9

<210> SEQ ID NO 598
<211> LENGTH: 36
<212> TYPE: DNA
<213> ORGANISM: Artificial sequence
<220> FEATURE:
<223> OTHER INFORMATION: Synthetic antibody sequence

<400> SEQUENCE: 598
caaagctatt atggtagtag tactactggt aatggt 36

<210> SEQ ID NO 599
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 599
gataatgttt atagtaataa ctac 24

<210> SEQ ID NO 600
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 600 tatgcggcc 9

<210> SEQ ID NO 601
<211> LENGTH: 36
<212> TYPE: DNA
<213> ORGANISM: Artificial sequence
<220> FEATURE:
<223> OTHER INFORMATION: Synthetic antibody sequence

<400> SEQUENCE: 601
tcaggccata aagattatag tgatgatggt agtact 36

<210> SEQ ID NO 602
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 602
gataatgttt atagtaataa ctac 24

<210> SEQ ID NO 603
<211> LENGTH: 9
<212> TYPE: DNA

<213> ORGANISM: Artificial sequence
<220> FEATURE:
<223> OTHER INFORMATION: Synthetic antibody sequence

<400> SEQUENCE: 603 tatgcggcc 9

<210> SEQ ID NO 604
<211> LENGTH: 36
<212> TYPE: DNA
<213> ORGANISM: Artificial sequence
<220> FEATURE:
<223> OTHER INFORMATION: Synthetic antibody sequence

<400> SEQUENCE: 604
tcaggccata aagattatag tgatgatggt agtact 36

<210> SEQ ID NO 605
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 605
gaggatatta gtagtaat 18

<210> SEQ ID NO 606
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 606 ggtgcatcc 9

<210> SEQ ID NO 607
<211> LENGTH: 30
<212> TYPE: DNA
<213> ORGANISM: Artificial sequence
<220> FEATURE:
<223> OTHER INFORMATION: Synthetic antibody sequence

<400> SEQUENCE: 607
caaggcgctt attatggtag tagttatggt 30

<210> SEQ ID NO 608
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 608
cagagcatta gcaatgaa 18

<210> SEQ ID NO 609
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 609 ctggcatcc 9

<210> SEQ ID NO 610
<211> LENGTH: 42
<212> TYPE: DNA
<213> ORGANISM: Artificial sequence
<220> FEATURE:
<223> OTHER INFORMATION: Synthetic antibody sequence

<400> SEQUENCE: 610
caaagtcatt attatggtgg tagtagtgat tatggatggg ct 42

<210> SEQ ID NO 611
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 611
caaagtgttt acaataacaa ccaa 24

<210> SEQ ID NO 612
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 612 ggtgcatcc 9

<210> SEQ ID NO 613
<211> LENGTH: 30
<212> TYPE: DNA
<213> ORGANISM: Artificial sequence
<220> FEATURE:
<223> OTHER INFORMATION: Synthetic antibody sequence

<400> SEQUENCE: 613
caaggcgctg ttagtagtga ttactatcct 30

<210> SEQ ID NO 614
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 614
cagagtattg gtagctat 18

<210> SEQ ID NO 615
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 615 tatgcttcc 9

<210> SEQ ID NO 616
<211> LENGTH: 36
<212> TYPE: DNA
<213> ORGANISM: Artificial sequence
<220> FEATURE:

<223> OTHER INFORMATION: Synthetic antibody sequence

<400> SEQUENCE: 616
caaagtaatc gtcttagtag tagtgacgtt aatgct 36

<210> SEQ ID NO 617
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 617
cagaacattt acagcaat 18

<210> SEQ ID NO 618
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 618 tctgcatcc 9

<210> SEQ ID NO 619
<211> LENGTH: 36
<212> TYPE: DNA
<213> ORGANISM: Artificial sequence
<220> FEATURE:
<223> OTHER INFORMATION: Synthetic antibody sequence

<400> SEQUENCE: 619
caaagctatt attatactgc tagtgctgat actact 36

<210> SEQ ID NO 620
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 620
cagagcattg gtagctac 18

<210> SEQ ID NO 621
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 621 aaggcatcc 9

<210> SEQ ID NO 622
<211> LENGTH: 30
<212> TYPE: DNA
<213> ORGANISM: Artificial sequence
<220> FEATURE:
<223> OTHER INFORMATION: Synthetic antibody sequence

<400> SEQUENCE: 622
caatatacta gttatagtag tggtggggct 30

<210> SEQ ID NO 623
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 623
gaggacattg ataggtat 18

<210> SEQ ID NO 624
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 624 agggcatcc 9

<210> SEQ ID NO 625
<211> LENGTH: 36
<212> TYPE: DNA
<213> ORGANISM: Artificial sequence
<220> FEATURE:
<223> OTHER INFORMATION: Synthetic antibody sequence

<400> SEQUENCE: 625
caaggcgatt ttattggtag tagttatggc gttgct 36

<210> SEQ ID NO 626
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 626
cagagcatta gtagttac 18

<210> SEQ ID NO 627
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 627 aaggcttcc 9

<210> SEQ ID NO 628
<211> LENGTH: 45
<212> TYPE: DNA
<213> ORGANISM: Artificial sequence
<220> FEATURE:
<223> OTHER INFORMATION: Synthetic antibody sequence

<400> SEQUENCE: 628
caaaacaatt atcatagtgg tagtagtaat ggtggtggtt ttgct 45

<210> SEQ ID NO 629
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 629
cagaccattt ataccaat 18

<210> SEQ ID NO 630
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 630 gctgcatcc 9

<210> SEQ ID NO 631
<211> LENGTH: 36
<212> TYPE: DNA
<213> ORGANISM: Artificial sequence
<220> FEATURE:
<223> OTHER INFORMATION: Synthetic antibody sequence

<400> SEQUENCE: 631
caaagctatt atggtagtag tactactggt aatggt 36

<210> SEQ ID NO 632
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 632
gagagtgttt atggtaacaa ccgt 24

<210> SEQ ID NO 633
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 633 caggcttcc 9

<210> SEQ ID NO 634
<211> LENGTH: 36
<212> TYPE: DNA
<213> ORGANISM: Artificial sequence
<220> FEATURE:
<223> OTHER INFORMATION: Synthetic antibody sequence

<400> SEQUENCE: 634
gcaggacata aaggaactac taatgatggg aatgat 36

<210> SEQ ID NO 635
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 635
cagagcatta ccaatgca 18

<210> SEQ ID NO 636
<211> LENGTH: 9

<212> TYPE: DNA
<213> ORGANISM: Artificial sequence
<220> FEATURE:
<223> OTHER INFORMATION: Synthetic antibody sequence

<400> SEQUENCE: 636 agggcatcc 9

<210> SEQ ID NO 637
<211> LENGTH: 39
<212> TYPE: DNA
<213> ORGANISM: Artificial sequence
<220> FEATURE:
<223> OTHER INFORMATION: Synthetic antibody sequence

<400> SEQUENCE: 637
caatgtagtt attatggtag tacttatttt gggagtcct 39

<210> SEQ ID NO 638
<211> LENGTH: 21
<212> TYPE: DNA
<213> ORGANISM: Artificial sequence
<220> FEATURE:
<223> OTHER INFORMATION: Synthetic antibody sequence

<400> SEQUENCE: 638
cagagcatta gtagtagcta c 21

<210> SEQ ID NO 639
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 639 tctgcatcc 9

<210> SEQ ID NO 640
<211> LENGTH: 39
<212> TYPE: DNA
<213> ORGANISM: Artificial sequence
<220> FEATURE:
<223> OTHER INFORMATION: Synthetic antibody sequence

<400> SEQUENCE: 640
caaagcactt atattagtag tagtaattat ggtgctgct 39

<210> SEQ ID NO 641
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 641
cagagcattg gtagtaat 18

<210> SEQ ID NO 642
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 642 aaggcatcc 9

<210> SEQ ID NO 643
<211> LENGTH: 33
<212> TYPE: DNA
<213> ORGANISM: Artificial sequence
<220> FEATURE:
<223> OTHER INFORMATION: Synthetic antibody sequence

<400> SEQUENCE: 643
caaaacaata attattggag taatggtaac cat 33

<210> SEQ ID NO 644
<211> LENGTH: 24
<212> TYPE: DNA
<213> ORGANISM: Artificial sequence
<220> FEATURE:
<223> OTHER INFORMATION: Synthetic antibody sequence

<400> SEQUENCE: 644
gagaatgttt atagtaataa ctac 24

<210> SEQ ID NO 645
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 645 tatgcggcc 9

<210> SEQ ID NO 646
<211> LENGTH: 36
<212> TYPE: DNA
<213> ORGANISM: Artificial sequence
<220> FEATURE:
<223> OTHER INFORMATION: Synthetic antibody sequence

<400> SEQUENCE: 646
tcaggccata aagattatag tgatgatggt agtact 36

<210> SEQ ID NO 647
<211> LENGTH: 18
<212> TYPE: DNA
<213> ORGANISM: Artificial sequence
<220> FEATURE:
<223> OTHER INFORMATION: Synthetic antibody sequence

<400> SEQUENCE: 647
cagagcattg ctagcgac 18

<210> SEQ ID NO 648
<211> LENGTH: 9
<212> TYPE: DNA
<213> ORGANISM: Artificial sequence
<220> FEATURE:
<223> OTHER INFORMATION: Synthetic antibody sequence

<400> SEQUENCE: 648 gctgcatcc 9

<210> SEQ ID NO 649
<211> LENGTH: 36
<212> TYPE: DNA
<213> ORGANISM: Artificial sequence
<220> FEATURE:
<223> OTHER INFORMATION: Synthetic antibody sequence

<400> SEQUENCE: 649
caaagctatt atggtagtag tactactggt aatggt 36

<210> SEQ ID NO 650
<211> LENGTH: 375
<212> TYPE: DNA
<213> ORGANISM: Artificial sequence
<220> FEATURE:
<223> OTHER INFORMATION: Synthetic antibody sequence

<400> SEQUENCE: 650
cagtcgttgg aggagtccga gggagacctg gtcaagcctg agggatccct gacactcacc 60
tgcaaagcct ctggattcga cttcagtagt gatgcaatgt gctgggtccg ccaggctcca 120
gggaaggggc tggagtggat cggatgcatt tataatggtg atgaaattac agaccacgcg 180
agctgggcga aaggccgatt caccatctcc aaaacctcgc cgaccacggt gactctgcaa 240
atgaccagtc tgacagtcgc ggacacggcc acctatttct gtgcgagagc tgtctatagt 300
gatggtggtg ctggttatcc ttatatgtat ggcatggacc tctggggccc agggaccctc 360
gtcaccgtct cttca 375

<210> SEQ ID NO 651
<211> LENGTH: 342
<212> TYPE: DNA
<213> ORGANISM: Artificial sequence
<220> FEATURE:
<223> OTHER INFORMATION: Synthetic antibody sequence

<400> SEQUENCE: 651
cgagcagtcg ggaaggagtc cgggggaggc ctggtcaagc ctggggcatc cctgacactc 60
acctgcaaag cctctggatt cgacttcagt ggcatttatt gggtatgctg ggtccgccag 120
gctccaggga aggggctgga gtggatcgcg tgttttgatg ctgaaaggac tggtaacact 180
tattacgcga cctgggcgaa aggccgcttc accatctcca gaacctcgtc gaccacggtg 240
actctgcaaa tgaccagtct gacagccgcg gacacggcca cctatttctg tgcgagatca 300
tattatatgt ggggcccagg caccctggtc accgtctctt ca 342

<210> SEQ ID NO 652
<211> LENGTH: 360
<212> TYPE: DNA
<213> ORGANISM: Artificial sequence
<220> FEATURE:
<223> OTHER INFORMATION: Synthetic antibody sequence

<400> SEQUENCE: 652
gagcagtcgt tggaggagtc cgggggagac ctggtcaagc ctgagggatc cctgacactc 60
acctgcacag cctctgaatt gtccttcagt agcgcctact acatgtgctg ggtccgccag 120
gctccaggga aggggctgga gtggatcgga tgcatttata gtggtgatgg tgacacttac 180
tacgcgaact gggcgaaagg ccgattcacc atctccaaaa cctcgtcgac cacggtgact 240
ctgcaaatga ccagtctgac agacgcggac acggccacct atttctgtgc gagggctctg 300
gatagtcatt attcttcctt tgacttgtgg ggcccaggca ccctggtcac catctcttca 360

<210> SEQ ID NO 653
<211> LENGTH: 345
<212> TYPE: DNA

<213> ORGANISM: Artificial sequence
<220> FEATURE:
<223> OTHER INFORMATION: Synthetic antibody sequence

<400> SEQUENCE: 653
gagcagtcgt tggaggagtc cgggggaggc ctggtcaagc ctggggcatc cctgacagtc 60
acctgcgcag tctctggatt ctccctcaat agctatgcaa taacttgggt ccgccaggct 120
ccagggaaag ggctggaata catcggatac attgatactg gtgctagtat cacagactac 180
gcgagctggg cgaaaggccg attcaccatc tccaaaacct cgtcgaccac ggtgactctg 240
gaaatgacca gtctgacaga cgcggacacg gccacctatt tctgtgcgag ggtttttcg 300 atgtttaagt tgtggggccc aggcaccctg gtcaccatct cttca 345

<210> SEQ ID NO 654
<211> LENGTH: 357
<212> TYPE: DNA
<213> ORGANISM: Artificial sequence
<220> FEATURE:
<223> OTHER INFORMATION: Synthetic antibody sequence

<400> SEQUENCE: 654
gagcagtcgg tggaggagtc cgggggaggc ctggtcaagc ctgagggatc cctgacactc 60
acctgcaaag cctctgggtt agacttcagt agcagctact ggatatgctg ggtccgccag 120
gctccaggga aggggctgga gtggatcgca tgcattgata ctggtagtag tggtagcact 180
tactacgcga gctgggcgaa aggccgattc accgtctcca aaacctcgtc gaccacggtg 240
tctctgcaaa tgaccagtct gacagccgcg gacacggcca cctatttctg tgcgagtact 300
cctaatagtc taggttacga cttatggggc ccaggcaccc tggtcaccat ctcttca 357

<210> SEQ ID NO 655
<211> LENGTH: 381
<212> TYPE: DNA
<213> ORGANISM: Artificial sequence
<220> FEATURE:
<223> OTHER INFORMATION: Synthetic antibody sequence

<400> SEQUENCE: 655
gagcagtcgg tggaggagtc cgggggagac ctggtcaagc ctggggcatc cctgacactc 60
acctgcacag cctctggatt ctcctccagt agtagcgcct atatgtgctg ggtccgccag 120
gctccaggga aggggctgga gtggatcgca tgtattttta ttggtagtgg tagtgactct 180
tactacgcga cctgggcgaa aggccgattc accatctcca aaacctcgtc gaccacggtg 240
actctgcaaa tgaccagtct gacagccgcg gacacggcca cctatttctg tgcgagaaat 300
acttatgatt ggaatggtta tatttatggc ccgtgttatt ttggcttgtg gggcccaggc 360
accctggtca ccatctcctc a 381

<210> SEQ ID NO 656
<211> LENGTH: 345
<212> TYPE: DNA
<213> ORGANISM: Artificial sequence
<220> FEATURE:
<223> OTHER INFORMATION: Synthetic antibody sequence

<400> SEQUENCE: 656
gagcagtcgg tgaaggagtc cgggggaggc ctggtcaagc ctggaggaac cctgacactc 60
acctgcatag tctctggatt ctccctcagt aggtatgcag tcacctgggt ccgccaggct 120
ccagggaagg ggcctgagtg gatcggatac attgacacta gtagtggtaa caaagactac 180
gcgaactggg tgaatggccg attcaccatc tccaaaacct cgtcgaccac ggtgactctg 240
caaatgacca gtctgacagc cgcggacacg gccacctatt tctgtgcgag aggtttttct 300
atgtttaagt tgtggggccc aggcaccctg gtcaccatct cttca 345

<210> SEQ ID NO 657
<211> LENGTH: 360
<212> TYPE: DNA
<213> ORGANISM: Artificial sequence
<220> FEATURE:
<223> OTHER INFORMATION: Synthetic antibody sequence

<400> SEQUENCE: 657
gagcagtcgg tggaggagtc cgggggaggc ctggtcaagc ctgagggatc cctgacactc 60
acctgcaaag cctctggatt ggacttcagt agcagctatt ggagctgctg ggtccgccag 120
actccaggga gggggctgga gtggatcgga tgcattgatg ttgggagtag tggtggctca 180
tactacgcga gctgggcgag aggccgattc accgtctcca aaggctcgtc gaccacggtg 240
actctgcaaa tgaccagtct gacagccgcg gacacggcca cctatttctg tgcgagcact 300
acgactaatg ttttcggtta cgacttatgg ggcccaggca ctctggtcac cgtctcttca 360

<210> SEQ ID NO 658
<211> LENGTH: 381
<212> TYPE: DNA
<213> ORGANISM: Artificial sequence
<220> FEATURE:
<223> OTHER INFORMATION: Synthetic antibody sequence

<400> SEQUENCE: 658
gagcagtcgt tggaggagtc cgggggaggc ctggtcaagc ctggggcatc cctgacactc 60
acctgcaaag cctctggatt cgacttcagt agtaatgact acatgtgctg ggtccgccag 120
gctccaggga aggggctgga gtggatcgga tgcatttatg gtggtgatgg gcacacttac 180
tacgcgacct gggcgaaagg ccgattcacc atctccaaag cctcgtcgac cacggtgacg 240
ctgcaaatga ccagtctgac agccgcggac acggccagct atttctgtgc gaggggatat 300
agttatggtg atactggata tgctgatgct attcttacct tggacttgtg gggcccaggc 360
accctggtca ccgtctcttc a 381

<210> SEQ ID NO 659
<211> LENGTH: 369
<212> TYPE: DNA
<213> ORGANISM: Artificial sequence
<220> FEATURE:
<223> OTHER INFORMATION: Synthetic antibody sequence

<400> SEQUENCE: 659
gagcagtcgg tgaaggagtc cgggggaggc ctggtccagc ctgagggatc cctgacactc 60
acctgcaaag tctctggaat cgacttcaat tattacaact actactacat gtgctgggtc 120
cgccaggctc cagggaaggg gctggagtgg atcggatgca tgtccactgc cagtgcgaat 180
atttaccttg cgagctgggc gaaaggccga ttcaccatct ccgaggcctc gtcgaccacg 240
gtgactctgc aaatgaccag tctgacagcc gcggacacgg ccacctattt ctgtgcgaaa 300
tcccatggtg gtgatggtgg ttatggggtt gtattatggg gcccaggcac cctggtcacc 360
atctcctca 369

<210> SEQ ID NO 660

<211> LENGTH: 366
<212> TYPE: DNA
<213> ORGANISM: Artificial sequence
<220> FEATURE:
<223> OTHER INFORMATION: Synthetic antibody sequence

<400> SEQUENCE: 660

```
gagcagtcgg tgaaggagtc cgggggaggc ctggtccagc ctgagggatc cctgacactc     60

acctgcacag tctctggatt ctccttcagt ggcagctact ggatatgctg ggtccgccag    120

gctccaggga aggggctgga gtggatcgca tgcatttatg gtgatagtat tgccacttac    180

tacccgaact gggcgaaagg ccgattcacc atctccaaaa cctcgtcgac cacggtgact    240

ctacaaatgg ccagtctgac aggcgcggac acggccacct atttctgtgc gagagatcga    300

aatggtggtt ctggtgctta tggttgggac ttgtggggcc caggcaccct ggtcaccatc    360

tcctca                                                                366
```

<210> SEQ ID NO 661
<211> LENGTH: 357
<212> TYPE: DNA
<213> ORGANISM: Artificial sequence
<220> FEATURE:
<223> OTHER INFORMATION: Synthetic antibody sequence

<400> SEQUENCE: 661

```
gagcagtcgt tggaggagtc cgggggaggc ctggtcaagc ctggggcatc cctgacactc     60

acctgcaaag cctctggatt ctccttcagt agcgactatg acatgtgctg ggtccgccag    120

gctccaggga aggggctgga gtggatcgga tgcattgtga ctggttttag tggtcgtatt    180

tattacgcga cctgggcgag aggccgattc accttctcca gaacctcgtc gaccacgctg    240

actctgcaaa tgaccagtct gacagccgcg gacacggcca cttatttctg tgcgagagat    300

agtggtaatt ataattggga cttgtggggc ccaggcaccc tggtcaccat ctcttca       357
```

<210> SEQ ID NO 662
<211> LENGTH: 372
<212> TYPE: DNA
<213> ORGANISM: Artificial sequence
<220> FEATURE:
<223> OTHER INFORMATION: Synthetic antibody sequence

<400> SEQUENCE: 662

```
gagcagtcgg tggaggagtc cgagggaggc ctggtccagc ctgagggatc cctgacactc     60

acctgcacag cttctggatt ctccttcagt aacgactact ggatatgctg ggtccgccag    120

gctccaggga aggggctgga gtggatcgga tgcggacata taggtagttt tcgtaccact    180

tactacgcga gctgggcgaa aggccgattc agcatctcca aaacctcgtc gaccacggtg    240

actctgcaaa tgaccagtct gacaggcgcg gacacggcca cctatttctg tgcgaggtcc    300

ccatatgatg atggttatgg tggtttcact tttaatttat ggggcccagg caccctggtc    360

accatctctt ca                                                         372
```

<210> SEQ ID NO 663
<211> LENGTH: 363
<212> TYPE: DNA
<213> ORGANISM: Artificial sequence
<220> FEATURE:
<223> OTHER INFORMATION: Synthetic antibody sequence

<400> SEQUENCE: 663

```
cagtcggtga aggagtccgg gggagacctg gtcaagcctg ggcatccct gacactcacc     60
```

tgcacagcct ctggattctc cttcagtagc agctactgga tatgctgggt ccgccaggct 120
ccagggaagg ggctggagtg gatcgcatgc atttatgctg gtagtagtgg tagcacttac 180
tacgcgagct gggcgaaagg ccgattcacc atctccaaaa cctcgtcgac cacggtgact 240
ctgcaaatga ccagtctgac agccgcggac acggccacct atttctgtgc gagatcgact 300
agtggtagtt atggtgcggg tttgggcttg tggggcccag gcaccctggt caccatctcc 360
tca 363

<210> SEQ ID NO 664
<211> LENGTH: 357
<212> TYPE: DNA
<213> ORGANISM: Artificial sequence
<220> FEATURE:
<223> OTHER INFORMATION: Synthetic antibody sequence

<400> SEQUENCE: 664
cagtcgctgg aggagtccgg gggagacctg gtccagcctg agggatccct gacactcacc 60
tgcacagctt ctggattctc cttcagtatc aacttataca tgtgctgggt ccgccaggct 120
ccagggaagg ggctggagtg gatcgcatgc atttatggta ataataatgc taacacttac 180
tacacaacct gggcgaaagg ccgattcacc atctccaaaa cctcgccgac cacggtgact 240
ctgcaaatga ccagtctgac aggcgcggac acggccacct atttctgtgc gagagatact 300
gctgcttatt acgcctttag cttatggggc ccaggcaccc tggtcaccat ctcctca 357

<210> SEQ ID NO 665
<211> LENGTH: 357
<212> TYPE: DNA
<213> ORGANISM: Artificial sequence
<220> FEATURE:
<223> OTHER INFORMATION: Synthetic antibody sequence

<400> SEQUENCE: 665
cagtcgttgg aggagtccgg gggtcgcctg gtcaatcctg acgaatccct gacactcacc 60
tgcacagcct ctggattcac cttcagtggc tactacatgt actgggtccg ccaggctcca 120
gggaaggggc tggagtggat cggatggatt tatgttggta gtggtggtag cacttactac 180
gcgagctggg cgaaaggccg attcaccatc tccaaaacct cgtcgaccac ggtgactctg 240
caaatgccca gtctgacagc cgcggacacg gccacctatt tctgtgcgag ggtgttaat 300 gattatggtt gggcccttaa gttgtggggc ccaggcactc tggtcaccgt ctcttca 357

<210> SEQ ID NO 666
<211> LENGTH: 363
<212> TYPE: DNA
<213> ORGANISM: Artificial sequence
<220> FEATURE:
<223> OTHER INFORMATION: Synthetic antibody sequence

<400> SEQUENCE: 666
gagcagtcgt tggaggagtc cgggggagac ctggtcaagc ctggggcatc cctgacactc 60
acctgcacag cttctgcgtt ctccttcagt agcagttcct ggatatgctg ggtccgccag 120
gctccaggga aggggctgga gtggatcgca tgcatttatg gtggtagtgt tggtactact 180
tactacgcga gttgggcgaa aggccgattc accatctcca aaccctcgtc gaccacggtg 240
actctgcaaa tgaccagtct ggcagccgcg gacacggcca cctatttctg tgcgaccaat 300
acggatagta gtaggtctta ttataatttg tggggcccag gcaccctggt caccatctcc 360
tca 363

<210> SEQ ID NO 667
<211> LENGTH: 381
<212> TYPE: DNA
<213> ORGANISM: Artificial sequence
<220> FEATURE:
<223> OTHER INFORMATION: Synthetic antibody sequence

<400> SEQUENCE: 667
cagtcggtga aggagtccgg gggaggcctg gtccagcctg agggatccct ggcactcacc 60
tgcaaagcct ctggaatcga cctcagtaac tattggtaca tgtgctgggt ccgccaggct 120
ccagggaagg ggctggagtg gatcggatgc gttgctactg atagtagtcg cacgcattac 180
gcgacctggg cgaaaggccg attcaccgtc tccaagacct cgtcgaccac ggtgactctg 240
caaatgacca gtctgacagc ggcggacacg gccacctatt tctgtgcgag aggatccggt 300
gctagcacca atggtgtttg gtgggtaatg ggagacggca tggacctctg ggggcccaggg 360 accctcgtca ccatctcctc a 381

<210> SEQ ID NO 668
<211> LENGTH: 354
<212> TYPE: DNA
<213> ORGANISM: Artificial sequence
<220> FEATURE:
<223> OTHER INFORMATION: Synthetic antibody sequence

<400> SEQUENCE: 668
cagtcgttgg aggagtccgg gggaggcctg gtcaagcctg ggcttccct gacactcacc 60 tgcacagctt ctggattcag cctcaataga tactatatgt gctgggtccg ccaggctcca 120
gggaaggggc tggagtggat cggatgcatt tattctggta gtggtagcac ttactacgcg 180
agctgggcga aaggccgatt caccatctcc aaaacctcgt cgaccacggt gactctgcaa 240
atgaccagtc tgccagccgc ggacacggcc acctatttct gtgggagatt ggattatcgt 300
gttatttatg cctttaattt gtggggccca ggcaccctgg tcaccatctc ctca 354

<210> SEQ ID NO 669
<211> LENGTH: 366
<212> TYPE: DNA
<213> ORGANISM: Artificial sequence
<220> FEATURE:
<223> OTHER INFORMATION: Synthetic antibody sequence

<400> SEQUENCE: 669
gagcagtcgg tggaggagtc cgggggaggc ctggtccagc ctgagggatc cctgacactc 60
acctgcacag cttctggatt ctccttcagt ggcagctgcg acatgtcctg ggtccgccag 120
gctccaggga aggggctgga gtggatcgca tgcatcgtgc ttagtaatgg taatacatac 180
tacgcgggct gggcgcaagg ccgattcacc atctccaaaa tctcgtcgac cacggtgact 240
ctggaaatga ccagtctgac agccgcggac acggccacgt atttctgtgc gagagagcgc 300
tatcctggtg ctttttcaag tggattggat ctctggggcc agggcaccct ggtcaccgtc 360
tcttca 366

<210> SEQ ID NO 670
<211> LENGTH: 360
<212> TYPE: DNA
<213> ORGANISM: Artificial sequence
<220> FEATURE:
<223> OTHER INFORMATION: Synthetic antibody sequence

<400> SEQUENCE: 670
cagtcgttgg aggagtccgg gggaggcctg gtccagcctg agggatccct gacactcacc 60
tgcacagtct ctggtttctc cttcagtagc agctggtaca tgtgctgggt ccgccaggct 120
ccagggaagg ggctggaatg gatcgcatgc atttatactc ttagaagtgg tgccgcgcat 180
tacgcgaact gggcgaaagg ccgattcacc atctccaaag cctcgtcgac cacggtgact 240
ctgcaaatga acagtctgac agccgcggac acggccacct atttctgtgc gagagcgact 300
tatgcttatg ctggtgctgg ggacttgtgg ggcccaggca ccctggtcac cgtctcttca 360

<210> SEQ ID NO 671
<211> LENGTH: 363
<212> TYPE: DNA
<213> ORGANISM: Artificial sequence
<220> FEATURE:
<223> OTHER INFORMATION: Synthetic antibody sequence

<400> SEQUENCE: 671
gagcagtcgt tgaaggagtc cgggggagac ctggtcaagc ctggggcatc cctgacactc 60
acctgcacag cttctgcgtt ctccttcagt agcagttcct ggatatgctg ggtccgccag 120
gctccaggga aggggctgga gtggatcgca tgcatttatg gtggtagtgt tgctactact 180
tactacgcga cttgggcgaa aggccgattc accatctcca aaccctcgtc gaccacggtg 240
actctgcaaa tgaccagtct gccagccgcg gacacggcca cctatttctg tgcgaccaat 300
acggatagta gtaggtctta ttataatttg tggggcccag gcaccctggt caccgtctcc 360
tca 363

<210> SEQ ID NO 672
<211> LENGTH: 372
<212> TYPE: DNA
<213> ORGANISM: Artificial sequence
<220> FEATURE:
<223> OTHER INFORMATION: Synthetic antibody sequence

<400> SEQUENCE: 672
gagcagtcgg tggaggagtc cgggggagac ctggtcaagc ctgggacatc cctgacactc 60
acctgcacag cttctggatt ctccttcagt ggcaatacaa tttgctgggt ccgccaggct 120
ccagggaaga ggcctgaatg gatcgcatgc atttatccta gcagtacttc tattactacc 180
tacgcgacct gggcgaaagg ccgattcacc gtctccaaaa cctcgtcgac cacggtgact 240
ctgcaaatga ccagtctgac agccgcggac acggccacct atttctgtgc gcgaagatat 300
gctgcttttc ttacttatgg tagtggggct tttgatccct ggggcccagg caccctagtc 360
accatctctt ca 372

<210> SEQ ID NO 673
<211> LENGTH: 354
<212> TYPE: DNA
<213> ORGANISM: Artificial sequence
<220> FEATURE:
<223> OTHER INFORMATION: Synthetic antibody sequence

<400> SEQUENCE: 673
gagcagtcgt tggaggagtc cgggggagac ctggtcaagc ctgagggatc cctgacactc 60
acctgcacag cctctggatt ctccttcagt agcagctact ggatatgctg ggtccgccag 120
gctccaggga agggactgga gtggatcgca tgcgttgcta ctggtagtgg taccactgac 180

```
tacgcgagct gggcgaaagg ccgattcacc atgtccaaaa cctcgtcgac cacggtgact    240

ctgcaaatga ccagtctgac agtcgcggac acggccacct atttctgtgc gagaattggt    300

gctttttatt cctttagatt atggggccca ggcaccctgg tcaccatctc ttca          354
```

<210> SEQ ID NO 674
<211> LENGTH: 360
<212> TYPE: DNA
<213> ORGANISM: Artificial sequence
<220> FEATURE:
<223> OTHER INFORMATION: Synthetic antibody sequence

<400> SEQUENCE: 674

```
cagtcgttgg aggagtccgg gggagacctg gtcaagcctg agggatccct gacactcacc     60

tgcacagcct ctggattctc cttcagtagc agctactgga tatgctgggt ccgccaggct    120

ccagggaagg ggctggagtg gatcggatgc atttatgctg gtaatagtgc taacacttat    180

tacgcgagct gggcgaaagg ccgattcacc atctccaaaa cctcgtcgac cacggtgact    240

ctgcaactga ccagtctgac agccgcggac acggccacct atttctgtgc gagccgaaat    300

ggtggtgcgc ctgatggttt gaacttgtgg ggcccaggca ccctggtcac catctcttca    360
```

<210> SEQ ID NO 675
<211> LENGTH: 354
<212> TYPE: DNA
<213> ORGANISM: Artificial sequence
<220> FEATURE:
<223> OTHER INFORMATION: Synthetic antibody sequence

<400> SEQUENCE: 675

```
gagcagtcgg tgaaggagtc cgggggaggc ctggtccagc ctgagggatc cctgacactc     60

acctgcacag cttctggatt ctccttcagt agcagctact ggatatgctg ggtccgccag    120

gctccaggga aggggctgga gtggatcgga tgcattgcta ctggtactgg tagcacttac    180

tacgcgaact gggtgaatgg ccgattcacc atgtccaaac cctcgtcgac cacggtgact    240

ctgcaaatga ccactctgac agccgcggac acggccacct atttctgtgc gagaggtggt    300

ggttattggt cttttagttt gtggggccca ggcaccctgg tcaccatctc ttca          354
```

<210> SEQ ID NO 676
<211> LENGTH: 381
<212> TYPE: DNA
<213> ORGANISM: Artificial sequence
<220> FEATURE:
<223> OTHER INFORMATION: Synthetic antibody sequence

<400> SEQUENCE: 676

```
gagcagtcgt tggaggagtc cgggggagac ctggtcaagc ctgagggatc cctgacactc     60

acctgcacag cctctggatt ctccttcagt agtagttatt atatgtgttg gatccgccag    120

cctccaggga gggggctgga gtggctcgca tgcatttata ctggtagtga tagcacttac    180

tacgcgccct gggcgaaagg ccgattcacc atctccagaa cctcgtcgac cacggtgact    240

ctgcaaatga ccagtctgac agccgcggac acggccacct atttctgtgc gggagattgg    300

gattatgctg atgctgctgg ttattatgtt gcgagaggtt ttaacttgtg gggcccaggc    360

accctggtca ccatctcctc a                                              381
```

<210> SEQ ID NO 677
<211> LENGTH: 351
<212> TYPE: DNA
<213> ORGANISM: Artificial sequence
<220> FEATURE:
<223> OTHER INFORMATION: Synthetic antibody sequence

<400> SEQUENCE: 677

```
gagcagtcgt tggaggagtc cgggggaggc ctggtccagc ctgagggatc cctgacactc     60

acctgcacag cttctggatt ctccttcact aaaaactact acatgtgctg ggtccgccag    120

gctccaggga aggggctgga gtggatcgga tgcatttatg ctggtagtac taatacattt    180

tacgcgagct gggcgaaagg ccgattcacc atctccaaag cctcgtcgac cacggtggat    240

ctgaaaatga ccagtctgac agtcgcggac acggccacct atttctgtgc gagagatttc    300

gttagttatt tgaatttgtg gggcccaggc accctggtca ccgtctcttc a             351
```

<210> SEQ ID NO 678
<211> LENGTH: 381
<212> TYPE: DNA
<213> ORGANISM: Artificial sequence
<220> FEATURE:
<223> OTHER INFORMATION: Synthetic antibody sequence

<400> SEQUENCE: 678

```
cgagcagtcg ggaaggagtc cgggggagac ctggtcacgc ttgggggatc cctgaaactc     60

tcctgcaaag cctctggaat cgacctcagt aacttttact acatgtgctg ggtccgccag    120

gctccaggga aggggctgga gtggatcgga tgcgttgcta gtgatagtag ccgcacgcat    180

tacgcgacct ggccgaaagg ccgattcacc atctccaaaa cctcgtcgac cacggtgact    240

ctgcaaatga ccagtctgac agcggcggac acggccacct atttctgtgc gagaggatcc    300

ggtgctagta ccaatggtgt ttggtgggta atgggagacg gcatggacct ctggggccca    360

gggaccctcg tcaccgtctc c                                              381
```

<210> SEQ ID NO 679
<211> LENGTH: 369
<212> TYPE: DNA
<213> ORGANISM: Artificial sequence
<220> FEATURE:
<223> OTHER INFORMATION: Synthetic antibody sequence

<400> SEQUENCE: 679

```
cagtcggtga aggagtccgg gggagacctg gtcaagcctg ggcatccct gacactcacc     60

tgcaaagcct ctggattctc cttcagtagc ggccactaca tgtactgggt ccgccaggct    120

ccagggaagg ggctggagtg gatcgcatgt atttatgctg gtagtgatac tggtagcaca    180

tggtacgcga gctgggcgaa aggccgattc accatctcca aaacctcgtc gaccacggtg    240

actctgcaaa tgaccagtct gacagccgcg gatacggcca cctatttctg tgcgagatct    300

agtaatagtt atggtaatta tggtgtttct aacttgtggg gcccaggcac cctggtcacc    360

gtctcttca                                                            369
```

<210> SEQ ID NO 680
<211> LENGTH: 354
<212> TYPE: DNA
<213> ORGANISM: Artificial sequence
<220> FEATURE:
<223> OTHER INFORMATION: Synthetic antibody sequence

<400> SEQUENCE: 680

```
caggagcagc tggtggagtc cgggggaggc ctggtccagc ctgagggatc cctgacactc     60

acctgcaaag cctctggaat cgacttcagt agcggctact ggatatgctg ggtccgccag    120
```

gctccaggga aggggctgga attgatcgca tgcattttta ctagtagtgg taccacttac 180
tacgcgagct gggcgaaagg ccgattcacc atctccaaaa cctcgtcgac cacggtgact 240
ctgcaaatga ccagtctgac agccgcggac acggccacct atttctgtgc gagagatatc 300
tattcctacg gcatggacct ctggggccca gggaccctcg tcaccgtctc ttca 354

<210> SEQ ID NO 681
<211> LENGTH: 351
<212> TYPE: DNA
<213> ORGANISM: Artificial sequence
<220> FEATURE:
<223> OTHER INFORMATION: Synthetic antibody sequence

<400> SEQUENCE: 681
cagtcggtga aggagtccga gggaggcctg gtccagcctg gggggatccct gacactctcc 60 tgcaaagcct ctggaatcga cttcagtagc gcctatatga gctgggtccg ccaggctcca 120
gggaaggggc tggagtggat cggaaagatg cgtattaatg atagaagtca ctacgcgaac 180
tgggtgaatg gccgattcac catctccaac cacaatgacc agaacacggt ggagctgcaa 240
ctgaacagtc tgacagccgc ggacacggcc acctatttct gtgcgagaat cgctactggt 300
actaatgttg atgacttctg gggcccaggc accctggtca ccatctcctc a 351

<210> SEQ ID NO 682
<211> LENGTH: 345
<212> TYPE: DNA
<213> ORGANISM: Artificial sequence
<220> FEATURE:
<223> OTHER INFORMATION: Synthetic antibody sequence

<400> SEQUENCE: 682
caggagcagc tggtggagtc cgggggaggc ctggtaacgc ctggaggatc cctgacactc 60
acctgcacag cctctggatt ctccttcagt agcaagcaat acatttcctg ggtccgccgg 120
gctccaggga aggggctgga gtggatcggg gccattgtca ctgttaataa taaagtccac 180
tacgcgaact gggcgaaagg ccggttcacc atctccgaag cctcgtcgac cacggtgact 240
ctacaaatga ccagtctgac agccgcggac acggccacct atttctgtgc gagatggcgg 300
acttttggct tgtggggccc aggcaccctg gtcaccgtct cttca 345

<210> SEQ ID NO 683
<211> LENGTH: 363
<212> TYPE: DNA
<213> ORGANISM: Artificial sequence
<220> FEATURE:
<223> OTHER INFORMATION: Synthetic antibody sequence

<400> SEQUENCE: 683
gagcagctga tggaggagtc cgggggaggc ctggtccagc ctgagggatc cctgacactc 60
acctgcacgg cttctagatt ctccctcagt aacatgaacg tgatgtgctg ggtccgccag 120
gctccaggga aggggctgga gtggatcgga tgcattaata ttggcggtac taatatatgg 180
tacgcgagct gggcgaaagg ccgattcacc atctccaaaa cctcgtcgac cacggtgact 240
ctgcaaatga ccagtctgac agtcgcggac acggccacct atttctgtgc gagatcatat 300
attactgatc gtatttatga ttacgacttt tggggcccag gcaccctggt caccatctct 360
tca 363

<210> SEQ ID NO 684
<211> LENGTH: 357

<212> TYPE: DNA
<213> ORGANISM: Artificial sequence
<220> FEATURE:
<223> OTHER INFORMATION: Synthetic antibody sequence

<400> SEQUENCE: 684
cagtcggtgg aggagtccgg gggaggcctg gtcaagcctg gggcatccct gacactctcc 60
tgcacagcct ctggattcga cttcagtagc aaatactaca tgtggtgggt ccgccaggct 120
ccagggaagg ggctggagtg gatcgcgcgc atttatggtg gtagtagtga tagtacagac 180
tacgcgacct gggcgagagg ccggttcgcc atctccagaa cctcgtcgac cacggtgact 240
ctgcgaatga ccagtctgac agccgcggac acggccacct atttctgtgg gagagtaatt 300
gatggtgctt gtggttatga cttgtggggc ccaggcaccc tggtcaccgt ctcttca 357

<210> SEQ ID NO 685
<211> LENGTH: 360
<212> TYPE: DNA
<213> ORGANISM: Artificial sequence
<220> FEATURE:
<223> OTHER INFORMATION: Synthetic antibody sequence

<400> SEQUENCE: 685
cagtcggtgg aggagtccgg gggagacctg gtcaagcctg gggcatccct gacactcacc 60
tgcacagcct ctggattcga cttcagtagc aatgcctact tgtgctgggt ccgccaggct 120
ccagggaagg ggctggagtg gatcggatgc atttatgatg gtacaagtgg tgacacttac 180
tacgcgaact gggcgaaagg ccgattcacc atctccagaa gttcgtcgac tacggtgact 240
ctccaaatga ccagtctgac agccgcggac acggccacct atttctgtgc gagggatact 300
cggagtagta attattattt taatttgtgg ggcccaggca ccctggtcac catctcttca 360

<210> SEQ ID NO 686
<211> LENGTH: 354
<212> TYPE: DNA
<213> ORGANISM: Artificial sequence
<220> FEATURE:
<223> OTHER INFORMATION: Synthetic antibody sequence

<400> SEQUENCE: 686
gagtccgagg gaggcctggt caagcctgga ggaaccctga cactcacctg caaagtctct 60
ggaatcgact tcaatagcta caagtactac tacatgtgct gggtccgcca ggctccaggg 120
aaggggctgg agtggatcgg atgcatgtcc actgccagtc gtaatattta ctacgcgagc 180
tgggcgaaag gccgattcac catctccgaa acctcgtcga cctcggtgac tctgcaaatg 240
accactctga cagccgcgga cacggccacc tatttctgtg cgaaatccca tggtggtgat 300
ggtggttatg ggttgtgtt atggggccca ggcaccctgg tcaccatctc ctca 354

<210> SEQ ID NO 687
<211> LENGTH: 378
<212> TYPE: DNA
<213> ORGANISM: Artificial sequence
<220> FEATURE:
<223> OTHER INFORMATION: Synthetic antibody sequence

<400> SEQUENCE: 687
cagtcgttgg aggagtccga gggaggcctg gtcaagcctg gaggaaccct gacactcacc 60
tgcacagcct ctggattctc cttcagtagc agctactgta tgtgttgggt ccgccaggct 120
ccagggaagg ggctggagtt gatcgcatgc atttatactg atagtagtgg tgccacttac 180

```
tacgcgagct gggcgaaagg ccgattcacc atctccaagt cctcgtcgac cacgataact    240

ctgcaaatga ccagtctgac agccgcggac acggccacct atttctgtgc gagggggtgg    300

gattacgagg atcctggtta tactgatact acctactttt ccttgtgggg cccaggcacc    360

ctggtcaccg tctcttca                                                  378


<210> SEQ ID NO 688
<211> LENGTH: 357
<212> TYPE: DNA
<213> ORGANISM: Artificial sequence
<220> FEATURE:
<223> OTHER INFORMATION: Synthetic antibody sequence

<400> SEQUENCE: 688

cagaagcagc tggtggagtc cgggggaggc ctggtccagc ctgagggatc cctggcactc     60

acctgcacag cttctggatt ctccttcagt agcagctact ggatatgctg ggtccgccag    120

gctccaggga aggggctgga gtggatcgca tgcatttatg ctggtagtag tggtagcact    180

tactacgcga gctgggtgaa tggccgattc accgtcttca aaacctcgtc gaccacggtg    240

actctgcaaa tgaccagtct gacagccgcg gacacggcca cctatttctg tgcgagaggt    300

ggtactagtt accgccttga tttgtggggc ccaggcaccc tggtcaccgt ctcttca       357


<210> SEQ ID NO 689
<211> LENGTH: 375
<212> TYPE: DNA
<213> ORGANISM: Artificial sequence
<220> FEATURE:
<223> OTHER INFORMATION: Synthetic antibody sequence

<400> SEQUENCE: 689

tcgcagcagc tgaaggagtc cgggggaggc ctggtcaagc ctggaggaac cctgacactc     60

acctgcaaag cctctggaat cgacttcaat aatgactata acatctgctg ggtccgccag    120

cctccaggga aggggctgga atggatcgga tgcatttata ctggtagtga tagtacagac    180

tacgcgagct gggtgaatgg ccgattcacc atctccgaaa gcaccagcct aaacacggtg    240

gatctgaaag tgaccagtct gacagacgcg gacacggcca cgtatttctg tgccagagat    300

cttgttactg gttatgctac ttatggttat ggatttatct tatggggccc aggcaccctg    360

gtcaccgtct cctca                                                     375


<210> SEQ ID NO 690

<400> SEQUENCE: 690

000


<210> SEQ ID NO 691
<211> LENGTH: 360
<212> TYPE: DNA
<213> ORGANISM: Artificial sequence
<220> FEATURE:
<223> OTHER INFORMATION: Synthetic antibody sequence

<400> SEQUENCE: 691

caggagcagc tgaaggagtc cgggggagac ctggtcaagc ctgagggatc cctgacactc     60

acctgcacag cctctggatt ctccttcagt agcgactatt gggtatgctg ggtccgccag    120

gctccaggga aggggccgga gtggatcgga tgcatttata ctggtgatga tgacacatac    180

tacgcgagct gggcgaaagg ccgattcacc atctccaaaa cctcgtcgac cacggtgact    240
```

ctggaagtga ccagtctgac agccgcggac acggccacct atttctgtgc gagaggactc 300
actattggta ctgctgagtt gtacttctgg ggcccaggca ctgtggtcac cgtctcttca 360

<210> SEQ ID NO 692
<211> LENGTH: 351
<212> TYPE: DNA
<213> ORGANISM: Artificial sequence
<220> FEATURE:
<223> OTHER INFORMATION: Synthetic antibody sequence

<400> SEQUENCE: 692
caggagcagc tggtggagtc cgggggaggc ctggtccagc ctgagggatc cctgacactc 60
acctgcacag attctggatt ctccttcact aaaaactact acatgtgctg ggtccgccag 120
gctccaggga aggggctgga gtggatcgga tgcatttatg ctggtagtac taatacattt 180
tacgcgagct gggcgaaagg ccgattcacc atctccaaag cctcgtcgac cacggtggat 240
ctgaaaatga ccagtctgac agtcgcggac acggccacct atttctgtgc gagagatttc 300
gttagttatt tgaatttgtg gggcccaggc accctggtca ccgtctcctc a 351

<210> SEQ ID NO 693
<211> LENGTH: 366
<212> TYPE: DNA
<213> ORGANISM: Artificial sequence
<220> FEATURE:
<223> OTHER INFORMATION: Synthetic antibody sequence

<400> SEQUENCE: 693
cagtcgttgg aggagtccgg gggtggcctg gtcaagcctg agggatccct gacactcacc 60
tgcacagcct ctggatttga cctcagtaac aactactaca tctgctgggt ccgccaggct 120
ccagggaagg ggctggaatt gatcgcatgt gttgattctg atcttactga tagtgcagac 180
tacgcgagct gggcgaaagg ccgattcacc atctccaaaa cctcgtcgac cacggtgact 240
ctgcaaatga ccagtctgac agccgcggac acggccacct atttctgtgc gggaagtggg 300
agtggttatt attattacta cggcatggat ctctggggcc cagggaccct cgtcaccatc 360
tcctca 366

<210> SEQ ID NO 694
<211> LENGTH: 358
<212> TYPE: DNA
<213> ORGANISM: Artificial sequence
<220> FEATURE:
<223> OTHER INFORMATION: Synthetic antibody sequence

<400> SEQUENCE: 694
tcgcagtcgt tggaggagtc cgggggaggc ctggtcaagc ctggggcatc cctgacactc 60
acctgcaaag gctctggatt ctccttcaat ggcgactatt atatgtgctg ggtccgccag 120
actccaggga aggggctgga gtggatcggg tgcatttatg ctgctggtga tgacacttac 180
tacgcgacct gggcgaaagg ccgattcacc atctccaaaa cctcgtcgac cacggtgact 240
ctgcaaatga ccagtctgac agccgcggac acggccacct atttttgtgc gagagatcag 300
gctgacagtt atgcctttgg tttgtggggc ccaggcacac tggtcaccat ctcctcag 358

<210> SEQ ID NO 695
<211> LENGTH: 348
<212> TYPE: DNA
<213> ORGANISM: Artificial sequence
<220> FEATURE:
<223> OTHER INFORMATION: Synthetic antibody sequence

<400> SEQUENCE: 695
cagtcgttga aggagtccga gggagacctg gtcaagcctg gggcatccct gacactcacc 60
tgcacagcct ctggattctc cttcagtagc agctactgga tatgctgggt ccgccaggct 120
ccagggaagg ggctagagtg gatcgcatgc atttatgctg gtagtagtgg tagcacttac 180
tacgcgagct gggcgaaagg ccgattcacc atctccaaaa cctcgtcgac cacggtgact 240
ctggaaatga ccagtctgac agacgcggac acggccacct atttctgtgc gaggggtttt 300
tcgatgttta agttgtgggg cccaggcacc ctggtcacca tctcttca 348

<210> SEQ ID NO 696
<211> LENGTH: 378
<212> TYPE: DNA
<213> ORGANISM: Artificial sequence
<220> FEATURE:
<223> OTHER INFORMATION: Synthetic antibody sequence

<400> SEQUENCE: 696
cagtcggtga aggagtccgg gggaggcctg gtcaagcctg gaggaaccct gacactcacc 60
tgcacagcct ctggattctc cttcagtagc agctactgta tgtgttgggt ccgccaggct 120
ccagggaagg ggctggagtt gatcgcatgc atttatactg atagtagtgg tgccacttac 180
tacgcgagct gggcgaaagg ccgattcacc atctccaagt cctcgtcgac cacgataact 240
ctgcaaatga ccagtctgac agccgcggac acggccacct atttctgtgc gagggggtgg 300
gattacgagg atcctggtta tactgatact acctactttt ccttgtgggg cccaggcacc 360
ctggtcaccg tctcttca 378

<210> SEQ ID NO 697
<211> LENGTH: 384
<212> TYPE: DNA
<213> ORGANISM: Artificial sequence
<220> FEATURE:
<223> OTHER INFORMATION: Synthetic antibody sequence

<400> SEQUENCE: 697
tcgcagtcgg tggaggagtc cgggggagac ctggtcaagc ctggaggaac cctgacactc 60
acctgcacag cctctagaat cgacctcaac aactattatt acatatcctg ggtccgccag 120
gctccaggga agggactgga gtggatcgga gtcgttgcta ctgatagtag tgtcacatgg 180
tacgcgagct gggcgaaagg ccagttcacc atctccaaaa cctcgtcgac cacggtgact 240
ctgcaaatga ccagtctgac agcggcggac acggccacct atttctgtgc gagaggatcc 300
ggtgctgcta ctaatggtgt ttggtgggtg atgggagacg gcatggacct ctggggccca 360
gggaccctcg tcaccgtctc ttca 384

<210> SEQ ID NO 698
<211> LENGTH: 348
<212> TYPE: DNA
<213> ORGANISM: Artificial sequence
<220> FEATURE:
<223> OTHER INFORMATION: Synthetic antibody sequence

<400> SEQUENCE: 698
cagtcggtgg aggagtccga gggtcgcctg gtcacgcctg gaggatccct gacactcacc 60
tgcacagtct ctggaatcga cctcagtagc tatgcaatgg gctgggtccg ccaggctcca 120
gggaaggggc tggaatggat cggggtcatt ggtaaaagtg gaaccacata ctacgcgaac 180

```
tgggcgaaag gccgattcac catctccaag acctcgacca cggtggatct gcaaatcgcc    240

agtccgacaa ccgaggacac ggccacctat ttctgtgcca gggcaggtgc tagtaggagt    300

atttattatg acttgtgggg ccaaggcacc ctggtcacca tctcctca                348


<210> SEQ ID NO 699
<211> LENGTH: 354
<212> TYPE: DNA
<213> ORGANISM: Artificial sequence
<220> FEATURE:
<223> OTHER INFORMATION: Synthetic antibody sequence

<400> SEQUENCE: 699

cagtcggtgg aggagtccgg gggaggcctg gtccagcctg agggatccct gacactcacc     60

tgcacagctt ctggattctc cttcagtggc attgtctata tgtgttgggt ccgccaggct    120

ccagggaagg ggctggagtg gatcgcatgt gcttttgttg gtagtggtgg tagcacttac    180

tacgcgacct gggcgacagg ccgattcacc atctccaaaa cctcgtcgac cacggtgact    240

ctacagatga ccagtctgac agccgcggac acggccacct atttctgtgc gaaatcttat    300

aattataatg gtttaggctt gtggggccca ggcaccctgg tcaccgtctc ctca          354


<210> SEQ ID NO 700
<211> LENGTH: 367
<212> TYPE: DNA
<213> ORGANISM: Artificial sequence
<220> FEATURE:
<223> OTHER INFORMATION: Synthetic antibody sequence

<400> SEQUENCE: 700

cagtcgttgg aggagtccgg gggagacctg gtcaagcctg ggcatccct gacactcacc     60

tgcacagcct ctggattctc cttcagtagc agctactaca tgtgctgggt ccgccaggct    120

ccagggaagg ggctggagtg gatcgcatgc atttatggtg gtagtactgg taccacttac    180

tacgcgagct gggcgaaagg ccgattcacc atctccaaaa cctcgtcgac cacggtgact    240

ctgcaaatga ccagtctgac aggcgcagac acggccacct atttctgtgc gagatcatat    300

aatagtgcta gtagtggtta ttattgggac ttgtggggcc caggcaccct ggtcaccgtc    360

tcttcag                                                             367


<210> SEQ ID NO 701
<211> LENGTH: 354
<212> TYPE: DNA
<213> ORGANISM: Artificial sequence
<220> FEATURE:
<223> OTHER INFORMATION: Synthetic antibody sequence

<400> SEQUENCE: 701

gagcagtcgg tggaggagtc cgggggaggc ctggtccagc ctgagggatc cctgacactc     60

acctgcacag cctctggaat cgacttcagt agcggcgcct ggatatgctg ggtccgccag    120

gctccaggga aggggctgga gttgatcgca tgcattttta ctactagtgg tttcacttac    180

tacgcgagct gggcgaaagg ccgattcacc atctccaaaa cctcgtcgac cacggtgact    240

ctgcaaatga ccagtctgac agccgcggac acggccacct atttctgtgc gagagatatc    300

tattcctacg gcatggacct ctggggccca gggaccctcg tcaccatctc ttca          354


<210> SEQ ID NO 702
<211> LENGTH: 345
<212> TYPE: DNA
<213> ORGANISM: Artificial sequence
```

<220> FEATURE:
<223> OTHER INFORMATION: Synthetic antibody sequence

<400> SEQUENCE: 702

```
caggagcagc tggtggagtc cgggggaggc ctggtccagc ctgagggatc cctgacactc     60

acctgcacag cttctggatt ctccttcagt agcaggcaat acatttcctg ggtccgccgg    120

gctccaggga aggggctgga gtggatcggg gccattgtca ctgttaataa taaagtccac    180

tacgccaact gggcgaaagg ccggttcacc atctccgaag cctcgtcgac cacggtgact    240

ctgcaaatga ccagtctgac agccgcggac acggccacct atttctgtgc gagatggcgg    300

acttttggct tgtggggccc aggcaccctg gtcaccgtct cttca                   345
```

<210> SEQ ID NO 703
<211> LENGTH: 378
<212> TYPE: DNA
<213> ORGANISM: Artificial sequence
<220> FEATURE:
<223> OTHER INFORMATION: Synthetic antibody sequence

<400> SEQUENCE: 703

```
cagtcggtga aggagtccgg gggaggcctg gtcaagcctg gaggaaccct gacactcacc     60

tgcacagcct ctggattctc cttcagtagc agctactgta tgtgttgggt ccgccaggct    120

ccagggaagg ggctggagtt gatcgcatgc atttatactg atagtagtgg tgccacttac    180

tacgcgagct gggcgaaagg ccgattcacc atctccaagt cctcgtcgac cacgataact    240

ctgcaaatga ccagtctgac agccgcggac acggccacct atttctgtgc gagggggtgg    300

gattacgagg atcctggtta tactgatact acctactttt ccttgtgggg cccaggcacc    360

ctggtcaccg tctcttca                                                  378
```

<210> SEQ ID NO 704
<211> LENGTH: 125
<212> TYPE: PRT
<213> ORGANISM: Artificial sequence
<220> FEATURE:
<223> OTHER INFORMATION: Synthetic antibody sequence

<400> SEQUENCE: 704

```
Gln Ser Leu Glu Glu Ser Glu Gly Asp Leu Val Lys Pro Glu Gly Ser
1               5                   10                  15

Leu Thr Leu Thr Cys Lys Ala Ser Gly Phe Asp Phe Ser Ser Asp Ala
            20                  25                  30

Met Cys Trp Val Arg Gln Ala Pro Gly Lys Gly Leu Glu Trp Ile Gly
        35                  40                  45

Cys Ile Tyr Asn Gly Asp Glu Ile Thr Asp His Ala Ser Trp Ala Lys
    50                  55                  60

Gly Arg Phe Thr Ile Ser Lys Thr Ser Pro Thr Thr Val Thr Leu Gln
65                  70                  75                  80

Met Thr Ser Leu Thr Val Ala Asp Thr Ala Thr Tyr Phe Cys Ala Arg
                85                  90                  95

Ala Val Tyr Ser Asp Gly Gly Ala Gly Tyr Pro Tyr Met Tyr Gly Met
            100                 105                 110

Asp Leu Trp Gly Pro Gly Thr Leu Val Thr Val Ser Ser
        115                 120                 125
```

<210> SEQ ID NO 705
<211> LENGTH: 114
<212> TYPE: PRT

<213> ORGANISM: Artificial sequence
<220> FEATURE:
<223> OTHER INFORMATION: Synthetic antibody sequence

<400> SEQUENCE: 705

Arg Ala Val Gly Lys Glu Ser Gly Gly Gly Leu Val Lys Pro Gly Ala
1 5 10 15

Ser Leu Thr Leu Thr Cys Lys Ala Ser Gly Phe Asp Phe Ser Gly Ile
20 25 30

Tyr Trp Val Cys Trp Val Arg Gln Ala Pro Gly Lys Gly Leu Glu Trp
35 40 45

Ile Ala Cys Phe Asp Ala Glu Arg Thr Gly Asn Thr Tyr Tyr Ala Thr
50 55 60

Trp Ala Lys Gly Arg Phe Thr Ile Ser Arg Thr Ser Ser Thr Thr Val
65 70 75 80

Thr Leu Gln Met Thr Ser Leu Thr Ala Ala Asp Thr Ala Thr Tyr Phe
85 90 95

Cys Ala Arg Ser Tyr Tyr Met Trp Gly Pro Gly Thr Leu Val Thr Val
100 105 110

Ser Ser

<210> SEQ ID NO 706
<211> LENGTH: 120
<212> TYPE: PRT
<213> ORGANISM: Artificial sequence
<220> FEATURE:
<223> OTHER INFORMATION: Synthetic antibody sequence

<400> SEQUENCE: 706

Glu Gln Ser Leu Glu Glu Ser Gly Gly Asp Leu Val Lys Pro Glu Gly
1 5 10 15

Ser Leu Thr Leu Thr Cys Thr Ala Ser Glu Leu Ser Phe Ser Ser Ala
20 25 30

Tyr Tyr Met Cys Trp Val Arg Gln Ala Pro Gly Lys Gly Leu Glu Trp
35 40 45

Ile Gly Cys Ile Tyr Ser Gly Asp Gly Asp Thr Tyr Tyr Ala Asn Trp
50 55 60

Ala Lys Gly Arg Phe Thr Ile Ser Lys Thr Ser Ser Thr Thr Val Thr
65 70 75 80

Leu Gln Met Thr Ser Leu Thr Asp Ala Asp Thr Ala Thr Tyr Phe Cys
85 90 95

Ala Arg Ala Leu Asp Ser His Tyr Ser Ser Phe Asp Leu Trp Gly Pro
100 105 110

Gly Thr Leu Val Thr Ile Ser Ser
115 120

<210> SEQ ID NO 707
<211> LENGTH: 115
<212> TYPE: PRT
<213> ORGANISM: Artificial sequence
<220> FEATURE:
<223> OTHER INFORMATION: Synthetic antibody sequence

<400> SEQUENCE: 707

Glu Gln Ser Leu Glu Glu Ser Gly Gly Gly Leu Val Lys Pro Gly Ala
1 5 10 15

Ser Leu Thr Val Thr Cys Ala Val Ser Gly Phe Ser Leu Asn Ser Tyr
20 25 30

```
Ala Ile Thr Trp Val Arg Gln Ala Pro Gly Lys Gly Leu Glu Tyr Ile
        35                  40                  45

Gly Tyr Ile Asp Thr Gly Ala Ser Ile Thr Asp Tyr Ala Ser Trp Ala
    50                  55                  60

Lys Gly Arg Phe Thr Ile Ser Lys Thr Ser Ser Thr Thr Val Thr Leu
65                  70                  75                  80

Glu Met Thr Ser Leu Thr Asp Ala Asp Thr Ala Thr Tyr Phe Cys Ala
                85                  90                  95

Arg Gly Phe Ser Met Phe Lys Leu Trp Gly Pro Gly Thr Leu Val Thr
            100                 105                 110

Ile Ser Ser
        115


<210> SEQ ID NO 708
<211> LENGTH: 119
<212> TYPE: PRT
<213> ORGANISM: Artificial sequence
<220> FEATURE:
<223> OTHER INFORMATION: Synthetic antibody sequence

<400> SEQUENCE: 708

Glu Gln Ser Val Glu Glu Ser Gly Gly Gly Leu Val Lys Pro Glu Gly
1               5                   10                  15

Ser Leu Thr Leu Thr Cys Lys Ala Ser Gly Leu Asp Phe Ser Ser Ser
            20                  25                  30

Tyr Trp Ile Cys Trp Val Arg Gln Ala Pro Gly Lys Gly Leu Glu Trp
        35                  40                  45

Ile Ala Cys Ile Asp Thr Gly Ser Ser Gly Ser Thr Tyr Tyr Ala Ser
    50                  55                  60

Trp Ala Lys Gly Arg Phe Thr Val Ser Lys Thr Ser Ser Thr Thr Val
65                  70                  75                  80

Ser Leu Gln Met Thr Ser Leu Thr Ala Ala Asp Thr Ala Thr Tyr Phe
                85                  90                  95

Cys Ala Ser Thr Pro Asn Ser Leu Gly Tyr Asp Leu Trp Gly Pro Gly
            100                 105                 110

Thr Leu Val Thr Ile Ser Ser
        115


<210> SEQ ID NO 709
<211> LENGTH: 127
<212> TYPE: PRT
<213> ORGANISM: Artificial sequence
<220> FEATURE:
<223> OTHER INFORMATION: Synthetic antibody sequence

<400> SEQUENCE: 709

Glu Gln Ser Val Glu Glu Ser Gly Gly Asp Leu Val Lys Pro Gly Ala
1               5                   10                  15

Ser Leu Thr Leu Thr Cys Thr Ala Ser Gly Phe Ser Ser Ser Ser Ser
            20                  25                  30

Ala Tyr Met Cys Trp Val Arg Gln Ala Pro Gly Lys Gly Leu Glu Trp
        35                  40                  45

Ile Ala Cys Ile Phe Ile Gly Ser Gly Ser Asp Ser Tyr Tyr Ala Thr
    50                  55                  60

Trp Ala Lys Gly Arg Phe Thr Ile Ser Lys Thr Ser Ser Thr Thr Val
65                  70                  75                  80

Thr Leu Gln Met Thr Ser Leu Thr Ala Ala Asp Thr Ala Thr Tyr Phe
                85                  90                  95
```

```
Cys Ala Arg Asn Thr Tyr Asp Trp Asn Gly Tyr Ile Tyr Gly Pro Cys
            100                 105                 110

Tyr Phe Gly Leu Trp Gly Pro Gly Thr Leu Val Thr Ile Ser Ser
        115                 120                 125


<210> SEQ ID NO 710
<211> LENGTH: 115
<212> TYPE: PRT
<213> ORGANISM: Artificial sequence
<220> FEATURE:
<223> OTHER INFORMATION: Synthetic antibody sequence

<400> SEQUENCE: 710

Glu Gln Ser Val Lys Glu Ser Gly Gly Gly Leu Val Lys Pro Gly Gly
1               5                   10                  15

Thr Leu Thr Leu Thr Cys Ile Val Ser Gly Phe Ser Leu Ser Arg Tyr
            20                  25                  30

Ala Val Thr Trp Val Arg Gln Ala Pro Gly Lys Gly Pro Glu Trp Ile
        35                  40                  45

Gly Tyr Ile Asp Thr Ser Ser Gly Asn Lys Asp Tyr Ala Asn Trp Val
    50                  55                  60

Asn Gly Arg Phe Thr Ile Ser Lys Thr Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Gly Phe Ser Met Phe Lys Leu Trp Gly Pro Gly Thr Leu Val Thr
            100                 105                 110

Ile Ser Ser
        115


<210> SEQ ID NO 711
<211> LENGTH: 120
<212> TYPE: PRT
<213> ORGANISM: Artificial sequence
<220> FEATURE:
<223> OTHER INFORMATION: Synthetic antibody sequence

<400> SEQUENCE: 711

Glu Gln Ser Val Glu Glu Ser Gly Gly Gly Leu Val Lys Pro Glu Gly
1               5                   10                  15

Ser Leu Thr Leu Thr Cys Lys Ala Ser Gly Leu Asp Phe Ser Ser Ser
            20                  25                  30

Tyr Trp Ser Cys Trp Val Arg Gln Thr Pro Gly Arg Gly Leu Glu Trp
        35                  40                  45

Ile Gly Cys Ile Asp Val Gly Ser Ser Gly Gly Ser Tyr Tyr Ala Ser
    50                  55                  60

Trp Ala Arg Gly Arg Phe Thr Val Ser Lys Gly Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Ser Thr Thr Thr Asn Val Phe Gly Tyr Asp Leu Trp Gly Pro
            100                 105                 110

Gly Thr Leu Val Thr Val Ser Ser
        115                 120


<210> SEQ ID NO 712
<211> LENGTH: 127
<212> TYPE: PRT
```

<213> ORGANISM: Artificial sequence
<220> FEATURE:
<223> OTHER INFORMATION: Synthetic antibody sequence

<400> SEQUENCE: 712

Glu Gln Ser Leu Glu Glu Ser Gly Gly Gly Leu Val Lys Pro Gly Ala
1 5 10 15

Ser Leu Thr Leu Thr Cys Lys Ala Ser Gly Phe Asp Phe Ser Ser Asn
20 25 30

Asp Tyr Met Cys Trp Val Arg Gln Ala Pro Gly Lys Gly Leu Glu Trp
35 40 45

Ile Gly Cys Ile Tyr Gly Gly Asp Gly His Thr Tyr Tyr Ala Thr Trp
50 55 60

Ala Lys Gly Arg Phe Thr Ile Ser Lys Ala Ser Ser Thr Thr Val Thr
65 70 75 80

Leu Gln Met Thr Ser Leu Thr Ala Ala Asp Thr Ala Ser Tyr Phe Cys
85 90 95

Ala Arg Gly Tyr Ser Tyr Gly Asp Thr Gly Tyr Ala Asp Ala Ile Leu
100 105 110

Thr Leu Asp Leu Trp Gly Pro Gly Thr Leu Val Thr Val Ser Ser
115 120 125

<210> SEQ ID NO 713
<211> LENGTH: 123
<212> TYPE: PRT
<213> ORGANISM: Artificial sequence
<220> FEATURE:
<223> OTHER INFORMATION: Synthetic antibody sequence

<400> SEQUENCE: 713

Glu Gln Ser Val Lys Glu Ser Gly Gly Gly Leu Val Gln Pro Glu Gly
1 5 10 15

Ser Leu Thr Leu Thr Cys Lys Val Ser Gly Ile Asp Phe Asn Tyr Tyr
20 25 30

Asn Tyr Tyr Tyr Met Cys Trp Val Arg Gln Ala Pro Gly Lys Gly Leu
35 40 45

Glu Trp Ile Gly Cys Met Ser Thr Ala Ser Ala Asn Ile Tyr Leu Ala
50 55 60

Ser Trp Ala Lys Gly Arg Phe Thr Ile Ser Glu Ala Ser Ser Thr Thr
65 70 75 80

Val Thr Leu Gln Met Thr Ser Leu Thr Ala Ala Asp Thr Ala Thr Tyr
85 90 95

Phe Cys Ala Lys Ser His Gly Gly Asp Gly Gly Tyr Gly Val Val Leu
100 105 110

Trp Gly Pro Gly Thr Leu Val Thr Ile Ser Ser
115 120

<210> SEQ ID NO 714
<211> LENGTH: 122
<212> TYPE: PRT
<213> ORGANISM: Artificial sequence
<220> FEATURE:
<223> OTHER INFORMATION: Synthetic antibody sequence

<400> SEQUENCE: 714

Glu Gln Ser Val Lys Glu Ser Gly Gly Gly Leu Val Gln Pro Glu Gly
1 5 10 15

Ser Leu Thr Leu Thr Cys Thr Val Ser Gly Phe Ser Phe Ser Gly Ser
20 25 30

```
Tyr Trp Ile Cys Trp Val Arg Gln Ala Pro Gly Lys Gly Leu Glu Trp
        35                  40                  45

Ile Ala Cys Ile Tyr Gly Asp Ser Ile Ala Thr Tyr Tyr Pro Asn Trp
    50                  55                  60

Ala Lys Gly Arg Phe Thr Ile Ser Lys Thr Ser Ser Thr Thr Val Thr
65                  70                  75                  80

Leu Gln Met Ala Ser Leu Thr Gly Ala Asp Thr Ala Thr Tyr Phe Cys
                85                  90                  95

Ala Arg Asp Arg Asn Gly Gly Ser Gly Ala Tyr Gly Trp Asp Leu Trp
            100                 105                 110

Gly Pro Gly Thr Leu Val Thr Ile Ser Ser
        115                 120


<210> SEQ ID NO 715
<211> LENGTH: 119
<212> TYPE: PRT
<213> ORGANISM: Artificial sequence
<220> FEATURE:
<223> OTHER INFORMATION: Synthetic antibody sequence

<400> SEQUENCE: 715

Glu Gln Ser Leu Glu Glu Ser Gly Gly Gly Leu Val Lys Pro Gly Ala
1               5                   10                  15

Ser Leu Thr Leu Thr Cys Lys Ala Ser Gly Phe Ser Phe Ser Ser Asp
            20                  25                  30

Tyr Asp Met Cys Trp Val Arg Gln Ala Pro Gly Lys Gly Leu Glu Trp
        35                  40                  45

Ile Gly Cys Ile Val Thr Gly Phe Ser Gly Arg Ile Tyr Tyr Ala Thr
    50                  55                  60

Trp Ala Arg Gly Arg Phe Thr Phe Ser Arg Thr Ser Ser Thr Thr Leu
65                  70                  75                  80

Thr Leu Gln Met Thr Ser Leu Thr Ala Ala Asp Thr Ala Thr Tyr Phe
                85                  90                  95

Cys Ala Arg Asp Ser Gly Asn Tyr Asn Trp Asp Leu Trp Gly Pro Gly
            100                 105                 110

Thr Leu Val Thr Ile Ser Ser
        115


<210> SEQ ID NO 716
<211> LENGTH: 124
<212> TYPE: PRT
<213> ORGANISM: Artificial sequence
<220> FEATURE:
<223> OTHER INFORMATION: Synthetic antibody sequence

<400> SEQUENCE: 716

Glu Gln Ser Val Glu Glu Ser Glu Gly Gly Leu Val Gln Pro Glu Gly
1               5                   10                  15

Ser Leu Thr Leu Thr Cys Thr Ala Ser Gly Phe Ser Phe Ser Asn Asp
            20                  25                  30

Tyr Trp Ile Cys Trp Val Arg Gln Ala Pro Gly Lys Gly Leu Glu Trp
        35                  40                  45

Ile Gly Cys Gly His Ile Gly Ser Phe Arg Thr Thr Tyr Tyr Ala Ser
    50                  55                  60

Trp Ala Lys Gly Arg Phe Ser Ile Ser Lys Thr Ser Ser Thr Thr Val
65                  70                  75                  80

Thr Leu Gln Met Thr Ser Leu Thr Gly Ala Asp Thr Ala Thr Tyr Phe
```

```
                85                  90                  95

Cys Ala Arg Ser Pro Tyr Asp Asp Gly Tyr Gly Gly Phe Thr Phe Asn
            100                 105                 110

Leu Trp Gly Pro Gly Thr Leu Val Thr Ile Ser Ser
        115                 120


<210> SEQ ID NO 717
<211> LENGTH: 121
<212> TYPE: PRT
<213> ORGANISM: Artificial sequence
<220> FEATURE:
<223> OTHER INFORMATION: Synthetic antibody sequence

<400> SEQUENCE: 717

Gln Ser Val Lys Glu Ser Gly Gly Asp Leu Val Lys Pro Gly Ala Ser
1               5                   10                  15

Leu Thr Leu Thr Cys Thr Ala Ser Gly Phe Ser Phe Ser Ser Ser Tyr
            20                  25                  30

Trp Ile Cys Trp Val Arg Gln Ala Pro Gly Lys Gly Leu Glu Trp Ile
        35                  40                  45

Ala Cys Ile Tyr Ala Gly Ser Ser Gly Ser Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Ser Thr Ser Gly Ser Tyr Gly Ala Gly Leu Gly Leu Trp Gly
            100                 105                 110

Pro Gly Thr Leu Val Thr Ile Ser Ser
        115                 120


<210> SEQ ID NO 718
<211> LENGTH: 119
<212> TYPE: PRT
<213> ORGANISM: Artificial sequence
<220> FEATURE:
<223> OTHER INFORMATION: Synthetic antibody sequence

<400> SEQUENCE: 718

Gln Ser Leu Glu Glu Ser Gly Gly Asp Leu Val Gln Pro Glu Gly Ser
1               5                   10                  15

Leu Thr Leu Thr Cys Thr Ala Ser Gly Phe Ser Phe Ser Ile Asn Leu
            20                  25                  30

Tyr Met Cys Trp Val Arg Gln Ala Pro Gly Lys Gly Leu Glu Trp Ile
        35                  40                  45

Ala Cys Ile Tyr Gly Asn Asn Asn Ala Asn Thr Tyr Tyr Thr Thr Trp
    50                  55                  60

Ala Lys Gly Arg Phe Thr Ile Ser Lys Thr Ser Pro Thr Thr Val Thr
65                  70                  75                  80

Leu Gln Met Thr Ser Leu Thr Gly Ala Asp Thr Ala Thr Tyr Phe Cys
                85                  90                  95

Ala Arg Asp Thr Ala Ala Tyr Tyr Ala Phe Ser Leu Trp Gly Pro Gly
            100                 105                 110

Thr Leu Val Thr Ile Ser Ser
        115


<210> SEQ ID NO 719
<211> LENGTH: 119
```

```
<212> TYPE: PRT
<213> ORGANISM: Artificial sequence
<220> FEATURE:
<223> OTHER INFORMATION: Synthetic antibody sequence

<400> SEQUENCE: 719

Gln Ser Leu Glu Glu Ser Gly Gly Arg Leu Val Asn Pro Asp Glu Ser
1               5                   10                  15

Leu Thr Leu Thr Cys Thr Ala Ser Gly Phe Thr Phe Ser Gly Tyr Tyr
            20                  25                  30

Met Tyr Trp Val Arg Gln Ala Pro Gly Lys Gly Leu Glu Trp Ile Gly
        35                  40                  45

Trp Ile Tyr Val Gly Ser Gly Gly Ser Thr Tyr Tyr Ala Ser Trp Ala
    50                  55                  60

Lys Gly Arg Phe Thr Ile Ser Lys Thr Ser Ser Thr Thr Val Thr Leu
65                  70                  75                  80

Gln Met Pro Ser Leu Thr Ala Ala Asp Thr Ala Thr Tyr Phe Cys Ala
                85                  90                  95

Arg Gly Val Asn Asp Tyr Gly Trp Ala Leu Lys Leu Trp Gly Pro Gly
            100                 105                 110

Thr Leu Val Thr Val Ser Ser
        115


<210> SEQ ID NO 720
<211> LENGTH: 121
<212> TYPE: PRT
<213> ORGANISM: Artificial sequence
<220> FEATURE:
<223> OTHER INFORMATION: Synthetic antibody sequence

<400> SEQUENCE: 720

Glu Gln Ser Leu Glu Glu Ser Gly Gly Asp Leu Val Lys Pro Gly Ala
1               5                   10                  15

Ser Leu Thr Leu Thr Cys Thr Ala Ser Ala Phe Ser Phe Ser Ser Ser
            20                  25                  30

Ser Trp Ile Cys Trp Val Arg Gln Ala Pro Gly Lys Gly Leu Glu Trp
        35                  40                  45

Ile Ala Cys Ile Tyr Gly Gly Ser Val Gly Thr Thr Tyr Tyr Ala Ser
    50                  55                  60

Trp Ala Lys Gly Arg Phe Thr Ile Ser Lys Pro Ser Ser Thr Thr Val
65                  70                  75                  80

Thr Leu Gln Met Thr Ser Leu Ala Ala Ala Asp Thr Ala Thr Tyr Phe
                85                  90                  95

Cys Ala Thr Asn Thr Asp Ser Ser Arg Ser Tyr Tyr Asn Leu Trp Gly
            100                 105                 110

Pro Gly Thr Leu Val Thr Ile Ser Ser
        115                 120


<210> SEQ ID NO 721
<211> LENGTH: 127
<212> TYPE: PRT
<213> ORGANISM: Artificial sequence
<220> FEATURE:
<223> OTHER INFORMATION: Synthetic antibody sequence

<400> SEQUENCE: 721

Gln Ser Val Lys Glu Ser Gly Gly Gly Leu Val Gln Pro Glu Gly Ser
1               5                   10                  15

Leu Ala Leu Thr Cys Lys Ala Ser Gly Ile Asp Leu Ser Asn Tyr Trp
```

```
            20                  25                  30

Tyr Met Cys Trp Val Arg Gln Ala Pro Gly Lys Gly Leu Glu Trp Ile
        35                  40                  45

Gly Cys Val Ala Thr Asp Ser Ser Arg Thr His Tyr Ala Thr Trp Ala
    50                  55                  60

Lys Gly Arg Phe Thr Val Ser Lys Thr Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Gly Ser Gly Ala Ser Thr Asn Gly Val Trp Trp Val Met Gly Asp
            100                 105                 110

Gly Met Asp Leu Trp Gly Pro Gly Thr Leu Val Thr Ile Ser Ser
        115                 120                 125


<210> SEQ ID NO 722
<211> LENGTH: 118
<212> TYPE: PRT
<213> ORGANISM: Artificial sequence
<220> FEATURE:
<223> OTHER INFORMATION: Synthetic antibody sequence

<400> SEQUENCE: 722

Gln Ser Leu Glu Glu Ser Gly Gly Gly Leu Val Lys Pro Gly Ala Ser
1               5                   10                  15

Leu Thr Leu Thr Cys Thr Ala Ser Gly Phe Ser Leu Asn Arg Tyr Tyr
            20                  25                  30

Met Cys Trp Val Arg Gln Ala Pro Gly Lys Gly Leu Glu Trp Ile Gly
        35                  40                  45

Cys Ile Tyr Ser Gly Ser Gly Ser Thr Tyr Tyr Ala Ser Trp Ala Lys
    50                  55                  60

Gly Arg Phe Thr Ile Ser Lys Thr Ser Ser Thr Thr Val Thr Leu Gln
65                  70                  75                  80

Met Thr Ser Leu Pro Ala Ala Asp Thr Ala Thr Tyr Phe Cys Gly Arg
                85                  90                  95

Leu Asp Tyr Arg Val Ile Tyr Ala Phe Asn Leu Trp Gly Pro Gly Thr
            100                 105                 110

Leu Val Thr Ile Ser Ser
        115


<210> SEQ ID NO 723
<211> LENGTH: 122
<212> TYPE: PRT
<213> ORGANISM: Artificial sequence
<220> FEATURE:
<223> OTHER INFORMATION: Synthetic antibody sequence

<400> SEQUENCE: 723

Glu Gln Ser Val Glu Glu Ser Gly Gly Gly Leu Val Gln Pro Glu Gly
1               5                   10                  15

Ser Leu Thr Leu Thr Cys Thr Ala Ser Gly Phe Ser Phe Ser Gly Ser
            20                  25                  30

Cys Asp Met Ser Trp Val Arg Gln Ala Pro Gly Lys Gly Leu Glu Trp
        35                  40                  45

Ile Ala Cys Ile Val Leu Ser Asn Gly Asn Thr Tyr Tyr Ala Gly Trp
    50                  55                  60

Ala Gln Gly Arg Phe Thr Ile Ser Lys Ile Ser Ser Thr Thr Val Thr
65                  70                  75                  80
```

```
Leu Glu Met Thr Ser Leu Thr Ala Ala Asp Thr Ala Thr Tyr Phe Cys
                85                  90                  95

Ala Arg Glu Arg Tyr Pro Gly Ala Phe Ser Ser Gly Leu Asp Leu Trp
            100                 105                 110

Gly Gln Gly Thr Leu Val Thr Val Ser Ser
        115                 120


<210> SEQ ID NO 724
<211> LENGTH: 120
<212> TYPE: PRT
<213> ORGANISM: Artificial sequence
<220> FEATURE:
<223> OTHER INFORMATION: Synthetic antibody sequence

<400> SEQUENCE: 724

Gln Ser Leu Glu Glu Ser Gly Gly Gly Leu Val Gln Pro Glu Gly Ser
1               5                   10                  15

Leu Thr Leu Thr Cys Thr Val Ser Gly Phe Ser Phe Ser Ser Ser Trp
            20                  25                  30

Tyr Met Cys Trp Val Arg Gln Ala Pro Gly Lys Gly Leu Glu Trp Ile
        35                  40                  45

Ala Cys Ile Tyr Thr Leu Arg Ser Gly Ala Ala His Tyr Ala Asn Trp
    50                  55                  60

Ala Lys Gly Arg Phe Thr Ile Ser Lys Ala Ser Ser Thr Thr Val Thr
65                  70                  75                  80

Leu Gln Met Asn Ser Leu Thr Ala Ala Asp Thr Ala Thr Tyr Phe Cys
                85                  90                  95

Ala Arg Ala Thr Tyr Ala Tyr Ala Gly Ala Gly Asp Leu Trp Gly Pro
            100                 105                 110

Gly Thr Leu Val Thr Val Ser Ser
        115                 120


<210> SEQ ID NO 725
<211> LENGTH: 121
<212> TYPE: PRT
<213> ORGANISM: Artificial sequence
<220> FEATURE:
<223> OTHER INFORMATION: Synthetic antibody sequence

<400> SEQUENCE: 725

Glu Gln Ser Leu Lys Glu Ser Gly Gly Asp Leu Val Lys Pro Gly Ala
1               5                   10                  15

Ser Leu Thr Leu Thr Cys Thr Ala Ser Ala Phe Ser Phe Ser Ser Ser
            20                  25                  30

Ser Trp Ile Cys Trp Val Arg Gln Ala Pro Gly Lys Gly Leu Glu Trp
        35                  40                  45

Ile Ala Cys Ile Tyr Gly Gly Ser Val Ala Thr Thr Tyr Tyr Ala Thr
    50                  55                  60

Trp Ala Lys Gly Arg Phe Thr Ile Ser Lys Pro Ser Ser Thr Thr Val
65                  70                  75                  80

Thr Leu Gln Met Thr Ser Leu Pro Ala Ala Asp Thr Ala Thr Tyr Phe
                85                  90                  95

Cys Ala Thr Asn Thr Asp Ser Ser Arg Ser Tyr Tyr Asn Leu Trp Gly
            100                 105                 110

Pro Gly Thr Leu Val Thr Val Ser Ser
        115                 120


<210> SEQ ID NO 726
```

<211> LENGTH: 124
<212> TYPE: PRT
<213> ORGANISM: Artificial sequence
<220> FEATURE:
<223> OTHER INFORMATION: Synthetic antibody sequence

<400> SEQUENCE: 726

```
Glu Gln Ser Val Glu Glu Ser Gly Gly Asp Leu Val Lys Pro Gly Thr
1               5                   10                  15

Ser Leu Thr Leu Thr Cys Thr Ala Ser Gly Phe Ser Phe Ser Gly Asn
            20                  25                  30

Thr Ile Cys Trp Val Arg Gln Ala Pro Gly Lys Arg Pro Glu Trp Ile
        35                  40                  45

Ala Cys Ile Tyr Pro Ser Ser Thr Ser Ile Thr Thr Tyr Ala Thr Trp
    50                  55                  60

Ala Lys Gly Arg Phe Thr Val Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Arg Tyr Ala Ala Phe Leu Thr Tyr Gly Ser Gly Ala Phe Asp
            100                 105                 110

Pro Trp Gly Pro Gly Thr Leu Val Thr Ile Ser Ser
        115                 120
```

<210> SEQ ID NO 727
<211> LENGTH: 118
<212> TYPE: PRT
<213> ORGANISM: Artificial sequence
<220> FEATURE:
<223> OTHER INFORMATION: Synthetic antibody sequence

<400> SEQUENCE: 727

```
Glu Gln Ser Leu Glu Glu Ser Gly Gly Asp Leu Val Lys Pro Glu Gly
1               5                   10                  15

Ser Leu Thr Leu Thr Cys Thr Ala Ser Gly Phe Ser Phe Ser Ser Ser
            20                  25                  30

Tyr Trp Ile Cys Trp Val Arg Gln Ala Pro Gly Lys Gly Leu Glu Trp
        35                  40                  45

Ile Ala Cys Val Ala Thr Gly Ser Gly Thr Thr Asp Tyr Ala Ser Trp
    50                  55                  60

Ala Lys Gly Arg Phe Thr Met Ser Lys Thr Ser Ser Thr Thr Val Thr
65                  70                  75                  80

Leu Gln Met Thr Ser Leu Thr Val Ala Asp Thr Ala Thr Tyr Phe Cys
                85                  90                  95

Ala Arg Ile Gly Ala Phe Tyr Ser Phe Arg Leu Trp Gly Pro Gly Thr
            100                 105                 110

Leu Val Thr Ile Ser Ser
        115
```

<210> SEQ ID NO 728
<211> LENGTH: 120
<212> TYPE: PRT
<213> ORGANISM: Artificial sequence
<220> FEATURE:
<223> OTHER INFORMATION: Synthetic antibody sequence

<400> SEQUENCE: 728

```
Gln Ser Leu Glu Glu Ser Gly Gly Asp Leu Val Lys Pro Glu Gly Ser
1               5                   10                  15
```

```
Leu Thr Leu Thr Cys Thr Ala Ser Gly Phe Ser Phe Ser Ser Ser Tyr
            20                  25                  30

Trp Ile Cys Trp Val Arg Gln Ala Pro Gly Lys Gly Leu Glu Trp Ile
        35                  40                  45

Gly Cys Ile Tyr Ala Gly Asn Ser Ala Asn Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Leu Thr Ser Leu Thr Ala Ala Asp Thr Ala Thr Tyr Phe Cys
                85                  90                  95

Ala Ser Arg Asn Gly Gly Ala Pro Asp Gly Leu Asn Leu Trp Gly Pro
            100                 105                 110

Gly Thr Leu Val Thr Ile Ser Ser
        115                 120
```

<210> SEQ ID NO 729
<211> LENGTH: 118
<212> TYPE: PRT
<213> ORGANISM: Artificial sequence
<220> FEATURE:
<223> OTHER INFORMATION: Synthetic antibody sequence

<400> SEQUENCE: 729

```
Glu Gln Ser Val Lys Glu Ser Gly Gly Gly Leu Val Gln Pro Glu Gly
1               5                   10                  15

Ser Leu Thr Leu Thr Cys Thr Ala Ser Gly Phe Ser Phe Ser Ser Ser
            20                  25                  30

Tyr Trp Ile Cys Trp Val Arg Gln Ala Pro Gly Lys Gly Leu Glu Trp
        35                  40                  45

Ile Gly Cys Ile Ala Thr Gly Thr Gly Ser Thr Tyr Tyr Ala Asn Trp
    50                  55                  60

Val Asn Gly Arg Phe Thr Met Ser Lys Pro Ser Ser Thr Thr Val Thr
65                  70                  75                  80

Leu Gln Met Thr Thr Leu Thr Ala Ala Asp Thr Ala Thr Tyr Phe Cys
                85                  90                  95

Ala Arg Gly Gly Gly Tyr Trp Ser Phe Ser Leu Trp Gly Pro Gly Thr
            100                 105                 110

Leu Val Thr Ile Ser Ser
        115
```

<210> SEQ ID NO 730
<211> LENGTH: 127
<212> TYPE: PRT
<213> ORGANISM: Artificial sequence
<220> FEATURE:
<223> OTHER INFORMATION: Synthetic antibody sequence

<400> SEQUENCE: 730

```
Glu Gln Ser Leu Glu Glu Ser Gly Gly Asp Leu Val Lys Pro Glu Gly
1               5                   10                  15

Ser Leu Thr Leu Thr Cys Thr Ala Ser Gly Phe Ser Phe Ser Ser Ser
            20                  25                  30

Tyr Tyr Met Cys Trp Ile Arg Gln Pro Pro Gly Arg Gly Leu Glu Trp
        35                  40                  45

Leu Ala Cys Ile Tyr Thr Gly Ser Asp Ser Thr Tyr Tyr Ala Pro Trp
    50                  55                  60

Ala Lys Gly Arg Phe Thr Ile Ser Arg Thr Ser Ser Thr Thr Val Thr
65                  70                  75                  80
```

```
Leu Gln Met Thr Ser Leu Thr Ala Ala Asp Thr Ala Thr Tyr Phe Cys
                85                  90                  95

Ala Gly Asp Trp Asp Tyr Ala Asp Ala Ala Gly Tyr Tyr Val Ala Arg
            100                 105                 110

Gly Phe Asn Leu Trp Gly Pro Gly Thr Leu Val Thr Ile Ser Ser
        115                 120                 125


<210> SEQ ID NO 731
<211> LENGTH: 117
<212> TYPE: PRT
<213> ORGANISM: Artificial sequence
<220> FEATURE:
<223> OTHER INFORMATION: Synthetic antibody sequence

<400> SEQUENCE: 731

Glu Gln Ser Leu Glu Glu Ser Gly Gly Gly Leu Val Gln Pro Glu Gly
1               5                   10                  15

Ser Leu Thr Leu Thr Cys Thr Ala Ser Gly Phe Ser Phe Thr Lys Asn
            20                  25                  30

Tyr Tyr Met Cys Trp Val Arg Gln Ala Pro Gly Lys Gly Leu Glu Trp
        35                  40                  45

Ile Gly Cys Ile Tyr Ala Gly Ser Thr Asn Thr Phe Tyr Ala Ser Trp
    50                  55                  60

Ala Lys Gly Arg Phe Thr Ile Ser Lys Ala Ser Ser Thr Thr Val Asp
65                  70                  75                  80

Leu Lys Met Thr Ser Leu Thr Val Ala Asp Thr Ala Thr Tyr Phe Cys
                85                  90                  95

Ala Arg Asp Phe Val Ser Tyr Leu Asn Leu Trp Gly Pro Gly Thr Leu
            100                 105                 110

Val Thr Val Ser Ser
        115


<210> SEQ ID NO 732
<211> LENGTH: 128
<212> TYPE: PRT
<213> ORGANISM: Artificial sequence
<220> FEATURE:
<223> OTHER INFORMATION: Synthetic antibody sequence

<400> SEQUENCE: 732

Arg Ala Val Gly Lys Glu Ser Gly Gly Asp Leu Val Thr Leu Gly Gly
1               5                   10                  15

Ser Leu Lys Leu Ser Cys Lys Ala Ser Gly Ile Asp Leu Ser Asn Phe
            20                  25                  30

Tyr Tyr Met Cys Trp Val Arg Gln Ala Pro Gly Lys Gly Leu Glu Trp
        35                  40                  45

Ile Gly Cys Val Ala Ser Asp Ser Ser Arg Thr His Tyr Ala Thr Trp
    50                  55                  60

Pro Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Gly Ser Gly Ala Ser Thr Asn Gly Val Trp Trp Val Met Gly
            100                 105                 110

Asp Gly Met Asp Leu Trp Gly Pro Gly Thr Leu Val Thr Val Ser Ser
        115                 120                 125
```

```
<210> SEQ ID NO 733
<211> LENGTH: 123
<212> TYPE: PRT
<213> ORGANISM: Artificial sequence
<220> FEATURE:
<223> OTHER INFORMATION: Synthetic antibody sequence

<400> SEQUENCE: 733

Gln Ser Val Lys Glu Ser Gly Gly Asp Leu Val Lys Pro Gly Ala Ser
1               5                   10                  15

Leu Thr Leu Thr Cys Lys Ala Ser Gly Phe Ser Phe Ser Ser Gly His
            20                  25                  30

Tyr Met Tyr Trp Val Arg Gln Ala Pro Gly Lys Gly Leu Glu Trp Ile
        35                  40                  45

Ala Cys Ile Tyr Ala Gly Ser Asp Thr Gly Ser Thr Trp Tyr Ala Ser
    50                  55                  60

Trp Ala Lys Gly Arg Phe Thr Ile Ser Lys Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Ser Ser Asn Ser Tyr Gly Asn Tyr Gly Val Ser Asn Leu
            100                 105                 110

Trp Gly Pro Gly Thr Leu Val Thr Val Ser Ser
        115                 120


<210> SEQ ID NO 734
<211> LENGTH: 118
<212> TYPE: PRT
<213> ORGANISM: Artificial sequence
<220> FEATURE:
<223> OTHER INFORMATION: Synthetic antibody sequence

<400> SEQUENCE: 734

Gln Glu Gln Leu Val Glu Ser Gly Gly Gly Leu Val Gln Pro Glu Gly
1               5                   10                  15

Ser Leu Thr Leu Thr Cys Lys Ala Ser Gly Ile Asp Phe Ser Ser Gly
            20                  25                  30

Tyr Trp Ile Cys Trp Val Arg Gln Ala Pro Gly Lys Gly Leu Glu Leu
        35                  40                  45

Ile Ala Cys Ile Phe Thr Ser Ser Gly Thr Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Ile Tyr Ser Tyr Gly Met Asp Leu Trp Gly Pro Gly Thr
            100                 105                 110

Leu Val Thr Val Ser Ser
        115


<210> SEQ ID NO 735
<211> LENGTH: 117
<212> TYPE: PRT
<213> ORGANISM: Artificial sequence
<220> FEATURE:
<223> OTHER INFORMATION: Synthetic antibody sequence

<400> SEQUENCE: 735

Gln Ser Val Lys Glu Ser Glu Gly Gly Leu Val Gln Pro Gly Gly Ser
1               5                   10                  15
```

```
Leu Thr Leu Ser Cys Lys Ala Ser Gly Ile Asp Phe Ser Ser Ala Tyr
            20                  25                  30

Met Ser Trp Val Arg Gln Ala Pro Gly Lys Gly Leu Glu Trp Ile Gly
        35                  40                  45

Lys Met Arg Ile Asn Asp Arg Ser His Tyr Ala Asn Trp Val Asn Gly
    50                  55                  60

Arg Phe Thr Ile Ser Asn His Asn Asp Gln Asn Thr Val Glu Leu Gln
65                  70                  75                  80

Leu Asn Ser Leu Thr Ala Ala Asp Thr Ala Thr Tyr Phe Cys Ala Arg
                85                  90                  95

Ile Ala Thr Gly Thr Asn Val Asp Asp Phe Trp Gly Pro Gly Thr Leu
            100                 105                 110

Val Thr Ile Ser Ser
        115


<210> SEQ ID NO 736
<211> LENGTH: 115
<212> TYPE: PRT
<213> ORGANISM: Artificial sequence
<220> FEATURE:
<223> OTHER INFORMATION: Synthetic antibody sequence

<400> SEQUENCE: 736

Gln Glu Gln Leu Val Glu Ser Gly Gly Gly Leu Val Thr Pro Gly Gly
1               5                   10                  15

Ser Leu Thr Leu Thr Cys Thr Ala Ser Gly Phe Ser Phe Ser Ser Lys
            20                  25                  30

Gln Tyr Ile Ser Trp Val Arg Arg Ala Pro Gly Lys Gly Leu Glu Trp
        35                  40                  45

Ile Gly Ala Ile Val Thr Val Asn Asn Lys Val His Tyr Ala Asn Trp
    50                  55                  60

Ala Lys Gly Arg Phe Thr Ile Ser Glu Ala Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Trp Arg Thr Phe Gly Leu Trp Gly Pro Gly Thr Leu Val Thr
            100                 105                 110

Val Ser Ser
        115


<210> SEQ ID NO 737
<211> LENGTH: 121
<212> TYPE: PRT
<213> ORGANISM: Artificial sequence
<220> FEATURE:
<223> OTHER INFORMATION: Synthetic antibody sequence

<400> SEQUENCE: 737

Glu Gln Leu Met Glu Glu Ser Gly Gly Gly Leu Val Gln Pro Glu Gly
1               5                   10                  15

Ser Leu Thr Leu Thr Cys Thr Ala Ser Arg Phe Ser Leu Ser Asn Met
            20                  25                  30

Asn Val Met Cys Trp Val Arg Gln Ala Pro Gly Lys Gly Leu Glu Trp
        35                  40                  45

Ile Gly Cys Ile Asn Ile Gly Gly Thr Asn Ile Trp Tyr Ala Ser Trp
    50                  55                  60

Ala Lys Gly Arg Phe Thr Ile Ser Lys Thr Ser Ser Thr Thr Val Thr
```

```
65                  70                  75                  80

Leu Gln Met Thr Ser Leu Thr Val Ala Asp Thr Ala Thr Tyr Phe Cys
                85                  90                  95

Ala Arg Ser Tyr Ile Thr Asp Arg Ile Tyr Asp Tyr Asp Phe Trp Gly
            100                 105                 110

Pro Gly Thr Leu Val Thr Ile Ser Ser
        115                 120


<210> SEQ ID NO 738
<211> LENGTH: 119
<212> TYPE: PRT
<213> ORGANISM: Artificial sequence
<220> FEATURE:
<223> OTHER INFORMATION: Synthetic antibody sequence

<400> SEQUENCE: 738

Gln Ser Val Glu Glu Ser Gly Gly Gly Leu Val Lys Pro Gly Ala Ser
1               5                   10                  15

Leu Thr Leu Ser Cys Thr Ala Ser Gly Phe Asp Phe Ser Ser Lys Tyr
            20                  25                  30

Tyr Met Trp Trp Val Arg Gln Ala Pro Gly Lys Gly Leu Glu Trp Ile
        35                  40                  45

Ala Arg Ile Tyr Gly Gly Ser Ser Asp Ser Thr Asp Tyr Ala Thr Trp
    50                  55                  60

Ala Arg Gly Arg Phe Ala Ile Ser Arg Thr Ser Ser Thr Thr Val Thr
65                  70                  75                  80

Leu Arg Met Thr Ser Leu Thr Ala Ala Asp Thr Ala Thr Tyr Phe Cys
                85                  90                  95

Gly Arg Val Ile Asp Gly Ala Cys Gly Tyr Asp Leu Trp Gly Pro Gly
            100                 105                 110

Thr Leu Val Thr Val Ser Ser
        115


<210> SEQ ID NO 739
<211> LENGTH: 120
<212> TYPE: PRT
<213> ORGANISM: Artificial sequence
<220> FEATURE:
<223> OTHER INFORMATION: Synthetic antibody sequence

<400> SEQUENCE: 739

Gln Ser Val Glu Glu Ser Gly Gly Asp Leu Val Lys Pro Gly Ala Ser
1               5                   10                  15

Leu Thr Leu Thr Cys Thr Ala Ser Gly Phe Asp Phe Ser Ser Asn Ala
            20                  25                  30

Tyr Leu Cys Trp Val Arg Gln Ala Pro Gly Lys Gly Leu Glu Trp Ile
        35                  40                  45

Gly Cys Ile Tyr Asp Gly Thr Ser Gly Asp Thr Tyr Tyr Ala Asn Trp
    50                  55                  60

Ala Lys Gly Arg Phe Thr Ile Ser Arg Ser Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Thr Arg Ser Ser Asn Tyr Tyr Phe Asn Leu Trp Gly Pro
            100                 105                 110

Gly Thr Leu Val Thr Ile Ser Ser
        115                 120
```

<210> SEQ ID NO 740
<211> LENGTH: 118
<212> TYPE: PRT
<213> ORGANISM: Artificial sequence
<220> FEATURE:
<223> OTHER INFORMATION: Synthetic antibody sequence

<400> SEQUENCE: 740

```
Glu Ser Glu Gly Gly Leu Val Lys Pro Gly Gly Thr Leu Thr Leu Thr
1               5                   10                  15

Cys Lys Val Ser Gly Ile Asp Phe Asn Ser Tyr Lys Tyr Tyr Tyr Met
            20                  25                  30

Cys Trp Val Arg Gln Ala Pro Gly Lys Gly Leu Glu Trp Ile Gly Cys
        35                  40                  45

Met Ser Thr Ala Ser Arg Asn Ile Tyr Tyr Ala Ser Trp Ala Lys Gly
    50                  55                  60

Arg Phe Thr Ile Ser Glu Thr Ser Ser Thr Ser Val Thr Leu Gln Met
65                  70                  75                  80

Thr Thr Leu Thr Ala Ala Asp Thr Ala Thr Tyr Phe Cys Ala Lys Ser
                85                  90                  95

His Gly Gly Asp Gly Gly Tyr Gly Val Val Leu Trp Gly Pro Gly Thr
            100                 105                 110

Leu Val Thr Ile Ser Ser
        115
```

<210> SEQ ID NO 741
<211> LENGTH: 126
<212> TYPE: PRT
<213> ORGANISM: Artificial sequence
<220> FEATURE:
<223> OTHER INFORMATION: Synthetic antibody sequence

<400> SEQUENCE: 741

```
Gln Ser Leu Glu Glu Ser Glu Gly Gly Leu Val Lys Pro Gly Gly Thr
1               5                   10                  15

Leu Thr Leu Thr Cys Thr Ala Ser Gly Phe Ser Phe Ser Ser Ser Tyr
            20                  25                  30

Cys Met Cys Trp Val Arg Gln Ala Pro Gly Lys Gly Leu Glu Leu Ile
        35                  40                  45

Ala Cys Ile Tyr Thr Asp Ser Ser Gly Ala Thr Tyr Tyr Ala Ser Trp
    50                  55                  60

Ala Lys Gly Arg Phe Thr Ile Ser Lys Ser Ser Ser Thr Thr Ile Thr
65                  70                  75                  80

Leu Gln Met Thr Ser Leu Thr Ala Ala Asp Thr Ala Thr Tyr Phe Cys
                85                  90                  95

Ala Arg Gly Trp Asp Tyr Glu Asp Pro Gly Tyr Thr Asp Thr Thr Tyr
            100                 105                 110

Phe Ser Leu Trp Gly Pro Gly Thr Leu Val Thr Val Ser Ser
        115                 120                 125
```

<210> SEQ ID NO 742
<211> LENGTH: 119
<212> TYPE: PRT
<213> ORGANISM: Artificial sequence
<220> FEATURE:
<223> OTHER INFORMATION: Synthetic antibody sequence

<400> SEQUENCE: 742

```
Gln Lys Gln Leu Val Glu Ser Gly Gly Gly Leu Val Gln Pro Glu Gly
```

```
1               5                   10                  15

Ser Leu Ala Leu Thr Cys Thr Ala Ser Gly Phe Ser Phe Ser Ser Ser
            20                  25                  30

Tyr Trp Ile Cys Trp Val Arg Gln Ala Pro Gly Lys Gly Leu Glu Trp
        35                  40                  45

Ile Ala Cys Ile Tyr Ala Gly Ser Ser Gly Ser Thr Tyr Tyr Ala Ser
    50                  55                  60

Trp Val Asn Gly Arg Phe Thr Val Phe Lys Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Gly Gly Thr Ser Tyr Arg Leu Asp Leu Trp Gly Pro Gly
            100                 105                 110

Thr Leu Val Thr Val Ser Ser
        115
```

<210> SEQ ID NO 743
<211> LENGTH: 125
<212> TYPE: PRT
<213> ORGANISM: Artificial sequence
<220> FEATURE:
<223> OTHER INFORMATION: Synthetic antibody sequence

<400> SEQUENCE: 743

```
Ser Gln Gln Leu Lys Glu Ser Gly Gly Gly Leu Val Lys Pro Gly Gly
1               5                   10                  15

Thr Leu Thr Leu Thr Cys Lys Ala Ser Gly Ile Asp Phe Asn Asn Asp
            20                  25                  30

Tyr Asn Ile Cys Trp Val Arg Gln Pro Pro Gly Lys Gly Leu Glu Trp
        35                  40                  45

Ile Gly Cys Ile Tyr Thr Gly Ser Asp Ser Thr Asp Tyr Ala Ser Trp
    50                  55                  60

Val Asn Gly Arg Phe Thr Ile Ser Glu Ser Thr Ser Leu Asn Thr Val
65                  70                  75                  80

Asp Leu Lys Val Thr Ser Leu Thr Asp Ala Asp Thr Ala Thr Tyr Phe
                85                  90                  95

Cys Ala Arg Asp Leu Val Thr Gly Tyr Ala Thr Tyr Gly Tyr Gly Phe
            100                 105                 110

Ile Leu Trp Gly Pro Gly Thr Leu Val Thr Val Ser Ser
        115                 120                 125
```

<210> SEQ ID NO 744

<400> SEQUENCE: 744

000

<210> SEQ ID NO 745
<211> LENGTH: 120
<212> TYPE: PRT
<213> ORGANISM: Artificial sequence
<220> FEATURE:
<223> OTHER INFORMATION: Synthetic antibody sequence

<400> SEQUENCE: 745

```
Gln Glu Gln Leu Lys Glu Ser Gly Gly Asp Leu Val Lys Pro Glu Gly
1               5                   10                  15

Ser Leu Thr Leu Thr Cys Thr Ala Ser Gly Phe Ser Phe Ser Ser Asp
            20                  25                  30
```

```
Tyr Trp Val Cys Trp Val Arg Gln Ala Pro Gly Lys Gly Pro Glu Trp
        35                  40                  45

Ile Gly Cys Ile Tyr Thr Gly Asp Asp Asp Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Glu Val Thr Ser Leu Thr Ala Ala Asp Thr Ala Thr Tyr Phe Cys
                85                  90                  95

Ala Arg Gly Leu Thr Ile Gly Thr Ala Glu Leu Tyr Phe Trp Gly Pro
            100                 105                 110

Gly Thr Val Val Thr Val Ser Ser
        115                 120


<210> SEQ ID NO 746
<211> LENGTH: 117
<212> TYPE: PRT
<213> ORGANISM: Artificial sequence
<220> FEATURE:
<223> OTHER INFORMATION: Synthetic antibody sequence

<400> SEQUENCE: 746

Gln Glu Gln Leu Val Glu Ser Gly Gly Gly Leu Val Gln Pro Glu Gly
1               5                   10                  15

Ser Leu Thr Leu Thr Cys Thr Asp Ser Gly Phe Ser Phe Thr Lys Asn
            20                  25                  30

Tyr Tyr Met Cys Trp Val Arg Gln Ala Pro Gly Lys Gly Leu Glu Trp
        35                  40                  45

Ile Gly Cys Ile Tyr Ala Gly Ser Thr Asn Thr Phe Tyr Ala Ser Trp
    50                  55                  60

Ala Lys Gly Arg Phe Thr Ile Ser Lys Ala Ser Ser Thr Thr Val Asp
65                  70                  75                  80

Leu Lys Met Thr Ser Leu Thr Val Ala Asp Thr Ala Thr Tyr Phe Cys
                85                  90                  95

Ala Arg Asp Phe Val Ser Tyr Leu Asn Leu Trp Gly Pro Gly Thr Leu
            100                 105                 110

Val Thr Val Ser Ser
        115


<210> SEQ ID NO 747
<211> LENGTH: 122
<212> TYPE: PRT
<213> ORGANISM: Artificial sequence
<220> FEATURE:
<223> OTHER INFORMATION: Synthetic antibody sequence

<400> SEQUENCE: 747

Gln Ser Leu Glu Glu Ser Gly Gly Gly Leu Val Lys Pro Glu Gly Ser
1               5                   10                  15

Leu Thr Leu Thr Cys Thr Ala Ser Gly Phe Asp Leu Ser Asn Asn Tyr
            20                  25                  30

Tyr Ile Cys Trp Val Arg Gln Ala Pro Gly Lys Gly Leu Glu Leu Ile
        35                  40                  45

Ala Cys Val Asp Ser Asp Leu Thr Asp Ser Ala Asp Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
```

```
                85                  90                  95

Ala Gly Ser Gly Ser Gly Tyr Tyr Tyr Tyr Tyr Gly Met Asp Leu Trp
            100                 105                 110

Gly Pro Gly Thr Leu Val Thr Ile Ser Ser
        115                 120
```

<210> SEQ ID NO 748
<211> LENGTH: 119
<212> TYPE: PRT
<213> ORGANISM: Artificial sequence
<220> FEATURE:
<223> OTHER INFORMATION: Synthetic antibody sequence

<400> SEQUENCE: 748

```
Ser Gln Ser Leu Glu Glu Ser Gly Gly Gly Leu Val Lys Pro Gly Ala
1               5                   10                  15

Ser Leu Thr Leu Thr Cys Lys Gly Ser Gly Phe Ser Phe Asn Gly Asp
            20                  25                  30

Tyr Tyr Met Cys Trp Val Arg Gln Thr Pro Gly Lys Gly Leu Glu Trp
        35                  40                  45

Ile Gly Cys Ile Tyr Ala Ala Gly Asp Asp Thr Tyr Tyr Ala Thr Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Gln Ala Asp Ser Tyr Ala Phe Gly Leu Trp Gly Pro Gly
            100                 105                 110

Thr Leu Val Thr Ile Ser Ser
        115
```

<210> SEQ ID NO 749
<211> LENGTH: 116
<212> TYPE: PRT
<213> ORGANISM: Artificial sequence
<220> FEATURE:
<223> OTHER INFORMATION: Synthetic antibody sequence

<400> SEQUENCE: 749

```
Gln Ser Leu Lys Glu Ser Glu Gly Asp Leu Val Lys Pro Gly Ala Ser
1               5                   10                  15

Leu Thr Leu Thr Cys Thr Ala Ser Gly Phe Ser Phe Ser Ser Ser Tyr
            20                  25                  30

Trp Ile Cys Trp Val Arg Gln Ala Pro Gly Lys Gly Leu Glu Trp Ile
        35                  40                  45

Ala Cys Ile Tyr Ala Gly Ser Ser Gly Ser Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Glu Met Thr Ser Leu Thr Asp Ala Asp Thr Ala Thr Tyr Phe Cys
                85                  90                  95

Ala Arg Gly Phe Ser Met Phe Lys Leu Trp Gly Pro Gly Thr Leu Val
            100                 105                 110

Thr Ile Ser Ser
        115
```

<210> SEQ ID NO 750
<211> LENGTH: 126

<212> TYPE: PRT
<213> ORGANISM: Artificial sequence
<220> FEATURE:
<223> OTHER INFORMATION: Synthetic antibody sequence

<400> SEQUENCE: 750

```
Gln Ser Val Lys Glu Ser Gly Gly Gly Leu Val Lys Pro Gly Gly Thr
1               5                   10                  15

Leu Thr Leu Thr Cys Thr Ala Ser Gly Phe Ser Phe Ser Ser Ser Tyr
            20                  25                  30

Cys Met Cys Trp Val Arg Gln Ala Pro Gly Lys Gly Leu Glu Leu Ile
        35                  40                  45

Ala Cys Ile Tyr Thr Asp Ser Ser Gly Ala Thr Tyr Tyr Ala Ser Trp
    50                  55                  60

Ala Lys Gly Arg Phe Thr Ile Ser Lys Ser Ser Ser Thr Thr Ile Thr
65                  70                  75                  80

Leu Gln Met Thr Ser Leu Thr Ala Ala Asp Thr Ala Thr Tyr Phe Cys
                85                  90                  95

Ala Arg Gly Trp Asp Tyr Glu Asp Pro Gly Tyr Thr Asp Thr Thr Tyr
            100                 105                 110

Phe Ser Leu Trp Gly Pro Gly Thr Leu Val Thr Val Ser Ser
        115                 120                 125
```

<210> SEQ ID NO 751
<211> LENGTH: 128
<212> TYPE: PRT
<213> ORGANISM: Artificial sequence
<220> FEATURE:
<223> OTHER INFORMATION: Synthetic antibody sequence

<400> SEQUENCE: 751

```
Ser Gln Ser Val Glu Glu Ser Gly Gly Asp Leu Val Lys Pro Gly Gly
1               5                   10                  15

Thr Leu Thr Leu Thr Cys Thr Ala Ser Arg Ile Asp Leu Asn Asn Tyr
            20                  25                  30

Tyr Tyr Ile Ser Trp Val Arg Gln Ala Pro Gly Lys Gly Leu Glu Trp
        35                  40                  45

Ile Gly Val Val Ala Thr Asp Ser Ser Val Thr Trp Tyr Ala Ser Trp
    50                  55                  60

Ala Lys Gly Gln Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Gly Ser Gly Ala Ala Thr Asn Gly Val Trp Trp Val Met Gly
            100                 105                 110

Asp Gly Met Asp Leu Trp Gly Pro Gly Thr Leu Val Thr Val Ser Ser
        115                 120                 125
```

<210> SEQ ID NO 752
<211> LENGTH: 116
<212> TYPE: PRT
<213> ORGANISM: Artificial sequence
<220> FEATURE:
<223> OTHER INFORMATION: Synthetic antibody sequence

<400> SEQUENCE: 752

```
Gln Ser Val Glu Glu Ser Glu Gly Arg Leu Val Thr Pro Gly Gly Ser
1               5                   10                  15

Leu Thr Leu Thr Cys Thr Val Ser Gly Ile Asp Leu Ser Ser Tyr Ala
```

```
            20                  25                  30

Met Gly Trp Val Arg Gln Ala Pro Gly Lys Gly Leu Glu Trp Ile Gly
        35                  40                  45

Val Ile Gly Lys Ser Gly Thr Thr Tyr Tyr Ala Asn Trp Ala Lys Gly
    50                  55                  60

Arg Phe Thr Ile Ser Lys Thr Ser Thr Thr Val Asp Leu Gln Ile Ala
65                  70                  75                  80

Ser Pro Thr Thr Glu Asp Thr Ala Thr Tyr Phe Cys Ala Arg Ala Gly
                85                  90                  95

Ala Ser Arg Ser Ile Tyr Tyr Asp Leu Trp Gly Gln Gly Thr Leu Val
            100                 105                 110

Thr Ile Ser Ser
        115


<210> SEQ ID NO 753
<211> LENGTH: 118
<212> TYPE: PRT
<213> ORGANISM: Artificial sequence
<220> FEATURE:
<223> OTHER INFORMATION: Synthetic antibody sequence

<400> SEQUENCE: 753

Gln Ser Val Glu Glu Ser Gly Gly Gly Leu Val Gln Pro Glu Gly Ser
1               5                   10                  15

Leu Thr Leu Thr Cys Thr Ala Ser Gly Phe Ser Phe Ser Gly Ile Val
            20                  25                  30

Tyr Met Cys Trp Val Arg Gln Ala Pro Gly Lys Gly Leu Glu Trp Ile
        35                  40                  45

Ala Cys Ala Phe Val Gly Ser Gly Gly Ser Thr Tyr Tyr Ala Thr Trp
    50                  55                  60

Ala Thr Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Lys Ser Tyr Asn Tyr Asn Gly Leu Gly Leu Trp Gly Pro Gly Thr
            100                 105                 110

Leu Val Thr Val Ser Ser
        115


<210> SEQ ID NO 754
<211> LENGTH: 122
<212> TYPE: PRT
<213> ORGANISM: Artificial sequence
<220> FEATURE:
<223> OTHER INFORMATION: Synthetic antibody sequence

<400> SEQUENCE: 754

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Ser Tyr
            20                  25                  30

Tyr Met Cys Trp Val Arg Gln Ala Pro Gly Lys Gly Leu Glu Trp Ile
        35                  40                  45

Ala Cys Ile Tyr Gly Gly Ser Thr Gly Thr Thr Tyr Tyr Ala Ser Trp
    50                  55                  60

Ala Lys Gly Arg Phe Thr Ile Ser Lys Thr Ser Ser Thr Thr Val Thr
65                  70                  75                  80
```

```
Leu Gln Met Thr Ser Leu Thr Gly Ala Asp Thr Ala Thr Tyr Phe Cys
                85                  90                  95

Ala Arg Ser Tyr Asn Ser Ala Ser Ser Gly Tyr Tyr Trp Asp Leu Trp
            100                 105                 110

Gly Pro Gly Thr Leu Val Thr Val Ser Ser
        115                 120


<210> SEQ ID NO 755
<211> LENGTH: 118
<212> TYPE: PRT
<213> ORGANISM: Artificial sequence
<220> FEATURE:
<223> OTHER INFORMATION: Synthetic antibody sequence

<400> SEQUENCE: 755

Glu Gln Ser Val Glu Glu Ser Gly Gly Gly Leu Val Gln Pro Glu Gly
1               5                   10                  15

Ser Leu Thr Leu Thr Cys Thr Ala Ser Gly Ile Asp Phe Ser Ser Gly
            20                  25                  30

Ala Trp Ile Cys Trp Val Arg Gln Ala Pro Gly Lys Gly Leu Glu Leu
        35                  40                  45

Ile Ala Cys Ile Phe Thr Thr Ser Gly Phe Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Ile Tyr Ser Tyr Gly Met Asp Leu Trp Gly Pro Gly Thr
            100                 105                 110

Leu Val Thr Ile Ser Ser
        115


<210> SEQ ID NO 756
<211> LENGTH: 115
<212> TYPE: PRT
<213> ORGANISM: Artificial sequence
<220> FEATURE:
<223> OTHER INFORMATION: Synthetic antibody sequence

<400> SEQUENCE: 756

Gln Glu Gln Leu Val Glu Ser Gly Gly Gly Leu Val Gln Pro Glu Gly
1               5                   10                  15

Ser Leu Thr Leu Thr Cys Thr Ala Ser Gly Phe Ser Phe Ser Ser Arg
            20                  25                  30

Gln Tyr Ile Ser Trp Val Arg Arg Ala Pro Gly Lys Gly Leu Glu Trp
        35                  40                  45

Ile Gly Ala Ile Val Thr Val Asn Asn Lys Val His Tyr Ala Asn Trp
    50                  55                  60

Ala Lys Gly Arg Phe Thr Ile Ser Glu Ala Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Trp Arg Thr Phe Gly Leu Trp Gly Pro Gly Thr Leu Val Thr
            100                 105                 110

Val Ser Ser
        115


<210> SEQ ID NO 757
```

```
<211> LENGTH: 126
<212> TYPE: PRT
<213> ORGANISM: Artificial sequence
<220> FEATURE:
<223> OTHER INFORMATION: Synthetic antibody sequence

<400> SEQUENCE: 757

Gln Ser Val Lys Glu Ser Gly Gly Gly Leu Val Lys Pro Gly Gly Thr
1               5                   10                  15

Leu Thr Leu Thr Cys Thr Ala Ser Gly Phe Ser Phe Ser Ser Ser Tyr
            20                  25                  30

Cys Met Cys Trp Val Arg Gln Ala Pro Gly Lys Gly Leu Glu Leu Ile
        35                  40                  45

Ala Cys Ile Tyr Thr Asp Ser Ser Gly Ala Thr Tyr Tyr Ala Ser Trp
    50                  55                  60

Ala Lys Gly Arg Phe Thr Ile Ser Lys Ser Ser Ser Thr Thr Ile Thr
65                  70                  75                  80

Leu Gln Met Thr Ser Leu Thr Ala Ala Asp Thr Ala Thr Tyr Phe Cys
                85                  90                  95

Ala Arg Gly Trp Asp Tyr Glu Asp Pro Gly Tyr Thr Asp Thr Thr Tyr
            100                 105                 110

Phe Ser Leu Trp Gly Pro Gly Thr Leu Val Thr Val Ser Ser
        115                 120                 125


<210> SEQ ID NO 758
<211> LENGTH: 128
<212> TYPE: PRT
<213> ORGANISM: Artificial sequence
<220> FEATURE:
<223> OTHER INFORMATION: Synthetic antibody sequence

<400> SEQUENCE: 758

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Ser
            20                  25                  30

Tyr Cys Met Cys Trp Val Arg Gln Ala Pro Gly Lys Gly Leu Glu Trp
        35                  40                  45

Val Ser Cys Ile Tyr Thr Asp Ser Ser Gly Ala Thr Tyr Tyr Ala Ser
    50                  55                  60

Trp Ala Lys Gly Arg Phe Thr Ile Ser Arg His Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Gly Trp Asp Tyr Glu Asp Pro Gly Tyr Thr Asp Thr
            100                 105                 110

Thr Tyr Phe Ser Leu Trp Gly Arg Gly Thr Leu Val Thr Val Ser Ser
        115                 120                 125


<210> SEQ ID NO 759
<211> LENGTH: 128
<212> TYPE: PRT
<213> ORGANISM: Artificial sequence
<220> FEATURE:
<223> OTHER INFORMATION: Synthetic antibody sequence

<400> SEQUENCE: 759

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Ser Phe Ser Ser Ser
            20                  25                  30

Tyr Cys Met Cys Trp Val Arg Gln Ala Pro Gly Lys Gly Leu Glu Leu
        35                  40                  45

Val Ser Cys Ile Tyr Thr Asp Ser Ser Gly Ala Thr Tyr Tyr Ala Ser
    50                  55                  60

Trp Ala Lys Gly Arg Phe Thr Ile Ser Arg His Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Gly Trp Asp Tyr Glu Asp Pro Gly Tyr Thr Asp Thr
            100                 105                 110

Thr Tyr Phe Ser Leu Trp Gly Arg Gly Thr Leu Val Thr Val Ser Ser
        115                 120                 125


<210> SEQ ID NO 760
<211> LENGTH: 339
<212> TYPE: DNA
<213> ORGANISM: Artificial sequence
<220> FEATURE:
<223> OTHER INFORMATION: Synthetic antibody sequence

<400> SEQUENCE: 760

gagctcgata tgacccagac tccagcctcc gtggaggcgg ctgtgggagg cacagtcacc     60

atcaagtgcc aggccagtca gaacatttac agctacttag tctggtatca gcagaaacca    120

gggcagcctc ccaagctcct aatctcaaag gcatccactc tggcatctgg ggtctcatcg    180

cggttcaaag gcagtggatc tgggacagag ttcactctca ccatcaacga cctggagtgt    240

gccgatgctg ccacttacta ctgtcaaacc aattatttta gtagtactag tcattttggt    300

gtttttactt tcggcggagg gaccgagctg gaaatcaaa                           339


<210> SEQ ID NO 761
<211> LENGTH: 339
<212> TYPE: DNA
<213> ORGANISM: Artificial sequence
<220> FEATURE:
<223> OTHER INFORMATION: Synthetic antibody sequence

<400> SEQUENCE: 761

gagctcgtgc tgacccagac tccatcccct gtgtctgcag ttgtgggagg ctcagtcacc     60

atcaattgcc agtccagtca gagtctttat aatgcgaacg acttatcctg gtatcagcag    120

aaaccagggc agcctcccaa gcaactgatc tactgggcat ccactctggc atctggggtc    180

ccatcgcggt tcaaaggcag tggatctggg acacagttca ctctcagcat cagcgacgtg    240

cagtgtgacg atgctgccac ttactactgt ctaggcgaat ttagttgcag tagttttgat    300

tgtcatgttt tcggcggagg gaccgaggtg gtggtcaaa                           339


<210> SEQ ID NO 762
<211> LENGTH: 330
<212> TYPE: DNA
<213> ORGANISM: Artificial sequence
<220> FEATURE:
<223> OTHER INFORMATION: Synthetic antibody sequence

<400> SEQUENCE: 762

gagctcgata tgacccagac tccatcctcc gtgtctgcag ctgtgggaga cacagtcacc     60

atcaagtgcc aggccagtca gagcatttac aggtacttag cctggtatca acagaaacca    120
```

gggcagcgtc ccagcctcct aatatattat ggatccgatc tggcatctgg ggtcccatcg 180
cggttcagcg gcagtggatc tgggacagag ttcactctca ccatcagcga cctggagtgt 240
gccgatgctg ccagttacta ctgtcaaacc acttatgatg attatcataa tggttgggct 300
ttcggcggag ggaccaatgt ggaaatcaac 330

<210> SEQ ID NO 763
<211> LENGTH: 330
<212> TYPE: DNA
<213> ORGANISM: Artificial sequence
<220> FEATURE:
<223> OTHER INFORMATION: Synthetic antibody sequence

<400> SEQUENCE: 763
gagctcgatc tgacccagac tccatcgtcc gtgtctgcag ctgtgggagg cacagtcacc 60
atcagttgcc aggccagtca gagtgtttat ggtaacaacc gcttagcctg gtatcatcag 120
aaaccaggac agcctcccaa acgcctgatc tatctggcat ccactctgga ttctggggtc 180
ccatcacggt tcaaaggcgc tggatctggg acacagttca ctctcaccat cagcgacctg 240
gagtgtgacg atgctgccac ttactactgt gcaggcggtt atgctgggaa tttcaatgct 300
ttcggcggag ggaccgaggt ggaaatcaaa 330

<210> SEQ ID NO 764
<211> LENGTH: 333
<212> TYPE: DNA
<213> ORGANISM: Artificial sequence
<220> FEATURE:
<223> OTHER INFORMATION: Synthetic antibody sequence

<400> SEQUENCE: 764
gagctcgatc tgacccagac tccagcctcc gtgtctgcag ctgtgggagg cacagtcacc 60
atcaagtgcc aggccagtca gaacattgtc agtaatttag cctggtatca gcagaaacca 120
gggcagcgtc ccaagctcct gatctattat gcatccactc tggcatctgg ggtcccatcg 180
cggttcaaag gcagtggatc tgggacagag tacactctca ccatcagcga cctggagtgt 240
gccgatgctg ccacttacta ctgtcaaaac aatgctggta tttatggtaa ttatggtcat 300
ggtttcggcg gagggaccga gctggaaatc aaa 333

<210> SEQ ID NO 765
<211> LENGTH: 327
<212> TYPE: DNA
<213> ORGANISM: Artificial sequence
<220> FEATURE:
<223> OTHER INFORMATION: Synthetic antibody sequence

<400> SEQUENCE: 765
gagctcgatc tgacccagac tccatcctcc gtggaggcag ctgtgggagg cacagtcacc 60
atcaagtgcc aggccagtca gagcatttac aactacttag cctggtatca gcagaaacca 120
gggcactctc ctaagctcct gatctacgat gtatccaaat tggcatctgg ggtctcatcg 180
cggttcaaag gtagtggatc tgggacagag ttcactctca ccatcagcga cctggagtgt 240
gccgatgctg ccacttatta ctgtcaaagt tattatggta atactgtttc ttttactttc 300
ggcggaggga ccgaggtgga aatcaaa 327

<210> SEQ ID NO 766
<211> LENGTH: 330
<212> TYPE: DNA
<213> ORGANISM: Artificial sequence
<220> FEATURE:
<223> OTHER INFORMATION: Synthetic antibody sequence

<400> SEQUENCE: 766
gagctcgtga tgacccagac tccatcgtcc gtgtctgcag ctgtgggagg cacagtcacc 60
atcagttgcc aggccagtca gagtgtttat aataacaaca acttagcctg gtatcagcag 120
aaaccagggc agcctcccaa acgcctgatc tattctgcat ccactctgga ttctggggtc 180
ccatcgcggt tcagcggcag tggatctggg acacagttca ctctcaccat cagcgacctg 240
gagtgtgacg atgctgccac ttactattgt gcaggcggtt atacttacaa tatcaatatt 300
ttcggcggag ggaccgaggt ggaaatcaaa 330

<210> SEQ ID NO 767
<211> LENGTH: 333
<212> TYPE: DNA
<213> ORGANISM: Artificial sequence
<220> FEATURE:
<223> OTHER INFORMATION: Synthetic antibody sequence

<400> SEQUENCE: 767
gagctcgatc tgacccagac accagcctct gtgtctgaac ctgtgggagg cacagtcacc 60
atcaagtgcc aggccagtca gaacatttac aacaatttag cctggtatca gcagaaacca 120
gggcagcctc ccaagctcct gatctattat gcatccactc tggcatctgg ggtcccaccg 180
cggttcagcg gcagtggatc tgggacagag tatactctca ccatcagcga cctcgagtgt 240
gacgatgctg ccacttacta ctgtcaaaac aatgctggta tttatggtgg ttatggtcat 300
ggtttcggcg gagggaccga ggtggtggtc aaa 333

<210> SEQ ID NO 768
<211> LENGTH: 336
<212> TYPE: DNA
<213> ORGANISM: Artificial sequence
<220> FEATURE:
<223> OTHER INFORMATION: Synthetic antibody sequence

<400> SEQUENCE: 768
gagctcgatc tgacccagac tccagcctcc gtagaggcag ctgtgggagg cacagtcacc 60
atcaagtgcc aggccagtca gactattggt agctacctat cctggtatca gcagaaacca 120
gggcagcgtc ccaaactcct gatctatgaa gcatccaaac tggcatctgg ggtcccatcg 180
tggttcaaag gcagtggatc tgggacagag ttcactctca ccatcagcga cctggagtgt 240
gccgatgctg ccacttacta ctgtcaaagc aattattatc gtgctggtgg taattatggt 300
ggagctttcg gcggagggac cgaggtggaa atcaaa 336

<210> SEQ ID NO 769
<211> LENGTH: 336
<212> TYPE: DNA
<213> ORGANISM: Artificial sequence
<220> FEATURE:
<223> OTHER INFORMATION: Synthetic antibody sequence

<400> SEQUENCE: 769
gagctcgatc tgacccagac tccattctcc gtgtctgcag ctgtgggagg cacagtcacc 60
atcaagtgcc aggccagtga gaccattagt aatagattag cctggtatca gcagaaacca 120
gggcagcctc ccaagctcct gatctattct gcatccactc tggaatctgg ggtcccatcg 180
cggttcaaag gcagtggatc tgggacagag ttcactctca ccatcagcga cctggagtgt 240
gccgatgctg ccacttatta ttgtcaaagt attcgtagta gtagtggtat tgttcatccg 300
aatactttcg gcggagggac cgaggtggaa atcaaa 336

<210> SEQ ID NO 770
<211> LENGTH: 333
<212> TYPE: DNA
<213> ORGANISM: Artificial sequence
<220> FEATURE:
<223> OTHER INFORMATION: Synthetic antibody sequence

<400> SEQUENCE: 770
gagctcgatc tgacccagac tccagcctct gtgtctgaac ctgtgggagg cacagtcacc 60
atcacgtgcc aggccagtca gagcattagt agttacttat cctggtatca gcagacacca 120
gggcagcctc ccaagctcct aatctacaag gcatccactc tggcatctgg ggtcccatcg 180
cggttcaaag gcagtggatc tgggacagag ttcactctca ccatcagcga cctggagtgt 240
gccgatgctg ccacttacta ctgtcaaagc tattactata ttagtgctac tgttgataat 300
actttcggcg gagggaccga ggtggaaatc aaa 333

<210> SEQ ID NO 771
<211> LENGTH: 327
<212> TYPE: DNA
<213> ORGANISM: Artificial sequence
<220> FEATURE:
<223> OTHER INFORMATION: Synthetic antibody sequence

<400> SEQUENCE: 771
gagctcgatc tgacccagac tccaacctcc gtgtctgcag ctgtgggagg cacagtcacc 60
atcaagtgcc aggccagtca gagcattagt gattacttat cctggtatca gcagaaacca 120
gggcagcctc ccaagctcct gatctacagg gcatccactc tggcatctgg ggtcccatcg 180
cggttcaaag gcagtggatc tgggacagag ttcactctca ccatcagcga cctggagtgt 240
gccgatgctg ccacttacta ttgtcaaagt aattattatg gtagtcaggg ttgtactttc 300
ggcggaggga ccgaggtgga aatcaaa 327

<210> SEQ ID NO 772
<211> LENGTH: 324
<212> TYPE: DNA
<213> ORGANISM: Artificial sequence
<220> FEATURE:
<223> OTHER INFORMATION: Synthetic antibody sequence

<400> SEQUENCE: 772
gagctcgata tgacccagac tccatcctcc gtggaggcag ctgtgggagg cacagtcacc 60
gtcaagtgcc aggtcagtca gagcattggc aatgcaatag cctggtatca gcagaaacca 120
gggcagcctc ccaagctcct gatctacaag gcatccactc tggcatctgg ggtcccatcg 180
cggttcaaag gcagtggatc tgggacagaa ttcactctca ccatcagcga cctggagtgt 240
gccgatgctg ccacttacta ctgtcaaaac tattattata gtaatactaa tagtttcggc 300
ggagggaccg aggtggtggt caaa 324

<210> SEQ ID NO 773
<211> LENGTH: 333
<212> TYPE: DNA
<213> ORGANISM: Artificial sequence
<220> FEATURE:
<223> OTHER INFORMATION: Synthetic antibody sequence

<400> SEQUENCE: 773

```
gagctcgata tgacccagac tgcatccccc gtgtctggag ctgtgggagg cacagtcacc     60

atcaagtgcc aggccagtca gaacatttat aataacatag ggtggtatca gcagaaacca    120

gggcagcctc ccaacctcct gatctatggt ccatcctatc tggcatctgg ggtcccatcg    180

cggttcaaag gcagtagatc tgggacagag tacactctca ccatcagcga cctggagtgt    240

gccgatgctg ccacttacta ctgtcaaagt gatgattgga tgagtatcag tcctgatatt    300

gttttcggcg gagggaccga ggtggaaatc aaa                                 333
```

<210> SEQ ID NO 774
<211> LENGTH: 330
<212> TYPE: DNA
<213> ORGANISM: Artificial sequence
<220> FEATURE:
<223> OTHER INFORMATION: Synthetic antibody sequence

<400> SEQUENCE: 774

```
gagctcgtga tgacccagac accatcatcc tcgtctgcag ctgtgggagg cacagtcacc     60

atcaagtgcc aggccagtca gagtattggt agtagattcg cctggtatca gcagaaacca    120

gggcagcgtc ccaagctcct gatctatgaa gcatccaaac tgccatctgg ggtcccatcg    180

cggttcaaag gcagtggatc tgggacagag ttcacgctca ccatcagcga cctggagtgt    240

gccgatgctg ccatttatta ctgtcaatgt acttattatg aaagtagtag tggtggtggt    300

ttcggcggag ggaccgaggt ggtggtcaaa                                     330
```

<210> SEQ ID NO 775
<211> LENGTH: 333
<212> TYPE: DNA
<213> ORGANISM: Artificial sequence
<220> FEATURE:
<223> OTHER INFORMATION: Synthetic antibody sequence

<400> SEQUENCE: 775

```
gagctcgtgc tgacccagac tccatcctcc gtggaggtag ctgtgggagg cgcagtcacc     60

atcaagtgcc aggccagtca tatcattact aactacttag cctggtatca gcagagacca    120

gggcagcctc ccaagctcct gatctacgat gcatcgaagc tggcatctgg ggtcccatcg    180

cggttcaaag gcagtggatc tgggacagag ttcactctca ccatcagcga cctggagtgt    240

gccgatgctg ccacttacta ctgtcaaaac tatctttatt ttagtagtgg tgattggaat    300

gttttcggcg gagggaccga ggtggtggtc aaa                                 333
```

<210> SEQ ID NO 776

<400> SEQUENCE: 776

000

<210> SEQ ID NO 777
<211> LENGTH: 339
<212> TYPE: DNA
<213> ORGANISM: Artificial sequence
<220> FEATURE:
<223> OTHER INFORMATION: Synthetic antibody sequence

<400> SEQUENCE: 777

```
gagctcgtga tgacccagac tccatcctcc gtgtctgcag ctgtgggagg cacagtcacc     60

atcaagtgcc aggccagtcc gagcattagt acttacttgt cctggtatca gcagaaacca    120

gggcagcctc ccaagcgcct gatcaacagg gcatccactc tggcatctgg ggtcccaccg    180
```

cggttcaaag gcagtggagc tgggacacag ttcactctca ccatcagcga cctggagtgt 240
gccgatgctg ccacttatta ttgtcaaaac aattaccata gtggtagtag taatggtggt 300
ggtgttgctt tcggcggagg gaccgaggtg gaaatcaaa 339

<210> SEQ ID NO 778
<211> LENGTH: 333
<212> TYPE: DNA
<213> ORGANISM: Artificial sequence
<220> FEATURE:
<223> OTHER INFORMATION: Synthetic antibody sequence

<400> SEQUENCE: 778
gagctcgtgc tgacccagac tccagcctcc gtgtctgcgg ctgtgggagg cacagtcacc 60
atcaattgcc aggccagtca gagtattggt agtggtaatt tagcctggta tcagcagaaa 120
ccagggcagc ctcccaagct cctgatctat ctggcatcca ctctggcatc tggggtccca 180
ccgcggttca aaggcagtgg atctgggaca gagttcactc tcaccatcag cgacctggag 240
tgtgacgatg ctgccactta ctactgtcaa tatacttatt atggtactac ttatgataat 300
gctttcggcg gagggaccga gctggaaatc aaa 333

<210> SEQ ID NO 779
<211> LENGTH: 330
<212> TYPE: DNA
<213> ORGANISM: Artificial sequence
<220> FEATURE:
<223> OTHER INFORMATION: Synthetic antibody sequence

<400> SEQUENCE: 779
gagctcgatc tgacccagac tccatcccca gtgtctgcag ctgtgggagg cacagtcacc 60
atcaattgcc aggccagtca gattgttgct aacggccgct tagcctggta tcagcagaaa 120
ccagggcagc ctcccaagct cctgatctat gctacatcca ctctggcatc tggggtccca 180
tcgcggttca agggcagtgg atctgggaca cagttcactc tcaccatcaa cggtgtgcag 240
tgtgacgatg ctgccactta ctactgtcaa ggcgcttata gtagtgggga tgttcggact 300
ttcggcggag ggaccgaggt ggtggtcaaa 330

<210> SEQ ID NO 780
<211> LENGTH: 324
<212> TYPE: DNA
<213> ORGANISM: Artificial sequence
<220> FEATURE:
<223> OTHER INFORMATION: Synthetic antibody sequence

<400> SEQUENCE: 780
gagctcgtgc tgacccagac accatcctcc gtgtctgcag ctgtgggagg cacagtcacc 60
atcaattgcc aggccagtga ggacattgat aggtatttag cctggtatca acagaaacca 120
gggcagcgtc ccaagctcct gatcgtcgat gcatccactc tgccatctgg ggtcccatcg 180
cggttcaaag gcagtggatc tgggacagag ttcactctca ccatcagcga cctggagtgt 240
gccgatggtg ccacttacta ctgtcaaagc tatgataata gtgataataa tggtttcggc 300
ggagggaccg aggtggtggt caaa 324

<210> SEQ ID NO 781
<211> LENGTH: 333
<212> TYPE: DNA
<213> ORGANISM: Artificial sequence
<220> FEATURE:

<223> OTHER INFORMATION: Synthetic antibody sequence

<400> SEQUENCE: 781
gagctcgatc tgacccagac tccatcctcc gtggaggtag ctgtgggagg cgcagtcacc 60
atcaagtgcc aggccagtca tatcattact aactacttag cctggtatca gcagagacca 120
gggcagcctc ccaagctcct gatctacgat gcatcgaagc tggcatctgg ggtcccatcg 180
cggttcaaag gcagtggatc tgggacagag ttcactctca ccatcagcga cctggagtgt 240
gccgatgctg ccacttacta ctgtcaaaac tatctttatt ttagtagtgg tgattggaat 300
gttttcggcg gagggaccga ggtggtggtc aaa 333

<210> SEQ ID NO 782
<211> LENGTH: 333
<212> TYPE: DNA
<213> ORGANISM: Artificial sequence
<220> FEATURE:
<223> OTHER INFORMATION: Synthetic antibody sequence

<400> SEQUENCE: 782
gagctcgatc tgacccagac tccagcctcc gtgtctgcag ctgtgggagg cacagtcacc 60
atcaattgcc aggccagtga gagcattggc agtgcattag cctggtatca gcagaaacca 120
gggcagcctc ccaagctcct gatctattct gcatccgctc tggcatctgg ggtcccatcg 180
cggttcaaag gcagtggatc tgggacagag tacactctca ccatcagcga cttggagtgt 240
gccgatgctg ccacttatta ctgtcaaagt tattatggaa gtggtacgac tgctttagat 300
actttcggcg gagggaccga ggtggaaatc aaa 333

<210> SEQ ID NO 783
<211> LENGTH: 333
<212> TYPE: DNA
<213> ORGANISM: Artificial sequence
<220> FEATURE:
<223> OTHER INFORMATION: Synthetic antibody sequence

<400> SEQUENCE: 783
gagctcgatc tgacccagac tccaggctcc gtggaggcag ctgtgggagg cacagtcacc 60
atcaagtgcc aggccggtca gagcatttac aactacttat cctggtatca gcagaaacca 120
gggcagcctc ccaagctcct gatctattct gcatccactc tggaatctgg ggtcccaccg 180
cggttcagcg gcagtggatc tgggacagag ttcactctca ccatcagcga cctggagtgt 240
gccgatgctg ccacttactc ctgtcaaaac aattatggta ttggtagtaa ttatggtcct 300
ggtttcggcg gagggaccga ggtggaaatc aaa 333

<210> SEQ ID NO 784
<211> LENGTH: 327
<212> TYPE: DNA
<213> ORGANISM: Artificial sequence
<220> FEATURE:
<223> OTHER INFORMATION: Synthetic antibody sequence

<400> SEQUENCE: 784
gagctcgatc tgacccagac tccagcctcc gtggaggcag ctgtgggagg cacagtcacc 60
atcaagtgcc aggccagtct gaacattaat agttggttgg cctggtatca gcagaaacca 120
gggcagcctc ccaagctcct gatctcttat acatccagtc tggcatctgg ggtcccatcg 180
cggttcaaag gcagtggatc tgggacagag tacactctca ccatcaacga cctggagtgt 240
gccgatgctg ccacttacta ctgtcaaacc acatattttg gtactaatgg tggtggtttc 300
ggcggaggga ccgaggtgga aatcaaa 327

<210> SEQ ID NO 785
<211> LENGTH: 321
<212> TYPE: DNA
<213> ORGANISM: Artificial sequence
<220> FEATURE:
<223> OTHER INFORMATION: Synthetic antibody sequence

<400> SEQUENCE: 785
gagctcgtga tgacccagac accatcctcc gtggaggcag ctgtgggagg cacagtcacc 60
aacaagtgcc aggccagtga ggacatttat agcaatttag cctggtatca gcagaaacca 120
gggcagcctc ccaagctcct gatctatggt gcaaccactc tggcatctgg ggtcccatcg 180
cggttcaaag gcagtggatc tgggacagag ttcactctca ccatcagcga cctggagtgt 240
gccgatgctg ccacttacta ttgtcaggcc gaaagtaatg atgtttgggc tttcggcgga 300
gggaccgagg tggtggtcaa a 321

<210> SEQ ID NO 786
<211> LENGTH: 330
<212> TYPE: DNA
<213> ORGANISM: Artificial sequence
<220> FEATURE:
<223> OTHER INFORMATION: Synthetic antibody sequence

<400> SEQUENCE: 786
gagctcgatc tgacccagac accagcctcc gtgtctgcag ctgtgggagg cacagtcacc 60
atcaagtgcc aggccagtga ggatatttat agtaatttag cctggtatca gcagaaacca 120
gggcagcctc ccaagctcct gatctacaag gcatccactc tggcatctgg ggtcccaccg 180
cggttcaaag gcagtggatc tgggacagaa tacactctca ccatcagcgg tgtgcagtgt 240
gacgatgctg ccacttacgc ctgtcagact acttattgga ctactactga tgataatcct 300
ttcggcggag ggaccgaggt ggaaatcaaa 330

<210> SEQ ID NO 787
<211> LENGTH: 336
<212> TYPE: DNA
<213> ORGANISM: Artificial sequence
<220> FEATURE:
<223> OTHER INFORMATION: Synthetic antibody sequence

<400> SEQUENCE: 787
gagctcgatc tgacccagac tccatcatcc tcgtctgcag ctgtgggagg cacagtcacc 60
atcaattgcc aggccagtca gagtgtttat aataagaact acttatcctg gtttcagcag 120
aaaccagggc agcctcccaa gctcctgatc tattatgctt ccactctggc atctggggtc 180
ccatcgcggt tcaaaggcag tggatctggg acagagttca ctctcaccat cagcgatgtg 240
gtgtgtgacg atgctgccac ttactactgt gcagcttata aaggtgttag tgatgatggt 300
atttctttcg gcggagggac cgaggtggaa atcaaa 336

<210> SEQ ID NO 788
<211> LENGTH: 339
<212> TYPE: DNA
<213> ORGANISM: Artificial sequence
<220> FEATURE:
<223> OTHER INFORMATION: Synthetic antibody sequence

<400> SEQUENCE: 788

```
gagctcgata tgacccagac tccatcctcc gtgtctgcag ctgtgggggg cacagtcacc     60

atcaagtgcc aggccagtca gagcattagt agttacttat cctggtatca gcagaaacca    120

gggcagcctc ccaagcgcct gatctacaag gcatccactc tgccatctgg ggtcccaccg    180

cggtttaaag gcagtggatc tgggacagag ttcactctca ccatcagcga cctggagtgt    240

gccgatgctg ccacttacta ctgtcaaaac aattatcata gtggtagtag taatggtggt    300

ggttttgctt tcggcggagg gacccaggtg gaaatcaaa                            339
```

```
<210> SEQ ID NO 789
<211> LENGTH: 336
<212> TYPE: DNA
<213> ORGANISM: Artificial sequence
<220> FEATURE:
<223> OTHER INFORMATION: Synthetic antibody sequence

<400> SEQUENCE: 789

gagctcgatc tgacccagac tccagcctcc gtggaggcag ctgtgagagg cacagtcacc     60

atcaagtgcc aggccagtca gagcattagt tactacttag cctggtatca gcagaaacca    120

gggcagcctc ccaaggtcct gatctacaag gcatccactc tggcatctgg ggtcccaccg    180

cggttcaaag gcagtggatt tgggacagag ttcactctca ccatcagcga cctggagtgt    240

gccgatgctg ccacttatta ctgtcaaagc acttatggta gggataataa tgatcttttt    300

ttcgctttcg gcggagggac cgaggtggaa atcaaa                               336
```

```
<210> SEQ ID NO 790
<211> LENGTH: 336
<212> TYPE: DNA
<213> ORGANISM: Artificial sequence
<220> FEATURE:
<223> OTHER INFORMATION: Synthetic antibody sequence

<400> SEQUENCE: 790

gagctcgatc tgacccagac tccagcctcc gtgtctgcag ctgtgggagg cacggtcacc     60

atcaagtgcc aggccagtca gagtattagt agtagctact tagcctggta tcagcagaaa    120

ccagggcagc ctcccaagct cctgatctat tctgcgtcca gtacggcatc tggggtccca    180

tcgcggttca aaggcagtgg atctgggaca cagttcactc tcaccatcag cgacctggag    240

tgtgccgatg ctgccactta ctactgtcaa agcacttata ttagtagtag taagtatggt    300

gctgttttcg gcggagggac cgagctggaa atcaaa                               336
```

```
<210> SEQ ID NO 791
<211> LENGTH: 330
<212> TYPE: DNA
<213> ORGANISM: Artificial sequence
<220> FEATURE:
<223> OTHER INFORMATION: Synthetic antibody sequence

<400> SEQUENCE: 791

gagctcgtga tgacccagac tgcatcgccc gtgtctgcag ctgtgggagg cacagtcacc     60

atcagttgcc agtccagtca gagtgtttat agtaacaact ggttatcctg gtatcagcag    120

aaaccagggc agcctcccaa acgcctgatc tacaaggcat ccactctgga aactggggtc    180

ccatcgcggt tcaaaggcag tggatctggg aaacagttca ctctcaccat cagcgacctg    240

gagtgtgacg atgctgccac ttattactgt gcaggcgggt atagtggtga tctttatgct    300

ttcggcggag ggaccgaggt ggtggtcaaa                                      330
```

<210> SEQ ID NO 792
<211> LENGTH: 339
<212> TYPE: DNA
<213> ORGANISM: Artificial sequence
<220> FEATURE:
<223> OTHER INFORMATION: Synthetic antibody sequence

<400> SEQUENCE: 792
gagctcgata tgacccagac tccatctccc gtgtctgcag ctgtgggagg ctcagtcacc 60
atcagttgcc aggccagtca gactatttat aataacaaaa atttggcctg gtatcagcag 120
aaaccagggc aacctcccaa gctcctgatc taccaggcat ccaaactggc atctggggtc 180
tcatcgcggt tcagtggcag tggatctggg acacagttca ctctcaccat cagcggcgtg 240
cagtgtgacg atgctgccac ttactactgt caaggcgaat ttagttgtag tagtggtgat 300
tgtactactt tcggcggagg gaccgaggtg gtggtcaaa 339

<210> SEQ ID NO 793
<211> LENGTH: 330
<212> TYPE: DNA
<213> ORGANISM: Artificial sequence
<220> FEATURE:
<223> OTHER INFORMATION: Synthetic antibody sequence

<400> SEQUENCE: 793
gagctcgata tgacccagac tccagcctcc gtgtctgaac ctgtgggagg cacagtcacc 60
atcaagtgcc aggccagtga gaacatttat agctacttag cctggtatca gcagaaacca 120
gggcagcctc ccaagctcct gatctattct gcatccactc tggcatctgg ggtcccatcg 180
cggttcaaag gcagtggatc tgggacacag ttcactctca ccatcagcga cctggagtgt 240
gccgatgctg ccacttacta ttgtcaatat agtaatttta gggtgaatga tcctagtgtt 300
ttcggcggag ggaccgaggt ggaaatcaaa 330

<210> SEQ ID NO 794
<211> LENGTH: 351
<212> TYPE: DNA
<213> ORGANISM: Artificial sequence
<220> FEATURE:
<223> OTHER INFORMATION: Synthetic antibody sequence

<400> SEQUENCE: 794
gagctcgatc tgacccagac tccagcctcc gtgtctgcag ctgtgggagg cacagtcacc 60
atcagttgcc agtccagtca gagcgttcat catagtcaga ccgttcataa taatcaatgg 120
ttagcctggt atcagcagaa accagggcag cctcccaagc tcctgatcta tgatgcatcc 180
aaactggcat ctggggtccc atcgcggttc acaggtagtg gatctgggac acagttctct 240
ctcaccatca gtgcagtgca gtgtgacgat gctgccactt actactgtca aggcggttat 300
agttatggtg atgtgtatgg tttcggcgga gggaccgagc tggaaatcaa g 351

<210> SEQ ID NO 795
<211> LENGTH: 342
<212> TYPE: DNA
<213> ORGANISM: Artificial sequence
<220> FEATURE:
<223> OTHER INFORMATION: Synthetic antibody sequence

<400> SEQUENCE: 795
gagctcgtgc tgacccagac tccatcttcc acgtctgcgg ctgtgggagg cacagtcacc 60
atcaattgcc aggccagtca aagtgttgat aacaacaaac aattatcctg gtatcagcag 120

```
aaaccagggc agcctcccaa gcaactgatc tactctgcat ccaaactggc atctggggtc    180

ccatcgcggt tcaaaggcag tggatctggg acacagttca ctctcaccat cagcgacctg    240

gagtgtgacg atgctgccac ttactactgt gcaggctatt attatagtgg tagtgccact    300

gatgcgtggg ctttcggcgg agcgaccgag gtggaaatca ac                       342


<210> SEQ ID NO 796
<211> LENGTH: 336
<212> TYPE: DNA
<213> ORGANISM: Artificial sequence
<220> FEATURE:
<223> OTHER INFORMATION: Synthetic antibody sequence

<400> SEQUENCE: 796

gagctcgtga tgacccagac tccatcctcc gtgtctgcag ctgtgggaga cacactcacc     60

atcaattgcc aggccagtga gaccattagt aatagattag cctggtatca acagaaacca    120

gggcagcctc ccaagctcct gatctattct gcatccactc tggaatctgg ggtcccatcg    180

cggttcagag gcagtggatc tgggacacag ttcactctca ccataagtga cctggagtgt    240

gccgatgctg ccacttatta ttgtcaaagt attcgtagta gtagtggtgt tgtgcatcca    300

aatactttcg gcggagggac cgaggtggaa atcaaa                              336


<210> SEQ ID NO 797
<211> LENGTH: 330
<212> TYPE: DNA
<213> ORGANISM: Artificial sequence
<220> FEATURE:
<223> OTHER INFORMATION: Synthetic antibody sequence

<400> SEQUENCE: 797

gagctcgatc tgacccagac tccatcctcc gtggaggcag ctgtgggagg cacagtcacc     60

atcaagtgcc aggccagtca gaccatttat accaatttag cctggtatca gcagaaacca    120

gggcagcctc ccaacctcct gatctatgct gcatccactc tggcatctgg ggtctcatcg    180

cggttcaaag gcagtggatc cgggacagag ttcactctca ccatcagcga cctggagtgt    240

gccgatgctg ccacttacta ctgtcaaagc tattatggta gtagtactac tggtaatggt    300

ttcggcggag ggaccgaggt ggaaatcaaa                                     330


<210> SEQ ID NO 798
<211> LENGTH: 336
<212> TYPE: DNA
<213> ORGANISM: Artificial sequence
<220> FEATURE:
<223> OTHER INFORMATION: Synthetic antibody sequence

<400> SEQUENCE: 798

gagctcgtgc tgacccagac accatcttcc aagtctgtcg ctgtgggaga cacagtcacc     60

atcaattgcc aggccagtga taatgtttat agtaataact acacatcctg gtttcagcag    120

aaaccagggc agcctcccaa acaactgctc tattatgcgg cctatcgggc atctggggtc    180

ccatcgcggt tcaaaggcag tggatctggg acagagttca ctctctccat cagcgatgtg    240

gtgtgtgacg atgctgccac ttactattgt tcaggccata aagattatag tgatgatggt    300

agtactttcg gcggagggac cgaggtggaa atcaaa                              336


<210> SEQ ID NO 799
<211> LENGTH: 336
<212> TYPE: DNA
<213> ORGANISM: Artificial sequence
```

<220> FEATURE:
<223> OTHER INFORMATION: Synthetic antibody sequence

<400> SEQUENCE: 799
gagctcgtgc tgacccagac accatcttcc aagtctgtcg ctgtgggaga cacagtcacc 60
atcaattgcc aggccagtga taatgtttat agtaataact acacatcctg gtttcagcag 120
aaaccagggc agcctcccaa acaactgctc tattatgcgg cctatcgggc atctggggtc 180
ccatcgcggt tcaaaggcag tggatctggg acagagttca ctctctccat cagcgatgtg 240
gtgtgtgacg atgctgccac ttactattgt tcaggccata aagattatag tgatgatggt 300
agtactttcg gcggagggac cgaggtggaa atcaaa 336

<210> SEQ ID NO 800
<211> LENGTH: 324
<212> TYPE: DNA
<213> ORGANISM: Artificial sequence
<220> FEATURE:
<223> OTHER INFORMATION: Synthetic antibody sequence

<400> SEQUENCE: 800
gagctcgtga tgacccagac accagcctcc gtgtctgcag ctgtgggagg cacagtcacc 60
atcaattgcc aggccagtga ggatattagt agtaatttag cctggtatca gcagaaacca 120
gggcagcctc ccaagctcct gatcagtggt gcatccactc tggcatctgg ggtcccatcg 180
cggttcaaag gcagtggatc tgggacagac ttcactctca ccatgagcga cctggagtgt 240
gccgatgctg ccacttacta ctgtcaaggc gcttattatg gtagtagtta tggtttcggg 300
ggagggaccg aggtggtggt caaa 324

<210> SEQ ID NO 801
<211> LENGTH: 336
<212> TYPE: DNA
<213> ORGANISM: Artificial sequence
<220> FEATURE:
<223> OTHER INFORMATION: Synthetic antibody sequence

<400> SEQUENCE: 801
gagctcgtgc tgacccagac accatccccc gtgtctgcag ctgtgggagg cacagtcacc 60
atcaattgcc aggccagtca gagcattagc aatgaattat cctggtatca acagaaacca 120
gggcagcctc ccaagctcct gatctatctg gcatccactc tggattctgg ggtcccatcg 180
cggttcaaag gcagtggatc tgggacccag ttcactctca ccatcagcga cctggagtgt 240
gccgacgctg ccacttacta ctgtcaaagt cattattatg gtggtagtag tgattatgga 300
tgggctttcg gcggagggac cgaggtggtg gtcaaa 336

<210> SEQ ID NO 802
<211> LENGTH: 330
<212> TYPE: DNA
<213> ORGANISM: Artificial sequence
<220> FEATURE:
<223> OTHER INFORMATION: Synthetic antibody sequence

<400> SEQUENCE: 802
gagctcgata tgacccagac tccatcttcc acgtctgcag ctgtgggagg cacagtcacc 60
atcaagtgcc aggccagtca aagtgtttac aataacaacc aattatcctg gtttcagcag 120
aaaccagggc agcctcccaa acgcctgatc tatggtgcat ccactctgga atctggggtc 180
ccatcgcggt tcagcggcag tggatctggg acacagttca ctctcaccat tagtgacctg 240
gagtgtgacg atgctgccac ttactactgt caaggcgctg ttagtagtga ttactatcct 300
ttcggcggag ggaccgaggt ggaaatcaaa 330

<210> SEQ ID NO 803
<211> LENGTH: 330
<212> TYPE: DNA
<213> ORGANISM: Artificial sequence
<220> FEATURE:
<223> OTHER INFORMATION: Synthetic antibody sequence

<400> SEQUENCE: 803
gagctcgata tgacccagac accagcctcc gtgtctgaac ctgtgggagg cacagtcacc 60
atcaagtgcc aggccagtca gagtattggt agctatttag cctggtatca gcagaaacca 120
gggcagcctc ccaagctcct ggccttttat gcttccactc tgaagtctgg ggtcccaccg 180
cggttcaaag gcagtggatc tgggacagag ttcactctca ccatcagcga cctggagtgt 240
gccgatgctg ccacttatta ctgtcaaagt aatcgtctta gtagtagtga cgttaatgct 300
ttcggcggag ggaccgaggt ggaaatcaaa 330

<210> SEQ ID NO 804
<211> LENGTH: 330
<212> TYPE: DNA
<213> ORGANISM: Artificial sequence
<220> FEATURE:
<223> OTHER INFORMATION: Synthetic antibody sequence

<400> SEQUENCE: 804
gagctcgtgc tgacccagac tgcatccccc gtgtctggag ctgtgggagg cacagtcacc 60
atcaagtgcc aggccagtca gaacatttac agcaatttag cctggtatca gcagaaacca 120
gggcagcctc ccaagctcct gatctattct gcatccaaac tggcatctgg ggtcccatcg 180
cggttcaaag gcagtggatc tgggacagag tacactctca ccatcagcgg cgtgcagtgt 240
gaagatgctg ccacttacta ctgtcaaagc tattattata ctgctagtgc tgatactact 300
ttcggcggag ggaccgaggt ggaaatcaaa 330

<210> SEQ ID NO 805
<211> LENGTH: 324
<212> TYPE: DNA
<213> ORGANISM: Artificial sequence
<220> FEATURE:
<223> OTHER INFORMATION: Synthetic antibody sequence

<400> SEQUENCE: 805
gagctcgtgc tgacccagac tccatcctcc gtggaggcag ctgtgggagg cacagtcacc 60
atcaagtgcc aggccagtca gagcattggt agctacttag cctggtatca gcagaaacca 120
gggcagcctc ccaagctcct gatctacaag gcatccactc tgtcatctgg ggtctcatca 180
cggtacaaag gcagtggatc tgggacagag ttcactctca ccatcagcga cctggagtgt 240
gacgatgctg ccacttacta ctgtcaatat actagttata gtagtggtgg ggctttcggc 300
ggagggaccg aggtggtggt caaa 324

<210> SEQ ID NO 806
<211> LENGTH: 330
<212> TYPE: DNA
<213> ORGANISM: Artificial sequence
<220> FEATURE:
<223> OTHER INFORMATION: Synthetic antibody sequence

<400> SEQUENCE: 806

```
gagctcgata tgacccagac tccatcctcc gtggaggcag ctgtgggagg cacagtcacc     60

atcaagtgcc aggccagtca gaccatttat accaatttag cctggtatca gcagaaacca    120

gggcagcctc ccaacctcct gatctatgct gcatccactc tggcatctgg ggtctcatcg    180

cggttcaaag gcagtggatc cgggacagag ttcactctca ccatcagcga cctggagtgt    240

gccgatgctg ccacttacta ctgtcaaagc tattatggta gtagtactac tggtaatggt    300

ttcggcggag ggaccgaggt ggaaatcaac                                      330
```

<210> SEQ ID NO 807
<211> LENGTH: 339
<212> TYPE: DNA
<213> ORGANISM: Artificial sequence
<220> FEATURE:
<223> OTHER INFORMATION: Synthetic antibody sequence

<400> SEQUENCE: 807

```
gagctcgtga tgacccagac tccagcctct gtgtctgaac ctgtgggagg cacagtcacc     60

atcaagtgcc aggccagtca gagcattagt agttacttat cctggtatca gcagaaacca    120

gggcagcctc ccaagcgcct gatctacaag gcttccactc tggcatctgg ggtcccatcg    180

cggttcaaag gcagtggatc tgggacagag ttcactctca ccatcagcgg cgtgcagtgt    240

gccgatgctg ccacttacta ctgtcaaaac aattatcata gtggtagtag taatggtggt    300

ggttttgctt tcggcggagg gaccgaggtg gaaatcaaa                            339
```

<210> SEQ ID NO 808
<211> LENGTH: 336
<212> TYPE: DNA
<213> ORGANISM: Artificial sequence
<220> FEATURE:
<223> OTHER INFORMATION: Synthetic antibody sequence

<400> SEQUENCE: 808

```
gagctcgtgc tgacccagac tccatcttcc aagtctgtcg ctgtgggaga cacagtcacc     60

atcaattgcc aggccagtga gagtgtttat ggtaacaacc gttgctcctg gtatcagcag    120

aaaccagggc agcctcccaa gctcctgatc taccaggctt ccactctggc ctctggggtc    180

ccatcgcggt tcagcggcag tggatctggg acacagttca ctctcaccat cagcgatgtg    240

gtgtgtgacg atgctgccac ttactactgt gcaggacata aaggaactac taatgatggg    300

aatgatttcg gcggagggac cgaggtggaa atcaaa                               336
```

<210> SEQ ID NO 809
<211> LENGTH: 333
<212> TYPE: DNA
<213> ORGANISM: Artificial sequence
<220> FEATURE:
<223> OTHER INFORMATION: Synthetic antibody sequence

<400> SEQUENCE: 809

```
gagctcgata tgacccagac tccagcctcc gtgtctgcag ctgtgggagg cacagtcacc     60

atcaagtgcc aggccagtca gagcattacc aatgcattag cctggtatca acagaaacca    120

gggcagcctc ccaagctcct gatctacagg gcatccactc tggcatctgg ggtctcatcg    180

cggttcaaag gcagcggatc tgggacagag ttcactctca ccatcagtga ccttgagtgt    240

gccgatgctg ccacttacta ttgtcaatgt agttattatg gtagtactta ttttgggagt    300

cctttcggcg gagggaccga ggtggaaatc aaa                                  333
```

<210> SEQ ID NO 810
<211> LENGTH: 336
<212> TYPE: DNA
<213> ORGANISM: Artificial sequence
<220> FEATURE:
<223> OTHER INFORMATION: Synthetic antibody sequence

<400> SEQUENCE: 810
gagctcgtgc tgacccagac tccatcctcc gtgtctgaac ctgtgggagg cacagtcacc 60
atcaagtgcc aggccagtca gagcattagt agtagctact tagcctggta tcagcagaaa 120
ccagggcagc ctcccaagtt cctgatctat tctgcatcca ctctggcatc tggggtccca 180
tcgcggttca aaggcagtgg atctgggaca gagttcactc tcaccatcag cgacctggag 240
tgtgccgatg ctgccactta ctactgtcaa agcacttata ttagtagtag taattatggt 300
gctgctttcg gcggagggac cgaggtggaa atcaaa 336

<210> SEQ ID NO 811
<211> LENGTH: 327
<212> TYPE: DNA
<213> ORGANISM: Artificial sequence
<220> FEATURE:
<223> OTHER INFORMATION: Synthetic antibody sequence

<400> SEQUENCE: 811
gagctcgatc tgacccagac tccatcctcc gtggaggcag ctgtgggagg cacagtcacc 60
atcaagtgcc aggccagtca gagcattggt agtaatttag cctggtatca gcagaaacca 120
gggcagcctc ccaaggtcct gatctacaag gcatccactc tggcatctgg ggtcccatcg 180
cggttcaaag gcagtggatc tgggacacag ttcactctca ccatcagcga cctggagtgt 240
gccgatgctg ccacttatta ctgtcaaaac aataattatt ggagtaatgg taaccatttc 300
ggcggaggga ccgaggtggt ggtcaaa 327

<210> SEQ ID NO 812
<211> LENGTH: 336
<212> TYPE: DNA
<213> ORGANISM: Artificial sequence
<220> FEATURE:
<223> OTHER INFORMATION: Synthetic antibody sequence

<400> SEQUENCE: 812
gagctcgtgc tgacccagac tccatcttcc aagtctgtcg ctgtgggaga cacagtcacc 60
atcaattgcc aggccagtga gaatgtttat agtaataact acacatcctg gtttcagcag 120
aaaccagggc agcctcccaa acaactgctc tattatgcgg cctatcgggc atctggggtc 180
ccatcgcggt tcaaaggcag tggatctggg acagagttca ctctctccat cagcgatgtg 240
gtgtgtgacg atgctgccac ttactattgt tcaggccata aagattatag tgatgatggt 300
agtactttcg gcggagggac cgaggtggtg gtcaaa 336

<210> SEQ ID NO 813
<211> LENGTH: 330
<212> TYPE: DNA
<213> ORGANISM: Artificial sequence
<220> FEATURE:
<223> OTHER INFORMATION: Synthetic antibody sequence

<400> SEQUENCE: 813
gagctcgatc tgacccagac tgcatccccc gtgtctggag ctgtgggagg cacagtcacc 60
atcaagtgcc aggccagtca gagcattgct agcgacttag cctggtatca gcagaaacca 120

```
gggcagcctc ccaacctcct gatctatgct gcatccactc tggcatctgg ggtctcatcg    180

cggttcaaag gcagtggatc cgggacagag ttcactctca ccatcagcga cctggagtgt    240

gccgatgctg ccacttacta ctgtcaaagc tattatggta gtagtactac tggtaatggt    300

ttcggcggag ggaccgaggt ggtggtcaaa                                     330


<210> SEQ ID NO 814
<211> LENGTH: 113
<212> TYPE: PRT
<213> ORGANISM: Artificial sequence
<220> FEATURE:
<223> OTHER INFORMATION: Synthetic antibody sequence

<400> SEQUENCE: 814

Glu Leu Asp Met Thr Gln Thr Pro Ala Ser Val Glu Ala Ala Val Gly
1               5                   10                  15

Gly Thr Val Thr Ile Lys Cys Gln Ala Ser Gln Asn Ile Tyr Ser Tyr
            20                  25                  30

Leu Val Trp Tyr Gln Gln Lys Pro Gly Gln Pro Pro Lys Leu Leu Ile
        35                  40                  45

Ser Lys Ala Ser Thr Leu Ala Ser Gly Val Ser Ser Arg Phe Lys Gly
    50                  55                  60

Ser Gly Ser Gly Thr Glu Phe Thr Leu Thr Ile Asn Asp Leu Glu Cys
65                  70                  75                  80

Ala Asp Ala Ala Thr Tyr Tyr Cys Gln Thr Asn Tyr Phe Ser Ser Thr
                85                  90                  95

Ser His Phe Gly Val Phe Thr Phe Gly Gly Gly Thr Glu Leu Glu Ile
            100                 105                 110

Lys


<210> SEQ ID NO 815
<211> LENGTH: 113
<212> TYPE: PRT
<213> ORGANISM: Artificial sequence
<220> FEATURE:
<223> OTHER INFORMATION: Synthetic antibody sequence

<400> SEQUENCE: 815

Glu Leu Val Leu Thr Gln Thr Pro Ser Pro Val Ser Ala Val Val Gly
1               5                   10                  15

Gly Ser Val Thr Ile Asn Cys Gln Ser Ser Gln Ser Leu Tyr Asn Ala
            20                  25                  30

Asn Asp Leu Ser Trp Tyr Gln Gln Lys Pro Gly Gln Pro Pro Lys Gln
        35                  40                  45

Leu Ile Tyr Trp Ala Ser Thr Leu Ala Ser Gly Val Pro Ser Arg Phe
    50                  55                  60

Lys Gly Ser Gly Ser Gly Thr Gln Phe Thr Leu Ser Ile Ser Asp Val
65                  70                  75                  80

Gln Cys Asp Asp Ala Ala Thr Tyr Tyr Cys Leu Gly Glu Phe Ser Cys
                85                  90                  95

Ser Ser Phe Asp Cys His Val Phe Gly Gly Gly Thr Glu Val Val Val
            100                 105                 110

Lys


<210> SEQ ID NO 816
<211> LENGTH: 110
<212> TYPE: PRT
```

```
<213> ORGANISM: Artificial sequence
<220> FEATURE:
<223> OTHER INFORMATION: Synthetic antibody sequence

<400> SEQUENCE: 816

Glu Leu Asp Met Thr Gln Thr Pro Ser Ser Val Ser Ala Ala Val Gly
1               5                   10                  15

Asp Thr Val Thr Ile Lys Cys Gln Ala Ser Gln Ser Ile Tyr Arg Tyr
            20                  25                  30

Leu Ala Trp Tyr Gln Gln Lys Pro Gly Gln Arg Pro Ser Leu Leu Ile
        35                  40                  45

Tyr Tyr Gly Ser Asp Leu Ala Ser Gly Val Pro Ser Arg Phe Ser Gly
    50                  55                  60

Ser Gly Ser Gly Thr Glu Phe Thr Leu Thr Ile Ser Asp Leu Glu Cys
65                  70                  75                  80

Ala Asp Ala Ala Ser Tyr Tyr Cys Gln Thr Thr Tyr Asp Asp Tyr His
                85                  90                  95

Asn Gly Trp Ala Phe Gly Gly Gly Thr Asn Val Glu Ile Asn
            100                 105                 110


<210> SEQ ID NO 817
<211> LENGTH: 110
<212> TYPE: PRT
<213> ORGANISM: Artificial sequence
<220> FEATURE:
<223> OTHER INFORMATION: Synthetic antibody sequence

<400> SEQUENCE: 817

Glu Leu Asp Leu Thr Gln Thr Pro Ser Ser Val Ser Ala Ala Val Gly
1               5                   10                  15

Gly Thr Val Thr Ile Ser Cys Gln Ala Ser Gln Ser Val Tyr Gly Asn
            20                  25                  30

Asn Arg Leu Ala Trp Tyr His Gln Lys Pro Gly Gln Pro Pro Lys Arg
        35                  40                  45

Leu Ile Tyr Leu Ala Ser Thr Leu Asp Ser Gly Val Pro Ser Arg Phe
    50                  55                  60

Lys Gly Ala Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Gly Tyr Ala Gly
                85                  90                  95

Asn Phe Asn Ala Phe Gly Gly Gly Thr Glu Val Glu Ile Lys
            100                 105                 110


<210> SEQ ID NO 818
<211> LENGTH: 111
<212> TYPE: PRT
<213> ORGANISM: Artificial sequence
<220> FEATURE:
<223> OTHER INFORMATION: Synthetic antibody sequence

<400> SEQUENCE: 818

Glu Leu Asp Leu Thr Gln Thr Pro Ala Ser Val Ser Ala Ala Val Gly
1               5                   10                  15

Gly Thr Val Thr Ile Lys Cys Gln Ala Ser Gln Asn Ile Val Ser Asn
            20                  25                  30

Leu Ala Trp Tyr Gln Gln Lys Pro Gly Gln Arg Pro Lys Leu Leu Ile
        35                  40                  45

Tyr Tyr Ala Ser Thr Leu Ala Ser Gly Val Pro Ser Arg Phe Lys Gly
    50                  55                  60
```

```
Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Asn Asn Ala Gly Ile Tyr Gly
                85                  90                  95

Asn Tyr Gly His Gly Phe Gly Gly Gly Thr Glu Leu Glu Ile Lys
            100                 105                 110


<210> SEQ ID NO 819
<211> LENGTH: 109
<212> TYPE: PRT
<213> ORGANISM: Artificial sequence
<220> FEATURE:
<223> OTHER INFORMATION: Synthetic antibody sequence

<400> SEQUENCE: 819

Glu Leu Asp Leu Thr Gln Thr Pro Ser Ser Val Glu Ala Ala Val Gly
1               5                   10                  15

Gly Thr Val Thr Ile Lys Cys Gln Ala Ser Gln Ser Ile Tyr Asn Tyr
            20                  25                  30

Leu Ala Trp Tyr Gln Gln Lys Pro Gly His Ser Pro Lys Leu Leu Ile
        35                  40                  45

Tyr Asp Val Ser Lys Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Tyr Tyr Gly Asn Thr Val
                85                  90                  95

Ser Phe Thr Phe Gly Gly Gly Thr Glu Val Glu Ile Lys
            100                 105


<210> SEQ ID NO 820
<211> LENGTH: 110
<212> TYPE: PRT
<213> ORGANISM: Artificial sequence
<220> FEATURE:
<223> OTHER INFORMATION: Synthetic antibody sequence

<400> SEQUENCE: 820

Glu Leu Val Met Thr Gln Thr Pro Ser Ser Val Ser Ala Ala Val Gly
1               5                   10                  15

Gly Thr Val Thr Ile Ser Cys Gln Ala Ser Gln Ser Val Tyr Asn Asn
            20                  25                  30

Asn Asn Leu Ala Trp Tyr Gln Gln Lys Pro Gly Gln Pro Pro Lys Arg
        35                  40                  45

Leu Ile Tyr Ser Ala Ser Thr Leu Asp Ser Gly Val Pro Ser Arg Phe
    50                  55                  60

Ser Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Gly Tyr Thr Tyr
                85                  90                  95

Asn Ile Asn Ile Phe Gly Gly Gly Thr Glu Val Glu Ile Lys
            100                 105                 110


<210> SEQ ID NO 821
<211> LENGTH: 111
<212> TYPE: PRT
<213> ORGANISM: Artificial sequence
<220> FEATURE:
<223> OTHER INFORMATION: Synthetic antibody sequence
```

<400> SEQUENCE: 821

```
Glu Leu Asp Leu Thr Gln Thr Pro Ala Ser Val Ser Glu Pro Val Gly
1               5                   10                  15

Gly Thr Val Thr Ile Lys Cys Gln Ala Ser Gln Asn Ile Tyr Asn Asn
            20                  25                  30

Leu Ala Trp Tyr Gln Gln Lys Pro Gly Gln Pro Pro Lys Leu Leu Ile
        35                  40                  45

Tyr Tyr Ala Ser Thr Leu Ala Ser Gly Val Pro Pro Arg Phe Ser Gly
    50                  55                  60

Ser Gly Ser Gly Thr Glu Tyr Thr Leu Thr Ile Ser Asp Leu Glu Cys
65                  70                  75                  80

Asp Asp Ala Ala Thr Tyr Tyr Cys Gln Asn Asn Ala Gly Ile Tyr Gly
                85                  90                  95

Gly Tyr Gly His Gly Phe Gly Gly Gly Thr Glu Val Val Val Lys
            100                 105                 110
```

<210> SEQ ID NO 822
<211> LENGTH: 112
<212> TYPE: PRT
<213> ORGANISM: Artificial sequence
<220> FEATURE:
<223> OTHER INFORMATION: Synthetic antibody sequence

<400> SEQUENCE: 822

```
Glu Leu Asp Leu Thr Gln Thr Pro Ala Ser Val Glu Ala Ala Val Gly
1               5                   10                  15

Gly Thr Val Thr Ile Lys Cys Gln Ala Ser Gln Thr Ile Gly Ser Tyr
            20                  25                  30

Leu Ser Trp Tyr Gln Gln Lys Pro Gly Gln Arg Pro Lys Leu Leu Ile
        35                  40                  45

Tyr Glu Ala Ser Lys Leu Ala Ser Gly Val Pro Ser Trp Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Asn Tyr Tyr Arg Ala Gly
                85                  90                  95

Gly Asn Tyr Gly Gly Ala Phe Gly Gly Gly Thr Glu Val Glu Ile Lys
            100                 105                 110
```

<210> SEQ ID NO 823
<211> LENGTH: 112
<212> TYPE: PRT
<213> ORGANISM: Artificial sequence
<220> FEATURE:
<223> OTHER INFORMATION: Synthetic antibody sequence

<400> SEQUENCE: 823

```
Glu Leu Asp Leu Thr Gln Thr Pro Phe Ser Val Ser Ala Ala Val Gly
1               5                   10                  15

Gly Thr Val Thr Ile Lys Cys Gln Ala Ser Glu Thr Ile Ser Asn Arg
            20                  25                  30

Leu Ala Trp Tyr Gln Gln Lys Pro Gly Gln Pro Pro Lys Leu Leu Ile
        35                  40                  45

Tyr Ser Ala Ser Thr Leu Glu Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80
```

```
Ala Asp Ala Ala Thr Tyr Tyr Cys Gln Ser Ile Arg Ser Ser Ser Gly
                85                  90                  95

Ile Val His Pro Asn Thr Phe Gly Gly Gly Thr Glu Val Glu Ile Lys
            100                 105                 110


<210> SEQ ID NO 824
<211> LENGTH: 111
<212> TYPE: PRT
<213> ORGANISM: Artificial sequence
<220> FEATURE:
<223> OTHER INFORMATION: Synthetic antibody sequence

<400> SEQUENCE: 824

Glu Leu Asp Leu Thr Gln Thr Pro Ala Ser Val Ser Glu Pro Val Gly
1               5                   10                  15

Gly Thr Val Thr Ile Thr Cys Gln Ala Ser Gln Ser Ile Ser Ser Tyr
            20                  25                  30

Leu Ser Trp Tyr Gln Gln Thr Pro Gly Gln Pro Pro Lys Leu Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Tyr Tyr Tyr Ile Ser Ala
                85                  90                  95

Thr Val Asp Asn Thr Phe Gly Gly Gly Thr Glu Val Glu Ile Lys
            100                 105                 110


<210> SEQ ID NO 825
<211> LENGTH: 109
<212> TYPE: PRT
<213> ORGANISM: Artificial sequence
<220> FEATURE:
<223> OTHER INFORMATION: Synthetic antibody sequence

<400> SEQUENCE: 825

Glu Leu Asp Leu Thr Gln Thr Pro Thr Ser Val Ser Ala Ala Val Gly
1               5                   10                  15

Gly Thr Val Thr Ile Lys Cys Gln Ala Ser Gln Ser Ile Ser Asp Tyr
            20                  25                  30

Leu Ser Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Asn Tyr Tyr Gly Ser Gln
                85                  90                  95

Gly Cys Thr Phe Gly Gly Gly Thr Glu Val Glu Ile Lys
            100                 105


<210> SEQ ID NO 826
<211> LENGTH: 108
<212> TYPE: PRT
<213> ORGANISM: Artificial sequence
<220> FEATURE:
<223> OTHER INFORMATION: Synthetic antibody sequence

<400> SEQUENCE: 826
```

```
Glu Leu Asp Met Thr Gln Thr Pro Ser Ser Val Glu Ala Ala Val Gly
1               5                   10                  15

Gly Thr Val Thr Val Lys Cys Gln Val Ser Gln Ser Ile Gly Asn Ala
            20                  25                  30

Ile Ala Trp Tyr Gln Gln Lys Pro Gly Gln Pro Pro Lys Leu Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Asn Tyr Tyr Tyr Ser Asn Thr
                85                  90                  95

Asn Ser Phe Gly Gly Gly Thr Glu Val Val Val Lys
            100                 105


<210> SEQ ID NO 827
<211> LENGTH: 111
<212> TYPE: PRT
<213> ORGANISM: Artificial sequence
<220> FEATURE:
<223> OTHER INFORMATION: Synthetic antibody sequence

<400> SEQUENCE: 827

Glu Leu Asp Met Thr Gln Thr Ala Ser Pro Val Ser Gly Ala Val Gly
1               5                   10                  15

Gly Thr Val Thr Ile Lys Cys Gln Ala Ser Gln Asn Ile Tyr Asn Asn
            20                  25                  30

Ile Gly Trp Tyr Gln Gln Lys Pro Gly Gln Pro Pro Asn Leu Leu Ile
        35                  40                  45

Tyr Gly Pro Ser Tyr Leu Ala Ser Gly Val Pro Ser Arg Phe Lys Gly
    50                  55                  60

Ser Arg Ser Gly Thr Glu Tyr Thr Leu Thr Ile Ser Asp Leu Glu Cys
65                  70                  75                  80

Ala Asp Ala Ala Thr Tyr Tyr Cys Gln Ser Asp Asp Trp Met Ser Ile
                85                  90                  95

Ser Pro Asp Ile Val Phe Gly Gly Gly Thr Glu Val Glu Ile Lys
            100                 105                 110


<210> SEQ ID NO 828
<211> LENGTH: 110
<212> TYPE: PRT
<213> ORGANISM: Artificial sequence
<220> FEATURE:
<223> OTHER INFORMATION: Synthetic antibody sequence

<400> SEQUENCE: 828

Glu Leu Val Met Thr Gln Thr Pro Ser Ser Ser Ser Ala Ala Val Gly
1               5                   10                  15

Gly Thr Val Thr Ile Lys Cys Gln Ala Ser Gln Ser Ile Gly Ser Arg
            20                  25                  30

Phe Ala Trp Tyr Gln Gln Lys Pro Gly Gln Arg Pro Lys Leu Leu Ile
        35                  40                  45

Tyr Glu Ala Ser Lys Leu Pro Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Ile Tyr Tyr Cys Gln Cys Thr Tyr Tyr Glu Ser Ser
                85                  90                  95
```

```
Ser Gly Gly Gly Phe Gly Gly Gly Thr Glu Val Val Val Lys
            100                 105                 110


<210> SEQ ID NO 829
<211> LENGTH: 111
<212> TYPE: PRT
<213> ORGANISM: Artificial sequence
<220> FEATURE:
<223> OTHER INFORMATION: Synthetic antibody sequence

<400> SEQUENCE: 829

Glu Leu Val Leu Thr Gln Thr Pro Ser Ser Val Glu Val Ala Val Gly
1               5                   10                  15

Gly Ala Val Thr Ile Lys Cys Gln Ala Ser His Ile Ile Thr Asn Tyr
            20                  25                  30

Leu Ala Trp Tyr Gln Gln Arg Pro Gly Gln Pro Pro Lys Leu Leu Ile
        35                  40                  45

Tyr Asp Ala Ser Lys Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Asn Tyr Leu Tyr Phe Ser Ser
                85                  90                  95

Gly Asp Trp Asn Val Phe Gly Gly Gly Thr Glu Val Val Val Lys
            100                 105                 110


<210> SEQ ID NO 830
<211> LENGTH: 113
<212> TYPE: PRT
<213> ORGANISM: Artificial sequence
<220> FEATURE:
<223> OTHER INFORMATION: Synthetic antibody sequence

<400> SEQUENCE: 830

Glu Leu Val Met Thr Gln Thr Pro Ser Ser Val Ser Ala Ala Val Gly
1               5                   10                  15

Gly Thr Val Thr Ile Lys Cys Gln Ala Ser Pro Ser Ile Ser Thr Tyr
            20                  25                  30

Leu Ser Trp Tyr Gln Gln Lys Pro Gly Gln Pro Pro Lys Arg Leu Ile
        35                  40                  45

Asn Arg Ala Ser Thr Leu Ala Ser Gly Val Pro Pro Arg Phe Lys Gly
    50                  55                  60

Ser Gly Ala Gly Thr Gln Phe Thr Leu Thr Ile Ser Asp Leu Glu Cys
65                  70                  75                  80

Ala Asp Ala Ala Thr Tyr Tyr Cys Gln Asn Asn Tyr His Ser Gly Ser
                85                  90                  95

Ser Asn Gly Gly Gly Val Ala Phe Gly Gly Gly Thr Glu Val Glu Ile
            100                 105                 110

Lys


<210> SEQ ID NO 831
<211> LENGTH: 111
<212> TYPE: PRT
<213> ORGANISM: Artificial sequence
<220> FEATURE:
<223> OTHER INFORMATION: Synthetic antibody sequence

<400> SEQUENCE: 831

Glu Leu Val Leu Thr Gln Thr Pro Ala Ser Val Ser Ala Ala Val Gly
```

```
1               5                   10                  15

Gly Thr Val Thr Ile Asn Cys Gln Ala Ser Gln Ser Ile Gly Ser Gly
            20                  25                  30

Asn Leu Ala Trp Tyr Gln Gln Lys Pro Gly Gln Pro Pro Lys Leu Leu
        35                  40                  45

Ile Tyr Leu Ala Ser Thr Leu Ala Ser Gly Val Pro Pro Arg Phe Lys
    50                  55                  60

Gly Ser Gly Ser Gly Thr Glu Phe Thr Leu Thr Ile Ser Asp Leu Glu
65                  70                  75                  80

Cys Asp Asp Ala Ala Thr Tyr Tyr Cys Gln Tyr Thr Tyr Tyr Gly Thr
                85                  90                  95

Thr Tyr Asp Asn Ala Phe Gly Gly Gly Thr Glu Leu Glu Ile Lys
            100                 105                 110


<210> SEQ ID NO 832
<211> LENGTH: 110
<212> TYPE: PRT
<213> ORGANISM: Artificial sequence
<220> FEATURE:
<223> OTHER INFORMATION: Synthetic antibody sequence

<400> SEQUENCE: 832

Glu Leu Asp Leu Thr Gln Thr Pro Ser Pro Val Ser Ala Ala Val Gly
1               5                   10                  15

Gly Thr Val Thr Ile Asn Cys Gln Ala Ser Gln Ile Val Ala Asn Gly
            20                  25                  30

Arg Leu Ala Trp Tyr Gln Gln Lys Pro Gly Gln Pro Pro Lys Leu Leu
        35                  40                  45

Ile Tyr Ala Thr Ser Thr Leu Ala Ser Gly Val Pro Ser Arg Phe Lys
    50                  55                  60

Gly Ser Gly Ser Gly Thr Gln Phe Thr Leu Thr Ile Asn Gly Val Gln
65                  70                  75                  80

Cys Asp Asp Ala Ala Thr Tyr Tyr Cys Gln Gly Ala Tyr Ser Ser Gly
                85                  90                  95

Asp Val Arg Thr Phe Gly Gly Gly Thr Glu Val Val Val Lys
            100                 105                 110


<210> SEQ ID NO 833
<211> LENGTH: 108
<212> TYPE: PRT
<213> ORGANISM: Artificial sequence
<220> FEATURE:
<223> OTHER INFORMATION: Synthetic antibody sequence

<400> SEQUENCE: 833

Glu Leu Val Leu Thr Gln Thr Pro Ser Ser Val Ser Ala Ala Val Gly
1               5                   10                  15

Gly Thr Val Thr Ile Asn Cys Gln Ala Ser Glu Asp Ile Asp Arg Tyr
            20                  25                  30

Leu Ala Trp Tyr Gln Gln Lys Pro Gly Gln Arg Pro Lys Leu Leu Ile
        35                  40                  45

Val Asp Ala Ser Thr Leu Pro Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Gly Ala Thr Tyr Tyr Cys Gln Ser Tyr Asp Asn Ser Asp Asn
                85                  90                  95
```

```
Asn Gly Phe Gly Gly Gly Thr Glu Val Val Val Lys
            100                 105


<210> SEQ ID NO 834
<211> LENGTH: 111
<212> TYPE: PRT
<213> ORGANISM: Artificial sequence
<220> FEATURE:
<223> OTHER INFORMATION: Synthetic antibody sequence

<400> SEQUENCE: 834

Glu Leu Asp Leu Thr Gln Thr Pro Ser Ser Val Glu Val Ala Val Gly
1               5                   10                  15

Gly Ala Val Thr Ile Lys Cys Gln Ala Ser His Ile Ile Thr Asn Tyr
            20                  25                  30

Leu Ala Trp Tyr Gln Gln Arg Pro Gly Gln Pro Pro Lys Leu Leu Ile
        35                  40                  45

Tyr Asp Ala Ser Lys Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Asn Tyr Leu Tyr Phe Ser Ser
                85                  90                  95

Gly Asp Trp Asn Val Phe Gly Gly Gly Thr Glu Val Val Val Lys
            100                 105                 110


<210> SEQ ID NO 835
<211> LENGTH: 111
<212> TYPE: PRT
<213> ORGANISM: Artificial sequence
<220> FEATURE:
<223> OTHER INFORMATION: Synthetic antibody sequence

<400> SEQUENCE: 835

Glu Leu Asp Leu Thr Gln Thr Pro Ala Ser Val Ser Ala Ala Val Gly
1               5                   10                  15

Gly Thr Val Thr Ile Asn Cys Gln Ala Ser Glu Ser Ile Gly Ser Ala
            20                  25                  30

Leu Ala Trp Tyr Gln Gln Lys Pro Gly Gln Pro Pro Lys Leu Leu Ile
        35                  40                  45

Tyr Ser Ala Ser Ala Leu Ala Ser Gly Val Pro Ser Arg Phe Lys Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Ser Tyr Tyr Gly Ser Gly Thr
                85                  90                  95

Thr Ala Leu Asp Thr Phe Gly Gly Gly Thr Glu Val Glu Ile Lys
            100                 105                 110


<210> SEQ ID NO 836
<211> LENGTH: 111
<212> TYPE: PRT
<213> ORGANISM: Artificial sequence
<220> FEATURE:
<223> OTHER INFORMATION: Synthetic antibody sequence

<400> SEQUENCE: 836

Glu Leu Asp Leu Thr Gln Thr Pro Gly Ser Val Glu Ala Ala Val Gly
1               5                   10                  15

Gly Thr Val Thr Ile Lys Cys Gln Ala Gly Gln Ser Ile Tyr Asn Tyr
```

```
            20                  25                  30

Leu Ser Trp Tyr Gln Gln Lys Pro Gly Gln Pro Pro Lys Leu Leu Ile
        35                  40                  45

Tyr Ser Ala Ser Thr Leu Glu Ser Gly Val Pro Pro Arg Phe Ser Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Ser Cys Gln Asn Asn Tyr Gly Ile Gly Ser
                85                  90                  95

Asn Tyr Gly Pro Gly Phe Gly Gly Gly Thr Glu Val Glu Ile Lys
            100                 105                 110


<210> SEQ ID NO 837
<211> LENGTH: 109
<212> TYPE: PRT
<213> ORGANISM: Artificial sequence
<220> FEATURE:
<223> OTHER INFORMATION: Synthetic antibody sequence

<400> SEQUENCE: 837

Glu Leu Asp Leu Thr Gln Thr Pro Ala Ser Val Glu Ala Ala Val Gly
1               5                   10                  15

Gly Thr Val Thr Ile Lys Cys Gln Ala Ser Leu Asn Ile Asn Ser Trp
            20                  25                  30

Leu Ala Trp Tyr Gln Gln Lys Pro Gly Gln Pro Pro Lys Leu Leu Ile
        35                  40                  45

Ser Tyr Thr Ser Ser Leu Ala Ser Gly Val Pro Ser Arg Phe Lys Gly
    50                  55                  60

Ser Gly Ser Gly Thr Glu Tyr Thr Leu Thr Ile Asn Asp Leu Glu Cys
65                  70                  75                  80

Ala Asp Ala Ala Thr Tyr Tyr Cys Gln Thr Thr Tyr Phe Gly Thr Asn
                85                  90                  95

Gly Gly Gly Phe Gly Gly Gly Thr Glu Val Glu Ile Lys
            100                 105


<210> SEQ ID NO 838
<211> LENGTH: 107
<212> TYPE: PRT
<213> ORGANISM: Artificial sequence
<220> FEATURE:
<223> OTHER INFORMATION: Synthetic antibody sequence

<400> SEQUENCE: 838

Glu Leu Val Met Thr Gln Thr Pro Ser Ser Val Glu Ala Ala Val Gly
1               5                   10                  15

Gly Thr Val Thr Asn Lys Cys Gln Ala Ser Glu Asp Ile Tyr Ser Asn
            20                  25                  30

Leu Ala Trp Tyr Gln Gln Lys Pro Gly Gln Pro Pro Lys Leu Leu Ile
        35                  40                  45

Tyr Gly Ala Thr Thr Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ala Glu Ser Asn Asp Val Trp
                85                  90                  95

Ala Phe Gly Gly Gly Thr Glu Val Val Val Lys
            100                 105
```

<210> SEQ ID NO 839
<211> LENGTH: 110
<212> TYPE: PRT
<213> ORGANISM: Artificial sequence
<220> FEATURE:
<223> OTHER INFORMATION: Synthetic antibody sequence

<400> SEQUENCE: 839

```
Glu Leu Asp Leu Thr Gln Thr Pro Ala Ser Val Ser Ala Ala Val Gly
1               5                   10                  15

Gly Thr Val Thr Ile Lys Cys Gln Ala Ser Glu Asp Ile Tyr Ser Asn
            20                  25                  30

Leu Ala Trp Tyr Gln Gln Lys Pro Gly Gln Pro Pro Lys Leu Leu Ile
        35                  40                  45

Tyr Lys Ala Ser Thr Leu Ala Ser Gly Val Pro Pro Arg Phe Lys Gly
    50                  55                  60

Ser Gly Ser Gly Thr Glu Tyr Thr Leu Thr Ile Ser Gly Val Gln Cys
65                  70                  75                  80

Asp Asp Ala Ala Thr Tyr Ala Cys Gln Thr Thr Tyr Trp Thr Thr Thr
                85                  90                  95

Asp Asp Asn Pro Phe Gly Gly Gly Thr Glu Val Glu Ile Lys
            100                 105                 110
```

<210> SEQ ID NO 840
<211> LENGTH: 112
<212> TYPE: PRT
<213> ORGANISM: Artificial sequence
<220> FEATURE:
<223> OTHER INFORMATION: Synthetic antibody sequence

<400> SEQUENCE: 840

```
Glu Leu Asp Leu Thr Gln Thr Pro Ser Ser Ser Ser Ala Ala Val Gly
1               5                   10                  15

Gly Thr Val Thr Ile Asn Cys Gln Ala Ser Gln Ser Val Tyr Asn Lys
            20                  25                  30

Asn Tyr Leu Ser Trp Phe Gln Gln Lys Pro Gly Gln Pro Pro Lys Leu
        35                  40                  45

Leu Ile Tyr Tyr Ala Ser Thr Leu Ala Ser Gly Val Pro Ser Arg Phe
    50                  55                  60

Lys Gly Ser Gly Ser Gly Thr Glu Phe Thr Leu Thr Ile Ser Asp Val
65                  70                  75                  80

Val Cys Asp Asp Ala Ala Thr Tyr Tyr Cys Ala Ala Tyr Lys Gly Val
                85                  90                  95

Ser Asp Asp Gly Ile Ser Phe Gly Gly Gly Thr Glu Val Glu Ile Lys
            100                 105                 110
```

<210> SEQ ID NO 841
<211> LENGTH: 113
<212> TYPE: PRT
<213> ORGANISM: Artificial sequence
<220> FEATURE:
<223> OTHER INFORMATION: Synthetic antibody sequence

<400> SEQUENCE: 841

```
Glu Leu Asp Met Thr Gln Thr Pro Ser Ser Val Ser Ala Ala Val Gly
1               5                   10                  15

Gly Thr Val Thr Ile Lys Cys Gln Ala Ser Gln Ser Ile Ser Ser Tyr
            20                  25                  30

Leu Ser Trp Tyr Gln Gln Lys Pro Gly Gln Pro Pro Lys Arg Leu Ile
```

```
        35                  40                  45

Tyr Lys Ala Ser Thr Leu Pro Ser Gly Val Pro Pro Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Asn Asn Tyr His Ser Gly Ser
                85                  90                  95

Ser Asn Gly Gly Gly Phe Ala Phe Gly Gly Gly Thr Gln Val Glu Ile
            100                 105                 110

Lys


<210> SEQ ID NO 842
<211> LENGTH: 112
<212> TYPE: PRT
<213> ORGANISM: Artificial sequence
<220> FEATURE:
<223> OTHER INFORMATION: Synthetic antibody sequence

<400> SEQUENCE: 842

Glu Leu Asp Leu Thr Gln Thr Pro Ala Ser Val Glu Ala Ala Val Arg
1               5                   10                  15

Gly Thr Val Thr Ile Lys Cys Gln Ala Ser Gln Ser Ile Ser Tyr Tyr
            20                  25                  30

Leu Ala Trp Tyr Gln Gln Lys Pro Gly Gln Pro Pro Lys Val Leu Ile
        35                  40                  45

Tyr Lys Ala Ser Thr Leu Ala Ser Gly Val Pro Pro Arg Phe Lys Gly
    50                  55                  60

Ser Gly Phe Gly Thr Glu Phe Thr Leu Thr Ile Ser Asp Leu Glu Cys
65                  70                  75                  80

Ala Asp Ala Ala Thr Tyr Tyr Cys Gln Ser Thr Tyr Gly Arg Asp Asn
                85                  90                  95

Asn Asp Leu Phe Phe Ala Phe Gly Gly Gly Thr Glu Val Glu Ile Lys
            100                 105                 110


<210> SEQ ID NO 843
<211> LENGTH: 112
<212> TYPE: PRT
<213> ORGANISM: Artificial sequence
<220> FEATURE:
<223> OTHER INFORMATION: Synthetic antibody sequence

<400> SEQUENCE: 843

Glu Leu Asp Leu Thr Gln Thr Pro Ala Ser Val Ser Ala Ala Val Gly
1               5                   10                  15

Gly Thr Val Thr Ile Lys Cys Gln Ala Ser Gln Ser Ile Ser Ser Ser
            20                  25                  30

Tyr Leu Ala Trp Tyr Gln Gln Lys Pro Gly Gln Pro Pro Lys Leu Leu
        35                  40                  45

Ile Tyr Ser Ala Ser Ser Thr Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Ala Asp Ala Ala Thr Tyr Tyr Cys Gln Ser Thr Tyr Ile Ser Ser
                85                  90                  95

Ser Lys Tyr Gly Ala Val Phe Gly Gly Gly Thr Glu Leu Glu Ile Lys
            100                 105                 110
```

<210> SEQ ID NO 844
<211> LENGTH: 110
<212> TYPE: PRT
<213> ORGANISM: Artificial sequence
<220> FEATURE:
<223> OTHER INFORMATION: Synthetic antibody sequence

<400> SEQUENCE: 844

```
Glu Leu Val Met Thr Gln Thr Ala Ser Pro Val Ser Ala Ala Val Gly
1               5                   10                  15

Gly Thr Val Thr Ile Ser Cys Gln Ser Ser Gln Ser Val Tyr Ser Asn
            20                  25                  30

Asn Trp Leu Ser Trp Tyr Gln Gln Lys Pro Gly Gln Pro Pro Lys Arg
        35                  40                  45

Leu Ile Tyr Lys Ala Ser Thr Leu Glu Thr Gly Val Pro Ser Arg Phe
    50                  55                  60

Lys Gly Ser Gly Ser Gly Lys Gln Phe Thr Leu Thr Ile Ser Asp Leu
65                  70                  75                  80

Glu Cys Asp Asp Ala Ala Thr Tyr Tyr Cys Ala Gly Gly Tyr Ser Gly
                85                  90                  95

Asp Leu Tyr Ala Phe Gly Gly Gly Thr Glu Val Val Val Lys
            100                 105                 110
```

<210> SEQ ID NO 845
<211> LENGTH: 113
<212> TYPE: PRT
<213> ORGANISM: Artificial sequence
<220> FEATURE:
<223> OTHER INFORMATION: Synthetic antibody sequence

<400> SEQUENCE: 845

```
Glu Leu Asp Met Thr Gln Thr Pro Ser Pro Val Ser Ala Ala Val Gly
1               5                   10                  15

Gly Ser Val Thr Ile Ser Cys Gln Ala Ser Gln Thr Ile Tyr Asn Asn
            20                  25                  30

Lys Asn Leu Ala Trp Tyr Gln Gln Lys Pro Gly Gln Pro Pro Lys Leu
        35                  40                  45

Leu Ile Tyr Gln Ala Ser Lys Leu Ala Ser Gly Val Ser Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Glu Phe Ser Cys
                85                  90                  95

Ser Ser Gly Asp Cys Thr Thr Phe Gly Gly Gly Thr Glu Val Val Val
            100                 105                 110

Lys
```

<210> SEQ ID NO 846
<211> LENGTH: 110
<212> TYPE: PRT
<213> ORGANISM: Artificial sequence
<220> FEATURE:
<223> OTHER INFORMATION: Synthetic antibody sequence

<400> SEQUENCE: 846

```
Glu Leu Asp Met Thr Gln Thr Pro Ala Ser Val Ser Glu Pro Val Gly
1               5                   10                  15

Gly Thr Val Thr Ile Lys Cys Gln Ala Ser Glu Asn Ile Tyr Ser Tyr
            20                  25                  30
```

```
Leu Ala Trp Tyr Gln Gln Lys Pro Gly Gln Pro Pro Lys Leu Leu Ile
        35                  40                  45

Tyr Ser Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Tyr Ser Asn Phe Arg Val Asn
                85                  90                  95

Asp Pro Ser Val Phe Gly Gly Gly Thr Glu Val Glu Ile Lys
            100                 105                 110


<210> SEQ ID NO 847
<211> LENGTH: 117
<212> TYPE: PRT
<213> ORGANISM: Artificial sequence
<220> FEATURE:
<223> OTHER INFORMATION: Synthetic antibody sequence

<400> SEQUENCE: 847

Glu Leu Asp Leu Thr Gln Thr Pro Ala Ser Val Ser Ala Ala Val Gly
1               5                   10                  15

Gly Thr Val Thr Ile Ser Cys Gln Ser Ser Gln Ser Val His His Ser
            20                  25                  30

Gln Thr Val His Asn Asn Gln Trp Leu Ala Trp Tyr Gln Gln Lys Pro
        35                  40                  45

Gly Gln Pro Pro Lys Leu Leu Ile Tyr Asp Ala Ser Lys Leu Ala Ser
    50                  55                  60

Gly Val Pro Ser Arg Phe Thr Gly Ser Gly Ser Gly Thr Gln Phe Ser
65                  70                  75                  80

Leu Thr Ile Ser Ala Val Gln Cys Asp Asp Ala Ala Thr Tyr Tyr Cys
                85                  90                  95

Gln Gly Gly Tyr Ser Tyr Gly Asp Val Tyr Gly Phe Gly Gly Gly Thr
            100                 105                 110

Glu Leu Glu Ile Lys
        115


<210> SEQ ID NO 848
<211> LENGTH: 114
<212> TYPE: PRT
<213> ORGANISM: Artificial sequence
<220> FEATURE:
<223> OTHER INFORMATION: Synthetic antibody sequence

<400> SEQUENCE: 848

Glu Leu Val Leu Thr Gln Thr Pro Ser Ser Thr Ser Ala Ala Val Gly
1               5                   10                  15

Gly Thr Val Thr Ile Asn Cys Gln Ala Ser Gln Ser Val Asp Asn Asn
            20                  25                  30

Lys Gln Leu Ser Trp Tyr Gln Gln Lys Pro Gly Gln Pro Pro Lys Gln
        35                  40                  45

Leu Ile Tyr Ser Ala Ser Lys Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Tyr Tyr Tyr Ser
                85                  90                  95

Gly Ser Ala Thr Asp Ala Trp Ala Phe Gly Gly Ala Thr Glu Val Glu
            100                 105                 110
```

Ile Asn

<210> SEQ ID NO 849
<211> LENGTH: 112
<212> TYPE: PRT
<213> ORGANISM: Artificial sequence
<220> FEATURE:
<223> OTHER INFORMATION: Synthetic antibody sequence

<400> SEQUENCE: 849

Glu Leu Val Met Thr Gln Thr Pro Ser Ser Val Ser Ala Ala Val Gly
1 5 10 15

Asp Thr Leu Thr Ile Asn Cys Gln Ala Ser Glu Thr Ile Ser Asn Arg
20 25 30

Leu Ala Trp Tyr Gln Gln Lys Pro Gly Gln Pro Pro Lys Leu Leu Ile
35 40 45

Tyr Ser Ala Ser Thr Leu Glu Ser Gly Val Pro Ser Arg Phe Arg Gly
50 55 60

Ser Gly Ser Gly Thr Gln Phe Thr Leu Thr Ile Ser Asp Leu Glu Cys
65 70 75 80

Ala Asp Ala Ala Thr Tyr Tyr Cys Gln Ser Ile Arg Ser Ser Ser Gly
85 90 95

Val Val His Pro Asn Thr Phe Gly Gly Gly Thr Glu Val Glu Ile Lys
100 105 110

<210> SEQ ID NO 850
<211> LENGTH: 110
<212> TYPE: PRT
<213> ORGANISM: Artificial sequence
<220> FEATURE:
<223> OTHER INFORMATION: Synthetic antibody sequence

<400> SEQUENCE: 850

Glu Leu Asp Leu Thr Gln Thr Pro Ser Ser Val Glu Ala Ala Val Gly
1 5 10 15

Gly Thr Val Thr Ile Lys Cys Gln Ala Ser Gln Thr Ile Tyr Thr Asn
20 25 30

Leu Ala Trp Tyr Gln Gln Lys Pro Gly Gln Pro Pro Asn Leu Leu Ile
35 40 45

Tyr Ala Ala Ser Thr Leu Ala Ser Gly Val Ser Ser Arg Phe Lys Gly
50 55 60

Ser Gly Ser Gly Thr Glu Phe Thr Leu Thr Ile Ser Asp Leu Glu Cys
65 70 75 80

Ala Asp Ala Ala Thr Tyr Tyr Cys Gln Ser Tyr Tyr Gly Ser Ser Thr
85 90 95

Thr Gly Asn Gly Phe Gly Gly Gly Thr Glu Val Glu Ile Lys
100 105 110

<210> SEQ ID NO 851
<211> LENGTH: 112
<212> TYPE: PRT
<213> ORGANISM: Artificial sequence
<220> FEATURE:
<223> OTHER INFORMATION: Synthetic antibody sequence

<400> SEQUENCE: 851

Glu Leu Val Leu Thr Gln Thr Pro Ser Ser Lys Ser Val Ala Val Gly
1 5 10 15

Asp Thr Val Thr Ile Asn Cys Gln Ala Ser Asp Asn Val Tyr Ser Asn

```
            20                  25                  30

Asn Tyr Thr Ser Trp Phe Gln Gln Lys Pro Gly Gln Pro Pro Lys Gln
        35                  40                  45

Leu Leu Tyr Tyr Ala Ala Tyr Arg Ala Ser Gly Val Pro Ser Arg Phe
    50                  55                  60

Lys Gly Ser Gly Ser Gly Thr Glu Phe Thr Leu Ser Ile Ser Asp Val
65                  70                  75                  80

Val Cys Asp Asp Ala Ala Thr Tyr Tyr Cys Ser Gly His Lys Asp Tyr
                85                  90                  95

Ser Asp Asp Gly Ser Thr Phe Gly Gly Gly Thr Glu Val Glu Ile Lys
            100                 105                 110


<210> SEQ ID NO 852
<211> LENGTH: 112
<212> TYPE: PRT
<213> ORGANISM: Artificial sequence
<220> FEATURE:
<223> OTHER INFORMATION: Synthetic antibody sequence

<400> SEQUENCE: 852

Glu Leu Val Leu Thr Gln Thr Pro Ser Ser Lys Ser Val Ala Val Gly
1               5                   10                  15

Asp Thr Val Thr Ile Asn Cys Gln Ala Ser Asp Asn Val Tyr Ser Asn
            20                  25                  30

Asn Tyr Thr Ser Trp Phe Gln Gln Lys Pro Gly Gln Pro Pro Lys Gln
        35                  40                  45

Leu Leu Tyr Tyr Ala Ala Tyr Arg Ala Ser Gly Val Pro Ser Arg Phe
    50                  55                  60

Lys Gly Ser Gly Ser Gly Thr Glu Phe Thr Leu Ser Ile Ser Asp Val
65                  70                  75                  80

Val Cys Asp Asp Ala Ala Thr Tyr Tyr Cys Ser Gly His Lys Asp Tyr
                85                  90                  95

Ser Asp Asp Gly Ser Thr Phe Gly Gly Gly Thr Glu Val Glu Ile Lys
            100                 105                 110


<210> SEQ ID NO 853
<211> LENGTH: 108
<212> TYPE: PRT
<213> ORGANISM: Artificial sequence
<220> FEATURE:
<223> OTHER INFORMATION: Synthetic antibody sequence

<400> SEQUENCE: 853

Glu Leu Val Met Thr Gln Thr Pro Ala Ser Val Ser Ala Ala Val Gly
1               5                   10                  15

Gly Thr Val Thr Ile Asn Cys Gln Ala Ser Glu Asp Ile Ser Ser Asn
            20                  25                  30

Leu Ala Trp Tyr Gln Gln Lys Pro Gly Gln Pro Pro Lys Leu Leu Ile
        35                  40                  45

Ser Gly Ala Ser Thr Leu Ala Ser Gly Val Pro Ser Arg Phe Lys Gly
    50                  55                  60

Ser Gly Ser Gly Thr Asp Phe Thr Leu Thr Met Ser Asp Leu Glu Cys
65                  70                  75                  80

Ala Asp Ala Ala Thr Tyr Tyr Cys Gln Gly Ala Tyr Tyr Gly Ser Ser
                85                  90                  95

Tyr Gly Phe Gly Gly Gly Thr Glu Val Val Val Lys
            100                 105
```

<210> SEQ ID NO 854
<211> LENGTH: 112
<212> TYPE: PRT
<213> ORGANISM: Artificial sequence
<220> FEATURE:
<223> OTHER INFORMATION: Synthetic antibody sequence

<400> SEQUENCE: 854

```
Glu Leu Val Leu Thr Gln Thr Pro Ser Pro Val Ser Ala Ala Val Gly
1               5                   10                  15

Gly Thr Val Thr Ile Asn Cys Gln Ala Ser Gln Ser Ile Ser Asn Glu
            20                  25                  30

Leu Ser Trp Tyr Gln Gln Lys Pro Gly Gln Pro Pro Lys Leu Leu Ile
        35                  40                  45

Tyr Leu Ala Ser Thr Leu Asp Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Ser His Tyr Tyr Gly Gly Ser
                85                  90                  95

Ser Asp Tyr Gly Trp Ala Phe Gly Gly Gly Thr Glu Val Val Val Lys
            100                 105                 110
```

<210> SEQ ID NO 855
<211> LENGTH: 110
<212> TYPE: PRT
<213> ORGANISM: Artificial sequence
<220> FEATURE:
<223> OTHER INFORMATION: Synthetic antibody sequence

<400> SEQUENCE: 855

```
Glu Leu Asp Met Thr Gln Thr Pro Ser Ser Thr Ser Ala Ala Val Gly
1               5                   10                  15

Gly Thr Val Thr Ile Lys Cys Gln Ala Ser Gln Ser Val Tyr Asn Asn
            20                  25                  30

Asn Gln Leu Ser Trp Phe Gln Gln Lys Pro Gly Gln Pro Pro Lys Arg
        35                  40                  45

Leu Ile Tyr Gly Ala Ser Thr Leu Glu Ser Gly Val Pro Ser Arg Phe
    50                  55                  60

Ser Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Gln Gly Ala Val Ser Ser
                85                  90                  95

Asp Tyr Tyr Pro Phe Gly Gly Gly Thr Glu Val Glu Ile Lys
            100                 105                 110
```

<210> SEQ ID NO 856
<211> LENGTH: 110
<212> TYPE: PRT
<213> ORGANISM: Artificial sequence
<220> FEATURE:
<223> OTHER INFORMATION: Synthetic antibody sequence

<400> SEQUENCE: 856

```
Glu Leu Asp Met Thr Gln Thr Pro Ala Ser Val Ser Glu Pro Val Gly
1               5                   10                  15

Gly Thr Val Thr Ile Lys Cys Gln Ala Ser Gln Ser Ile Gly Ser Tyr
            20                  25                  30

Leu Ala Trp Tyr Gln Gln Lys Pro Gly Gln Pro Pro Lys Leu Leu Ala
```

```
        35                  40                  45

Phe Tyr Ala Ser Thr Leu Lys Ser Gly Val Pro Pro Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Asn Arg Leu Ser Ser Ser
                85                  90                  95

Asp Val Asn Ala Phe Gly Gly Gly Thr Glu Val Glu Ile Lys
            100                 105                 110


<210> SEQ ID NO 857
<211> LENGTH: 110
<212> TYPE: PRT
<213> ORGANISM: Artificial sequence
<220> FEATURE:
<223> OTHER INFORMATION: Synthetic antibody sequence

<400> SEQUENCE: 857

Glu Leu Val Leu Thr Gln Thr Ala Ser Pro Val Ser Gly Ala Val Gly
1               5                   10                  15

Gly Thr Val Thr Ile Lys Cys Gln Ala Ser Gln Asn Ile Tyr Ser Asn
            20                  25                  30

Leu Ala Trp Tyr Gln Gln Lys Pro Gly Gln Pro Pro Lys Leu Leu Ile
        35                  40                  45

Tyr Ser Ala Ser Lys Leu Ala Ser Gly Val Pro Ser Arg Phe Lys Gly
    50                  55                  60

Ser Gly Ser Gly Thr Glu Tyr Thr Leu Thr Ile Ser Gly Val Gln Cys
65                  70                  75                  80

Glu Asp Ala Ala Thr Tyr Tyr Cys Gln Ser Tyr Tyr Tyr Thr Ala Ser
                85                  90                  95

Ala Asp Thr Thr Phe Gly Gly Gly Thr Glu Val Glu Ile Lys
            100                 105                 110


<210> SEQ ID NO 858
<211> LENGTH: 108
<212> TYPE: PRT
<213> ORGANISM: Artificial sequence
<220> FEATURE:
<223> OTHER INFORMATION: Synthetic antibody sequence

<400> SEQUENCE: 858

Glu Leu Val Leu Thr Gln Thr Pro Ser Ser Val Glu Ala Ala Val Gly
1               5                   10                  15

Gly Thr Val Thr Ile Lys Cys Gln Ala Ser Gln Ser Ile Gly Ser Tyr
            20                  25                  30

Leu Ala Trp Tyr Gln Gln Lys Pro Gly Gln Pro Pro Lys Leu Leu Ile
        35                  40                  45

Tyr Lys Ala Ser Thr Leu Ser Ser Gly Val Ser Ser Arg Tyr Lys Gly
    50                  55                  60

Ser Gly Ser Gly Thr Glu Phe Thr Leu Thr Ile Ser Asp Leu Glu Cys
65                  70                  75                  80

Asp Asp Ala Ala Thr Tyr Tyr Cys Gln Tyr Thr Ser Tyr Ser Ser Gly
                85                  90                  95

Gly Ala Phe Gly Gly Gly Thr Glu Val Val Val Lys
            100                 105


<210> SEQ ID NO 859
<211> LENGTH: 113
```

<212> TYPE: PRT
<213> ORGANISM: Artificial sequence
<220> FEATURE:
<223> OTHER INFORMATION: Synthetic antibody sequence

<400> SEQUENCE: 859

Glu Leu Val Met Thr Gln Thr Pro Ala Ser Val Ser Glu Pro Val Gly
1 5 10 15

Gly Thr Val Thr Ile Lys Cys Gln Ala Ser Gln Ser Ile Ser Ser Tyr
20 25 30

Leu Ser Trp Tyr Gln Gln Lys Pro Gly Gln Pro Pro Lys Arg Leu Ile
35 40 45

Tyr Lys Ala Ser Thr Leu Ala Ser Gly Val Pro Ser Arg Phe Lys Gly
50 55 60

Ser Gly Ser Gly Thr Glu Phe Thr Leu Thr Ile Ser Gly Val Gln Cys
65 70 75 80

Ala Asp Ala Ala Thr Tyr Tyr Cys Gln Asn Asn Tyr His Ser Gly Ser
85 90 95

Ser Asn Gly Gly Gly Phe Ala Phe Gly Gly Gly Thr Glu Val Glu Ile
100 105 110

Lys

<210> SEQ ID NO 860
<211> LENGTH: 110
<212> TYPE: PRT
<213> ORGANISM: Artificial sequence
<220> FEATURE:
<223> OTHER INFORMATION: Synthetic antibody sequence

<400> SEQUENCE: 860

Glu Leu Asp Met Thr Gln Thr Pro Ser Ser Val Glu Ala Ala Val Gly
1 5 10 15

Gly Thr Val Thr Ile Lys Cys Gln Ala Ser Gln Thr Ile Tyr Thr Asn
20 25 30

Leu Ala Trp Tyr Gln Gln Lys Pro Gly Gln Pro Pro Asn Leu Leu Ile
35 40 45

Tyr Ala Ala Ser Thr Leu Ala Ser Gly Val Ser Ser Arg Phe Lys Gly
50 55 60

Ser Gly Ser Gly Thr Glu Phe Thr Leu Thr Ile Ser Asp Leu Glu Cys
65 70 75 80

Ala Asp Ala Ala Thr Tyr Tyr Cys Gln Ser Tyr Tyr Gly Ser Ser Thr
85 90 95

Thr Gly Asn Gly Phe Gly Gly Gly Thr Glu Val Glu Ile Asn
100 105 110

<210> SEQ ID NO 861
<211> LENGTH: 112
<212> TYPE: PRT
<213> ORGANISM: Artificial sequence
<220> FEATURE:
<223> OTHER INFORMATION: Synthetic antibody sequence

<400> SEQUENCE: 861

Glu Leu Val Leu Thr Gln Thr Pro Ser Ser Lys Ser Val Ala Val Gly
1 5 10 15

Asp Thr Val Thr Ile Asn Cys Gln Ala Ser Glu Ser Val Tyr Gly Asn
20 25 30

Asn Arg Cys Ser Trp Tyr Gln Gln Lys Pro Gly Gln Pro Pro Lys Leu
35 40 45

```
Leu Ile Tyr Gln Ala Ser Thr Leu Ala Ser Gly Val Pro Ser Arg Phe
    50                  55                  60

Ser Gly Ser Gly Ser Gly Thr Gln Phe Thr Leu Thr Ile Ser Asp Val
65                  70                  75                  80

Val Cys Asp Asp Ala Ala Thr Tyr Tyr Cys Ala Gly His Lys Gly Thr
                85                  90                  95

Thr Asn Asp Gly Asn Asp Phe Gly Gly Gly Thr Glu Val Glu Ile Lys
            100                 105                 110


<210> SEQ ID NO 862
<211> LENGTH: 111
<212> TYPE: PRT
<213> ORGANISM: Artificial sequence
<220> FEATURE:
<223> OTHER INFORMATION: Synthetic antibody sequence

<400> SEQUENCE: 862

Glu Leu Asp Met Thr Gln Thr Pro Ala Ser Val Ser Ala Ala Val Gly
1               5                   10                  15

Gly Thr Val Thr Ile Lys Cys Gln Ala Ser Gln Ser Ile Thr Asn Ala
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Cys Ser Tyr Tyr Gly Ser Thr
                85                  90                  95

Tyr Phe Gly Ser Pro Phe Gly Gly Gly Thr Glu Val Glu Ile Lys
            100                 105                 110


<210> SEQ ID NO 863
<211> LENGTH: 112
<212> TYPE: PRT
<213> ORGANISM: Artificial sequence
<220> FEATURE:
<223> OTHER INFORMATION: Synthetic antibody sequence

<400> SEQUENCE: 863

Glu Leu Val Leu Thr Gln Thr Pro Ser Ser Val Ser Glu Pro Val Gly
1               5                   10                  15

Gly Thr Val Thr Ile Lys Cys Gln Ala Ser Gln Ser Ile Ser Ser Ser
            20                  25                  30

Tyr Leu Ala Trp Tyr Gln Gln Lys Pro Gly Gln Pro Pro Lys Phe Leu
        35                  40                  45

Ile Tyr Ser Ala Ser Thr Leu Ala Ser Gly Val Pro Ser Arg Phe Lys
    50                  55                  60

Gly Ser Gly Ser Gly Thr Glu Phe Thr Leu Thr Ile Ser Asp Leu Glu
65                  70                  75                  80

Cys Ala Asp Ala Ala Thr Tyr Tyr Cys Gln Ser Thr Tyr Ile Ser Ser
                85                  90                  95

Ser Asn Tyr Gly Ala Ala Phe Gly Gly Gly Thr Glu Val Glu Ile Lys
            100                 105                 110


<210> SEQ ID NO 864
<211> LENGTH: 109
<212> TYPE: PRT
```

```
<213> ORGANISM: Artificial sequence
<220> FEATURE:
<223> OTHER INFORMATION: Synthetic antibody sequence

<400> SEQUENCE: 864

Glu Leu Asp Leu Thr Gln Thr Pro Ser Ser Val Glu Ala Ala Val Gly
1               5                   10                  15

Gly Thr Val Thr Ile Lys Cys Gln Ala Ser Gln Ser Ile Gly Ser Asn
            20                  25                  30

Leu Ala Trp Tyr Gln Gln Lys Pro Gly Gln Pro Pro Lys Val Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Asn Asn Asn Tyr Trp Ser Asn
                85                  90                  95

Gly Asn His Phe Gly Gly Gly Thr Glu Val Val Val Lys
            100                 105


<210> SEQ ID NO 865
<211> LENGTH: 112
<212> TYPE: PRT
<213> ORGANISM: Artificial sequence
<220> FEATURE:
<223> OTHER INFORMATION: Synthetic antibody sequence

<400> SEQUENCE: 865

Glu Leu Val Leu Thr Gln Thr Pro Ser Ser Lys Ser Val Ala Val Gly
1               5                   10                  15

Asp Thr Val Thr Ile Asn Cys Gln Ala Ser Glu Asn Val Tyr Ser Asn
            20                  25                  30

Asn Tyr Thr Ser Trp Phe Gln Gln Lys Pro Gly Gln Pro Pro Lys Gln
        35                  40                  45

Leu Leu Tyr Tyr Ala Ala Tyr Arg Ala Ser Gly Val Pro Ser Arg Phe
    50                  55                  60

Lys Gly Ser Gly Ser Gly Thr Glu Phe Thr Leu Ser Ile Ser Asp Val
65                  70                  75                  80

Val Cys Asp Asp Ala Ala Thr Tyr Tyr Cys Ser Gly His Lys Asp Tyr
                85                  90                  95

Ser Asp Asp Gly Ser Thr Phe Gly Gly Gly Thr Glu Val Val Val Lys
            100                 105                 110


<210> SEQ ID NO 866
<211> LENGTH: 110
<212> TYPE: PRT
<213> ORGANISM: Artificial sequence
<220> FEATURE:
<223> OTHER INFORMATION: Synthetic antibody sequence

<400> SEQUENCE: 866

Glu Leu Asp Leu Thr Gln Thr Ala Ser Pro Val Ser Gly Ala Val Gly
1               5                   10                  15

Gly Thr Val Thr Ile Lys Cys Gln Ala Ser Gln Ser Ile Ala Ser Asp
            20                  25                  30

Leu Ala Trp Tyr Gln Gln Lys Pro Gly Gln Pro Pro Asn Leu Leu Ile
        35                  40                  45

Tyr Ala Ala Ser Thr Leu Ala Ser Gly Val Ser Ser Arg Phe Lys Gly
    50                  55                  60
```

```
Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Tyr Tyr Gly Ser Ser Thr
                85                  90                  95

Thr Gly Asn Gly Phe Gly Gly Gly Thr Glu Val Val Val Lys
            100                 105                 110
```

```
<210> SEQ ID NO 867
<211> LENGTH: 110
<212> TYPE: PRT
<213> ORGANISM: Artificial sequence
<220> FEATURE:
<223> OTHER INFORMATION: Synthetic antibody sequence

<400> SEQUENCE: 867

Asp Ile Gln Leu Thr Gln Ser Pro Ser Phe Leu Ser Ala Ser Val Gly
1               5                   10                  15

Asp Arg Val Thr Ile Thr Cys Gln Ala Ser Gln Thr Ile Tyr Thr Asn
            20                  25                  30

Leu Ala Trp Tyr Gln Gln Lys Pro Gly Lys Ala Pro Lys Leu Leu Ile
        35                  40                  45

Tyr Ala Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Ser Tyr Tyr Gly Ser Ser Thr
                85                  90                  95

Thr Gly Asn Gly Phe Gly Gly Gly Thr Lys Val Glu Ile Lys
            100                 105                 110
```

```
<210> SEQ ID NO 868
<211> LENGTH: 6
<212> TYPE: PRT
<213> ORGANISM: Artificial sequence
<220> FEATURE:
<223> OTHER INFORMATION: Synthetic antibody

<400> SEQUENCE: 868

His Ile Ile Thr Asn Tyr
1               5
```

```
<210> SEQ ID NO 869
<211> LENGTH: 3
<212> TYPE: PRT
<213> ORGANISM: Artificial sequence
<220> FEATURE:
<223> OTHER INFORMATION: Synthetic antibody

<400> SEQUENCE: 869

Asp Ala Ser
1
```

```
<210> SEQ ID NO 870
<211> LENGTH: 13
<212> TYPE: PRT
<213> ORGANISM: Artificial sequence
<220> FEATURE:
<223> OTHER INFORMATION: Synthetic antibody

<400> SEQUENCE: 870

Gln Asn Tyr Leu Tyr Phe Ser Ser Gly Asp Trp Asn Val
1               5                   10
```

<210> SEQ ID NO 871
<211> LENGTH: 384
<212> TYPE: DNA
<213> ORGANISM: Artificial sequence
<220> FEATURE:
<223> OTHER INFORMATION: Synthetic antibody

<400> SEQUENCE: 871
gaagtgcagc tggtggagag cggcggcggt ctggtacaac cgggcggcag cctgagactg 60
agctgcgccg ctagcggctt cagcttcagc agcagctact gcatgtgctg ggtgagacaa 120
gcccccggca agggcctgga gtgggtgagc tgcatctaca ccgacagcag cggcgccacc 180
tactacgcta gctgggccaa gggcagattc accatcagca gacacaacag caagaacacc 240
ctgtacctgc agatgaacag cctgagagcc gaggacaccg ccgtgtacta ctgcgctaga 300
ggctgggact acgaggaccc cggctacacc gacaccacct acttcagcct gtggggcaga 360
ggcaccctgg tgaccgtgag cagc 384

<210> SEQ ID NO 872
<211> LENGTH: 384
<212> TYPE: DNA
<213> ORGANISM: Artificial sequence
<220> FEATURE:
<223> OTHER INFORMATION: Synthetic antibody

<400> SEQUENCE: 872
gaagtgcagc tggtggagag cggcggcggt ctggtacaac cgggcggcag cctgagactg 60
agctgcgccg ctagcggctt cagcttcagc agcagctact gcatgtgctg ggtgagacaa 120
gcccccggca agggcctgga gctggtgagc tgcatctaca ccgacagcag cggcgccacc 180
tactacgcta gctgggccaa gggcagattc accatcagca gacacaacag caagaacacc 240
ctgtacctgc agatgaacag cctgagagcc gaggacaccg ccgtgtacta ctgcgctaga 300
ggctgggact acgaggaccc cggctacacc gacaccacct acttcagcct gtggggcaga 360
ggcaccctgg tgaccgtgag cagc 384

<210> SEQ ID NO 873
<211> LENGTH: 384
<212> TYPE: DNA
<213> ORGANISM: Artificial sequence
<220> FEATURE:
<223> OTHER INFORMATION: Synthetic antibody

<400> SEQUENCE: 873
gaagtgcagc tggtggagag cggcggcggt ctggtacaac cgggcggcag cctgagactg 60
agctgcgccg ctagcggctt cagcttcagc agcagctaca gcatgagctg ggtgagacaa 120
gcccccggca agggcctgga gtgggtgagc agcatctaca ccgacagcag cggcgccacc 180
tactacgcta gctgggccaa gggcagattc accatcagca gacacaacag caagaacacc 240
ctgtacctgc agatgaacag cctgagagcc gaggacaccg ccgtgtacta ctgcgctaga 300
ggctgggact acgaggaccc cggctacacc gacaccacct acttcagcct gtggggcaga 360
ggcaccctgg tgaccgtgag cagc 384

<210> SEQ ID NO 874
<211> LENGTH: 128
<212> TYPE: PRT
<213> ORGANISM: Artificial sequence
<220> FEATURE:

```
<223> OTHER INFORMATION: Synthetic antibody

<400> SEQUENCE: 874

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Ser
            20                  25                  30

Tyr Ser Met Ser Trp Val Arg Gln Ala Pro Gly Lys Gly Leu Glu Trp
        35                  40                  45

Val Ser Ser Ile Tyr Thr Asp Ser Ser Gly Ala Thr Tyr Tyr Ala Ser
    50                  55                  60

Trp Ala Lys Gly Arg Phe Thr Ile Ser Arg His Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Gly Trp Asp Tyr Glu Asp Pro Gly Tyr Thr Asp Thr
            100                 105                 110

Thr Tyr Phe Ser Leu Trp Gly Arg Gly Thr Leu Val Thr Val Ser Ser
        115                 120                 125


<210> SEQ ID NO 875
<211> LENGTH: 330
<212> TYPE: DNA
<213> ORGANISM: Artificial sequence
<220> FEATURE:
<223> OTHER INFORMATION: Synthetic antibody

<400> SEQUENCE: 875

gacattcagc tgacacagag ccctagcttc ctgagcgcta gcgtgggcga cagagtgacc      60

atcacctgcc aagcctctca gaccatctac accaacctgg cctggtatca gcagaagccc     120

ggcaaagccc ccaagctgct gatatacgcc gctagcaccc tggcgagcgg cgtgcctagc     180

agattcagcg gcagcggcag cggcaccgag ttcaccctga ccatcagcag cctgcagccc     240

gaggacttcg ccacctacta ctgtcagagc tactacggca gcagcaccac cggcaacggc     300

ttcggcggcg gcaccaaggt ggagatcaag                                      330
```

MONOCLONAL ANTIBODIES AGAINST LILRB1 FOR DIAGNOSTIC AND THERAPEUTIC USE

PRIORITY CLAIM

This application is a national phase application under 35 U.S.C. § 371 of International Application No. PCT/US2021/043128, filed Jul. 26, 2021, which claims benefit of priority to U.S. Provisional Application Ser. Nos. 63/057,601 and 63/124,516, filed Jul. 28, 2020 and Dec. 11, 2020, respectively, the entire contents of these applications being hereby incorporated by reference.

REFERENCE TO A SEQUENCE LISTING

The instant application contains a Sequence Listing, which has been submitted in ASCII format via EFS-Web and is hereby incorporated by reference in its entirety. Said ASCII copy, created on Jul. 23, 2021, is named UTFH_P0370WO_ST25.txt and is 319 kilobytes in size.

BACKGROUND

1. Field

The present disclosure relates generally to the fields of medicine, oncology, immunology and immuno-oncology. More particularly, it concerns agonistic and antagonistic antibodies that bind to LILRB1 and methods of their use.

2. Description of Related Art

NK cells play critical roles in anticancer immunity and their functions against cancer cells can be enhanced by engaging activating receptors or blocking inhibitory receptors 1. Among activating receptors, FcγRIII (CD16) plays critical roles in antibody-dependent cellular cytotoxicity (ADCC) induced by therapeutic monoclonal antibodies to treat both hematological malignancies (rituximab for lymphoma and daratumumab for multiple myeloma) and metastatic solid cancer (cetuximab and trastuzumab)[2 3]. Antibodies engaging activating receptors, such as NKG2D and NKp46, also showed NK-dependent tumor immunity in preclinical studies[4 5]. Importantly, it has also been demonstrated that antibodies that block inhibitory receptors on NK cells, such as KIR and NKG2A, enhance NK cell function against cancer cells[6 7]. Thus, developing antibodies to target immune receptors on NK cells can provide novel cancer immunotherapeutic strategies.

LILRB1, an ITIM-containing receptor, is expressed on a variety of human immune cells. This includes all B cells, monocytes and macrophages, DCs, and subsets of NK cells and T cells. LILRB1 ligands, including MHC class I molecules, activate LILRB1 and transduce a negative signal that down-regulates the immune response[8]. The percentage of LILRB1$^+$ NK cells is significantly higher in patients with advanced stage prostate and breast cancer than in healthy donors or patients with localized cancer[9-11]. Blockade of LILRB1 signaling in immune cells was capable of activating the activity of NK cells against solid tumor and leukemia[10 12], and activating T cells or macrophages against solid tumors[13-15] using in vitro models. However, it is unknown whether LILRB1 can be targeted to turn "on" immune cells in vivo for cancer treatment. In addition, it is also reported that LILRB1 is expressed on some tumor cells and stimulates immune response[16 17]. Thus, it is not clear whether the net outcome of blockade of LILRB1 signaling on both tumor cells and immune cells is to activate or suppress anti-tumor immune response.

SUMMARY

Thus, in one aspect, the present disclosure provides an isolated monoclonal antibody or an antigen-binding fragment thereof that binds specifically to LILRB1. In certain embodiments, the antibody or antigen-binding fragment, when bound to LILRB1, modulates the activation of LILRB1. In certain embodiments, the antibody or antigen-binding fragment, when bound to LILRB1, activates LILRB1. In certain embodiments, the antibody or antigen-binding fragment, when bound to LILRB1, suppresses activation of LILRB1. In certain embodiments, the antibody or antigen-binding fragment, when bound to LILRB1, specifically blocks binding of MHC and other ligands to LILRB1.

In one aspect, the isolated monoclonal antibody or an antigen-binding fragment thereof comprises a heavy chain (HC) variable region (VH) and a light chain (LC) variable region (VL) comprising the clone-paired CDR sequences as set forth in Tables 1 and 3; and variants thereof wherein one or more of the LC-CDRs has one, two, or three amino acid substitutions, additions, deletions, or combinations thereof. The isolated monoclonal antibody or an antigen binding fragment thereof may be a murine, a rodent, a rabbit, a chimeric, humanized, or human antibody. The isolated monoclonal antibody or an antigen-binding fragment thereof may have VH and VL chains with amino acid sequences at least 90% or 95% identical to the clone-paired sequences of Tables 6 and 8, respectively. The isolated monoclonal antibody or an antigen-binding fragment thereof may have VH and VL chains encoded by nucleic acid sequences at least 80% or 90% identical to the clone-paired sequences of Tables 5 and 7, respectively. The isolated monoclonal antibody or an antigen-binding fragment thereof of may have VH and VL chains with amino acid sequences identical to the clone-paired sequences of Tables 6 and 8, respectively. The isolated monoclonal antibody or an antigen binding fragment thereof may have VH and VL chains encoded by nucleic acid sequences identical to the clone-paired sequences of Tables 5 and 7, respectively.

The variants may be those where one or more of the HC-CDRs or LC-CDRs has one, two, or three amino acid substitutions, additions, deletions, or combinations thereof. In certain embodiments, each CDR is defined in accordance with Kabat definition, the Chothia definition, the combination of Kabat definition and Chothia definition, the AbM definition, or the contact definition of CDR.

In certain embodiments, the isolated monoclonal antibody described herein is a chimeric, humanized, or human antibody. In certain aspects, the humanized antibody has VH and VL chains having amino acid sequences at least 90% or 95% identical to clone-paired sequences of Hu-176 VH-1 and Hu-176-K, as shown in Tables 6 and 8, respectively. In certain aspects, the VH and VL chains have amino acid sequences identical to clone-paired sequences of Hu-176 VH-1 and Hu-176-K, as shown in Tables 6 and 8, respectively. In certain aspects, the humanized antibody has VH and VL chains having amino acid sequences at least 90% or 95% identical to clone-paired sequences of Hu-176 VH-1 (W48L) and Hu-176-K, as shown in Tables 6 and 8, respectively. In certain aspects, the VH and VL chains have amino acid sequences identical to clone-paired sequences of Hu-176 VH-1 (W48L) and Hu-176-K, as shown in Tables 6 and 8, respectively In certain aspects, the isolated monoclonal antibody described herein comprises amino acid modifications in the IgG Fc region. In some aspects, the IgG Fc region comprises an amino acid modification in one or more of amino acid positions 234, 235, 297, and 329. In some aspects, the IgG Fc region comprises an amino acid substitution N to A at amino acid position 297. In some aspects, the IgG Fc region comprises the amino acid substitutions L to A at amino acid position 234, L to A at amino acid position 235, and P to G at amino acid position 329.

In another aspect, the present disclosure provides an isolated monoclonal antibody or an antigen-binding fragment thereof, which competes for the same epitope with an antibody having clone-paired heavy and light chain CDR sequences from Tables 1 and 3. In certain embodiments, the epitope bound by the antibody or antigen-binding fragment is located within the linker region between the D1 and D2 domain of human LILRB1. In certain embodiments, the present disclosure provides an isolated monoclonal antibody or an antigen-binding fragment thereof, wherein, when bound to LILRB1, the monoclonal antibody binds to residues Y76 and R84 of LILRB1.

In certain embodiments, the isolated monoclonal antibody described herein is of the IgG1, IgG2, IgG3 or IgG4 type. In certain embodiments, the antigen-binding fragment described herein is a recombinant ScFv (single chain fragment variable) antibody, Fab fragment, F(ab')2 fragment, or Fv fragment.

In certain aspects, the isolated monoclonal antibody or an antigen binding fragment thereof described herein is conjugated or fused to an imaging agent or a cytotoxic agent. In certain aspects, the isolated monoclonal antibody or an antigen binding fragment thereof described herein is labeled, with, for example, a fluorescent label, an enzymatic label, or a radioactive label.

In another aspect, there is provided a pharmaceutical composition comprising an isolated monoclonal antibody or an antigen-binding fragment thereof as provided herein, and at least one pharmaceutically acceptable carrier.

In another aspect, there is provided an isolated nucleic acid that encodes the isolated monoclonal antibody or an antigen-binding fragment thereof as provided herein.

In another aspect, there is provided a vector comprising the isolated nucleic acid as provided herein.

In another aspect, there is provided a host cell comprising the vector as provided herein. The host cell may be a mammalian cell. The host cell may be a CHO cell.

In another aspect, there is provided a hybridoma encoding or producing the isolated monoclonal antibody as provided herein.

In another aspect, there is provided a process of producing an antibody. The method may comprise culturing the host cell as provided herein under conditions suitable for expressing the antibody and recovering the antibody.

In another aspect, there is provided a chimeric antigen receptor (CAR) protein comprising an antigen-binding fragment as provided herein.

In another aspect, there is provided an isolated nucleic acid that encodes a CAR protein as provided herein.

In another aspect, there is provided an engineered cell comprising the isolated nucleic acid as provided herein. In certain embodiments, the cell is a T cell, NK cell, or myeloid cell.

In another, there is provided a method of treating or ameliorating the effect of a cancer in a subject, the method comprising administering to the subject a therapeutically effective amount of an antibody or an antigen-binding fragment thereof as defined herein.

The method may reduce or eradicate the tumor burden in the subject, may reduce the number of tumor cells, may reduce tumor size, may reduce tumor infiltration, may reduce tumor metastasis, may eradicate the tumor in the subject. The cancer may be a solid tumor or hematologic malignancy.

In certain embodiments, the cancer is a solid tumor including adrenal cancer, bile duct carcinoma, bone cancer, brain cancer, breast cancer, cervical cancer, choriocarcinoma, colon cancer, colorectal cancer, esophageal cancer, eye cancer, gastric cancer, glioblastoma, head and neck cancer, kidney cancer, liver cancer, lung cancer, mesothelioma, melanoma, merkel cell cancer, nasopharyngeal carcinoma, neuroblastoma, oral cancer, ovarian cancer, pancreatic cancer, penile cancer, pinealoma, prostate cancer, renal cell cancer, retinoblastoma, sarcoma, skin cancer, testicular cancer, thymic carcinoma, thyroid cancer, uterine cancer, and vaginal cancer.

In some embodiments, the cancer is a metastatic, recurrent or drug-resistant cancer.

In some embodiments, said cancer is hematologic malignancies including acute lymphocytic leukemia (ALL), acute myeloid leukemia (AML), B-cell leukemia, blastic plasmacytoid dendritic cell neoplasm (BPDCN), chronic lymphoblastic leukemia (CLL), chronic myelomonocytic leukemia (CMML), chronic myelocytic leukemia (CML), pre-B acute lymphocytic leukemia (Pre-B ALL), diffuse large B-cell lymphoma (DLBCL), extranodal NK/T-cell lymphoma, hairy cell leukemia, HHV8-associated primary effusion lymphoma, plasmablastic lymphoma, primary CNS lymphoma, primary mediastinal large B-cell lymphoma, T-cell/histiocyte-rich B-cell lymphoma, heavy chain disease, Hodgkin's lymphoma, non-Hodgkin's lymphoma, Waldenstrom's macroglobulinemia, multiple myeloma (MM), myelodysplastic syndromes (MDS), myeloproliferative neoplasms, and polycythemia vera.

The antibody or an antigen-binding fragment thereof may be administered intravenously, intra-arterially, intra-tumorally, or subcutaneously.

In certain aspects, the subject's NK cells have been identified as expressing LILRB1. In certain aspects, the subject's NK cells have been identified as expressing an increased level of LILRB1 relative to a reference level. The reference level may be an average level as found in a segment of the healthy population. In certain aspects, wherein the subject's myeloma cells have been identified as not expressing LILRB1.

In certain embodiments, the method may further comprise administering to the subject one or more drugs selected from the group consisting of administering to the subject one or more drugs selected from the group consisting of a topoisomerase inhibitor, an anthracycline topoisomerase inhibitor, an anthracycline, a daunorubicin, a nucleoside metabolic inhibitor, a cytarabine, a hypomethylating agent, a low dose cytarabine (LDAC), a combination of daunorubicin and cytarabine, a daunorubicin and cytarabine liposome for injection, Vyxeos®, an azacytidine, Vidaza®, a decitabine, an all-trans-retinoic acid (ATRA), an arsenic, an arsenic trioxide, a histamine dihydrochloride, Ceplene®, an interleukin-2, an aldesleukin, Proleukin®, a gemtuzumab ozogamicin, Mylotarg®, an FLT-3 inhibitor, a midostaurin, Rydapt®, a clofarabine, a farnesyl transferase inhibitor, a decitabine, an IDH1 inhibitor, an ivosidenib, Tibsovo®, an IDH2 inhibitor, an enasidenib, Idhifa®, a smoothened (SMO) inhibitor, a glasdegib, an arginase inhibitor, an IDO inhibitor, an epacadostat, a BCL-2 inhibitor, a venetoclax, Venclexta®, a platinum complex derivative, oxaliplatin, a kinase inhibitor, a tyrosine kinase inhibitor, a PI3 kinase inhibitor, a BTK inhibitor, an ibrutinib, IMBRUVICA®, an acalabrutinib, CALQUENCE®, a zanubrutinib, a PD-1 antibody, a PD-L1 antibody, a CTLA-4 antibody, a LAG3 antibody, an ICOS antibody, a TIGIT antibody, a TIM3 antibody, a CD40 antibody, a 4-1BB antibody, a CD47 antibody, a SIRP1α antibody or fusions protein, a CD70 antibody, and CLL1 antibody, a CD123 antibody, an antagonist of E-selectin, an antibody binding to a tumor antigen, an antibody binding to a T-cell surface marker, an antibody binding to a myeloid cell or NK cell surface marker, an alkylating agent, a nitrosourea agent, an antimetabolite, an antitumor antibiotic, an alkaloid derived from a plant, a hormone therapy medicine, a hormone antagonist, an aromatase inhibitor, and a P-glycoprotein inhibitor.

The isolated monoclonal antibody or an antigen binding fragment thereof may comprise an antitumor drug linked thereto. The antitumor drug may be linked to said antibody through a photolabile linker. The antitumor drug may be linked to said antibody through an enzymatically cleaved linker. The antitumor drug may a toxin, a radioisotope, a cytokine, or an enzyme.

In another embodiment, there is provided a method of detecting a cancer cell or cancer stem cell in a sample or subject comprising (a) contacting a subject or a sample from the subject with the antibody or an antigen-binding fragment thereof as defined herein; and (b) detecting binding of said antibody to a cancer cell or cancer stem cell in said subject or sample. The sample may be a body fluid or biopsy, or blood, bone marrow, sputum, tears, saliva, mucous, serum, urine or feces. Detection may comprise immunohistochemistry, flow cytometry, immunoassays (including ELISA, RIA etc.) or Western blot. The method may further comprise performing steps (a) and (b) a second time and determining a change in detection levels as compared to the first time. The isolated monoclonal antibody or an antigen binding fragment thereof may further comprise a label, such as a peptide tag, an enzyme, a magnetic particle, a chromophore, a fluorescent molecule, a chemo-luminescent molecule, or a dye. The isolated monoclonal antibody or an antigen binding fragment thereof may be conjugated to a liposome or nanoparticle.

In still an additional aspect, there is provided a method of treating or ameliorating the effect of an autoimmune disease in a subject, the method comprising administering to the subject a therapeutically effective amount of the antibody or an antigen-binding fragment thereof as defined herein. The antibody or an antigen-binding fragment thereof may be administered intravenously, intra-arterially, intra-tumorally, or subcutaneously. The method may further comprise administering to the subject one or more drugs selected from the group consisting of a steroid or an NSAID. The autoimmune disease may be Guillain-Barre syndrome, Chronic inflammatory demyelinating polyneuropathy, ankylosing spondylitis, psoriatic arthritis, enteropathic arthritis, reactive arthritis, undifferentiated spondyloarthropathy, juvenile spondyloarthropathy, Behcet's disease, enthesitis, ulcerative colitis, Crohn's disease, irritable bowel syndrome, inflammatory bowel disease, fibromyalgia, chronic fatigue syndrome, pain conditions associated with systemic inflammatory disease, systemic lupus erythematosus, Sjogren's syndrome, rheumatoid arthritis, juvenile rheumatoid arthritis, juvenile onset diabetes mellitus (also known as Type I diabetes mellitus), Wegener's granulomatosis, polymyositis, dermatomyositis, inclusion body myositis, multiple endocrine failure, Schmidt's syndrome, autoimmune uveitis, Addison's disease, Grave's Disease, Hashimoto's thyroiditis, autoimmune thyroid disease, pernicious anemia, gastric atrophy, chronic hepatitis, lupoid hepatitis, atherosclerosis, multiple sclerosis, amyotrophic lateral sclerosis, hypoparathyroidism, Dressler's syndrome, myasthenia gravis, Eaton-Lambert syndrome, autoimmune thrombocytopenia, idiopathic thrombocytopenic purpura, hemolytic anemia, pemphigus vulgaris, pemphigus, dermatitis herpetiformis, alopecia, scleroderma, progressive systemic sclerosis, CREST syndrome (calcinosis, Raynaud's phenomenon, esophageal dysmotility, sclerodactyly, and telangtasia), adult onset diabetes mellitus (also known as Type II diabetes mellitus), mixed connective tissue disease, polyarteritis nodosa, systemic necrotizing vasculitis, glomerulonephritis, atopic dermatitis, atopic rhinitis, Goodpasture's syndrome, Chagas' disease, sarcoidosis, rheumatic fever, asthma, antiphospholipidsyndrome, erythema multiforme, Cushing's syndrome, autoimmune chronic active hepatitis, allergic disease, allergic encephalomyelitis, transfusion reaction, leprosy, malaria, leshmaniasis, trypanosomiasis, Takayasu's arteritis, polymyalgia rheumatica, temporal arteritis, shistosomiasis, giant cell arteritis, eczema, lymphomatoid granulomatosis, Kawasaki's disease, endophthalmitis, psoriasis, erythroblastosis fetalis, eosinophilic faciitis, Shulman's syndrome, Felty's syndrome, Fuch's cyclitis, IgA nephropathy, Henoch-Schonlein purpura, graft versus host disease, transplantation rejection, tularemia, periodic fever syndromes, pyogenic arthritis, Familial Mediterranean Fever, TNF-receptor associated periodic syndrome (TRAPS), Muckle-Wells syndrome, or hyper-IgD syndrome.

In another embodiment, provided herein are methods for increasing the immune functions of NK cells in a subject, the method comprising administering to the subject the antibody or an antigen-binding fragment thereof or an engineered cell as defined herein.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

FIGS. 1A-C. The expression of LILRB1 on NK cells from human peripheral blood. (FIG. 1A) PBMCs were isolated from healthy donors' buffy coats or peripheral blood of patients with multiple myeloma (MM) or prostate cancer by density gradient centrifugation using Ficoll-Paque PLUS medium, and then stained with anti-CD3-PE, anti-CD56-FITC, anti-LILRB1-APC or isotype-APC antibodies. NK cells were gated as $SSC^{low}FSC^{low}CD56^{+}CD3^{-}$. The LILRB1 expression on NK cell was gated according to the isotype-APC antibody. Representative flow cytometry plots showed that LILRB1 were mainly expressed on CD56$^{dim}$, instead of CD56$^{bright}$ NK cells. (FIG. 1B) The percentage of LILRB1$^{+}$ NK cells among CD56$^{dim}$ NK cells from healthy donors (n=12), patients with stage 2b or 2c prostate cancer (n=16), and stage 3b or 3c prostate cancer (n=17) were determined by flow cytometry. (FIG. 1C) The percentage of LILRB1$^{+}$ NK cells from healthy donors (same as FIG. 1B), patients with newly diagnosed MM (n=10), and patients with MM who had partial response or refractory disease (n=8) and good response to treatment (CR+VGPR, n=9) were determined by flow cytometry. CR=complete remission, VGPR=very good partial remission. *P<0.05; ***P<0.001.

FIGS. 2A-I. Generation and characterization of rabbit antagonistic anti-LILRB1 mAbs. (FIG. 2A) Left panel: The expression of HLA-G on cell surface of K562 and K562 cells overexpressed with HLA-G1 (K562-HLA-G) were stained with anti-HLA-G antibody (clone: MEM-G/9, Abcam) and analyzed by flow cytometry. Right panel: K562 or K562-HLA-G were co-cultured with LILRB1 reporter cells. K562/K562-HLA-G cells were stained with DDAOSE before co-culturing with LILRB1 reporter cells. The percentage of activated LILRB1 reporter cells (GFP) was analyzed by flow cytometry, 24 hours after co-culture. (FIG. 2B) Titration of antagonistic anti-LILRB1 mAbs in blocking the activation of LILRB1 reporter cells stimulated by K562-HLA-G. LILRB1 reporter cells were co-cultured with K562-HLA-G and incubated with different concentration of antagonistic anti-LILRB1 mAbs. (FIG. 2C) Representative flow cytometry plots showed that B1-176 binds to LILRB1 specifically. The LILR reporter cells were incubated with 0.5 μg/mL rabbit B1-176 at 4° C. for 30 min. Then, the reporter cells were incubated with anti-Rabbit-IgG PE antibody (Jackson Laboratory) and analyzed with flow cytometry. (FIG. 2D) Binding specificity of B1-176 rabbit antibody to LILRBs and LILRAs, determined by ELISA. (FIG. 2E) Affinity of B1-176 performed by Octet RED96. (FIG. 2F) Screening of B1-176 binding to LILRB1-Fc fusion proteins with different domain deletion, determined by ELISA. (FIG. 2G) Binding ability of B1-176 to LILRB1-D1D2 Fc fusion proteins with different mutant was determined by ELISA (top panel). Two amino acids (Y76 and R84) in LILRB1 were identified to be critical for the binding of B1-176 (bottom panel). (FIG. 2H) Detailed binding surface of LILRB1 by rabbit mAb B1-176 was generated by molecular docking using Discovery Studio. (FIG. 2I) Cross reactivities of B1-176 and commercial available anti-LILRB1 mAbs to LILRs expressed on 2B4 cells, as accessed by flow cytometry.

FIGS. 3A-D. Humanization of anti-LILRB1 blocking antibody 176. (FIG. 3A) A combined Kabat/IMGT/Chothia CDR-grafting strategy was used to humanize rabbit antibody 176. The heavy chain and light chain of rabbit antibody B1-176 were showed as Rab-176 VH, Rab-176 VL. The heavy chain and light chain of human antibody framework were showed as Hu IGHV3-53*04 and Hu IGKV1-9*01. Amino Acids different from rabbit original ones (shown in blue), which were near HCDR, were shown in green. The heavy chain of B1-176 was humanized based on the human antibody framework, showed as Hu-176 VH-1 or Hu-176 VH-2 (W48L), which has a mutation noted with asterisk. The light chain of B1-176 was humanized based on the human antibody framework, showed as Hu-176 VL. (FIG. 3B) The ELISA results showed that Rabbit amino acid L48 (noted with asterisk) in FR2 need to be remained at the same position to keep the binding activity of humanized B1-176 as same as rabbit B1-176. (FIG. 3C) Molecular docking data showed that the structures of rabbit B1-176 and humanized Hu B1-176-N297A are similar. (FIG. 3D) The affinities of rabbit human chimeric anti-LILRB1 antibody B1-176 N297A and humanized anti-LILRB1 antibody expressed in human IgG1 with N297A or LALAPG mutations were determined by Octet RED96 or ELISA.

FIGS. 4A-C. Antagonistic LILRB1 mAbs can block the activation of LILRB1 receptor cells stimulated by both hematological cancer and solid tumor cell lines. (FIG. 4A) The levels of MHC class I on hematological cancer cell lines (left panel) or solid cancer cell lines (right) was detected by flow cytometry, using anti-pan MHC class I antibody (clone: HP-1F7, Santa Cruz Biotechnology). Cancer cell lines (prestained with DDAOSE) were co-cultured with LILRB1 reporter cells to test cancer cells' ability to stimulate LILRB1. The percentage of activated LILRB1 reporter cells (GFP$^{+}$) were analyzed by flow cytometry. (FIG. 4B) Rabbit B1-176 (left panel) and humanized Hu B1-176-N297A (right panel) can block the activation of LILRB1 receptor cells induced by hematological cancer cell lines in a dose-dependent manner. LILRB1 reporter cells were co-cultured with K562-HLA-G, multiple myeloma cell line KMS27, or pre-B leukemia cell line 697, then incubated with anti-LILRB1 mAbs. The activation of LILRB1 reporter cells was analyzed by flow cytometry 24 hrs after treatment. (FIG. 4C) Rabbit B1-176 (left panel) and humanized Hu B1-176-N297A (right panel) were titrated to block the activation of LILRB1 receptor cells by solid tumor cell lines. LILRB1 reporter cells were co-cultured with lung carcinoma cell line H460, melanoma cell line Malme-3m or triple-negative breast cancer cell line MDA-MB-231, then incubated with anti-LILRB1 mAbs. The activation of LILRB1 reporter cells was analyzed by flow cytometry 24 hrs after treatment.

FIGS. 5A-F. Antagonistic LILRB1 mAbs can regulate functions of NKL cell lines against cancer cells in vitro. (FIG. 5A) Multiple myeloma cell line KMS27 was co-cultured with NKL and incubated with 10 μg/mL control human IgG (hIgG) or B1-176-N297A (left panel, n=3), Hu B1-176-N297A (middle panel, n=3), and Hu B1-176-LALAPG (right panel, n=2). 4 hrs later, cytotoxic activity of NKL against cancer cells was analyzed by flow cytometry. (FIG. 5B) Multiple myeloma cell lines OPM2, RPMI8226 or acute T cell leukemia Jurkat cells were co-cultured with NKL and incubated with 10 μg/mL B1-176-N297A or hIgG. n=3. (FIG. 5C) Pre-B leukemia 697 cells (left panel) or Burkitt lymphoma Raji cells (right) were overexpressed with MICA (697-MICA, Raji-MICA) and co-cultured with NKL. 10 μg/mL B1-176-N297A or hIgG was added into the culture. (FIG. 5D) 697-MICA was co-cultured with NKL (E:T=20) and incubated with different concentrations of B1-176-N297A. (FIG. 5E) Solid tumor cell lines MDA-MB-231 or MALME-3M were co-cultured with NKL and incubated with 10 μg/mL B1-176-N297A or hIgG. n=3. (FIG. 5F) KMS27, OPM2, RPMI8226, Jurkat cells or 697/697MICA cells were co-cultured with NKL (E:T ratio=1:1). 10 μg/mL control hIgG, B1-176-N297A (for RPMI8226, Jurkat and 697/697 MICA) or Hu B1-176-N297A (for KMS27 and OPM2 treatment) was added into cell culture. IFN-γ levels in cell culture supernatants were determined by ELISA 24 hrs later. n=3-4, Statistical significance was analyzed between anti-LILRB1 antibody and hIgG. *P<0.05; P<0.01; *P<0.001.

FIGS. 6A-B. Antagonistic LILRB1 mAbs can increase cytotoxic activities of primary NK cells against cancer cells in vitro. (FIG. 6A) Multiple myeloma cell lines KMS27 and OPM2, Pre-B leukemia cell line 697 or lymphoma cell line Raji and Daudi cells were co-cultured with FACS-sorted LILRB1+ NK cells isolated from healthy donors' PBMCs. 10 μg/mL control hIgG or B1-176N297A was added into cell culture. n=3, except Daudi cells n=2. (FIG. 6B) KMS27 cells were co-cultured with NK cells from one multiple myeloma patient (E:T ratio=2.5:1) and incubated with 10 μg/mL control hIgG or Hu B1-176-N297A. Cytotoxic activity of primary NK cells was analyzed by flow cytometry 4 hrs after co-culture. n=3, ***P<0.001.

FIGS. 7A-C. Antagonistic LILRB1 mAbs can increase cytotoxicity activities of NKL cells in vivo. (FIG. 7A) $5\times10^6$ CFSE-stained 697 (NKL resistant) and 697 MICA (NKL sensitive) cell mixtures were injected together with $5\times10^7$ NKL cells into the peritoneal cavity of NSG mice. 10 mg/kg of control hIgG or B1-176-N297A was injected into mice through retro-orbitally. 24 hrs later, peritoneal cells were harvested and stained with anti-MICA-APC antibody. The ratio of 697-MICA to 697 cells was quantified by flow cytometry with the representative flow plot. The ratio of 697-MICA to 697 was used to calculate the cytotoxic activity of NKL cells in vivo. n=3-4, *P<0.05. (FIG. 7B) $1\times10^6$ 697 MICA luciferase-overexpressing cells (697 MICA-luci) were mixed with $5\times10^6$ NKL cells and injected into NSG mice subcutaneously. 10 mg/kg of control hIgG or B1-176-N297A was administrated retro-orbitally. Bioluminescence imaging (BLI) was conducted 48 hrs later. Quantification of BLI data (Total flux (p/s)) from two independent experiments demonstrates that mice received B1-176-N297 showed significantly lower tumor burden compared to control hIgG-treated mice, suggesting that B1-176-N297 improves the cytotoxic function of NKL cells in vivo. n=8-10, P<0.01. (FIG. 7**C) NSG mice were irradiated sublethally and injected with $5\times10^5$ luciferase-overexpressing KMS27 and $5\times10^6$ NKL cells via tail vein injection on Day 0. Another $5\times10^6$ NKL cells were injected into NSG mice via tail vein injection on Day 14. Mice received 10 mg/kg of control hIgG or B1-176-N297A retro-orbitally on Day 0, Day 3 and Day 7, and then once a week for one month further. BLI was conducted on Day 28 and Day 35. Summary BLI data showed that B1-176-N297 significantly decreased tumor development in mice (left panel). n=4, data from one representative experiment. *P<0.05, statistical significance was calculated by one-tailed unpaired t-test. Survival analysis of multiple myeloma mouse xenograft showed that B1-176-N297 treated mice significantly improved survival compared to control hIgG-treated mice (right panel). n=9-10, pooled data from two representative experiments. ***P<0.001.

FIGS. 8A-D. Antagonistic LILRB1 mAbs can regulate functions of NK92mi cell lines against cancer cells in vitro. (FIGS. 8A-C) Leukemia cell lines (RS4-11, MHHCALL2, MOLM13, THP-1, 697, 697MICA), Solid tumor cell lines (MDA-MB-231, SW480, MALEM-3M) or multiple myeloma cell line (RMPI8226) were co-cultured with NK92mi and incubated with 10 μg/mL control human IgG (hIgG), B1-#3 or B1-176. Four hours later, cytotoxic activity of NKL against cancer cells was analyzed by flow cytometry. (FIG. 8D) Two cases of primary leukemia cell were co-cultured with NK92mi and incubated with 10 μg/mL control human IgG (hIgG) or B1-#3 N297A. Four hours later, cytotoxic activity of NK92mi against cancer cells was analyzed by flow cytometry.

FIG. 9. Agonistic LILRB1 mAbs can activate LILRB1 receptor cells. LILRB1. LILRB1 reporter cells were co-cultured with K562 cells, and treated with agonistic LILRB1 mAbs B1-7 or B1-41. 24 hrs later, Percentage of GFP+ reporter cells were analyzed by flow cytometry. N297A mutation in Fc abolished, while S267E mutation in Fc enhanced the activity of agonistic LILRB1 mAbs.

FIGS. 10A-D. Agonistic LILRB1 mAbs can inhibit cytotoxic activities of NK cells against cancer cells in vitro. NK92mi cells were cocultured with 697 (FIG. 10A) or THP1 cells (FIG. 10B) and treated with anti-LILRB1 mAbs. Antagonistic B1-3 increased, while agonistic B1-7 inhibited the cytotoxic activity of NK92mi against 697 and THP-1 cells. (FIG. 10C) NKL cells were cocultured with 697/697-MICA and treated with anti-LILRB1 mAbs. Antagonistic B1-3 increased, while agonistic B1-7 inhibited the cytotoxic activity of NKL against 697-MICA. (FIG. 10D) NKL cells were cocultured with 697-MICA and treated with B1-7, and B1-7 with mutation in Fc (N297A, S267E). N297A mutation in Fc abolished the activity of agonistic B1-7. Cytotoxic activity was analyzed 4 hours after cocultured, by flow cytometry.

FIG. 11. Agonistic LILRB1 mAbs can inhibit IFN-γ secretion from of NKL cells. NKL cells were cocultured with 697-MICA cells and treated with anti-LILRB1 mAbs. Antagonistic B1-3 increased, while agonistic B1-7 inhibited IFN-γ secretion from of NKL cells. Culture supernatants were collected 24 hours after coculture and the IFN-γ levels were determined by ELISA.

FIGS. 12A-G. Generation and screening of anti-LILRB1 mAbs. (FIG. 12A) Anti-LILRB1 specific rabbit memory B cell isolation, in vitro culture, and cloning strategy used to generate anti-LILRB1 mAbs. After cultured with rabbit CD40L feeder cells and a cocktail of rabbit cytokines in 96-well plates for 14 days, B cells supernatants were screened for binding to LILRB1 in ELISA. Antibody heavy and light chain variable genes were then cloned into rabbit IgG expression vector and recombinant antibodies were produced using a transient HEK293Expi-F cell expression system. (FIG. 12B) Flow chart of the screening of anti-LILRB1 mAbs. (FIG. 12C) $EC_{50}$ of 44 anti-LILRB1 rabbit mAbs were determined by ELISA. (FIG. 12D) A classic sandwich epitope binning assay (Octet RED96) was used to determine the 12 epitope bins of 44 anti-LILRB1 rabbit mAbs. (FIG. 12E) To screen antagonistic anti-LILRB1 antibodies, LILRB1 reporter cells were co-cultured with K562-HLA-G cells and incubated with anti-LILRB1 mAbs (10 μg/mL) for 24 hours. (FIG. 12F) Left panel: the homology of LILRB1 with other receptors in LILR family. The phylogenetic tree of D1-D2 coding amino acid sequences from all the LILRs, except only D1 domain was selected for LILRB4, was generated by MEGA version 7.0 using a Maximum Likelihood method. Right table: the specificity of anti-LILRB1 mAbs, analyzed by Octet RED96. (FIG. 12G) Affinity of commercial anti-LILRB1 monoclonal antibody HP-F1 and GHI/75, analyzed by Octet RED96.

FIGS. 13A-B. Characterization of B1-176. Fusion proteins of LILRB1 ECD mutants with Fc of hIgG1 were produced to characterize the binding epitope of B1-176. (FIG. 13A) Schematic of the LILRB1-fc mutations. (FIG. 13B) Single or multiple mutations of LILRB1 amino acids.

FIGS. 14A-D. The expression of LILRB1 on cell surface. (FIG. 14A) One representative flow plot of LILRB1 expression on NKL cells. (FIG. 14B) Representative flow plots showed multiple myeloma cell lines did not express LILRB1 on cell surface. (FIG. 14C) Representative flow plots showed majority of malignant plasma cells from a patient with MM did not express LILRB1 on cell surface. (FIG. 14D) Representative flow plots showed that pre-B ALL cell line 697, MHHCALL2, RS4;11, RCHACV, REH; acute monocytic leukemia cell line THP-1, MOLM13, MV4-11; and Raji cells expressed LILRB1 on cell membrane, while T cell leukemia Jurkat cells and chronic myelogenous leukemia cell line K562 did not expressed LILRB1. Cells were incubated with anti-LILRB1-APC (clone: HP-F1, eBioscience) on ice for 30 min and analyzed by flow cytometry.

DETAILED DESCRIPTION

Figure 2H:
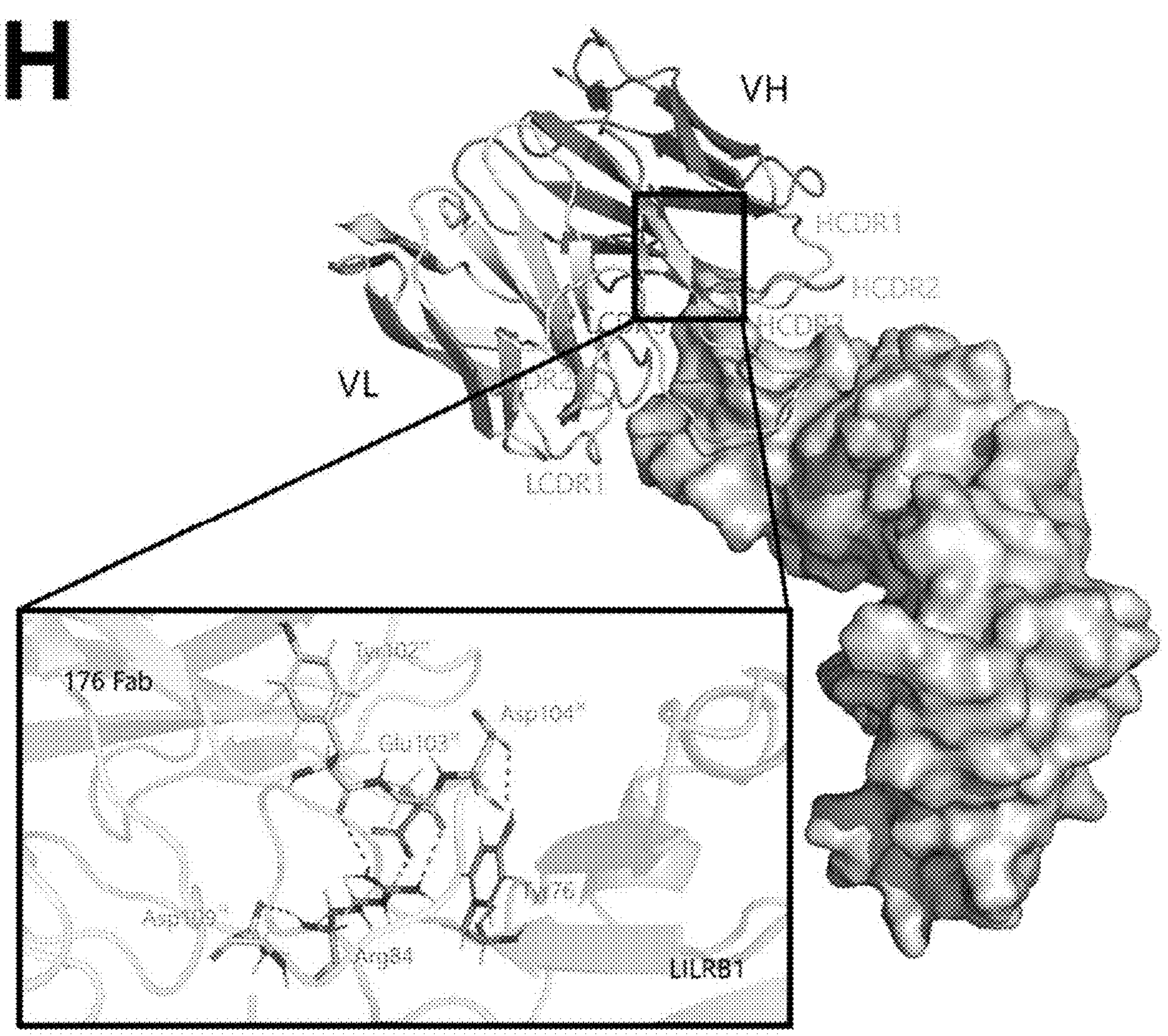

LILRB1, a member of the ITIM-containing LILR receptor family, plays critical roles in regulation of both innate and adaptive immunity. It is expressed on several types of immune cells, including NK cells, and acts as an immune checkpoint protein. LILRB expression in myeloid-derived suppressor cells (MDSCs) can promote tumor growth and result in a suppressive immune microenvironment for tumor progression and metastasis. On the other hand, activation of LILRB1 signaling using agonistic antibodies can reduce tissue inflammation and can be used for management of autoimmune diseases. Both agonistic and antagonistic human LILRB1 monoclonal antibodies are provided herein, with specific targeting properties for modulation of LILRB1 signaling. These LILRB1 antibodies can be used to treatment human diseases, including cancer and auto-immune disease.

I. Aspects of the Present Disclosure

LILRB1 is expressed on subsets of T cells and NK cells. LILRB1 is mainly expressed on $CD56^{dim}$ NK cells from healthy donors and patients with different malignancies. In addition, the percentage of LILRB1V NK cells from peripheral blood of patients with multiple myeloma (MM) with persistent disease while on treatment is significantly higher than that in NK cells from health donors or from patients with minimal disease or complete response. The percentage of LILRB1V NK cells is also significantly higher in the peripheral blood of patients with late stage prostate cancer (stage 3B and 3C) than in that of healthy donors. These results are in accordance with previous studies showing that LILRB1 level is higher on peripheral blood $CD56^{dim}$ NK cells than $CD56^{bright}$ NK cells[40]. Other prior studies also reported that the percentage of LILRB1V NK cells was significantly higher for NK cells in the peripheral blood of patients with metastatic prostate and breast cancers than for NK cells from healthy donors or patients with localized cancers[9 10]. Previous studies also reported that there is a strong association between the percentage of circulating $CD8^{+}$LILRB1 T cells and the recurrence risk of non-muscle-invasive bladder cancer[41]. Taken together, LILRB1 expression on NK cells and T cells has prognostic value. Although the precise mechanism of the LILRB1 polymorphism in human NK cells is unknown, the expression of LILRB1 on NK cells is linked to particular haplotypes and a polymorphic regulatory region[42]. The increase of $LILRB1^{+}$ NK cells from certain patients with cancer was well documented. NK cells upregulated LILRB1 expression when cultured with cancer cells in vitro[9]. HLA-G and soluble HLA-G were reported to upregulate LILRB1 expression on NK cells, T cells and antigen presenting cells[43]. Patients with elevated plasmatic soluble HLA-G may have high LILRB1 expression on NK cells[10]. Terminally differentiated NK cells, marked by the expression of CD57 or multiple KIRs, have high expression of LILRB1 and poor proliferative capacity[44]. The high number of circulating $CD57^{+}$ NK cells was associated with resistance to HER2-specific therapeutic antibodies in a patient with primary breast cancer[45], which may explain the increased LILRB1V NK cells in patients with cancer that have poor response to treatment.

Importantly, blockade of LILRB1 with antagonistic monoclonal antibodies increases the immune functions of NK cells against multiple myeloma cells both in vitro and in vivo. In an earlier study, Heidenreich and colleagues reported that blockade of LILRB1 on NK92 cell line did not increase their cytotoxic activity against multiple myeloma cell lines[46]. This discrepancy may be related to the use of the NK92 cell line, which may have more potent cytotoxic activity[47] than the NKL cell line and primary NK cells used herein. MHC class I, ligands of LILRB1, is strongly expressed on late-stage MM cell lines, with a direct correlation between expression levels and clinical stage of disease[48]. RPMI8226, the cell line used in the study of[46], and other MM cell lines, express high levels of MHC class I molecules at the cell surface and have a strong capacity to activate the LILRB1 reporter cells. These data indicate that MM cells may become NK cell-resistant by activating LILRB1 on NK cells through engagement of the MHC class I molecules expressed by MM cells.

NK cell function is determined by the balance of various activating signals and inhibitory signals in the cell. Targeting multiple immune receptors may optimize the function of NK cells against cancer cells. Combinatorial blockade of LILRB1 and activation of NKG2D receptor (by its ligand MICA), acts synergistically to increase the cytotoxic function of NK cells. These results are concordant with a previous report showing that overexpression of HLA-G on MICA-expressing M8 melanoma cell line blocked NKL cells' cytotoxic activity against the cancer cell line by activating LILRB1[49]. Several methods are being developed to increase the surface abundance of MICA on cancer cells[419]. Other studies have reported combinatorial effects of LILRB1 blockade with KIR blockade or ADCC-inducing mAbs in vitro[10 12]. Adoptively transferred allogeneic haploidentical NK cells are considered to have improved function because of the mismatch of MHC class I molecules and KIRs[1 50]. Since LILRB1 may still be activated on these allogeneic NK cells, there may be a combinatorial effect of LILRB1 blockade and allogeneic NK cell adoptive transfer.

Interestingly, there are reports that LILRB1 on cancer cells, such as transformed B lymphoid cancer cells and MGUS cells, may activate immune responses[16 17]. LILRB1 is expressed on pre-B leukemia cells and Burkitt lymphoma Raji cells. However, administration of anti-LILRB1 blocking antibodies increased the NK cell function against the LILRB1 positive cell line 697 cells and Raji cells, in agreement with a previous report that LILRB1 blockade increased the cytotoxic activity of NK cells against pre-B-ALL[12]. These results suggest that immune stimulating functions of LILRB1 may be context-dependent. As LILRB1 expression on NK cells is significantly higher in patients with persistent disease following treatment, LILRB1 blockade may increase the function of NK cells in patients with persistent MM. However, LILRB1 expression level on both myeloma cells and NK cells should be monitored before and during anti-LILRB1 antibody treatment. To minimize the risk of modulating LILRB1 receptor on myeloma cells, the anti-LILRB1 antibody treatment should prioritize those patients with high expression level of LILRB1 on NK cells and no LILRB1 expression on myeloma cells.

In conclusion, blockade of LILRB1 by antagonistic antibodies has potential as an immunotherapy approach for treatment of patients with various types of cancer, in particular those with high levels of expression of LILRB1 on NK cells.

II. Monoclonal Antibodies and Production Thereof

The monoclonal antibodies described herein can be prepared using standard methods, followed by screening, characterization and functional assessment. Variable regions can be sequenced and then subcloned into a human expression vector to produce the chimeric antibody genes, which are then expressed and purified. These chimeric antibodies can be tested for antigen binding, signaling blocking, and in xenograft experiments. The monoclonal antibodies described herein can also be prepared using phage display method, in which a large library of phage displayed human scFv is panned against the target protein. The human scFv selected to specifically binding to the target protein can be sequenced and then subcloned into a human expression vector to produce the desired human antibody.

A. General Methods

It will be understood that monoclonal antibodies binding to LILRB1 will have several applications. These include the production of diagnostic kits for use in detecting and diagnosing cancer, as well as for cancer therapies. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The classical methods for generating monoclonal antibodies (MAbs) generally begin along the same lines as those for preparing polyclonal antibodies. The first step for both these methods is immunization of an appropriate host. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984).

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). Fusion procedures usually produce viable hybrids at low frequencies, about $1\times10^{-6}$ to $1\times10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain is also used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Recently, additional methods for generating mAb, such as scFv phage display, have been developed (see CM Hammers and JR Stanley, Antibody phage display: technique and applications, J Invest Dermatol (2014) 134: e17). Generally, a panel of human mAbs that bind to a target protein, e.g., human LILRB1, are generated by panning a large diversity of human scFv phage displayed antibody library.

To generate the human scFv phage displayed antibody library, RNA is extracted from the chosen cell source, e.g., peripheral blood mononuclear cells. The RNA is then reversed-transcribed into cDNA, which is used for PCR of the VH and VL chains of the encoded antibodies. Defined sets of primers specific for the different VH and VL chain region gene families allow the amplification of all transcribed rearranged variable regions within a given immunoglobulin repertoire, reflecting all antibody specificities in a particular individual.

The VH and VL PCR products that represent the antibody repertoire are ligated into a phage display vector that is engineered to express the VH and VL as an scFv fused to the pIII minor capsid protein of a filamentous bacteriophage of *E. coli* that was originally derived from the M13 bacteriophage. This generates a library of phages, each of which expresses on its surface a scFv and harbors the vector with the respective nucleotide sequence within.

The library is then screened for phage binding to a target antigen through its expressed surface scFv by a technique called bio-panning. In short, the target protein is coated on solid phase for incubation with phage libraries. After washing and elution, antigen enriched phages are recovered and used for next rounds of phage panning. After at least three rounds of phage panning, single bacterial colonies are picked for phage ELISA and other functional/genetic analysis.

The positive hits are sequenced for the scFv region and are converted to full human IgG heavy and light chain constructs, which are used to generate the mAb of interest using the methods disclosed supra. For example, the IgG expressing plasmids are cotransfected into Expi293 cells using transfection reagent PEI. After 7 days of expression, supernatants are harvested, and antibodies are purified by affinity chromatography using protein A resin.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

1. Antibodies to LILRB1

Antibodies or antigen-binding fragments thereof according to the present disclosure may be defined, in the first instance, by their binding specificity, which in this case is for LILRB1. Those of skill in the art, by assessing the binding specificity/affinity of a given antibody using techniques well known to those of skill in the art, can determine whether such antibodies fall within the scope of the instant claims.

In one aspect, there are provided antibodies and antigen-binding fragments specifically bind to LILRB1. In some embodiments, when bound to LILRB1, such antibodies modulate the activation of LILRB1. In certain embodiments, the antibody or antigen-binding fragment, when bound to LILRB1, activates LILRB1. In certain embodiments, the antibody or antigen-binding fragment, when bound to LILRB1, suppresses activation of LILRB1. In certain embodiments, the antibody or antigen-binding fragment, when bound to LILRB1, can specifically interfere with, block or reduce the interaction between LILRB1 and its binding partners. In certain embodiments, the antibodies or antigen-binding fragments provided herein specifically or selectively bind to human LILRB1.

In some embodiments, the antibodies or antigen-binding fragments bind specifically to human LILRB1 and/or substantially inhibits binding of human LILRB1 to MHC class I molecules, such as HLA-G, by at least about 20%-40%, 40-60%, 60-80%, 80-85%, or more. In some embodiments, the antibody or antigen-binding fragment has a Kd of less (binding more tightly) than $10^{-6}$, $10^{-7}$, $10^{-8}$, $10^{-9}$, $10^{-10}$, $10^{-11}$, $10^{-12}$, $10^{-13}$ M. In some embodiments, the antibody or antigen-binding fragment has an IC50 for blocking the binding of MHC class I molecules, such as HLA-G, to LILRB1 of less than 10 uM, 10 uM to 1 uM, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM.

In some embodiments, the antibodies or antigen-binding fragments provided herein having the clone-paired CDRs illustrated in Tables 1 and 3.

In certain embodiments, the antibodies may be defined by their variable sequence, which include additional "framework" regions. The antibody is characterized by clone-paired heavy chain and light chain amino acid sequences from Tables 6 and 8. Furthermore, the antibodies sequences may vary from these sequences, particularly in regions outside the CDRs. For example, the amino acids may vary from those set out above by a given percentage, e.g., 80%, 85%, 90%, 91%, 92%, 93%, 94%, 95%, 96%, 97%, 98% or 99% homology, or the amino acids may vary from those set out above by permitting conservative substitutions (discussed below). Each of the foregoing apply to the amino acid sequences of Tables 6 and 8. In another embodiment, the antibody derivatives of the present disclosure comprise VL and VH domains having up to 0, 1, 2, 3, 4, 5, 6, 7, 8, 9, 10 or more conservative or non-conservative amino acid substitutions, while still exhibiting the desired binding and functional properties.

While the antibodies of the present disclosure were generated as IgG's, it may be useful to modify the constant regions to alter their function. The constant regions of the antibodies typically mediate the binding of the antibody to host tissues or factors, including various cells of the immune system (e.g., effector cells) and the first component (Clq) of the classical complement system. Thus, the term "antibody" includes intact immunoglobulins of types IgA, IgG, IgE, IgD, IgM (as well as subtypes thereof), wherein the light chains of the immunoglobulin may be of types kappa or lambda. Within light and heavy chains, the variable and constant regions are joined by a 35 "J" region of about 12 or more amino acids, with the heavy chain also including a "D" region of about 10 more amino acids. See generally, Fundamental Immunology Ch. 7 (Paul, W., ed., $2^{nd}$ ed. Raven Press, N.Y. (1989).

The present disclosure further comprises nucleic acids which hybridize to nucleic acids encoding the antibodies disclosed herein. In general, the nucleic acids hybridize under moderate or high stringency conditions to nucleic acids that encode antibodies disclosed herein and also encode antibodies that maintain the ability to specifically bind to an LILRB1. A first nucleic acid molecule is "hybridizable" to a second nucleic acid molecule when a single stranded form of the first nucleic acid molecule can anneal to the second nucleic acid molecule under the appropriate conditions of temperature and solution ionic strength (see Sambrook et al., Molecular Cloning: a Laboratory Manual, $3^{rd}$ ed., Cold Spring Harbor Press, Cold Spring Harbor, N.Y. 2001). The conditions of temperature and ionic strength determine the "stringency" of the hybridization. Typical moderate stringency hybridization conditions are 40% formamide, with 5× or 6×SSC and 0.1% SDS at 42° C. High stringency hybridization conditions are 50% formamide, 5× or 6×SSC (0.15M NaCl and 0.015M Na-citrate) at 42° C. or, optionally, at a higher temperature (e.g., 57° C., 59° C., 60° C., 62° C., 63° C., 65° C. or 68° C.). Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook et al., supra). For hybridization with shorter nucleic acids, e.g., oligonucleotides, the position of mismatches becomes more important, and the length of the oligonucleotide determines its specificity (see Sambrook et al., supra).

TABLE 1

Amino acid sequences of LILRB1 (B1) mAb heavy chain CDRs

| mAb ID | CDR1 | SEQ ID NO: | CDR2 | SEQ ID NO: | CDR3 | SEQ ID NO: |
|---|---|---|---|---|---|---|
| B1-#3-H | GFDFSSDA | 2 | IYNGDEI | 3 | ARAVYSDGGAGYPYMYGMDL | 4 |
| B1-#4-H | GFDFSGIYW | 5 | FDAERTGNT | 6 | ARSYYM | 7 |
| B1-#5-H | ELSFSSAYY | 8 | IYSGDGD | 9 | ARALDSHYSSFDL | 10 |
| B1-#7-H | GFSLNSYA | 11 | IDTGASI | 12 | ARGFSMFKL | 13 |
| B1-#10-H | GLDFSSSYW | 14 | IDTGSSGST | 15 | ASTPNSLGYDL | 16 |
| B1-#15-H | GFSSSSSAY | 17 | IFIGSGSDS | 18 | ARNTYDWNGYIYGPCYFGL | 19 |
| B1-#18-H | GFSLSRYA | 20 | IDTSSGN | 21 | ARGFSMFKL | 22 |
| B1-#19-H | GLDFSSSYW | 23 | IDVGSSGGS | 24 | ASTTTNVFGYDL | 25 |
| B1-#22-H | GFDFSSNDY | 26 | IYGGDGHT | 27 | RGYSYGDTGYADAILTLDL | 28 |
| B1-#25-H | FNYYNYYY | 29 | MSTASAN | 30 | AKSHGGDGGYGVVL | 31 |
| B1-#27-H | GFSFSGSYW | 32 | IYGDSIA | 33 | ARDRNGGSGAYGWDL | 34 |
| B1-#28-H | GFSFSSDYD | 35 | IVTGFSGRI | 36 | ARDSGNYNWDL | 37 |
| B1-#38-H | GFSFSNDYW | 38 | GHIGSFRTT | 39 | ARSPYDDGYGGFTFNL | 40 |
| B1-#41-1-H | GFSFSSSYW | 41 | IYAGSSGST | 42 | ARSTSGSYGAGLGL | 43 |
| B1-#56-H | GFSFSINLY | 44 | IYGNNNANT | 45 | ARDTAAYYAFSL | 46 |
| B1-#57-H | SGFTFSGYY | 47 | IYVGSGGST | 48 | ARGVNDYGWALKL | 49 |
| B1-#58-H | AFSFSSSSW | 50 | IYGGSVGTT | 51 | ATNTDSSRSYYNL | 52 |
| B1-#72-H | GIDLSNYWY | 53 | VATDSSRT | 54 | RGSGASTNGVWWVMGDGMDL | 55 |
| B1-#74-H | GFSLNRYY | 56 | IYSGSGS | 57 | GRLDYRVIYAFNL | 58 |
| B1-#76-H | GFSFSGSCD | 59 | IVLSNGN | 60 | ARERYPGAFSSGLDL | 61 |
| B1-#79-H | GFSFSSSWY | 62 | IYTLRSGAA | 63 | ARATYAYAGAGDL | 64 |

TABLE 1-continued

Amino acid sequences of LILRB1 (B1) mAb heavy chain CDRs

| mAb ID | CDR1 | SEQ ID NO: | CDR2 | SEQ ID NO: | CDR3 | SEQ ID NO: |
|---|---|---|---|---|---|---|
| B1-#83-H | AFSFSSSSW | 65 | IYGGSVATT | 66 | ATNTDSSRSYYNL | 67 |
| B1-#93-H | GFSFSGNT | 68 | IYPSSTSI | 69 | ARRYAAFLTYGSGAFDP | 70 |
| B1-#98-H | GFSFSSSYW | 71 | VATGSGT | 72 | ARIGAFYSFRL | 73 |
| B1-#110-H | GFSFSSSYW | 74 | IYAGNSANT | 75 | ASRNGGAPDGLNL | 76 |
| B1-#115-H | GFSFSSSYW | 77 | IATGTGS | 78 | ARGGGYWSFSL | 79 |
| B1-#117-H | GFSFSSSYY | 80 | IYTGSDST | 81 | GDWDYADAAGYYVARGFNL | 82 |
| B1-#125-H | GFSFTKNYY | 83 | IYAGSTNT | 84 | RDFVSYLNL | 85 |
| B1-#128-H | GIDLSNFYY | 86 | VASDSSR | 87 | ARGSGASTNGVWWVMGDGMDL | 88 |
| B1-#154-H | GFSFSSGHY | 89 | IYAGSDTGS | 90 | CARSSNSYGNYGVSNL | 91 |
| B1-#160-H | GIDFSSGYW | 92 | IFTSSGTT | 93 | RDIYSYGMDL | 94 |
| B1-#162-H | GIDFSSAY | 95 | MRINDRS | 96 | ARIATGTNVDDF | 97 |
| B1-#166-H | GFSFSSKQY | 98 | IVTVNNK | 99 | ARWRTFGL | 100 |
| B1-#167-H | RFSLSNMNV | 101 | INIGGTN | 102 | ARSYITDRIYDYDF | 103 |
| B1-#170-H | GFDFSSKYY | 104 | IYGGSSDST | 105 | GRVIDGACGYDL | 106 |
| B1-#173-2-H | GFDFSSNAY | 107 | IYDGTSGDT | 108 | ARDTRSSNYYFNL | 109 |
| B1-#175-H | NSYKYYYM | 110 | STASRNI | 111 | AKSHGGDGGYGVVL | 112 |
| B1-#176-H | GFSFSSSYC | 113 | IYTDSSGAT | 114 | ARGWDYEDPGYTDTTYFSL | 115 |
| B1-#178-H | GFSFSSSYW | 116 | IYAGSSGST | 117 | ARGGTSYRLDL | 118 |
| B1-#179-H | GFSFSSKQY | 119 | IVTVNNK | 120 | TRWRTFGL | 121 |

TABLE 1-continued

Amino acid sequences of LILRB1 (B1) mAb heavy chain CDRs

| mAb ID | CDR1 | SEQ ID NO: | CDR2 | SEQ ID NO: | CDR3 | SEQ ID NO: |
|---|---|---|---|---|---|---|
| B1-#185-H | GIDFNNDYN | 122 | IYTGSDST | 123 | ARDLVTGYATYGYGFIL | 124 |
| B1-#189-H | SSSYWICW | 125 | GIGSSGTT | 126 | ARVGGYWTFDL | 127 |
| B1-#190-H | GFSFSSDYW | 128 | IYTGDDD | 129 | ARGLTIGTAELYF | 130 |
| B1-#196-H | GFSFTKNYY | 131 | IYAGSTN | 132 | ARDFVSYLNL | 133 |
| B1-#198-H | GFDLSNNYY | 134 | VDSDLTDSA | 135 | AGSGSGYYYYYGMDL | 136 |
| B1-#202-H | GFSFNGDYY | 137 | IYAAGDD | 138 | ARDQADSYAFGL | 139 |
| B1-#203-H | GFSFSSSYW | 140 | IYAGSSGST | 141 | ARGFSMFKL | 142 |
| B1-#204-H | GFSFSSSYC | 143 | IYTDSSGAT | 144 | ARGWDYEDPGYTDTTYFSL | 145 |
| B1-#209-H | RIDLNNYYY | 146 | VATDSSVT | 147 | RGSGAATNGVWWVMGDGMDL | 148 |
| B1-#210-H | GIDLSSYA | 149 | IGKSGTT | 150 | ARAGASRSIYYDL | 151 |
| B1-#220-H | GFSFSGIVY | 152 | AFVGSGGST | 153 | AKSYNYNGLGL | 154 |
| B1-#221-H | GFSFSSSYY | 155 | IYGGSTGTT | 156 | ARSYNSASSGYYWDL | 157 |
| B1-#224-H | GIDFSSGAW | 158 | IFTTSGFT | 159 | RDIYSYGMDL | 160 |
| B1-#226-H | GFSFSSRQY | 161 | IVTVNNK | 162 | ARWRTFGL | 163 |
| B1-#227-H | GFSFSSSYC | 164 | IYTDSSGAT | 165 | ARGWDYEDPGYTDTTYFSL | 166 |

TABLE 2

Nucleic acid sequences of LILRB1 (B1) mAb heavy chain CDRs

| mAb ID | CDR1 | SEQ ID NO: | CDR2 | SEQ ID NO: | CDR3 | SEQ ID NO: |
|---|---|---|---|---|---|---|
| B1-#3-H | GGATTCGACTTCAGTAGTGATGCA | 167 | ATTTATAATGGTGATGAAATT | 168 | GCGAGAGCTGTCTATAGTGATGGTGGTGCTGGTTATCCTTATATGTATGGCATGGACCTC | 169 |
| B1-#4-H | GGATTCGACTTCAGTGGCATTTATTGG | 170 | TTTGATGCTGAAAGGACTGGTAACACT | 171 | GCGAGATCATATTATATG | 172 |
| B1-#5-H | GAATTGTCCTTCAGTAGCGCCTACTAC | 173 | ATTTATAGTGGTGATGGTGAC | 174 | GCGAGGGCTCTGGATAGTCATTATTCTTCCTTTGACTTG | 175 |
| B1-#7-H | GGATTCTCCCTCAATAGCTATGCA | 176 | ATTGATACTGGTGCTAGTATC | 177 | GCGAGGGGTTTTTCGATGTTTAAGTTG | 178 |
| B1-#10-H | GGGTTAGACTTCAGTAGCAGCTACTGG | 179 | ATTGATACTGGTAGTAGTGGTAGCACT | 180 | GCGAGTACTCCTAATAGTCTAGGTTACGACTTA | 181 |
| B1-#15-H | GGATTCTCCTCCAGTAGTAGCGCCTAT | 182 | ATTTTTATTGGTAGTGGTAGTGACTCT | 183 | GCGAGAAATACTTATGATTGGAATGGTTATATTTATGGCCCGTGTTATTTTGGCTTG | 184 |
| B1-#18-H | GGATTCTCCCTCAGTAGGTATGCA | 185 | ATTGACACTAGTAGTGGTAAC | 186 | GCGAGAGGTTTTTCTATGTTTAAGTTG | 187 |
| B1-#19-H | GGATTGGACTTCAGTAGCAGCTATTGG | 188 | ATTGATGTTGGGAGTAGTGGTGGCTCA | 189 | GCGAGCACTACGACTAATGTTTTCGGTTACGACTTA | 190 |
| B1-#22-H | GGATTGGACTTCAGTAGTAATGACTAC | 191 | ATTTATGGTGGTGATGGGCACACT | 192 | AGGGGATATAGTTATGGTGATACTGGATATGCTGATGCTATTCTTACCTTGGACTTG | 193 |
| B1-#25-H | TTCAATTATTACAACTACTACTAC | 194 | ATGTCCACTGCCAGTGCGAAT | 195 | GCGAAATCCCATGGTGGTGATGGTGGTTATGGGGTTGTATTA | 196 |
| B1-#27-H | GGATTCTCCTTCAGTGGCAGCTACTGG | 197 | ATTTATGGTGATAGTATTGCC | 198 | GCGAGAGATCGAAATGGTGGTTCTGGTGCTTATGGTTGGGACTTG | 199 |
| B1-#28-H | GGATTCTCCTTCAGTAGCGACTATGAC | 200 | ATTGTGACTGGTTTTAGTGGTCGTATT | 201 | GCGAGAGATAGTGGTAATTATAATTGGGACTTG | 202 |
| B1-#38-H | GGATTCTCCTTCAGTAACGACTACTGG | 203 | GGACATATAGGTAGTTTTCGTACCACT | 204 | GCGAGGTCCCCATATGATGATGGTTATGGTGGTTTCACTTTTAATTTA | 205 |
| B1-#41-H1 | GGATTCTCCTTCAGTAGCAGCTACTGG | 206 | ATTTATGGTGGTAGTAGTGGTAGCACT | 207 | GCGAGATCGACTAGTGGTAGTTATGGTGCGGGTTTGGGCTTG | 208 |
| B1-#56-H | GGATTCTCCTTCAGTATCAACTTATAC | 209 | ATTTATGGTAATAATAATGCTAACACT | 210 | GCGAGAGATACTGCTGCTTATTACGCCTTTAGCTTA | 211 |

TABLE 2-continued

Nucleic acid sequences of LILRB1 (B1) mAb heavy chain CDRs

| mAb ID | CDR1 | SEQ ID NO: | CDR2 | SEQ ID NO: | CDR3 | SEQ ID NO: |
|---|---|---|---|---|---|---|
| B1-#57-H | TCTGGATTCACCTTCAGTGGCTACTAC | 212 | ATTTATGTTGGTAGTGGTGGTAGCACT | 213 | GCGAGGGGTGTTAATGATTATGGTTGGGCCCTTAAGTTG | 214 |
| B1-#58-H | GCGTTCTCCTTCAGTAGCAGTTCCTGG | 215 | ATTTATGGTGGTAGTGTTGGTACTACT | 216 | GCGACCAATACGGATAGTAGTAGGTCTTATTATAATTTG | 217 |
| B1-#72-H | GGAATCGACCTCAGTAACTATTGGTAC | 218 | GTTGCTACTGATAGTAGTCGCACG | 219 | AGAGGATCCGGTGCTAGCACCAATGGTGTTTGGTGGGTAATGGGAGACGGCATGGACCTC | 220 |
| B1-#74-H | GGATTCAGCCTCAATAGATACTAT | 221 | ATTTATTCTGGTAGTGGTAGC | 222 | GGGAGATTGGATTATCGTGTTATTTATGCCTTTAATTTG | 223 |
| B1-#76-H | GGATTCTCCTTCAGTGGCAGCTGCGAC | 224 | ATCGTGCTTAGTAATGGTAAT | 225 | GCGAGAGAGCGCTATCCTGGTGCTTTTTCAAGTGGATTGGATCTC | 226 |
| B1-#79-H | GGTTTCTCCTTCAGTAGCAGCTGGTAC | 227 | ATTTATACTCTTAGAAGTGGTGCCGCG | 228 | GCGAGAGCGACTTATGCTTATGCTGGTGCTGGGGACTTG | 229 |
| B1-#83-H | GCGTTCTCCTTCAGTAGCAGTTCCTGG | 230 | ATTTATGGTGGTAGTGTTGCTACTACT | 231 | GCGACCAATACGGATAGTAGTAGGTCTTATTATAATTTG | 232 |
| B1-#93-H | GGATTCTCCTTCAGTGGCAATACA | 233 | ATTTATCCTAGCAGTACTTCTATT | 234 | GCGCGAAGATATGCTGCTTTTCTTACTTATGGTAGTGGGGCTTTTGATCCC | 235 |
| B1-#98-H | GGATTCTCCTTCAGTAGCAGCTACTGG | 236 | GTTGCTACTGGTAGTGGTACC | 237 | GCGAGAATTGGTGCTTTTTATTCCTTTAGATTA | 238 |
| B1-#110-H1 | GGATTCTCCTTCAGTAGCAGCTACTGG | 239 | ATTTATGGTGGTAATAGTGCTAACACT | 240 | GCGAGCCGAAATGGTGGTGCGCCTGATGGTTTGAACTTG | 241 |
| B1-#115-H | GGATTCTCCTTCAGTAGCAGCTACTGG | 242 | ATTGCTACTGGTAGTGGTAGC | 243 | GCGAGAGGTGGTGGTTATTGGTCTTTTAGTTTG | 244 |
| B1-#117-H | GGATTCTCCTTCAGTAGTAGTTATTAT | 245 | ATTTATACTGGTAGTGATAGCACT | 246 | GGAGATTGGGATTATGCTGATGCTGCTGGTTATTATGTTGCGAGAGGTTTTAACTTG | 247 |
| B1-#125-H | GGATTCTCCTTCACTAAAAACTACTAC | 248 | ATTTATGGTGGTAGTACTAATACA | 249 | AGAGATTTCGTTAGTTATTTGAATTTG | 250 |
| B1-#128-H2 | GGAATCGACCTCAGTAACTTTTACTAC | 251 | GTTGCTAGTGATAGTAGCCGC | 252 | GCGAGAGGATCCGGTGCTAGTACCAATGGTGTTTGGTGGGTAATGGGAGACGGCATGGACCTC | 253 |
| B1-#154-H | GGATTCTCCTTCAGTAGCGGCCACTAC | 254 | ATTTATGCTGGTAGTGATACTGGTAGC | 255 | TGTGCGAGATCTAGTAATAGTTATGGTAATTATGGTGTTTCTAACTTG | 256 |

TABLE 2-continued

Nucleic acid sequences of LILRB1 (B1) mAb heavy chain CDRs

| mAb ID | CDR1 | SEQ ID NO: | CDR2 | SEQ ID NO: | CDR3 | SEQ ID NO: |
|---|---|---|---|---|---|---|
| B1-#160-H | GGAATCGACTTCAGTAGCGGCTACTGG | 257 | ATTTTTACTAGTAGTGGTACCACT | 258 | AGAGATATCTATTCCTACGGCATGGACCTC | 259 |
| B1-#162-H | GGAATCGACTTCAGTAGCGGCTAT | 260 | ATGCGTATTAATGATAGAAGT | 261 | GCGAGAATCGCTACTGGTACTAATGTTGATGACTTC | 262 |
| B1-#166-H | GGATTCTCCTTCAGTAGCAAGCAATAC | 263 | ATTGTCACTGTTAATAATAAA | 264 | GCGAGATGGCGGACTTTTGGCTTG | 265 |
| B1-#167-H | AGATTCTCCCTCAGTAACATGAACGTG | 266 | ATTAATATTGGCGGTACTAAT | 267 | GCGAGATCATATATTACTGATCGTATTTATGATTACGACTTT | 268 |
| B1-#170-H | GGATTCGACTTCAGTAGCAAATACTAC | 269 | ATTTATGGTGGTAGTAGTGATAGTACA | 270 | GGGAGAGTAATTGATGGTGCTTGTGGTTATGACTTG | 271 |
| B1-#173-H2 | GGATTCGACTTCAGTAGCAATGCCTAC | 272 | ATTTATGATGGTACAAGTGGTGACACT | 273 | GCGAGGGATACTCGGAGTAGTAATTATTATTTTAATTTG | 274 |
| B1-#175-H | AATAGCTACAAGTACTACTACATG | 275 | TCCACTGCCAGTCGTAATATT | 276 | GCGAAATCCCATGGTGGTGATGGTGGTTATGGGGTTGTGTTA | 277 |
| B1-#176-H | GGATTCTCCTTCAGTAGCAGCTACTGT | 278 | ATTTATACTGATAGTAGTGGTGCCACT | 279 | GCGAGGGGGTGGGATTACGAGGATCCTGGTTATACTGATACTACCTACTTTTCCTTG | 280 |
| B1-#178-H | GGATTCTCCTTCAGTAGCAGCTACTGG | 281 | ATTTATGCTGGTAGTAGTGGTAGCACT | 282 | GCGAGAGGTGGTACTAGTTACCGCCTTGATTTG | 283 |
| B1-#179-H | GGATTCTCCTTCAGTAGCAAACAATAC | 284 | ATTGTCACTGTTAATAATAAA | 285 | ACGAGATGGCGGACTTTTGGCTTG | 286 |
| B1-#185-H | GGAATCGACTTCAATAATGACTATAAC | 287 | ATTTATACTGGTAGTGATAGTACA | 288 | GCCAGAGATCTTGTTACTGGTTATGCTACTTATGGTTATGGATTTATCTTA | 289 |
| B1-#189-H | AGTAGCAGCTACTGGATATGCTGG | 290 | GGTATTGGTAGTAGTGGTACCACT | 291 | GCGAGAGTTGGTGGTTACTGGACTTTTGACTTG | 292 |
| B1-#190-H | GGATTCTCCTTCAGTAGCGACTATTGG | 293 | ATTTATACTGGTGATGATGAC | 294 | GCGAGAGGACTCACTATTGGTACTGCTGAGTTGTACTTC | 295 |
| B1-#196-H | GGATTCTCCTTCACTAAAAACTACTAC | 296 | ATTTATGCTGGTAGTACTAAT | 297 | GCGAGAGATTTCGTTAGTTATTTGAATTTG | 298 |
| B1-#198-H | GGATTTGACCTCAGTAACAACTACTAC | 299 | GTTGATTCTGATCTTACTGATAGTGCA | 300 | GCGGGAAGTGGGAGTGGTTATTATTATTACTACGGCATGGATCTC | 301 |
| B1-#202-H | GGATTCTCCTTCAATGGCGACTATTAT | 302 | ATTTATGCTGCTGGTGATGAC | 303 | GCGAGAGATCAGGCTGACAGTTATGCCTTTGGTTTG | 304 |

TABLE 2-continued

Nucleic acid sequences of LILRB1 (B1) mAb heavy chain CDRs

| mAb ID | CDR1 | SEQ ID NO: | CDR2 | SEQ ID NO: | CDR3 | SEQ ID NO: |
|---|---|---|---|---|---|---|
| B1-#203-H | GGATTCTCCTTCAGTAGCAGCTACTGG | 305 | ATTTATGCTGGTAGTAGTGGTAGCACT | 306 | GCGAGGGGTTTTCGATGTTTAAGTTG | 307 |
| B1-#204-H | GGATTCTCCTTCAGTAGCAGCTACTGT | 308 | ATTTATACTGATAGTAGTGGTGCCACT | 309 | GCGAGGGGGTGGGATTACGAGGATCCTGGTTATACTGATACTACCTACTTTTCCTTG | 310 |
| B1-#209-H | AGAATCGACCTCAACAACTATTATTAC | 311 | GTTGCTACTGATAGTAGTGTCACA | 312 | AGAGGATCCGGTGCTGCTACTAATGGTGTTTGGTGGGTGATGGGAGACGGCATGGACCTC | 313 |
| B1-#210-H | GGAATCGACCTCAGTAGCTATGCA | 314 | ATTGGTAAAAGTGGAACCACA | 315 | GCCAGGGCAGGTGCTAGTAGGAGTATTTATTATGACTTG | 316 |
| B1-#220-H | GGATTCTCCTTCAGTGGCATTGTCTAT | 317 | GCTTTTGTTGGTAGTGGTGGTAGCACT | 318 | GCGAAATCTTATAATTATAATGGTTTAGGCTTG | 319 |
| B1-#221-H | GGATTCTCCTTCAGTAGCAGCTACTAC | 320 | ATTTATGGTGGTAGTACTGGTACCACT | 321 | GCGAGATCATATAATAGTGCTAGTAGTGGTTATTATTGGGACTTG | 322 |
| B1-#224-H | GGAATCGACTTCAGTAGCGGCGCCTGG | 323 | ATTTTTACTACTAGTGGTTTCACT | 324 | AGAGATATCTATTCCTACGGCATGGACCTC | 325 |
| B1-#226-H | GGATTCTCCTTCAGTAGCAGGCAATAC | 326 | ATTGTCACTGTTAATAATAAA | 327 | GCGAGATGGCGGACTTTTGGCTTG | 328 |
| B1-#227-H | GGATTCTCCTTCAGTAGCAGCTACTGT | 329 | ATTTATACTGATAGTAGTGGTGCCACT | 330 | GCGAGGGGGTGGGATTACGAGGATCCTGGTTATACTGATACTACCTACTTTTCCTTG | 331 |

TABLE 3

Amino acid sequences of LILRB1 (B1) mAb light chain CDRs

| mAb ID | CDR1 | SEQ ID NO: | CDR2 | SEQ ID NO: | CDR3 | SEQ ID NO: |
|---|---|---|---|---|---|---|
| B1-#3-K | QNIYSY | 332 | KAS | 333 | QTNYFSSTSHFGVFT | 334 |
| B1-#4-K | QSLYNAND | 335 | WAS | 336 | LGEFSCSSFDCHV | 337 |
| B1-#5-K | QSIYRY | 338 | YGS | 339 | QTTYDDYHNGWA | 340 |
| B1-#7-K | QSVYGNNR | 341 | LAS | 342 | AGGYAGNFNA | 343 |
| B1-#10-K | QNIVSN | 344 | YAS | 345 | QNNAGIYGNYGHG | 346 |
| B1-#15-K | QSIYNY | 347 | DVS | 348 | QSYYGNTVSFT | 349 |
| B1-#18-K | QSVYNNNN | 350 | SAS | 351 | AGGYTYNINI | 352 |
| B1-#19-K | QNIYNN | 353 | YAS | 354 | QNNAGIYGGYGHG | 355 |
| B1-#22-K | QTIGSY | 356 | EAS | 357 | QSNYYRAGGNYGGA | 358 |

TABLE 3-continued

| Amino acid sequences of LILRB1 (B1) mAb light chain CDRs | | | | | | |
|---|---|---|---|---|---|---|
| mAb ID | CDR1 | SEQ ID NO: | CDR2 | SEQ ID NO: | CDR3 | SEQ ID NO: |
| B1-#25-K | ETISNR | 359 | SAS | 360 | QSIRSSSGIVHPNT | 361 |
| B1-#27-K | QSISSY | 362 | KAS | 363 | QSYYYISATVDNT | 364 |
| B1-#28-K | QSISDY | 365 | RAS | 366 | QSNYYGSQGCT | 367 |
| B1-#38-K | QSIGNA | 368 | KAS | 369 | QNYYYSNTNS | 370 |
| B1-#41-1-K | QNIYNN | 371 | GPS | 372 | QSDDWMSISPDIV | 373 |
| B1-#56-K | QSIGSR | 374 | EAS | 375 | QCTYYESSSGGG | 376 |
| B1-#58-K1 | HIITNY | 868 | DAS | 869 | QNYLYFSSGDWNV | 870 |
| B1-#72-1-K | PSISTY | 377 | RAS | 378 | QNNYHSGSSNGGGVA | 379 |
| B1-#74-K | QSIGSGN | 380 | LAS | 381 | QYTYYGTTYDNA | 382 |
| B1-#76-K | QIVANGR | 383 | ATS | 384 | QGAYSSGDVRT | 385 |
| B1-#79-K | EDIDRY | 386 | DAS | 387 | QSYDNSDNNG | 388 |
| B1-#83-K | HIITNY | 389 | DAS | 390 | QNYLYFSSGDWNV | 391 |
| B1-#93-K | ESIGSA | 392 | SAS | 393 | QSYYGSGTTALDT | 394 |
| B1-#98-K | QSIYNY | 395 | SAS | 396 | QNNYGIGSNYGPG | 397 |
| B1-#110-K | LNINSW | 398 | YTS | 399 | QTTYFGTNGGG | 400 |
| B1-#115-K | EDIYSN | 401 | GAT | 402 | QAESNDVWA | 403 |
| B1-#125-K | QSVYNKNY | 404 | YAS | 405 | AAYKGVSDDGIS | 406 |
| B1-#128-K | QSISSY | 407 | KAS | 408 | QNNYHSGSSNGGGFA | 409 |
| B1-#154-K | QSISYY | 410 | KAS | 411 | QSTYGRDNNDLFFA | 412 |
| B1-#160-K | QSISSSY | 413 | SAS | 414 | QSTYISSSKYGAV | 415 |
| B1-#162-K | QSVYSNNW | 416 | KAS | 417 | AGGYSGDLYA | 418 |
| B1-#167-K | QTIYNNKN | 419 | QAS | 420 | QGEFSCSSGDCTT | 421 |
| B1-#169-K | ENIYSY | 422 | SAS | 423 | QYSNFRVNDPSV | 424 |
| B1-#170-K | QTVHNNQW | 425 | DAS | 426 | QGGYSYGDVYG | 427 |
| B1-#173-2-K | QSVDNNKQ | 428 | SAS | 429 | AGYYYSGSATDAWA | 430 |
| B1-#175-K | ETISNR | 431 | SAS | 432 | QSIRSSSGVVHPNT | 433 |
| B1-#176-K | QTIYTN | 434 | AAS | 435 | QSYYGSSTTGNG | 436 |
| B1-#178-2-K | DNVYSNNY | 437 | YAA | 438 | SGHKDYSDDGST | 439 |
| B1-#185-K | DNVYSNNY | 440 | YAA | 441 | SGHKDYSDDGST | 442 |
| B1-#189-K | EDISSN | 443 | GAS | 444 | QGAYYGSSYG | 445 |
| B1-#190-K | QSISNE | 446 | LAS | 447 | QSHYYGGSSDYGWA | 448 |
| B1-#196-K | QSVYNNNQ | 449 | GAS | 450 | QGAVSSDYYP | 451 |
| B1-#198-K | QSIGSY | 452 | YAS | 453 | QSNRLSSSDVNA | 454 |
| B1-#202-2K | QNIYSN | 455 | SAS | 456 | QSYYYTASADTT | 457 |
| B1-#203-1K | QSIGSY | 458 | KAS | 459 | QYTSYSSGGA | 460 |
| B1-#205-K | EDIDRY | 461 | RAS | 462 | QGDFIGSSYGVA | 463 |
| B1-#209-K | QSISSY | 464 | KAS | 465 | QNNYHSGSSNGGGFA | 466 |

TABLE 3-continued

| Amino acid sequences of LILRB1 (B1) mAb light chain CDRs | | | | | | |
|---|---|---|---|---|---|---|
| mAb ID | CDR1 | SEQ ID NO: | CDR2 | SEQ ID NO: | CDR3 | SEQ ID NO: |
| B1-#204-K | QTIYTN | 467 | AAS | 468 | QSYYGSSTTGNG | 469 |
| B1-210-K | ESVYGNNR | 470 | QAS | 471 | AGHKGTTNDGND | 472 |
| B1-#220-K | QSITNA | 473 | RAS | 474 | QCSYYGSTYFGSP | 475 |
| B1-#224-K | QSISSSY | 476 | SAS | 477 | QSTYISSSNYGAA | 478 |
| B1-221-K | QSIGSN | 479 | KAS | 480 | QNNNYWSNGNH | 481 |
| B1-#226-K | ENVYSNNY | 482 | YAA | 483 | SGHKDYSDDGST | 484 |
| B1-#227-K | QSIASD | 485 | AAS | 486 | QSYYGSSTTGNG | 487 |

TABLE 4

| Nucleic acid sequences of LILRB1 (B1) mAb CDRs | | | | | | |
|---|---|---|---|---|---|---|
| mAb ID | CDR1 | SEQ ID NO: | CDR2 | SEQ ID NO: | CDR3 | SEQ ID NO: |
| B1-#3-K | CAGAACATTT ACAGCTAC | 488 | AAGGCA TCC | 489 | CAAACCAATTATTTT AGTAGTACTAGTCAT TTTGGTGTTTTTACT | 490 |
| B1-#4-K | CAGAGTGTTT ATAATGCGAA CGAC | 491 | TGGGCA TCC | 492 | CTAGGCGAATTTAGT TGCAGTAGTTTTGAT TGTCATGTT | 493 |
| B1-#5-K | CAGAGCATTT ACAGGTAC | 494 | TATGGA TCC | 495 | CAAACCACTTATGAT GATTATCATAATGGT TGGGCT | 496 |
| B1-#7-K | CAGAGTGTTT ATGGTAACAA CCGC | 497 | CTGGCA TCC | 498 | GCAGGCGGTTATGCT GGGAATTTCAATGCT | 499 |
| B1-#10-K | CAGAACATTG TCAGTAAT | 500 | TATGCA TCC | 501 | CAAAACAATGCTGGT ATTTATGGTAATTAT GGTCATGGT | 502 |
| B1-#15-K | CAGAGCATTT ACAACTAC | 503 | GATGTA TCC | 504 | CAAAGTTATTATGGT AATACTGTTTCTTTT ACT | 505 |
| B1-#18-K | CAGAGTGTTT ATAATAACAA CAAC | 506 | TCTGCA TCC | 507 | GCAGGCGGTTATACT TACAATATCAATATT | 508 |
| B1-#19-K | CAGAACATTT ACAACAAT | 509 | TATGCA TCC | 510 | CAAAACAATGCTGGT ATTTATGGTGGTTAT GGTCATGGT | 511 |
| B1-#22-K | CAGACTATTG GTAGCTAC | 512 | GAAGCA TCC | 513 | CAAAGCAATTATTAT CGTGCTGGTGGTAAT TATGGTGGAGCT | 514 |
| B1-#25-K | GAGACCATTA GTAATAGA | 515 | TCTGCA TCC | 516 | CAAAGTATTCGTAGT AGTAGTGGTATTGTT CATCCGAATACT | 517 |
| B1-#27-K | CAGAGCATTA GTAGTTAC | 518 | AAGGCA TCC | 519 | CAAAGCTATTACTAT ATTAGTGCTACTGTT GATAATACT | 520 |
| B1-#28-K | CAGAGCATTA GTGATTAC | 521 | AGGGCA TCC | 522 | CAAAGTAATTATTAT GGTAGTCAGGGTTGT ACT | 523 |

TABLE 4-continued

| Nucleic acid sequences of LILRB1 (B1) mAb CDRs | | | | | | |
|---|---|---|---|---|---|---|
| mAb ID | CDR1 | SEQ ID NO: | CDR2 | SEQ ID NO: | CDR3 | SEQ ID NO: |
| B1-#38-K | CAGAGCATTGGCAATGCA | 524 | AAGGCATCC | 525 | CAAAACTATTATTATAGTAATACTAATAGT | 526 |
| B1-#41-K | CAGAACATTTATAATAAC | 527 | GGTCCATCC | 528 | CAAAGTGATGATTGGATGAGTATCAGTCCTGATATTGTT | 529 |
| B1-#56-K | CAGAGTATTGGTAGTAGA | 530 | GAAGCATCC | 531 | CAATGTACTTATTATGAAAGTAGTAGTGGTGGTGGT | 532 |
| B1-#58-K1 | CATATCATTACTAACTAC | 533 | GATGCATCG | 534 | CAAAACTATCTTTATTTTAGTAGTGGTGATTGGAATGTT | 535 |
| B1-#72-1K | CCGAGCATTAGTACTTAC | 536 | AGGGCATCC | 537 | CAAAACAATTACCATAGTGGTAGTAGTAATGGTGGTGGTGTTGCT | 538 |
| B1-#74-K | CAGAGTATTGGTAGTGGTAAT | 539 | CTGGCATCC | 540 | CAATATACTTATTATGGTACTACTTATGATAATGCT | 541 |
| B1-#76-K | CAGATTGTTGCTAACGGCCGC | 542 | GCTACATCC | 543 | CAAGGCGCTTATAGTAGTGGGGATGTTCGGACT | 544 |
| B1-#79-K | GAGGACATTGATAGGTAT | 545 | GATGCATCC | 546 | CAAAGCTATGATAATAGTGATAATAATGGT | 547 |
| B1-#83-K | CATATCATTACTAACTAC | 548 | GATGCATCG | 549 | CAAAACTATCTTTATTTTAGTAGTGGTGATTGGAATGTT | 550 |
| B1-#93-K | GAGAGCATTGGCAGTGCA | 551 | TCTGCATCC | 552 | CAAAGTTATTATGGAAGTGGTACGACTGCTTTAGATACT | 553 |
| B1-#98-K | CAGAGCATTTACAACTAC | 554 | TCTGCATCC | 555 | CAAAACAATTATGGTATTGGTAGTAATTATGGTCCTGGT | 556 |
| B1-#110-K | CTGAACATTAATAGTTGG | 557 | TATACATCC | 558 | CAAACCACATATTTTGGTACTAATGGTGGTGGT | 559 |
| B1-#115-K | GAGGACATTTATAGCAAT | 560 | GGTGCAACC | 561 | CAGGCCGAAAGTAATGATGTTTGGGCT | 562 |
| B1-#117-K | GAGGATATTTATAGTAAT | 563 | AAGGCATCC | 564 | CAGACTACTTATTGGACTACTACTGATGATAATCCT | 565 |
| B1-#125-K | CAGAGTGTTTATAATAAGAACTAC | 566 | TATGCTTCC | 567 | GCAGCTTATAAAGGTGTTAGTGATGATGGTATTTCT | 568 |
| B1-#128-K | CAGAGCATTAGTAGTTAC | 569 | AAGGCATCC | 570 | CAAAACAATTATCATAGTGGTAGTAGTAATGGTGGTGGTTTTGCT | 571 |
| B1-#154-K | CAGAGCATTAGTTACTAC | 572 | AAGGCATCC | 573 | CAAAGCACTTATGGTAGGGATAATAATGATCTTTTTTTCGCT | 574 |
| B1-#160-K | CAGAGTATTAGTAGTAGCTAC | 575 | TCTGCGTCC | 576 | CAAAGCACTTATATTAGTAGTAGTAAGTATGGTGCTGTT | 577 |
| B1-#162-K | CAGAGTGTTTATAGTAACAACTGG | 578 | AAGGCATCC | 579 | GCAGGCGGGTATAGTGGTGATCTTTATGCT | 580 |

TABLE 4-continued

Nucleic acid sequences of LILRB1 (B1) mAb CDRs

| mAb ID | CDR1 | SEQ ID NO: | CDR2 | SEQ ID NO: | CDR3 | SEQ ID NO: |
|---|---|---|---|---|---|---|
| B1-#167-K | CAGACTATTTATAATAACAAAAAT | 581 | CAGGCATCC | 582 | CAAGGCGAATTTAGTTGTAGTAGTGGTGATTGTACTACT | 583 |
| B1-#169-K | GAGAACATTTATAGCTAC | 584 | TCTGCATCC | 585 | CAATATAGTAATTTTAGGGTGAATGATCCTAGTGTT | 586 |
| B1-#170-K | CAGACCGTTCATAATAATCAATGG | 587 | GATGCATCC | 588 | CAAGGCGGTTATAGTTATGGTGATGTGTATGGT | 589 |
| B1-#173-2-K | CAAAGTGTTGATAACAACAAACAA | 590 | TCTGCATCC | 591 | GCAGGCTATTATTATAGTGGTAGTGCCACTGATGCGTGGGCT | 592 |
| B1-#175-K | GAGACCATTAGTAATAGA | 593 | TCTGCATCC | 594 | CAAAGTATTCGTAGTAGTAGTGGTGTTGTGCATCCAAATACT | 595 |
| B1-#176-K | CAGACCATTTATACCAAT | 596 | GGTGCATCC | 597 | CAAAGCTATTATGGTAGTAGTACTACTGGTAATGGT | 598 |
| B1-#178-2-K | GATAATGTTTATAGTAATAACTAC | 599 | TATGCGGCC | 600 | TCAGGCCATAAAGATTATAGTGATGATGGTAGTACT | 601 |
| B1-#185-K | GATAATGTTTATAGTAATAACTAC | 602 | TATGCGGCC | 603 | TCAGGCCATAAAGATTATAGTGATGATGGTAGTACT | 604 |
| B1-#189-K | GAGGATATTAGTAGTAAT | 605 | GGTGCATCC | 606 | CAAGGCGCTTATTATGGTAGTAGTTATGGT | 607 |
| B1-#190-K | CAGAGCATTAGCAATGAA | 608 | CTGGCATCC | 609 | CAAAGTCATTATTATGGTGGTAGTAGTGATTATGGATGGGCT | 610 |
| B1-#196-K | CAAAGTGTTTACAATAACAACCAA | 611 | GGTGCATCC | 612 | CAAGGCGCTGTTAGTAGTGATTACTATCCT | 613 |
| B1-#198-K | CAGAGTATTGGTAGCTAT | 614 | TATGCTTCC | 615 | CAAAGTAATCGTCTTAGTAGTAGTGACGTTAATGCT | 616 |
| B1-#202-2-K | GAGAACATTTACAGCAAT | 617 | TCTGCATCC | 618 | CAAAGCTATTATTATACTGCTAGTGCTGATACTACT | 619 |
| B1-#203-1-K | CAGAGCATTGGTAGCTAC | 620 | AAGGCATCC | 621 | CAATATACTAGTTATAGTAGTGGTGGGGCT | 622 |
| B1-#205-K | GAGGACATTGATAGGTAT | 623 | AGGGCATCC | 624 | CAAGGCGATTTTATTGGTAGTAGTTATGGCGTTGCT | 625 |
| B1-#209-K | CAGAGCATTAGTAGTTAC | 626 | AAGGCTTCC | 627 | CAAAACAATTATCATAGTGGTAGTAGTAATGGTGGTGGTTTTGCT | 628 |
| B1-#204-K | CAGACCATTTATACCAAT | 629 | GCTGCATCC | 630 | CAAAGCTATTATGGTAGTAGTACTACTGGTAATGGT | 631 |
| B1-210-K | GAGAGTGTTTATGGTAACAACCGT | 632 | CAGGCTTCC | 633 | GCAGGACATAAAGGAACTACTAATGATGGGAATGAT | 634 |
| B1-#220-K | CAGAGCATTACCAATGCA | 635 | AGGGCATCC | 636 | CAATGTAGTTATTATGGTAGTACTTATTTTGGGAGTCCT | 637 |

TABLE 4-continued

| Nucleic acid sequences of LILRB1 (B1) mAb CDRs | | | | | | |
|---|---|---|---|---|---|---|
| mAb ID | CDR1 | SEQ ID NO: | CDR2 | SEQ ID NO: | CDR3 | SEQ ID NO: |
| B1-#224-K | CAGAGCATTAGTAGTAGCTAC | 638 | TCTGCATCC | 639 | CAAAGCACTTATATTAGTAGTAGTAATTATGGTGCTGCT | 640 |
| B1-221-K | CAGAGCATTGGTAGTAAT | 641 | AAGGCATCC | 642 | CAAAACAATAATTATTGGAGTAATGGTAACCAT | 643 |
| B1-#226-K | GAGAATGTTTATAGTAATAACTAC | 644 | TATGCGGCC | 645 | TCAGGCCATAAAGATTATAGTGATGATGGTAGTACT | 646 |
| B1-#227-K | CAGAGCATTGCTAGCGAC | 647 | GCTGCATCC | 648 | CAAAGCTATTATGGTAGTAGTACTACTGGTAATGGT | 649 |

TABLE 5

| LILRB1 mAb heavy chain variable region nucleotide sequences | | |
|---|---|---|
| mAb ID | Heavy chain nucleotide sequences | SEQ ID NO: |
| >B1-#3-H | CAGTCGTTGGAGGAGTCCGAGGGAGACCTGGTCAAGCCTGAGGGATCCCTGACACTCACCTGCAAAGCCTCTGGATTCGACTTCAGTAGTGATGCAATGTGCTGGGTCCGCCAGGCTCCAGGGAAGGGGCTGGAGTGGATCGGATGCATTTATAATGGTGATGAAATTACAGACCACGCGAGCTGGGCGAAAGGCCGATTCACCATCTCCAAAACCTCGCCGACCACGGTGACTCTGCAAATGACCAGTCTGACAGTCGCGGACACGGCCACCTATTTCTGTGCGAGAGCTGTCTATAGTGATGGTGGTGCTGGTTATCCTTATATGTATGGCATGGACCTCTGGGGCCCAGGGACCCTCGTCACCGTCTCTTCA | 650 |
| >B1-#4-H | CGAGCAGTCGGGAAGGAGTCCGGGGGAGGCCTGGTCAAGCCTGGGGCATCCCTGACACTCACCTGCAAAGCCTCTGGATTCGACTTCAGTGGCATTTATTGGGTATGCTGGGTCCGCCAGGCTCCAGGGAAGGGGCTGGAGTGGATCGCGTGTTTTGATGCTGAAAGGACTGGTAACACTTATTACGCGACCTGGGCGAAAGGCCGCTTCACCATCTCCAGAACCTCGTCGACCACGGTGACTCTGCAAATGACCAGTCTGACAGCCGCGGACACGGCCACCTATTTCTGTGCGAGATCATATTATATGTGGGGCCCAGGCACCCTGGTCACCGTCTCTTCA | 651 |
| >B1-#5-H | GAGCAGTCGTTGGAGGAGTCCGGGGGAGACCTGGTCAAGCCTGAGGGATCCCTGACACTCACCTGCACAGCCTCTGAATTGTCCTTCAGTAGCGCCTACTACATGTGCTGGGTCCGCCAGGCTCCAGGGAAGGGGCTGGAGTGGATCGGATGCATTTATAGTGGTGATGGTGACACTTACTACGCGAACTGGGCGAAAGGCCGATTCACCATCTCCAAAACCTCGTCGACCACGGTGACTCTGCAAATGACCAGTCTGACAGACGCGGACACGGCCACCTATTTCTGTGCGAGGGCTCTGGATAGTCATTATTCTTCCTTTGACTTGTGGGGCCCAGGCACCCTGGTCACCATCTCTTCA | 652 |
| >B1-#7-H | GAGCAGTCGTTGGAGGAGTCCGGGGGAGGCCTGGTCAAGCCTGGGGCATCCCTGACAGTCACCTGCGCAGTCTCTGGATTCTCCCTCAATAGCTATGCAATAACTTGGGTCCGCCAGGCTCCAGGGAAAGGGCTGGAATACATCGGATACATTGATACTGGTGCTAGTATCACAGACTACGCGAGCTGGGCGAAAGGCCGATTCACCATCTCCAAAACCTCGTCGACCACGGTGACTCTGGAAATGACCAGTCTGACAGACGCGGACACGGCCACCTATTTCTGTGCGAGGGGTTTTTCGATGTTTAAGTTGTGGGGCCCAGGCACCCTGGTCACCATCTCTTCA | 653 |
| >B1-#10-H | GAGCAGTCGGTGGAGGAGTCCGGGGGAGGCCTGGTCAAGCCTGAGGGATCCCTGACACTCACCTGCAAAGCCTCTGGGTTAGACTTCAGTAGCAGCTACTGGATATGCTGGGTCCGCCAGGCTCCAGGGAAGGGGCTGGAGTGGATCGCATGCATTGATACTGGTAGTAGTGGTAGCACTTACTACGCGAGCTGGGCGAAAGGCCGATTCACCGTCTCCAAAACCTCGTCGACCACGGTGTCTCTGCAAATGACCAGTCTGACAGCCGCGGACACGGCCACCTATTTCTGTGCGAGTACTCCTAATAGTCTAGGTTACGACTTATGGGGCCCAGGCACCCTGGTCACCATCTCTTCA | 654 |

TABLE 5-continued

LILRB1 mAb heavy chain variable region nucleotide sequences

| mAb ID | Heavy chain nucleotide sequences | SEQ ID NO: |
|---|---|---|
| >B1-#15-H | GAGCAGTCGGTGGAGGAGTCCGGGGGAGACCTGGTCAAGCCTGG GGCATCCCTGACACTCACCTGCACAGCCTCTGGATTCTCCTCCA GTAGTAGCGCCTATATGTGCTGGGTCCGCCAGGCTCCAGGGAAG GGGCTGGAGTGGATCGCATGTATTTTTATTGGTAGTGGTAGTGA CTCTTACTACGCGACCTGGGCGAAAGGCCGATTCACCATCTCCA AAACCTCGTCGACCACGGTGACTCTGCAAATGACCAGTCTGACA GCCGCGGACACGGCCACCTATTTCTGTGCGAGAAATACTTATGA TTGGAATGGTTATATTTATGGCCCGTGTTATTTTGGCTTGTGGG GCCCAGGCACCCTGGTCACCATCTCCTCA | 655 |
| >B1-#18-H | GAGCAGTCGGTGAAGGAGTCCGGGGGAGGCCTGGTCAAGCCTGG AGGAACCCTGACACTCACCTGCATAGTCTCTGGATTCTCCCTCA GTAGGTATGCAGTCACCTGGGTCCGCCAGGCTCCAGGGAAGGGG CCTGAGTGGATCGGATACATTGACACTAGTAGTGGTAACAAAGA CTACGCGAACTGGGTGAATGGCCGATTCACCATCTCCAAAACCT CGTCGACCACGGTGACTCTGCAAATGACCAGTCTGACAGCCGCG GACACGGCCACCTATTTCTGTGCGAGAGGTTTTTCTATGTTTAA GTTGTGGGGCCCAGGCACCCTGGTCACCATCTCTTCA | 656 |
| >B1-#19-H | GAGCAGTCGGTGGAGGAGTCCGGGGGAGGCCTGGTCAAGCCTGA GGGATCCCTGACACTCACCTGCAAAGCCTCTGGATTGGACTTCA GTAGCAGCTATTGGAGCTGCTGGGTCCGCCAGACTCCAGGGAGG GGGCTGGAGTGGATCGGATGCATTGATGTTGGGAGTAGTGGTGG CTCATACTACGCGAGCTGGGCGAGAGGCCGATTCACCGTCTCCA AAGGCTCGTCGACCACGGTGACTCTGCAAATGACCAGTCTGACA GCCGCGGACACGGCCACCTATTTCTGTGCGAGCACTACGACTAA TGTTTTCGGTTACGACTTATGGGGCCCAGGCACTCTGGTCACCG TCTCTTCA | 657 |
| >B1-#22-H | GAGCAGTCGTTGGAGGAGTCCGGGGGAGGCCTGGTCAAGCCTGG GGCATCCCTGACACTCACCTGCAAAGCCTCTGGATTCGACTTCA GTAGTAATGACTACATGTGCTGGGTCCGCCAGGCTCCAGGGAAG GGGCTGGAGTGGATCGGATGCATTTATGGTGGTGATGGGCACAC TTACTACGCGACCTGGGCGAAAGGCCGATTCACCATCTCCAAAG CCTCGTCGACCACGGTGACGCTGCAAATGACCAGTCTGACAGCC GCGGACACGGCCAGCTATTTCTGTGCGAGGGGATATAGTTATGG TGATACTGGATATGCTGATGCTATTCTTACCTTGGACTTGTGGG GCCCAGGCACCCTGGTCACCGTCTCTTCA | 658 |
| >B1-#25-H | GAGCAGTCGGTGAAGGAGTCCGGGGGAGGCCTGGTCCAGCCTGA GGGATCCCTGACACTCACCTGCAAAGTCTCTGGAATCGACTTCA ATTATTACAACTACTACTACATGTGCTGGGTCCGCCAGGCTCCA GGGAAGGGGCTGGAGTGGATCGGATGCATGTCCACTGCCAGTGC GAATATTTACCTTGCGAGCTGGGCGAAAGGCCGATTCACCATCT CCGAGGCCTCGTCGACCACGGTGACTCTGCAAATGACCAGTCTG ACAGCCGCGGACACGGCCACCTATTTCTGTGCGAAATCCCATGG TGGTGATGGTGGTTATGGGGTTGTATTATGGGGCCCAGGCACCC TGGTCACCATCTCCTCA | 659 |
| >B1-#27-H | GAGCAGTCGGTGAAGGAGTCCGGGGGAGGCCTGGTCCAGCCTGA GGGATCCCTGACACTCACCTGCACAGTCTCTGGATTCTCCTTCA GTGGCAGCTACTGGATATGCTGGGTCCGCCAGGCTCCAGGGAAG GGGCTGGAGTGGATCGCATGCATTTATGGTGATAGTATTGCCAC TTACTACCCGAACTGGGCGAAAGGCCGATTCACCATCTCCAAAA CCTCGTCGACCACGGTGACTCTACAAATGGCCAGTCTGACAGGC GCGGACACGGCCACCTATTTCTGTGCGAGAGATCGAAATGGTGG TTCTGGTGCTTATGGTTGGGACTTGTGGGGCCCAGGCACCCTGG TCACCATCTCCTCA | 660 |
| >B1-#28-H | GAGCAGTCGTTGGAGGAGTCCGGGGGAGGCCTGGTCAAGCCTGG GGCATCCCTGACACTCACCTGCAAAGCCTCTGGATTCTCCTTCA GTAGCGACTATGACATGTGCTGGGTCCGCCAGGCTCCAGGGAAG GGGCTGGAGTGGATCGGATGCATTGTGACTGGTTTTAGTGGTCG TATTTATTACGCGACCTGGGCGAGAGGCCGATTCACCTTCTCCA GAACCTCGTCGACCACGCTGACTCTGCAAATGACCAGTCTGACA GCCGCGGACACGGCCACTTATTTCTGTGCGAGAGATAGTGGTAA TTATAATTGGGACTTGTGGGGCCCAGGCACCCTGGTCACCATCT CTTCA | 661 |
| >B1-#38-H | GAGCAGTCGGTGGAGGAGTCCGAGGGAGGCCTGGTCCAGCCTGA GGGATCCCTGACACTCACCTGCACAGCTTCTGGATTCTCCTTCA GTAACGACTACTGGATATGCTGGGTCCGCCAGGCTCCAGGGAAG GGGCTGGAGTGGATCGGATGCGGACATATAGGTAGTTTTCGTAC CACTTACTACGCGAGCTGGGCGAAAGGCCGATTCAGCATCTCCA AAACCTCGTCGACCACGGTGACTCTGCAAATGACCAGTCTGACA | 662 |

TABLE 5-continued

LILRB1 mAb heavy chain variable region nucleotide sequences

| mAb ID | Heavy chain nucleotide sequences | SEQ ID NO: |
|---|---|---|
| | GGCGCGGACACGGCCACCTATTTCTGTGCGAGGTCCCCATATGATGATGGTTATGGTGGTTTCACTTTTAATTTATGGGGCCCAGGCACCCTGGTCACCATCTCTTCA | |
| >B1-#41-1-H | CAGTCGGTGAAGGAGTCCGGGGGAGACCTGGTCAAGCCTGGGGCATCCCTGACACTCACCTGCACAGCCTCTGGATTCTCCTTCAGTAGCAGCTACTGGATATGCTGGGTCCGCCAGGCTCCAGGGAAGGGGCTGGAGTGGATCGCATGCATTTATGCTGGTAGTAGTGGTAGCACTTACTACGCGAGCTGGGCGAAAGGCCGATTCACCATCTCCAAAACCTCGTCGACCACGGTGACTCTGCAAATGACCAGTCTGACAGCCGCGGACACGGCCACCTATTTCTGTGCGAGATCGACTAGTGGTAGTTATGGTGCGGGTTTGGGCTTGTGGGGCCCAGGCACCCTGGTCACCATCTCCTCA | 663 |
| >B1-#56-H | CAGTCGCTGGAGGAGTCCGGGGGAGACCTGGTCCAGCCTGAGGGATCCCTGACACTCACCTGCACAGCTTCTGGATTCTCCTTCAGTATCAACTTATACATGTGCTGGGTCCGCCAGGCTCCAGGGAAGGGGCTGGAGTGGATCGCATGCATTTATGGTAATAATAATGCTAACACTTACTACACAACCTGGGCGAAAGGCCGATTCACCATCTCCAAAACCTCGCCGACCACGGTGACTCTGCAAATGACCAGTCTGACAGGCGCGGACACGGCCACCTATTTCTGTGCGAGAGATACTGCTGCTTATTACGCCTTTAGCTTATGGGGCCCAGGCACCCTGGTCACCATCTCCTCA | 664 |
| >B1-#57-H | CAGTCGTTGGAGGAGTCCGGGGGTCGCCTGGTCAATCCTGACGAATCCCTGACACTCACCTGCACAGCCTCTGGATTCACCTTCAGTGGCTACTACATGTACTGGGTCCGCCAGGCTCCAGGGAAGGGGCTGGAGTGGATCGGATGGATTTATGTTGGTAGTGGTGGTAGCACTTACTACGCGAGCTGGGCGAAAGGCCGATTCACCATCTCCAAAACCTCGTCGACCACGGTGACTCTGCAAATGCCCAGTCTGACAGCCGCGGACACGGCCACCTATTTCTGTGCGAGGGGTGTTAATGATTATGGTTGGGCCCTTAAGTTGTGGGGCCCAGGCACTCTGGTCACCGTCTCTTCA | 665 |
| >B1-#58-H | GAGCAGTCGTTGGAGGAGTCCGGGGGAGACCTGGTCAAGCCTGGGGCATCCCTGACACTCACCTGCACAGCTTCTGCGTTCTCCTTCAGTAGCAGTTCCTGGATATGCTGGGTCCGCCAGGCTCCAGGGAAGGGGCTGGAGTGGATCGCATGCATTTATGGTGGTAGTGTTGGTACTACTTACTACGCGAGTTGGGCGAAAGGCCGATTCACCATCTCCAAACCCTCGTCGACCACGGTGACTCTGCAAATGACCAGTCTGGCAGCCGCGGACACGGCCACCTATTTCTGTGCGACCAATACGGATAGTAGTAGGTCTTATTATAATTTGTGGGGCCCAGGCACCCTGGTCACCATCTCCTCA | 666 |
| >B1-#72-H | CAGTCGGTGAAGGAGTCCGGGGGAGGCCTGGTCCAGCCTGAGGGATCCCTGGCACTCACCTGCAAAGCCTCTGGAATCGACCTCAGTAACTATTGGTACATGTGCTGGGTCCGCCAGGCTCCAGGGAAGGGGCTGGAGTGGATCGGATGCGTTGCTACTGATAGTAGTCGCACGCATTACGCGACCTGGGCGAAAGGCCGATTCACCGTCTCCAAGACCTCGTCGACCACGGTGACTCTGCAAATGACCAGTCTGACAGCGGCGGACACGGCCACCTATTTCTGTGCGAGAGGATCCGGTGCTAGCACCAATGGTGTTTGGTGGGTAATGGGAGACGGCATGGACCTCTGGGGCCCAGGGACCCTCGTCACCATCTCCTCA | 667 |
| >B1-#74-H | CAGTCGTTGGAGGAGTCCGGGGGAGGCCTGGTCAAGCCTGGGGCTTCCCTGACACTCACCTGCACAGCTTCTGGATTCAGCCTCAATAGATACTATATGTGCTGGGTCCGCCAGGCTCCAGGGAAGGGGCTGGAGTGGATCGGATGCATTTATTCTGGTAGTGGTAGCACTTACTACGCGAGCTGGGCGAAAGGCCGATTCACCATCTCCAAAACCTCGTCGACCACGGTGACTCTGCAAATGACCAGTCTGCCAGCCGCGGACACGGCCACCTATTTCTGTGGGAGATTGGATTATCGTGTTATTTATGCCTTTAATTTGTGGGGCCCAGGCACCCTGGTCACCATCTCCTCA | 668 |
| >B1-#76-H | GAGCAGTCGGTGGAGGAGTCCGGGGGAGGCCTGGTCCAGCCTGAGGGATCCCTGACACTCACCTGCACAGCTTCTGGATTCTCCTTCAGTGGCAGCTGCGACATGTCCTGGGTCCGCCAGGCTCCAGGGAAGGGGCTGGAGTGGATCGCATGCATCGTGCTTAGTAATGGTAATACATACTACGCGGGCTGGGCGCAAGGCCGATTCACCATCTCCAAAATCTCGTCGACCACGGTGACTCTGGAAATGACCAGTCTGACAGCCGCGGACACGGCCACGTATTTCTGTGCGAGAGAGCGCTATCCTGGTGCTTTTTCAAGTGGATTGGATCTCTGGGGCCAGGGCACCCTGGTCACCGTCTCTTCA | 669 |

TABLE 5-continued

LILRB1 mAb heavy chain variable region nucleotide sequences

| mAb ID | Heavy chain nucleotide sequences | SEQ ID NO: |
|---|---|---|
| >B1-#79-H | CAGTCGTTGGAGGAGTCCGGGGGAGGCCTGGTCCAGCCTGAGGG ATCCCTGACACTCACCTGCACAGTCTCTGGTTTCTCCTTCAGTA GCAGCTGGTACATGTGCTGGGTCCGCCAGGCTCCAGGGAAGGGG CTGGAATGGATCGCATGCATTTATACTCTTAGAAGTGGTGCCGC GCATTACGCGAACTGGGCGAAAGGCCGATTCACCATCTCCAAAG CCTCGTCGACCACGGTGACTCTGCAAATGAACAGTCTGACAGCC GCGGACACGGCCACCTATTTCTGTGCGAGAGCGACTTATGCTTA TGCTGGTGCTGGGGACTTGTGGGGCCCAGGCACCCTGGTCACCG TCTCTTCA | 670 |
| >B1-#83-H | GAGCAGTCGTTGAAGGAGTCCGGGGGAGACCTGGTCAAGCCTGG GGCATCCCTGACACTCACCTGCACAGCTTCTGCGTTCTCCTTCA GTAGCAGTTCCTGGATATGCTGGGTCCGCCAGGCTCCAGGGAAG GGGCTGGAGTGGATCGCATGCATTTATGGTGGTAGTGTTGCTAC TACTTACTACGCGACTTGGGCGAAAGGCCGATTCACCATCTCCA AACCCTCGTCGACCACGGTGACTCTGCAAATGACCAGTCTGCCA GCCGCGGACACGGCCACCTATTTCTGTGCGACCAATACGGATAG TAGTAGGTCTTATTATAATTTGTGGGGCCCAGGCACCCTGGTCA CCGTCTCCTCA | 671 |
| >B1-#93-H | GAGCAGTCGGTGGAGGAGTCCGGGGGAGACCTGGTCAAGCCTGG GACATCCCTGACACTCACCTGCACAGCTTCTGGATTCTCCTTCA GTGGCAATACAATTTGCTGGGTCCGCCAGGCTCCAGGGAAGAGG CCTGAATGGATCGCATGCATTTATCCTAGCAGTACTTCTATTAC TACCTACGCGACCTGGGCGAAAGGCCGATTCACCGTCTCCAAAA CCTCGTCGACCACGGTGACTCTGCAAATGACCAGTCTGACAGCC GCGGACACGGCCACCTATTTCTGTGCGCGAAGATATGCTGCTTT TCTTACTTATGGTAGTGGGGCTTTTGATCCCTGGGGCCCAGGCA CCCTAGTCACCATCTCTTCA | 672 |
| >B1-#98-H | GAGCAGTCGTTGGAGGAGTCCGGGGGAGACCTGGTCAAGCCTGA GGGATCCCTGACACTCACCTGCACAGCCTCTGGATTCTCCTTCA GTAGCAGCTACTGGATATGCTGGGTCCGCCAGGCTCCAGGGAAG GGACTGGAGTGGATCGCATGCGTTGCTACTGGTAGTGGTACCAC TGACTACGCGAGCTGGGCGAAAGGCCGATTCACCATGTCCAAAA CCTCGTCGACCACGGTGACTCTGCAAATGACCAGTCTGACAGTC GCGGACACGGCCACCTATTTCTGTGCGAGAATTGGTGCTTTTTA TTCCTTTAGATTATGGGGCCCAGGCACCCTGGTCACCATCTCTT CA | 673 |
| >B1-#110-H | CAGTCGTTGGAGGAGTCCGGGGGAGACCTGGTCAAGCCTGAGGG ATCCCTGACACTCACCTGCACAGCCTCTGGATTCTCCTTCAGTA GCAGCTACTGGATATGCTGGGTCCGCCAGGCTCCAGGGAAGGGG CTGGAGTGGATCGGATGCATTTATGCTGGTAATAGTGCTAACAC TTATTACGCGAGCTGGGCGAAAGGCCGATTCACCATCTCCAAAA CCTCGTCGACCACGGTGACTCTGCAACTGACCAGTCTGACAGCC GCGGACACGGCCACCTATTTCTGTGCGAGCCGAAATGGTGGTGC GCCTGATGGTTTGAACTTGTGGGGCCCAGGCACCCTGGTCACCA TCTCTTCA | 674 |
| >B1-#115-H | GAGCAGTCGGTGAAGGAGTCCGGGGGAGGCCTGGTCCAGCCTGA GGGATCCCTGACACTCACCTGCACAGCTTCTGGATTCTCCTTCA GTAGCAGCTACTGGATATGCTGGGTCCGCCAGGCTCCAGGGAAG GGGCTGGAGTGGATCGGATGCATTGCTACTGGTACTGGTAGCAC TTACTACGCGAACTGGGTGAATGGCCGATTCACCATGTCCAAAC CCTCGTCGACCACGGTGACTCTGCAAATGACCACTCTGACAGCC GCGGACACGGCCACCTATTTCTGTGCGAGAGGTGGTGGTTATTG GTCTTTTAGTTTGTGGGGCCCAGGCACCCTGGTCACCATCTCTT CA | 675 |
| >B1-#117-H | GAGCAGTCGTTGGAGGAGTCCGGGGGAGACCTGGTCAAGCCTGA GGGATCCCTGACACTCACCTGCACAGCCTCTGGATTCTCCTTCA GTAGTAGTTATTATATGTGTTGGATCCGCCAGCCTCCAGGGAGG GGGCTGGAGTGGCTCGCATGCATTTATACTGGTAGTGATAGCAC TTACTACGCGCCCTGGGCGAAAGGCCGATTCACCATCTCCAGAA CCTCGTCGACCACGGTGACTCTGCAAATGACCAGTCTGACAGCC GCGGACACGGCCACCTATTTCTGTGCGGGAGATTGGGATTATGC TGATGCTGCTGGTTATTATGTTGCGAGAGGTTTTAACTTGTGGG GCCCAGGCACCCTGGTCACCATCTCCTCA | 676 |
| >B1-#125-H | GAGCAGTCGTTGGAGGAGTCCGGGGGAGGCCTGGTCCAGCCTGA GGGATCCCTGACACTCACCTGCACAGCTTCTGGATTCTCCTTCA CTAAAAACTACTACATGTGCTGGGTCCGCCAGGCTCCAGGGAAG GGGCTGGAGTGGATCGGATGCATTTATGCTGGTAGTACTAATAC ATTTTACGCGAGCTGGGCGAAAGGCCGATTCACCATCTCCAAAG | 677 |

TABLE 5-continued

| LILRB1 mAb heavy chain variable region nucleotide sequences | | |
|---|---|---|
| mAb ID | Heavy chain nucleotide sequences | SEQ ID NO: |
| | CCTCGTCGACCACGGTGGATCTGAAAATGACCAGTCTGACAGTC GCGGACACGGCCACCTATTTCTGTGCGAGAGATTTCGTTAGTTA TTTGAATTTGTGGGGCCCAGGCACCCTGGTCACCGTCTCTTCA | |
| >B1-#128-2-H | CGAGCAGTCGGGAAGGAGTCCGGGGGAGACCTGGTCACGCTTGG GGGATCCCTGAAACTCTCCTGCAAAGCCTCTGGAATCGACCTCA GTAACTTTTACTACATGTGCTGGGTCCGCCAGGCTCCAGGGAAG GGGCTGGAGTGGATCGGATGCGTTGCTAGTGATAGTAGCCGCAC GCATTACGCGACCTGGCCGAAAGGCCGATTCACCATCTCCAAAA CCTCGTCGACCACGGTGACTCTGCAAATGACCAGTCTGACAGCG GCGGACACGGCCACCTATTTCTGTGCGAGAGGATCCGGTGCTAG TACCAATGGTGTTTGGTGGGTAATGGGAGACGGCATGGACCTCT GGGGCCCAGGGACCCTCGTCACCGTCTCC | 678 |
| >B1-#154-H | CAGTCGGTGAAGGAGTCCGGGGGAGACCTGGTCAAGCCTGGGGC ATCCCTGACACTCACCTGCAAAGCCTCTGGATTCTCCTTCAGTA GCGGCCACTACATGTACTGGGTCCGCCAGGCTCCAGGGAAGGGG CTGGAGTGGATCGCATGTATTTATGCTGGTAGTGATACTGGTAG CACATGGTACGCGAGCTGGGCGAAAGGCCGATTCACCATCTCCA AAACCTCGTCGACCACGGTGACTCTGCAAATGACCAGTCTGACA GCCGCGGATACGGCCACCTATTTCTGTGCGAGATCTAGTAATAG TTATGGTAATTATGGTGTTTCTAACTTGTGGGGCCCAGGCACCC TGGTCACCGTCTCTTCA | 679 |
| >B1-#160-H | CAGGAGCAGCTGGTGGAGTCCGGGGGAGGCCTGGTCCAGCCTGA GGGATCCCTGACACTCACCTGCAAAGCCTCTGGAATCGACTTCA GTAGCGGCTACTGGATATGCTGGGTCCGCCAGGCTCCAGGGAAG GGGCTGGAATTGATCGCATGCATTTTTACTAGTAGTGGTACCAC TTACTACGCGAGCTGGGCGAAAGGCCGATTCACCATCTCCAAAA CCTCGTCGACCACGGTGACTCTGCAAATGACCAGTCTGACAGCC GCGGACACGGCCACCTATTTCTGTGCGAGAGATATCTATTCCTA CGGCATGGACCTCTGGGGCCCAGGGACCCTCGTCACCGTCTCTT CA | 680 |
| >B1-#162-H | CAGTCGGTGAAGGAGTCCGAGGGAGGCCTGGTCCAGCCTGGGGG ATCCCTGACACTCTCCTGCAAAGCCTCTGGAATCGACTTCAGTA GCGCCTATATGAGCTGGGTCCGCCAGGCTCCAGGGAAGGGGCTG GAGTGGATCGGAAAGATGCGTATTAATGATAGAAGTCACTACGC GAACTGGGTGAATGGCCGATTCACCATCTCCAACCACAATGACC AGAACACGGTGGAGCTGCAACTGAACAGTCTGACAGCCGCGGAC ACGGCCACCTATTTCTGTGCGAGAATCGCTACTGGTACTAATGT TGATGACTTCTGGGGCCCAGGCACCCTGGTCACCATCTCCTCA | 681 |
| >B1-#166-H | CAGGAGCAGCTGGTGGAGTCCGGGGGAGGCCTGGTAACGCCTGG AGGATCCCTGACACTCACCTGCACAGCCTCTGGATTCTCCTTCA GTAGCAAGCAATACATTTCCTGGGTCCGCCGGGCTCCAGGGAAG GGGCTGGAGTGGATCGGGGCCATTGTCACTGTTAATAATAAAGT CCACTACGCGAACTGGGCGAAAGGCCGGTTCACCATCTCCGAAG CCTCGTCGACCACGGTGACTCTACAAATGACCAGTCTGACAGCC GCGGACACGGCCACCTATTTCTGTGCGAGATGGCGGACTTTTGG CTTGTGGGGCCCAGGCACCCTGGTCACCGTCTCTTCA | 682 |
| >B1-#167-H | GAGCAGCTGATGGAGGAGTCCGGGGGAGGCCTGGTCCAGCCTGA GGGATCCCTGACACTCACCTGCACGGCTTCTAGATTCTCCCTCA GTAACATGAACGTGATGTGCTGGGTCCGCCAGGCTCCAGGGAAG GGGCTGGAGTGGATCGGATGCATTAATATTGGCGGTACTAATAT ATGGTACGCGAGCTGGGCGAAAGGCCGATTCACCATCTCCAAAA CCTCGTCGACCACGGTGACTCTGCAAATGACCAGTCTGACAGTC GCGGACACGGCCACCTATTTCTGTGCGAGATCATATATTACTGA TCGTATTTATGATTACGACTTTTGGGGCCCAGGCACCCTGGTCA CCATCTCTTCA | 683 |
| >B1-#170-H | CAGTCGGTGGAGGAGTCCGGGGGAGGCCTGGTCAAGCCTGGGGC ATCCCTGACACTCTCCTGCACAGCCTCTGGATTCGACTTCAGTA GCAAATACTACATGTGGTGGGTCCGCCAGGCTCCAGGGAAGGGG CTGGAGTGGATCGCGCGCATTTATGGTGGTAGTAGTGATAGTAC AGACTACGCGACCTGGGCGAGAGGCCGGTTCGCCATCTCCAGAA CCTCGTCGACCACGGTGACTCTGCGAATGACCAGTCTGACAGCC GCGGACACGGCCACCTATTTCTGTGGGAGAGTAATTGATGGTGC TTGTGGTTATGACTTGTGGGGCCCAGGCACCCTGGTCACCGTCT CTTCA | 684 |
| >B1-#173-2-H | CAGTCGGTGGAGGAGTCCGGGGGAGACCTGGTCAAGCCTGGGGC ATCCCTGACACTCACCTGCACAGCCTCTGGATTCGACTTCAGTA GCAATGCCTACTTGTGCTGGGTCCGCCAGGCTCCAGGGAAGGGG | 685 |

TABLE 5-continued

LILRB1 mAb heavy chain variable region nucleotide sequences

| mAb ID | Heavy chain nucleotide sequences | SEQ ID NO: |
|---|---|---|
| | CTGGAGTGGATCGGATGCATTTATGATGGTACAAGTGGTGACAC TTACTACGCGAACTGGGCGAAAGGCCGATTCACCATCTCCAGAA GTTCGTCGACTACGGTGACTCTCCAAATGACCAGTCTGACAGCC GCGGACACGGCCACCTATTTCTGTGCGAGGGATACTCGGAGTAG TAATTATTATTTTAATTTGTGGGGCCCAGGCACCCTGGTCACCA TCTCTTCA | |
| >B1-#175-H | GAGTCCGAGGGAGGCCTGGTCAAGCCTGGAGGAACCCTGACACT CACCTGCAAAGTCTCTGGAATCGACTTCAATAGCTACAAGTACT ACTACATGTGCTGGGTCCGCCAGGCTCCAGGGAAGGGGCTGGAG TGGATCGGATGCATGTCCACTGCCAGTCGTAATATTTACTACGC GAGCTGGGCGAAAGGCCGATTCACCATCTCCGAAACCTCGTCGA CCTCGGTGACTCTGCAAATGACCACTCTGACAGCCGCGGACACG GCCACCTATTTCTGTGCGAAATCCCATGGTGGTGATGGTGGTTA TGGGGTTGTGTTATGGGGCCCAGGCACCCTGGTCACCATCTCCT CA | 686 |
| >B1-#176-H | CAGTCGTTGGAGGAGTCCGAGGGAGGCCTGGTCAAGCCTGGAGG AACCCTGACACTCACCTGCACAGCCTCTGGATTCTCCTTCAGTA GCAGCTACTGTATGTGTTGGGTCCGCCAGGCTCCAGGGAAGGGG CTGGAGTTGATCGCATGCATTTATACTGATAGTAGTGGTGCCAC TTACTACGCGAGCTGGGCGAAAGGCCGATTCACCATCTCCAAGT CCTCGTCGACCACGATAACTCTGCAAATGACCAGTCTGACAGCC GCGGACACGGCCACCTATTTCTGTGCGAGGGGGTGGGATTACGA GGATCCTGGTTATACTGATACTACCTACTTTTCCTTGTGGGGCC CAGGCACCCTGGTCACCGTCTCTTCA | 687 |
| >B1-#178-H | CAGAAGCAGCTGGTGGAGTCCGGGGGAGGCCTGGTCCAGCCTGA GGGATCCCTGGCACTCACCTGCACAGCTTCTGGATTCTCCTTCA GTAGCAGCTACTGGATATGCTGGGTCCGCCAGGCTCCAGGGAAG GGGCTGGAGTGGATCGCATGCATTTATGCTGGTAGTAGTGGTAG CACTTACTACGCGAGCTGGGTGAATGGCCGATTCACCGTCTTCA AAACCTCGTCGACCACGGTGACTCTGCAAATGACCAGTCTGACA GCCGCGGACACGGCCACCTATTTCTGTGCGAGAGGTGGTACTAG TTACCGCCTTGATTTGTGGGGCCCAGGCACCCTGGTCACCGTCT CTTCA | 688 |
| >B1-#185-H | TCGCAGCAGCTGAAGGAGTCCGGGGGAGGCCTGGTCAAGCCTGG AGGAACCCTGACACTCACCTGCAAAGCCTCTGGAATCGACTTCA ATAATGACTATAACATCTGCTGGGTCCGCCAGCCTCCAGGGAAG GGGCTGGAATGGATCGGATGCATTTATACTGGTAGTGATAGTAC AGACTACGCGAGCTGGGTGAATGGCCGATTCACCATCTCCGAAA GCACCAGCCTAAACACGGTGGATCTGAAAGTGACCAGTCTGACA GACGCGGACACGGCCACGTATTTCTGTGCCAGAGATCTTGTTAC TGGTTATGCTACTTATGGTTATGGATTTATCTTATGGGGCCCAG GCACCCTGGTCACCGTCTCCTCA | 689 |
| >B1-#190-H | CAGGAGCAGCTGAAGGAGTCCGGGGGAGACCTGGTCAAGCCTGA GGGATCCCTGACACTCACCTGCACAGCCTCTGGATTCTCCTTCA GTAGCGACTATTGGGTATGCTGGGTCCGCCAGGCTCCAGGGAAG GGGCCGGAGTGGATCGGATGCATTTATACTGGTGATGATGACAC ATACTACGCGAGCTGGGCGAAAGGCCGATTCACCATCTCCAAAA CCTCGTCGACCACGGTGACTCTGGAAGTGACCAGTCTGACAGCC GCGGACACGGCCACCTATTTCTGTGCGAGAGGACTCACTATTGG TACTGCTGAGTTGTACTTCTGGGGCCCAGGCACTGTGGTCACCG TCTCTTCA | 691 |
| >B1-#196-H | CAGGAGCAGCTGGTGGAGTCCGGGGGAGGCCTGGTCCAGCCTGA GGGATCCCTGACACTCACCTGCACAGATTCTGGATTCTCCTTCA CTAAAAACTACTACATGTGCTGGGTCCGCCAGGCTCCAGGGAAG GGGCTGGAGTGGATCGGATGCATTTATGCTGGTAGTACTAATAC ATTTTACGCGAGCTGGGCGAAAGGCCGATTCACCATCTCCAAAG CCTCGTCGACCACGGTGGATCTGAAAATGACCAGTCTGACAGTC GCGGACACGGCCACCTATTTCTGTGCGAGAGATTTCGTTAGTTA TTTGAATTTGTGGGGCCCAGGCACCCTGGTCACCGTCTCCTCA | 692 |
| >B1-#198-H | CAGTCGTTGGAGGAGTCCGGGGGTGGCCTGGTCAAGCCTGAGGG ATCCCTGACACTCACCTGCACAGCCTCTGGATTTGACCTCAGTA ACAACTACTACATCTGCTGGGTCCGCCAGGCTCCAGGGAAGGGG CTGGAATTGATCGCATGTGTTGATTCTGATCTTACTGATAGTGC AGACTACGCGAGCTGGGCGAAAGGCCGATTCACCATCTCCAAAA CCTCGTCGACCACGGTGACTCTGCAAATGACCAGTCTGACAGCC GCGGACACGGCCACCTATTTCTGTGCGGGAAGTGGGAGTGGTTA TTATTATTACTACGGCATGGATCTCTGGGGCCCAGGGACCCTCG TCACCATCTCCTCA | 693 |

TABLE 5-continued

LILRB1 mAb heavy chain variable region nucleotide sequences

| mAb ID | Heavy chain nucleotide sequences | SEQ ID NO: |
|---|---|---|
| >B1-#202-H | TCGCAGTCGTTGGAGGAGTCCGGGGGAGGCCTGGTCAAGCCTGG GGCATCCCTGACACTCACCTGCAAAGGCTCTGGATTCTCCTTCA ATGGCGACTATTATATGTGCTGGGTCCGCCAGACTCCAGGGAAG GGGCTGGAGTGGATCGGGTGCATTTATGCTGCTGGTGATGACAC TTACTACGCGACCTGGGCGAAAGGCCGATTCACCATCTCCAAAA CCTCGTCGACCACGGTGACTCTGCAAATGACCAGTCTGACAGCC GCGGACACGGCCACCTATTTTTGTGCGAGAGATCAGGCTGACAG TTATGCCTTTGGTTTGTGGGGCCCAGGCACACTGGTCACCATCT CCTCAG | 694 |
| >B1-#203-H | CAGTCGTTGAAGGAGTCCGAGGGAGACCTGGTCAAGCCTGGGGC ATCCCTGACACTCACCTGCACAGCCTCTGGATTCTCCTTCAGTA GCAGCTACTGGATATGCTGGGTCCGCCAGGCTCCAGGGAAGGGG CTAGAGTGGATCGCATGCATTTATGCTGGTAGTAGTGGTAGCAC TTACTACGCGAGCTGGGCGAAAGGCCGATTCACCATCTCCAAAA CCTCGTCGACCACGGTGACTCTGGAAATGACCAGTCTGACAGAC GCGGACACGGCCACCTATTTCTGTGCGAGGGGTTTTTCGATGTT TAAGTTGTGGGGCCCAGGCACCCTGGTCACCATCTCTTCA | 695 |
| >B1-#204-H | CAGTCGGTGAAGGAGTCCGGGGGAGGCCTGGTCAAGCCTGGAGG AACCCTGACACTCACCTGCACAGCCTCTGGATTCTCCTTCAGTA GCAGCTACTGTATGTGTTGGGTCCGCCAGGCTCCAGGGAAGGGG CTGGAGTTGATCGCATGCATTTATACTGATAGTAGTGGTGCCAC TTACTACGCGAGCTGGGCGAAAGGCCGATTCACCATCTCCAAGT CCTCGTCGACCACGATAACTCTGCAAATGACCAGTCTGACAGCC GCGGACACGGCCACCTATTTCTGTGCGAGGGGGTGGGATTACGA GGATCCTGGTTATACTGATACTACCTACTTTTCCTTGTGGGGCC CAGGCACCCTGGTCACCGTCTCTTCA | 696 |
| >B1-#209-H | TCGCAGTCGGTGGAGGAGTCCGGGGGAGACCTGGTCAAGCCTGG AGGAACCCTGACACTCACCTGCACAGCCTCTAGAATCGACCTCA ACAACTATTATTACATATCCTGGGTCCGCCAGGCTCCAGGGAAG GGACTGGAGTGGATCGGAGTCGTTGCTACTGATAGTAGTGTCAC ATGGTACGCGAGCTGGGCGAAAGGCCAGTTCACCATCTCCAAAA CCTCGTCGACCACGGTGACTCTGCAAATGACCAGTCTGACAGCG GCGGACACGGCCACCTATTTCTGTGCGAGAGGATCCGGTGCTGC TACTAATGGTGTTTGGTGGGTGATGGGAGACGGCATGGACCTCT GGGGCCCAGGGACCCTCGTCACCGTCTCTTCA | 697 |
| >B1-#210-H | CAGTCGGTGGAGGAGTCCGAGGGTCGCCTGGTCACGCCTGGAGG ATCCCTGACACTCACCTGCACAGTCTCTGGAATCGACCTCAGTA GCTATGCAATGGGCTGGGTCCGCCAGGCTCCAGGGAAGGGGCTG GAATGGATCGGGGTCATTGGTAAAAGTGGAACCACATACTACGC GAACTGGGCGAAAGGCCGATTCACCATCTCCAAGACCTCGACCA CGGTGGATCTGCAAATCGCCAGTCCGACAACCGAGGACACGGCC ACCTATTTCTGTGCCAGGGCAGGTGCTAGTAGGAGTATTTATTA TGACTTGTGGGGCCAAGGCACCCTGGTCACCATCTCCTCA | 698 |
| >B1-#220-H | CAGTCGGTGGAGGAGTCCGGGGGAGGCCTGGTCCAGCCTGAGGG ATCCCTGACACTCACCTGCACAGCTTCTGGATTCTCCTTCAGTG GCATTGTCTATATGTGTTGGGTCCGCCAGGCTCCAGGGAAGGGG CTGGAGTGGATCGCATGTGCTTTTGTTGGTAGTGGTGGTAGCAC TTACTACGCGACCTGGGCGACAGGCCGATTCACCATCTCCAAAA CCTCGTCGACCACGGTGACTCTACAGATGACCAGTCTGACAGCC GCGGACACGGCCACCTATTTCTGTGCGAAATCTTATAATTATAA TGGTTTAGGCTTGTGGGGCCCAGGCACCCTGGTCACCGTCTCCT CA | 699 |
| >B1-#221-H | CAGTCGTTGGAGGAGTCCGGGGGAGACCTGGTCAAGCCTGGGGC ATCCCTGACACTCACCTGCACAGCCTCTGGATTCTCCTTCAGTA GCAGCTACTACATGTGCTGGGTCCGCCAGGCTCCAGGGAAGGGG CTGGAGTGGATCGCATGCATTTATGGTGGTAGTACTGGTACCAC TTACTACGCGAGCTGGGCGAAAGGCCGATTCACCATCTCCAAAA CCTCGTCGACCACGGTGACTCTGCAAATGACCAGTCTGACAGGC GCAGACACGGCCACCTATTTCTGTGCGAGATCATATAATAGTGC TAGTAGTGGTTATTATTGGGACTTGTGGGGCCCAGGCACCCTGG TCACCGTCTCTTCAG | 700 |
| >B1-#224-H | GAGCAGTCGGTGGAGGAGTCCGGGGGAGGCCTGGTCCAGCCTGA GGGATCCCTGACACTCACCTGCACAGCCTCTGGAATCGACTTCA GTAGCGGCGCCTGGATATGCTGGGTCCGCCAGGCTCCAGGGAAG GGGCTGGAGTTGATCGCATGCATTTTTACTACTAGTGGTTTCAC TTACTACGCGAGCTGGGCGAAAGGCCGATTCACCATCTCCAAAA CCTCGTCGACCACGGTGACTCTGCAAATGACCAGTCTGACAGCC | 701 |

TABLE 5-continued

LILRB1 mAb heavy chain variable region nucleotide sequences

| mAb ID | Heavy chain nucleotide sequences | SEQ ID NO: |
|---|---|---|
| | GCGGACACGGCCACCTATTTCTGTGCGAGAGATATCTATTCCTACGGCATGGACCTCTGGGGCCCAGGGACCCTCGTCACCATCTCTTCA | |
| >B1-#226-H | CAGGAGCAGCTGGTGGAGTCCGGGGGAGGCCTGGTCCAGCCTGAGGGATCCCTGACACTCACCTGCACAGCTTCTGGATTCTCCTTCAGTAGCAGGCAATACATTTCCTGGGTCCGCCGGGCTCCAGGGAAGGGGCTGGAGTGGATCGGGGCCATTGTCACTGTTAATAATAAAGTCCACTACGCCAACTGGGCGAAAGGCCGGTTCACCATCTCCGAAGCCTCGTCGACCACGGTGACTCTGCAAATGACCAGTCTGACAGCCGCGGACACGGCCACCTATTTCTGTGCGAGATGGCGGACTTTTGGCTTGTGGGGCCCAGGCACCCTGGTCACCGTCTCTTCA | 702 |
| >B1-#227-H | CAGTCGGTGAAGGAGTCCGGGGGAGGCCTGGTCAAGCCTGGAGGAACCCTGACACTCACCTGCACAGCCTCTGGATTCTCCTTCAGTAGCAGCTACTGTATGTGTTGGGTCCGCCAGGCTCCAGGGAAGGGGCTGGAGTTGATCGCATGCATTTATACTGATAGTAGTGGTGCCACTTACTACGCGAGCTGGGCGAAAGGCCGATTCACCATCTCCAAGTCCTCGTCGACCACGATAACTCTGCAAATGACCAGTCTGACAGCCGCGGACACGGCCACCTATTTCTGTGCGAGGGGGTGGGATTACGAGGATCCTGGTTATACTGATACTACCTACTTTTCCTTGTGGGGCCCAGGCACCCTGGTCACCGTCTCTTCA | 703 |
| >Hu176-VH-1 | GAAGTGCAGCTGGTGGAGAGCGGCGGCGGTCTGGTACAACCGGGCGGCAGCCTGAGACTGAGCTGCGCCGCTAGCGGCTTCAGCTTCAGCAGCAGCTACTGCATGTGCTGGGTGAGACAAGCCCCCGGCAAGGGCCTGGAGTGGGTGAGCTGCATCTACACCGACAGCAGCGGCGCCACCTACTACGCTAGCTGGGCCAAGGGCAGATTCACCATCAGCAGACACAACAGCAAGAACACCCTGTACCTGCAGATGAACAGCCTGAGAGCCGAGGACACCGCCGTGTACTACTGCGCTAGAGGCTGGGACTACGAGGACCCCGGCTACACCGACACCACCTACTTCAGCCTGTGGGGCAGAGGCACCCTGGTGACCGTGAGCAGC | 871 |
| >Hu176-VH-2 (W48L) | GAAGTGCAGCTGGTGGAGAGCGGCGGCGGTCTGGTACAACCGGGCGGCAGCCTGAGACTGAGCTGCGCCGCTAGCGGCTTCAGCTTCAGCAGCAGCTACTGCATGTGCTGGGTGAGACAAGCCCCCGGCAAGGGCCTGGAGCTGGTGAGCTGCATCTACACCGACAGCAGCGGCGCCACCTACTACGCTAGCTGGGCCAAGGGCAGATTCACCATCAGCAGACACAACAGCAAGAACACCCTGTACCTGCAGATGAACAGCCTGAGAGCCGAGGACACCGCCGTGTACTACTGCGCTAGAGGCTGGGACTACGAGGACCCCGGCTACACCGACACCACCTACTTCAGCCTGTGGGGCAGAGGCACCCTGGTGACCGTGAGCAGC | 872 |
| >Hu176-H2M2 | GAAGTGCAGCTGGTGGAGAGCGGCGGCGGTCTGGTACAACCGGGCGGCAGCCTGAGACTGAGCTGCGCCGCTAGCGGCTTCAGCTTCAGCAGCAGCTACAGCATGAGCTGGGTGAGACAAGCCCCCGGCAAGGGCCTGGAGTGGGTGAGCAGCATCTACACCGACAGCAGCGGCGCCACCTACTACGCTAGCTGGGCCAAGGGCAGATTCACCATCAGCAGACACAACAGCAAGAACACCCTGTACCTGCAGATGAACAGCCTGAGAGCCGAGGACACCGCCGTGTACTACTGCGCTAGAGGCTGGGACTACGAGGACCCCGGCTACACCGACACCACCTACTTCAGCCTGTGGGGCAGAGGCACCCTGGTGACCGTGAGCAGC | 873 |

TABLE 6

LILRB1 mAb heavy chain variable region amino acid sequences

| mAb ID | Heavy chain amino acid sequences | SEQ ID NO: |
|---|---|---|
| >B1-#3-H | QSLEESEGDLVKPEGSLTLTCKASGFDFSSDAMCWVRQAPGKGLEWIGCIYNGDEITDHASWAKGRFTISKTSPTTVTLQMTSLTVADTATYFCARAVYSDGGAGYPYMYGMDLWGPGTLVTVSS | 704 |
| >B1-#4-H | RAVGKESGGGLVKPGASLTLTCKASGFDFSGIYWVCWVRQAPGKGLEWIACFDAERTGNTYYATWAKGRFTISRTSSTTVTLQMTSLTAADTATYFCARSYYMWGPGTLVTVSS | 705 |
| >B1-#5-H | EQSLEESGGDLVKPEGSLTLTCTASELSFSSAYYMCWVRQAPGKGLEWIGCIYSGDGDTYYANWAKGRFTISKTSSTTVTLQMTSLTDADTATYFCARALDSHYSSFDLWGPGTLVTISS | 706 |

TABLE 6-continued

LILRB1 mAb heavy chain variable region amino acid sequences

| mAb ID | Heavy chain amino acid sequences | SEQ ID NO: |
|---|---|---|
| >B1-#7-H | EQSLEESGGGLVKPGASLTVTCAVSGFSLNSYAITWVRQAPGKG LEYIGYIDTGASITDYASWAKGRFTISKTSSTTVTLEMTSLTDA DTATYFCARGFSMFKLWGPGTLVTISS | 707 |
| >B1-#10-H | EQSVEESGGGLVKPEGSLTLTCKASGLDFSSSYWICWVRQAPGK GLEWIACIDTGSSGSTYYASWAKGRFTVSKTSSTTVSLQMTSLT AADTATYFCASTPNSLGYDLWGPGTLVTISS | 708 |
| >B1-#15-H | EQSVEESGGDLVKPGASLTLTCTASGFSSSSSAYMCWVRQAPGK GLEWIACIFIGSGSDSYYATWAKGRFTISKTSSTTVTLQMTSLT AADTATYFCARNTYDWNGYIYGPCYFGLWGPGTLVTISS | 709 |
| >B1-#18-H | EQSVKESGGGLVKPGGTLTLTCIVSGFSLSRYAVTWVRQAPGKG PEWIGYIDTSSGNKDYANWVNGRFTISKTSSTTVTLQMTSLTAA DTATYFCARGFSMFKLWGPGTLVTISS | 710 |
| >B1-#19-H | EQSVEESGGGLVKPEGSLTLTCKASGLDFSSSYWSCWVRQTPGR GLEWIGCIDVGSSGGSYYASWARGRFTVSKGSSTTVTLQMTSLT AADTATYFCASTTTNVFGYDLWGPGTLVTVSS | 711 |
| >B1-#22-H | EQSLEESGGGLVKPGASLTLTCKASGFDFSSNDYMCWVRQAPGK GLEWIGCIYGGDGHTYYATWAKGRFTISKASSTTVTLQMTSLTA ADTASYFCARGYSYGDTGYADAILTLDLWGPGTLVTVSS | 712 |
| >B1-#25-H | EQSVKESGGGLVQPEGSLTLTCKVSGIDFNYYNYYYMCWVRQAP GKGLEWIGCMSTASANIYLASWAKGRFTISEASSTTVTLQMTSL TAADTATYFCAKSHGGDGGYGVVLWGPGTLVTISS | 713 |
| >B1-#27-H | EQSVKESGGGLVQPEGSLTLTCTVSGFSFSGSYWICWVRQAPGK GLEWIACIYGDSIATYYPNWAKGRFTISKTSSTTVTLQMASLTG ADTATYFCARDRNGGSGAYGWDLWGPGTLVTISS | 714 |
| >B1-#28-H | EQSLEESGGGLVKPGASLTLTCKASGFSFSSDYDMCWVRQAPGK GLEWIGCIVTGFSGRIYYATWARGRFTFSRTSSTTLTLQMTSLT AADTATYFCARDSGNYNWDLWGPGTLVTISS | 715 |
| >B1-#38-H | EQSVEESEGGLVQPEGSLTLTCTASGFSFSNDYWICWVRQAPGK GLEWIGCGHIGSFRTTYYASWAKGRFSISKTSSTTVTLQMTSLT GADTATYFCARSPYDDGYGGFTFNLWGPGTLVTISS | 716 |
| >B1-#41-1-H | QSVKESGGDLVKPGASLTLTCTASGFSFSSSYWICWVRQAPGKG LEWIACIYAGSSGSTYYASWAKGRFTISKTSSTTVTLQMTSLTA ADTATYFCARSTSGSYGAGLGLWGPGTLVTISS | 717 |
| >B1-#56-H | QSLEESGGDLVQPEGSLTLTCTASGFSFSINLYMCWVRQAPGKG LEWIACIYGNNNANTYYTTWAKGRFTISKTSPTTVTLQMTSLTG ADTATYFCARDTAAYYAFSLWGPGTLVTISS | 718 |
| >B1-#57-H | QSLEESGGRLVNPDESLTLTCTASGFTFSGYYMYWVRQAPGKGL EWIGWIYVGSGGSTYYASWAKGRFTISKTSSTTVTLQMPSLTAA DTATYFCARGVNDYGWALKLWGPGTLVTVSS | 719 |
| >B1-#58-H | EQSLEESGGDLVKPGASLTLTCTASAFSFSSSSWICWVRQAPGK GLEWIACIYGGSVGTTYYASWAKGRFTISKPSSTTVTLQMTSLA AADTATYFCATNTDSSRSYYNLWGPGTLVTISS | 720 |
| >B1-#72-H | QSVKESGGGLVQPEGSLALTCKASGIDLSNYWYMCWVRQAPGKG LEWIGCVATDSSRTHYATWAKGRFTVSKTSSTTVTLQMTSLTAA DTATYFCARGSGASTNGVWWVMGDGMDLWGPGTLVTISS | 721 |
| >B1-#74-H | QSLEESGGGLVKPGASLTLTCTASGFSLNRYYMCWVRQAPGKGL EWIGCIYSGSGSTYYASWAKGRFTISKTSSTTVTLQMTSLPAAD TATYFCGRLDYRVIYAFNLWGPGTLVTISS | 722 |
| >B1-#76-H | EQSVEESGGGLVQPEGSLTLTCTASGFSFSGSCDMSWVRQAPGK GLEWIACIVLSNGNTYYAGWAQGRFTISKISSTTVTLEMTSLTA ADTATYFCARERYPGAFSSGLDLWGQGTLVTVSS | 723 |
| >B1-#79-H | QSLEESGGGLVQPEGSLTLTCTVSGFSFSSSWYMCWVRQAPGKG LEWIACIYTLRSGAAHYANWAKGRFTISKASSTTVTLQMNSLTA ADTATYFCARATYAYAGAGDLWGPGTLVTVSS | 724 |
| >B1-#83-H | EQSLKESGGDLVKPGASLTLTCTASAFSFSSSSWICWVRQAPGK GLEWIACIYGGSVATTYYATWAKGRFTISKPSSTTVTLQMTSLP AADTATYFCATNTDSSRSYYNLWGPGTLVTVSS | 725 |

TABLE 6-continued

LILRB1 mAb heavy chain variable region amino acid sequences

| mAb ID | Heavy chain amino acid sequences | SEQ ID NO: |
|---|---|---|
| >B1-#93-H | EQSVEESGGDLVKPGTSLTLTCTASGFSFSGNTICWVRQAPGKR PEWIACIYPSSTSITTYATWAKGRFTVSKTSSTTVTLQMTSLTA ADTATYFCARRYAAFLTYGSGAFDPWGPGTLVTISS | 726 |
| >B1-#98-H | EQSLEESGGDLVKPEGSLTLTCTASGFSFSSSYWICWVRQAPGK GLEWIACVATGSGTTDYASWAKGRFTMSKTSSTTVTLQMTSLTV ADTATYFCARIGAFYSFRLWGPGTLVTISS | 727 |
| >B1-#110-H | QSLEESGGDLVKPEGSLTLTCTASGFSFSSSYWICWVRQAPGKG LEWIGCIYAGNSANTYYASWAKGRFTISKTSSTTVTLQLTSLTA ADTATYFCASRNGGAPDGLNLWGPGTLVTISS | 728 |
| >B1-#115-H | EQSVKESGGGLVQPEGSLTLTCTASGFSFSSSYWICWVRQAPGK GLEWIGCIATGTGSTYYANWVNGRFTMSKPSSTTVTLQMTTLTA ADTATYFCARGGGYWSFSLWGPGTLVTISS | 729 |
| >B1-#117-H | EQSLEESGGDLVKPEGSLTLTCTASGFSFSSSYYMCWIRQPPGR GLEWLACIYTGSDSTYYAPWAKGRFTISRTSSTTVTLQMTSLTA ADTATYFCAGDWDYADAAGYYVARGFNLWGPGTLVTISS | 730 |
| >B1-#125-H | EQSLEESGGGLVQPEGSLTLTCTASGFSFTKNYYMCWVRQAPGK GLEWIGCIYAGSTNTFYASWAKGRFTISKASSTTVDLKMTSLTV ADTATYFCARDFVSYLNLWGPGTLVTVSS | 731 |
| >B1-#128-H | RAVGKESGGDLVTLGGSLKLSCKASGIDLSNFYYMCWVRQAPGK GLEWIGCVASDSSRTHYATWPKGRFTISKTSSTTVTLQMTSLTA ADTATYFCARGSGASTNGVWWVMGDGMDLWGPGTLVTVSS | 732 |
| >B1-#154-H | QSVKESGGDLVKPGASLTLTCKASGFSFSSGHYMYWVRQAPGKG LEWIACIYAGSDTGSTWYASWAKGRFTISKTSSTTVTLQMTSLT AADTATYFCARSSNSYGNYGVSNLWGPGTLVTVSS | 733 |
| >B1-#160-H | QEQLVESGGGLVQPEGSLTLTCKASGIDFSSGYWICWVRQAPGK GLELIACIFTSSGTTYYASWAKGRFTISKTSSTTVTLQMTSLTA ADTATYFCARDIYSYGMDLWGPGTLVTVSS | 734 |
| >B1-#162-H | QSVKESEGGLVQPGGSLTLSCKASGIDFSSAYMSWVRQAPGKGL EWIGKMRINDRSHYANWVNGRFTISNHNDQNTVELQLNSLTAAD TATYFCARIATGTNVDDFWGPGTLVTISS | 735 |
| >B1-#166-H | QEQLVESGGGLVTPGGSLTLTCTASGFSFSSKQYISWVRRAPGK GLEWIGAIVTVNNKVHYANWAKGRFTISEASSTTVTLQMTSLTA ADTATYFCARWRTFGLWGPGTLVTVSS | 736 |
| >B1-#167-H | EQLMEESGGGLVQPEGSLTLTCTASRFSLSNMNVMCWVRQAPGK GLEWIGCINIGGTNIWYASWAKGRFTISKTSSTTVTLQMTSLTV ADTATYFCARSYITDRIYDYDFWGPGTLVTISS | 737 |
| >B1-#170-H | QSVEESGGGLVKPGASLTLSCTASGFDFSSKYYMWWVRQAPGKG LEWIARIYGGSSDSTDYATWARGRFAISRTSSTTVTLRMTSLTA ADTATYFCGRVIDGACGYDLWGPGTLVTVSS | 738 |
| >B1-#173-2-H | QSVEESGGDLVKPGASLTLTCTASGFDFSSNAYLCWVRQAPGKG LEWIGCIYDGTSGDTYYANWAKGRFTISRSSSTTVTLQMTSLTA ADTATYFCARDTRSSNYYFNLWGPGTLVTISS | 739 |
| >B1-#175-H | ESEGGLVKPGGTLTLTCKVSGIDFNSYKYYYMCWVRQAPGKGLE WIGCMSTASRNIYYASWAKGRFTISETSSTSVTLQMTTLTAADT ATYFCAKSHGGDGGYGVVLWGPGTLVTISS | 740 |
| >B1-#176-H | QSLEESEGGLVKPGGTLTLTCTASGFSFSSSYCMCWVRQAPGKG LELIACIYTDSSGATYYASWAKGRFTISKSSSTTITLQMTSLTA ADTATYFCARGWDYEDPGYTDTTYFSLWGPGTLVTVSS | 741 |
| >B1-#178-H | QKQLVESGGGLVQPEGSLALTCTASGFSFSSSYWICWVRQAPGK GLEWIACIYAGSSGSTYYASWVNGRFTVFKTSSTTVTLQMTSLT AADTATYFCARGGTSYRLDLWGPGTLVTVSS | 742 |
| >B1-#185-H | SQQLKESGGGLVKPGGTLTLTCKASGIDFNNDYNICWVRQPPGK GLEWIGCIYTGSDSTDYASWVNGRFTISESTSLNTVDLKVTSLT DADTATYFCARDLVTGYATYGYGFILWGPGTLVTVSS | 743 |

TABLE 6-continued

LILRB1 mAb heavy chain variable region amino acid sequences

| mAb ID | Heavy chain amino acid sequences | SEQ ID NO: |
|---|---|---|
| >B1-#190-H | QEQLKESGGDLVKPEGSLTLTCTASGFSFSSDYWVCWVRQAPGK GPEWIGCIYTGDDDTYYASWAKGRFTISKTSSTTVTLEVTSLTA ADTATYFCARGLTIGTAELYFWGPGTVVTVSS | 745 |
| >B1-#196-H | QEQLVESGGGLVQPEGSLTLTCTDSGFSFTKNYYMCWVRQAPGK GLEWIGCIYAGSTNTFYASWAKGRFTISKASSTTVDLKMTSLTV ADTATYFCARDFVSYLNLWGPGTLVTVSS | 746 |
| >B1-#198-H | QSLEESGGGLVKPEGSLTLTCTASGFDLSNNYYICWVRQAPGKG LELIACVDSDLTDSADYASWAKGRFTISKTSSTTVTLQMTSLTA ADTATYFCAGSGSGYYYYYGMDLWGPGTLVTISS | 747 |
| >B1-#202-H | SQSLEESGGGLVKPGASLTLTCKGSGFSFNGDYYMCWVRQTPGK GLEWIGCIYAAGDDTYYATWAKGRFTISKTSSTTVTLQMTSLTA ADTATYFCARDQADSYAFGLWGPGTLVTISS | 748 |
| >B1-#203-H | QSLKESEGDLVKPGASLTLTCTASGFSFSSSYWICWVRQAPGKG LEWIACIYAGSSGSTYYASWAKGRFTISKTSSTTVTLEMTSLTD ADTATYFCARGFSMFKLWGPGTLVTISS | 749 |
| >B1-#204-H | QSVKESGGGLVKPGGTLTLTCTASGFSFSSSYCMCWVRQAPGKG LELIACIYTDSSGATYYASWAKGRFTISKSSSTTITLQMTSLTA ADTATYFCARGWDYEDPGYTDTTYFSLWGPGTLVTVSS | 750 |
| >B1-#209-H | SQSVEESGGDLVKPGGTLTLTCTASRIDLNNYYYISWVRQAPGK GLEWIGVVATDSSVTWYASWAKGQFTISKTSSTTVTLQMTSLTA ADTATYFCARGSGAATNGVWWVMGDGMDLWGPGTLVTVSS | 751 |
| >B1-#210-H | QSVEESEGRLVTPGGSLTLTCTVSGIDLSSYAMGWVRQAPGKGL EWIGVIGKSGTTYYANWAKGRFTISKTSTTVDLQIASPTTEDTA TYFCARAGASRSIYYDLWGQGTLVTISS | 752 |
| >B1-#220-H | QSVEESGGGLVQPEGSLTLTCTASGFSFSGIVYMCWVRQAPGKG LEWIACAFVGSGGSTYYATWATGRFTISKTSSTTVTLQMTSLTA ADTATYFCAKSYNYNGLGLWGPGTLVTVSS | 753 |
| >B1-#221-H | QSLEESGGDLVKPGASLTLTCTASGFSFSSSYYMCWVRQAPGKG LEWIACIYGGSTGTTYYASWAKGRFTISKTSSTTVTLQMTSLTG ADTATYFCARSYNSASSGYYWDLWGPGTLVTVSS | 754 |
| >B1-#224-H | EQSVEESGGGLVQPEGSLTLTCTASGIDFSSGAWICWVRQAPGK GLELIACIFTTSGFTYYASWAKGRFTISKTSSTTVTLQMTSLTA ADTATYFCARDIYSYGMDLWGPGTLVTISS | 755 |
| >B1-#226-H | QEQLVESGGGLVQPEGSLTLTCTASGFSFSSRQYISWVRRAPGK GLEWIGAIVTVNNKVHYANWAKGRFTISEASSTTVTLQMTSLTA ADTATYFCARWRTFGLWGPGTLVTVSS | 756 |
| >B1-#227-H | QSVKESGGGLVKPGGTLTLTCTASGFSFSSSYCMCWVRQAPGKG LELIACIYTDSSGATYYASWAKGRFTISKSSSTTITLQMTSLTA ADTATYFCARGWDYEDPGYTDTTYFSLWGPGTLVTVSS | 757 |
| Hu-176 VH-1 | EVQLVESGGGLVQPGGSLRLSCAASGFSFSSSYCMCWVRQAPGK GLEWVSCIYTDSSGATYYASWAKGRFTISRHNSKNTLYLQMNSL RAEDTAVYYCARGWDYEDPGYTDTTYFSLWGRGTLVTVSS | 758 |
| Hu-176 VH-2 (W48L) | EVQLVESGGGLVQPGGSLRLSCAASGFSFSSSYCMCWVRQAPGK GLELVSCIYTDSSGATYYASWAKGRFTISRHNSKNTLYLQMNSL RAEDTAVYYCARGWDYEDPGYTDTTYFSLWGRGTLVTVSS | 759 |
| Hu-176 H2M2 | EVQLVESGGGLVQPGGSLRLSCAASGFSFSSSYSMSWVRQAPGK GLEWVSSIYTDSSGATYYASWAKGRFTISRHNSKNTLYLQMNSL RAEDTAVYYCARGWDYEDPGYTDTTYFSLWGRGTLVTVSS | 874 |

TABLE 7

| Nucleotide sequences of LILRB1 mAb light chain variable region | | |
|---|---|---|
| mAb ID | Light chain nucleotide sequences | SEQ ID NO: |
| >B1-3-K | GAGCTCGATATGACCCAGACTCCAGCCTCCGTGGAGGCGGCTGT GGGAGGCACAGTCACCATCAAGTGCCAGGCCAGTCAGAACATTT ACAGCTACTTAGTCTGGTATCAGCAGAAACCAGGGCAGCCTCCC AAGCTCCTAATCTCAAAGGCATCCACTCTGGCATCTGGGGTCTC ATCGCGGTTCAAAGGCAGTGGATCTGGGACAGAGTTCACTCTCA CCATCAACGACCTGGAGTGTGCCGATGCTGCCACTTACTACTGT CAAACCAATTATTTTAGTAGTACTAGTCATTTTGGTGTTTTTAC TTTCGGCGGAGGGACCGAGCTGGAAATCAAA | 760 |
| >B1-4-K | GAGCTCGTGCTGACCCAGACTCCATCCCCTGTGTCTGCAGTTGT GGGAGGCTCAGTCACCATCAATTGCCAGTCCAGTCAGAGTCTTT ATAATGCGAACGACTTATCCTGGTATCAGCAGAAACCAGGGCAG CCTCCCAAGCAACTGATCTACTGGGCATCCACTCTGGCATCTGG GGTCCCATCGCGGTTCAAAGGCAGTGGATCTGGGACACAGTTCA CTCTCAGCATCAGCGACGTGCAGTGTGACGATGCTGCCACTTAC TACTGTCTAGGCGAATTTAGTTGCAGTAGTTTTGATTGTCATGT TTTCGGCGGAGGGACCGAGGTGGTGGTCAAA | 761 |
| >B1-5-K | GAGCTCGATATGACCCAGACTCCATCCTCCGTGTCTGCAGCTGT GGGAGACACAGTCACCATCAAGTGCCAGGCCAGTCAGAGCATTT ACAGGTACTTAGCCTGGTATCAACAGAAACCAGGGCAGCGTCCC AGCCTCCTAATATATTATGGATCCGATCTGGCATCTGGGGTCCC ATCGCGGTTCAGCGGCAGTGGATCTGGGACAGAGTTCACTCTCA CCATCAGCGACCTGGAGTGTGCCGATGCTGCCAGTTACTACTGT CAAACCACTTATGATGATTATCATAATGGTTGGGCTTTCGGCGG AGGGACCAATGTGGAAATCAAC | 762 |
| >B1-7-K | GAGCTCGATCTGACCCAGACTCCATCGTCCGTGTCTGCAGCTGT GGGAGGCACAGTCACCATCAGTTGCCAGGCCAGTCAGAGTGTTT ATGGTAACAACCGCTTAGCCTGGTATCATCAGAAACCAGGACAG CCTCCCAAACGCCTGATCTATCTGGCATCCACTCTGGATTCTGG GGTCCCATCACGGTTCAAAGGCGCTGGATCTGGGACACAGTTCA CTCTCACCATCAGCGACCTGGAGTGTGACGATGCTGCCACTTAC TACTGTGCAGGCGGTTATGCTGGGAATTTCAATGCTTTCGGCGG AGGGACCGAGGTGGAAATCAAA | 763 |
| >B1-10-K | GAGCTCGATCTGACCCAGACTCCAGCCTCCGTGTCTGCAGCTGT GGGAGGCACAGTCACCATCAAGTGCCAGGCCAGTCAGAACATTG TCAGTAATTTAGCCTGGTATCAGCAGAAACCAGGGCAGCGTCCC AAGCTCCTGATCTATTATGCATCCACTCTGGCATCTGGGGTCCC ATCGCGGTTCAAAGGCAGTGGATCTGGGACAGAGTACACTCTCA CCATCAGCGACCTGGAGTGTGCCGATGCTGCCACTTACTACTGT CAAAACAATGCTGGTATTTATGGTAATTATGGTCATGGTTTCGG CGGAGGGACCGAGCTGGAAATCAAA | 764 |
| >B1-15-K | GAGCTCGATCTGACCCAGACTCCATCCTCCGTGGAGGCAGCTGT GGGAGGCACAGTCACCATCAAGTGCCAGGCCAGTCAGAGCATTT ACAACTACTTAGCCTGGTATCAGCAGAAACCAGGGCACTCTCCT AAGCTCCTGATCTACGATGTATCCAAATTGGCATCTGGGGTCTC ATCGCGGTTCAAAGGTAGTGGATCTGGGACAGAGTTCACTCTCA CCATCAGCGACCTGGAGTGTGCCGATGCTGCCACTTATTACTGT CAAAGTTATTATGGTAATACTGTTTCTTTTACTTTCGGCGGAGG GACCGAGGTGGAAATCAAA | 765 |
| >B1-18-K | GAGCTCGTGATGACCCAGACTCCATCGTCCGTGTCTGCAGCTGT GGGAGGCACAGTCACCATCAGTTGCCAGGCCAGTCAGAGTGTTT ATAATAACAACAACTTAGCCTGGTATCAGCAGAAACCAGGGCAG CCTCCCAAACGCCTGATCTATTCTGCATCCACTCTGGATTCTGG GGTCCCATCGCGGTTCAGCGGCAGTGGATCTGGGACACAGTTCA CTCTCACCATCAGCGACCTGGAGTGTGACGATGCTGCCACTTAC TATTGTGCAGGCGGTTATACTTACAATATCAATATTTTCGGCGG AGGGACCGAGGTGGAAATCAAA | 766 |
| >B1-19-K | GAGCTCGATCTGACCCAGACACCAGCCTCTGTGTCTGAACCTGT GGGAGGCACAGTCACCATCAAGTGCCAGGCCAGTCAGAACATTT ACAACAATTTAGCCTGGTATCAGCAGAAACCAGGGCAGCCTCCC AAGCTCCTGATCTATTATGCATCCACTCTGGCATCTGGGGTCCC ACCGCGGTTCAGCGGCAGTGGATCTGGGACAGAGTATACTCTCA CCATCAGCGACCTCGAGTGTGACGATGCTGCCACTTACTACTGT CAAAACAATGCTGGTATTTATGGTGGTTATGGTCATGGTTTCGG CGGAGGGACCGAGGTGGTGGTCAAA | 767 |

TABLE 7-continued

Nucleotide sequences of LILRB1 mAb light chain variable region

| mAb ID | Light chain nucleotide sequences | SEQ ID NO: |
|---|---|---|
| >B1-22-K | GAGCTCGATCTGACCCAGACTCCAGCCTCCGTAGAGGCAGCTGT<br>GGGAGGCACAGTCACCATCAAGTGCCAGGCCAGTCAGACTATTG<br>GTAGCTACCTATCCTGGTATCAGCAGAAACCAGGGCAGCGTCCC<br>AAACTCCTGATCTATGAAGCATCCAAACTGGCATCTGGGGTCCC<br>ATCGTGGTTCAAAGGCAGTGGATCTGGGACAGAGTTCACTCTCA<br>CCATCAGCGACCTGGAGTGTGCCGATGCTGCCACTTACTACTGT<br>CAAAGCAATTATTATCGTGCTGGTGGTAATTATGGTGGAGCTTT<br>CGGCGGAGGGACCGAGGTGGAAATCAAA | 768 |
| >B1-25-K | GAGCTCGATCTGACCCAGACTCCATTCTCCGTGTCTGCAGCTGT<br>GGGAGGCACAGTCACCATCAAGTGCCAGGCCAGTGAGACCATTA<br>GTAATAGATTAGCCTGGTATCAGCAGAAACCAGGGCAGCCTCCC<br>AAGCTCCTGATCTATTCTGCATCCACTCTGGAATCTGGGGTCCC<br>ATCGCGGTTCAAAGGCAGTGGATCTGGGACAGAGTTCACTCTCA<br>CCATCAGCGACCTGGAGTGTGCCGATGCTGCCACTTATTATTGT<br>CAAAGTATTCGTAGTAGTAGTGGTATTGTTCATCCGAATACTTT<br>CGGCGGAGGGACCGAGGTGGAAATCAAA | 769 |
| >B1-27-K | GAGCTCGATCTGACCCAGACTCCAGCCTCTGTGTCTGAACCTGT<br>GGGAGGCACAGTCACCATCACGTGCCAGGCCAGTCAGAGCATTA<br>GTAGTTACTTATCCTGGTATCAGCAGACACCAGGGCAGCCTCCC<br>AAGCTCCTAATCTACAAGGCATCCACTCTGGCATCTGGGGTCCC<br>ATCGCGGTTCAAAGGCAGTGGATCTGGGACAGAGTTCACTCTCA<br>CCATCAGCGACCTGGAGTGTGCCGATGCTGCCACTTACTACTGT<br>CAAAGCTATTACTATATTAGTGCTACTGTTGATAATACTTTCGG<br>CGGAGGGACCGAGGTGGAAATCAAA | 770 |
| >B1-28-K | GAGCTCGATCTGACCCAGACTCCAACCTCCGTGTCTGCAGCTGT<br>GGGAGGCACAGTCACCATCAAGTGCCAGGCCAGTCAGAGCATTA<br>GTGATTACTTATCCTGGTATCAGCAGAAACCAGGGCAGCCTCCC<br>AAGCTCCTGATCTACAGGGCATCCACTCTGGCATCTGGGGTCCC<br>ATCGCGGTTCAAAGGCAGTGGATCTGGGACAGAGTTCACTCTCA<br>CCATCAGCGACCTGGAGTGTGCCGATGCTGCCACTTACTATTGT<br>CAAAGTAATTATTATGGTAGTCAGGGTTGTACTTTCGGCGGAGG<br>GACCGAGGTGGAAATCAAA | 771 |
| >B1-38-K | GAGCTCGATATGACCCAGACTCCATCCTCCGTGGAGGCAGCTGT<br>GGGAGGCACAGTCACCGTCAAGTGCCAGGTCAGTCAGAGCATTG<br>GCAATGCAATAGCCTGGTATCAGCAGAAACCAGGGCAGCCTCCC<br>AAGCTCCTGATCTACAAGGCATCCACTCTGGCATCTGGGGTCCC<br>ATCGCGGTTCAAAGGCAGTGGATCTGGGACAGAATTCACTCTCA<br>CCATCAGCGACCTGGAGTGTGCCGATGCTGCCACTTACTACTGT<br>CAAAACTATTATTATAGTAATACTAATAGTTTCGGCGGAGGGAC<br>CGAGGTGGTGGTCAAA | 772 |
| >B1-41-1-K | GAGCTCGATATGACCCAGACTGCATCCCCCGTGTCTGGAGCTGT<br>GGGAGGCACAGTCACCATCAAGTGCCAGGCCAGTCAGAACATTT<br>ATAATAACATAGGGTGGTATCAGCAGAAACCAGGGCAGCCTCCC<br>AACCTCCTGATCTATGGTCCATCCTATCTGGCATCTGGGGTCCC<br>ATCGCGGTTCAAAGGCAGTAGATCTGGGACAGAGTACACTCTCA<br>CCATCAGCGACCTGGAGTGTGCCGATGCTGCCACTTACTACTGT<br>CAAAGTGATGATTGGATGAGTATCAGTCCTGATATTGTTTTCGG<br>CGGAGGGACCGAGGTGGAAATCAAA | 773 |
| >B1-56-K | GAGCTCGTGATGACCCAGACACCATCATCCTCGTCTGCAGCTGT<br>GGGAGGCACAGTCACCATCAAGTGCCAGGCCAGTCAGAGTATTG<br>GTAGTAGATTCGCCTGGTATCAGCAGAAACCAGGGCAGCGTCCC<br>AAGCTCCTGATCTATGAAGCATCCAAACTGCCATCTGGGGTCCC<br>ATCGCGGTTCAAAGGCAGTGGATCTGGGACAGAGTTCACGCTCA<br>CCATCAGCGACCTGGAGTGTGCCGATGCTGCCATTTATTACTGT<br>CAATGTACTTATTATGAAAGTAGTAGTGGTGGTGGTTTCGGCGG<br>AGGGACCGAGGTGGTGGTCAAA | 774 |
| >B1-58-K1 | GAGCTCGTGCTGACCCAGACTCCATCCTCCGTGGAGGTAGCTGT<br>GGGAGGCGCAGTCACCATCAAGTGCCAGGCCAGTCATATCATTA<br>CTAACTACTTAGCCTGGTATCAGCAGAGACCAGGGCAGCCTCCC<br>AAGCTCCTGATCTACGATGCATCGAAGCTGGCATCTGGGGTCCC<br>ATCGCGGTTCAAAGGCAGTGGATCTGGGACAGAGTTCACTCTCA<br>CCATCAGCGACCTGGAGTGTGCCGATGCTGCCACTTACTACTGT<br>CAAAACTATCTTTATTTTAGTAGTGGTGATTGGAATGTTTTCGG<br>CGGAGGGACCGAGGTGGTGGTCAAA | 775 |
| >B1-72-1-K | GAGCTCGTGATGACCCAGACTCCATCCTCCGTGTCTGCAGCTGT<br>GGGAGGCACAGTCACCATCAAGTGCCAGGCCAGTCCGAGCATTA | 777 |

TABLE 7-continued

Nucleotide sequences of LILRB1 mAb light chain variable region

| mAb ID | Light chain nucleotide sequences | SEQ ID NO: |
|---|---|---|
| | GTACTTACTTGTCCTGGTATCAGCAGAAACCAGGGCAGCCTCCC<br>AAGCGCCTGATCAACAGGGCATCCACTCTGGCATCTGGGGTCCC<br>ACCGCGGTTCAAAGGCAGTGGAGCTGGGACACAGTTCACTCTCA<br>CCATCAGCGACCTGGAGTGTGCCGATGCTGCCACTTATTATTGT<br>CAAAACAATTACCATAGTGGTAGTAGTAATGGTGGTGGTGTTGC<br>TTTCGGCGGAGGGACCGAGGTGGAAATCAAA | |
| >B1-74-K | GAGCTCGTGCTGACCCAGACTCCAGCCTCCGTGTCTGCGGCTGT<br>GGGAGGCACAGTCACCATCAATTGCCAGGCCAGTCAGAGTATTG<br>GTAGTGGTAATTTAGCCTGGTATCAGCAGAAACCAGGGCAGCCT<br>CCCAAGCTCCTGATCTATCTGGCATCCACTCTGGCATCTGGGGT<br>CCCACCGCGGTTCAAAGGCAGTGGATCTGGGACAGAGTTCACTC<br>TCACCATCAGCGACCTGGAGTGTGACGATGCTGCCACTTACTAC<br>TGTCAATATACTTATTATGGTACTACTTATGATAATGCTTTCGG<br>CGGAGGGACCGAGGTGGAAATCAAA | 778 |
| >B1-76-K | GAGCTCGATCTGACCCAGACTCCATCCCCAGTGTCTGCAGCTGT<br>GGGAGGCACAGTCACCATCAATTGCCAGGCCAGTCAGATTGTTG<br>CTAACGGCCGCTTAGCCTGGTATCAGCAGAAACCAGGGCAGCCT<br>CCCAAGCTCCTGATCTATGCTACATCCACTCTGGCATCTGGGGT<br>CCCATCGCGGTTCAAGGGCAGTGGATCTGGGACACAGTTCACTC<br>TCACCATCAACGGTGTGCAGTGTGACGATGCTGCCACTTACTAC<br>TGTCAAGGCGCTTATAGTAGTGGGGATGTTCGGACTTTCGGCGG<br>AGGGACCGAGGTGGTGGTCAAA | 779 |
| >B1-79-K | GAGCTCGTGCTGACCCAGACACCATCCTCCGTGTCTGCAGCTGT<br>GGGAGGCACAGTCACCATCAATTGCCAGGCCAGTGAGGACATTG<br>ATAGGTATTTAGCCTGGTATCAACAGAAACCAGGGCAGCGTCCC<br>AAGCTCCTGATCGTCGATGCATCCACTCTGCCATCTGGGGTCCC<br>ATCGCGGTTCAAAGGCAGTGGATCTGGGACAGAGTTCACTCTCA<br>CCATCAGCGACCTGGAGTGTGCCGATGGTGCCACTTACTACTGT<br>CAAAGCTATGATAATAGTGATAATAATGGTTTCGGCGGAGGGAC<br>CGAGGTGGTGGTCAAA | 780 |
| >B1-83-K | GAGCTCGATCTGACCCAGACTCCATCCTCCGTGGAGGTAGCTGT<br>GGGAGGCGCAGTCACCATCAAGTGCCAGGCCAGTCATATCATTA<br>CTAACTACTTAGCCTGGTATCAGCAGAGACCAGGGCAGCCTCCC<br>AAGCTCCTGATCTACGATGCATCGAAGCTGGCATCTGGGGTCCC<br>ATCGCGGTTCAAAGGCAGTGGATCTGGGACAGAGTTCACTCTCA<br>CCATCAGCGACCTGGAGTGTGCCGATGCTGCCACTTACTACTGT<br>CAAAACTATCTTTATTTTAGTAGTGGTGATTGGAATGTTTTCGG<br>CGGAGGGACCGAGGTGGTGGTCAAA | 781 |
| >B1-93-K | GAGCTCGATCTGACCCAGACTCCAGCCTCCGTGTCTGCAGCTGT<br>GGGAGGCACAGTCACCATCAATTGCCAGGCCAGTGAGAGCATTG<br>GCAGTGCATTAGCCTGGTATCAGCAGAAACCAGGGCAGCCTCCC<br>AAGCTCCTGATCTATTCTGCATCCGCTCTGGCATCTGGGGTCCC<br>ATCGCGGTTCAAAGGCAGTGGATCTGGGACAGAGTACACTCTCA<br>CCATCAGCGACTTGGAGTGTGCCGATGCTGCCACTTATTACTGT<br>CAAAGTTATTATGGAAGTGGTACGACTGCTTTAGATACTTTCGG<br>CGGAGGGACCGAGGTGGAAATCAAA | 782 |
| >B1-98-K | GAGCTCGATCTGACCCAGACTCCAGGCTCCGTGGAGGCAGCTGT<br>GGGAGGCACAGTCACCATCAAGTGCCAGGCCGGTCAGAGCATTT<br>ACAACTACTTATCCTGGTATCAGCAGAAACCAGGGCAGCCTCCC<br>AAGCTCCTGATCTATTCTGCATCCACTCTGGAATCTGGGGTCCC<br>ACCGCGGTTCAGCGGCAGTGGATCTGGGACAGAGTTCACTCTCA<br>CCATCAGCGACCTGGAGTGTGCCGATGCTGCCACTTACTCCTGT<br>CAAAACAATTATGGTATTGGTAGTAATTATGGTCCTGGTTTCGG<br>CGGAGGGACCGAGGTGGAAATCAAA | 783 |
| >B1-110-K | GAGCTCGATCTGACCCAGACTCCAGCCTCCGTGGAGGCAGCTGT<br>GGGAGGCACAGTCACCATCAAGTGCCAGGCCAGTCTGAACATTA<br>ATAGTTGGTTGGCCTGGTATCAGCAGAAACCAGGGCAGCCTCCC<br>AAGCTCCTGATCTCTTATACATCCAGTCTGGCATCTGGGGTCCC<br>ATCGCGGTTCAAAGGCAGTGGATCTGGGACAGAGTACACTCTCA<br>CCATCAACGACCTGGAGTGTGCCGATGCTGCCACTTACTACTGT<br>CAAACCACATATTTTGGTACTAATGGTGGTGGTTTCGGCGGAGG<br>GACCGAGGTGGAAATCAAA | 784 |
| >B1-115-K | GAGCTCGTGATGACCCAGACACCATCCTCCGTGGAGGCAGCTGT<br>GGGAGGCACAGTCACCAACAAGTGCCAGGCCAGTGAGGACATTT<br>ATAGCAATTTAGCCTGGTATCAGCAGAAACCAGGGCAGCCTCCC<br>AAGCTCCTGATCTATGGTGCAACCACTCTGGCATCTGGGGTCCC | 785 |

TABLE 7-continued

Nucleotide sequences of LILRB1 mAb light chain variable region

| mAb ID | Light chain nucleotide sequences | SEQ ID NO: |
|---|---|---|
| | ATCGCGGTTCAAAGGCAGTGGATCTGGGACAGAGTTCACTCTCA<br>CCATCAGCGACCTGGAGTGTGCCGATGCTGCCACTTACTATTGT<br>CAGGCCGAAAGTAATGATGTTTGGGCTTTCGGCGGAGGGACCGA<br>GGTGGTGGTCAAA | |
| >B1-117-K | GAGCTCGATCTGACCCAGACACCAGCCTCCGTGTCTGCAGCTGT<br>GGGAGGCACAGTCACCATCAAGTGCCAGGCCAGTGAGGATATTT<br>ATAGTAATTTAGCCTGGTATCAGCAGAAACCAGGGCAGCCTCCC<br>AAGCTCCTGATCTACAAGGCATCCACTCTGGCATCTGGGGTCCC<br>ACCGCGGTTCAAAGGCAGTGGATCTGGGACAGAATACACTCTCA<br>CCATCAGCGGTGTGCAGTGTGACGATGCTGCCACTTACGCCTGT<br>CAGACTACTTATTGGACTACTACTGATGATAATCCTTTCGGCGG<br>AGGGACCGAGGTGGAAATCAAA | 786 |
| >B1-125-K | GAGCTCGATCTGACCCAGACTCCATCATCCTCGTCTGCAGCTGT<br>GGGAGGCACAGTCACCATCAATTGCCAGGCCAGTCAGAGTGTTT<br>ATAATAAGAACTACTTATCCTGGTTTCAGCAGAAACCAGGGCAG<br>CCTCCCAAGCTCCTGATCTATTATGCTTCCACTCTGGCATCTGG<br>GGTCCCATCGCGGTTCAAAGGCAGTGGATCTGGGACAGAGTTCA<br>CTCTCACCATCAGCGATGTGGTGTGTGACGATGCTGCCACTTAC<br>TACTGTGCAGCTTATAAAGGTGTTAGTGATGATGGTATTTCTTT<br>CGGCGGAGGGACCGAGGTGGAAATCAAA | 787 |
| >B1-128-K | GAGCTCGATATGACCCAGACTCCATCCTCCGTGTCTGCAGCTGT<br>GGGGGGCACAGTCACCATCAAGTGCCAGGCCAGTCAGAGCATTA<br>GTAGTTACTTATCCTGGTATCAGCAGAAACCAGGGCAGCCTCCC<br>AAGCGCCTGATCTACAAGGCATCCACTCTGCCATCTGGGGTCCC<br>ACCGCGGTTTAAAGGCAGTGGATCTGGGACAGAGTTCACTCTCA<br>CCATCAGCGACCTGGAGTGTGCCGATGCTGCCACTTACTACTGT<br>CAAAACAATTATCATAGTGGTAGTAGTAATGGTGGTGGTTTTGC<br>TTTCGGCGGAGGGACCCAGGTGGAAATCAAA | 788 |
| >B1-154-K | GAGCTCGATCTGACCCAGACTCCAGCCTCCGTGGAGGCAGCTGT<br>GAGAGGCACAGTCACCATCAAGTGCCAGGCCAGTCAGAGCATTA<br>GTTACTACTTAGCCTGGTATCAGCAGAAACCAGGGCAGCCTCCC<br>AAGGTCCTGATCTACAAGGCATCCACTCTGGCATCTGGGGTCCC<br>ACCGCGGTTCAAAGGCAGTGGATTTGGGACAGAGTTCACTCTCA<br>CCATCAGCGACCTGGAGTGTGCCGATGCTGCCACTTATTACTGT<br>CAAAGCACTTATGGTAGGGATAATAATGATCTTTTTTTCGCTTT<br>CGGCGGAGGGACCGAGGTGGAAATCAAA | 789 |
| >B1-160-K | GAGCTCGATCTGACCCAGACTCCAGCCTCCGTGTCTGCAGCTGT<br>GGGAGGCACGGTCACCATCAAGTGCCAGGCCAGTCAGAGTATTA<br>GTAGTAGCTACTTAGCCTGGTATCAGCAGAAACCAGGGCAGCCT<br>CCCAAGCTCCTGATCTATTCTGCGTCCAGTACGGCATCTGGGGT<br>CCCATCGCGGTTCAAAGGCAGTGGATCTGGGACACAGTTCACTC<br>TCACCATCAGCGACCTGGAGTGTGCCGATGCTGCCACTTACTAC<br>TGTCAAAGCACTTATATTAGTAGTAGTAAGTATGGTGCTGTTTT<br>CGGCGGAGGGACCGAGGTGGAAATCAAA | 790 |
| >B1-162-K | GAGCTCGTGATGACCCAGACTGCATCGCCCGTGTCTGCAGCTGT<br>GGGAGGCACAGTCACCATCAGTTGCCAGTCCAGTCAGAGTGTTT<br>ATAGTAACAACTGGTTATCCTGGTATCAGCAGAAACCAGGGCAG<br>CCTCCCAAACGCCTGATCTACAAGGCATCCACTCTGGAAACTGG<br>GGTCCCATCGCGGTTCAAAGGCAGTGGATCTGGGAAACAGTTCA<br>CTCTCACCATCAGCGACCTGGAGTGTGACGATGCTGCCACTTAT<br>TACTGTGCAGGCGGGTATAGTGGTGATCTTTATGCTTTCGGCGG<br>AGGGACCGAGGTGGTGGTCAAA | 791 |
| >B1-167-K | GAGCTCGATATGACCCAGACTCCATCTCCCGTGTCTGCAGCTGT<br>GGGAGGCTCAGTCACCATCAGTTGCCAGGCCAGTCAGACTATTT<br>ATAATAACAAAAATTTGGCCTGGTATCAGCAGAAACCAGGGCAA<br>CCTCCCAAGCTCCTGATCTACCAGGCATCCAAACTGGCATCTGG<br>GGTCTCATCGCGGTTCAGTGGCAGTGGATCTGGGACACAGTTCA<br>CTCTCACCATCAGCGGCGTGCAGTGTGACGATGCTGCCACTTAC<br>TACTGTCAAGGCGAATTTAGTTGTAGTAGTGGTGATTGTACTAC<br>TTTCGGCGGAGGGACCGAGGTGGTGGTCAAA | 792 |
| >B1-169-K | GAGCTCGATATGACCCAGACTCCAGCCTCCGTGTCTGAACCTGT<br>GGGAGGCACAGTCACCATCAAGTGCCAGGCCAGTGAGAACATTT<br>ATAGCTACTTAGCCTGGTATCAGCAGAAACCAGGGCAGCCTCCC<br>AAGCTCCTGATCTATTCTGCATCCACTCTGGCATCTGGGGTCCC<br>ATCGCGGTTCAAAGGCAGTGGATCTGGGACACAGTTCACTCTCA<br>CCATCAGCGACCTGGAGTGTGCCGATGCTGCCACTTACTATTGT | 793 |

TABLE 7-continued

| Nucleotide sequences of LILRB1 mAb light chain variable region | | |
|---|---|---|
| mAb ID | Light chain nucleotide sequences | SEQ ID NO: |
| | CAATATAGTAATTTTAGGGTGAATGATCCTAGTGTTTTCGGCGG AGGGACCGAGGTGGAAATCAAA | |
| >B1-170-K | GAGCTCGATCTGACCCAGACTCCAGCCTCCGTGTCTGCAGCTGT GGGAGGCACAGTCACCATCAGTTGCCAGTCCAGTCAGAGCGTTC ATCATAGTCAGACCGTTCATAATAATCAATGGTTAGCCTGGTAT CAGCAGAAACCAGGGCAGCCTCCCAAGCTCCTGATCTATGATGC ATCCAAACTGGCATCTGGGGTCCCATCGCGGTTCACAGGTAGTG GATCTGGGACACAGTTCTCTCTCACCATCAGTGCAGTGCAGTGT GACGATGCTGCCACTTACTACTGTCAAGGCGGTTATAGTTATGG TGATGTGTATGGTTTCGGCGGAGGGACCGAGCTGGAAATCAAG | 794 |
| >B1-173-2-K | GAGCTCGTGCTGACCCAGACTCCATCTTCCACGTCTGCGGCTGT GGGAGGCACAGTCACCATCAATTGCCAGGCCAGTCAAAGTGTTG ATAACAACAAACAATTATCCTGGTATCAGCAGAAACCAGGGCAG CCTCCCAAGCAACTGATCTACTCTGCATCCAAACTGGCATCTGG GGTCCCATCGCGGTTCAAAGGCAGTGGATCTGGGACACAGTTCA CTCTCACCATCAGCGACCTGGAGTGTGACGATGCTGCCACTTAC TACTGTGCAGGCTATTATTATAGTGGTAGTGCCACTGATGCGTG GGCTTTCGGCGGAGCGACCGAGGTGGAAATCAAC | 795 |
| >B1-175-K | GAGCTCGTGATGACCCAGACTCCATCCTCCGTGTCTGCAGCTGT GGGAGACACACTCACCATCAATTGCCAGGCCAGTGAGACCATTA GTAATAGATTAGCCTGGTATCAACAGAAACCAGGGCAGCCTCCC AAGCTCCTGATCTATTCTGCATCCACTCTGGAATCTGGGGTCCC ATCGCGGTTCAGAGGCAGTGGATCTGGGACACAGTTCACTCTCA CCATAAGTGACCTGGAGTGTGCCGATGCTGCCACTTATTATTGT CAAAGTATTCGTAGTAGTAGTGGTGTTGTGCATCCAAATACTTT CGGCGGAGGGACCGAGGTGGAAATCAAA | 796 |
| >B1-176-K | GAGCTCGATCTGACCCAGACTCCATCCTCCGTGGAGGCAGCTGT GGGAGGCACAGTCACCATCAAGTGCCAGGCCAGTCAGACCATTT ATACCAATTTAGCCTGGTATCAGCAGAAACCAGGGCAGCCTCCC AACCTCCTGATCTATGCTGCATCCACTCTGGCATCTGGGGTCTC ATCGCGGTTCAAAGGCAGTGGATCCGGGACAGAGTTCACTCTCA CCATCAGCGACCTGGAGTGTGCCGATGCTGCCACTTACTACTGT CAAAGCTATTATGGTAGTAGTACTACTGGTAATGGTTTCGGCGG AGGGACCGAGGTGGAAATCAAA | 797 |
| >B1-178-2-K | GAGCTCGTGCTGACCCAGACACCATCTTCCAAGTCTGTCGCTGT GGGAGACACAGTCACCATCAATTGCCAGGCCAGTGATAATGTTT ATAGTAATAACTACACATCCTGGTTTCAGCAGAAACCAGGGCAG CCTCCCAAACAACTGCTCTATTATGCGGCCTATCGGGCATCTGG GGTCCCATCGCGGTTCAAAGGCAGTGGATCTGGGACAGAGTTCA CTCTCTCCATCAGCGATGTGGTGTGTGACGATGCTGCCACTTAC TATTGTTCAGGCCATAAAGATTATAGTGATGATGGTAGTACTTT CGGCGGAGGGACCGAGGTGGAAATCAAA | 798 |
| >B1-185-K | GAGCTCGTGCTGACCCAGACACCATCTTCCAAGTCTGTCGCTGT GGGAGACACAGTCACCATCAATTGCCAGGCCAGTGATAATGTTT ATAGTAATAACTACACATCCTGGTTTCAGCAGAAACCAGGGCAG CCTCCCAAACAACTGCTCTATTATGCGGCCTATCGGGCATCTGG GGTCCCATCGCGGTTCAAAGGCAGTGGATCTGGGACAGAGTTCA CTCTCTCCATCAGCGATGTGGTGTGTGACGATGCTGCCACTTAC TATTGTTCAGGCCATAAAGATTATAGTGATGATGGTAGTACTTT CGGCGGAGGGACCGAGGTGGAAATCAAA | 799 |
| >B1-189-K | GAGCTCGTGATGACCCAGACACCAGCCTCCGTGTCTGCAGCTGT GGGAGGCACAGTCACCATCAATTGCCAGGCCAGTGAGGATATTA GTAGTAATTTAGCCTGGTATCAGCAGAAACCAGGGCAGCCTCCC AAGCTCCTGATCAGTGGTGCATCCACTCTGGCATCTGGGGTCCC ATCGCGGTTCAAAGGCAGTGGATCTGGGACAGACTTCACTCTCA CCATGAGCGACCTGGAGTGTGCCGATGCTGCCACTTACTACTGT CAAGGCGCTTATTATGGTAGTAGTTATGGTTTCGGGGGAGGGAC CGAGGTGGTGGTCAAA | 800 |
| >B1-190-K | GAGCTCGTGCTGACCCAGACACCATCCCCCGTGTCTGCAGCTGT GGGAGGCACAGTCACCATCAATTGCCAGGCCAGTCAGAGCATTA GCAATGAATTATCCTGGTATCAACAGAAACCAGGGCAGCCTCCC AAGCTCCTGATCTATCTGGCATCCACTCTGGATTCTGGGGTCCC ATCGCGGTTCAAAGGCAGTGGATCTGGGACCCAGTTCACTCTCA CCATCAGCGACCTGGAGTGTGCCGACGCTGCCACTTACTACTGT CAAAGTCATTATTATGGTGGTAGTAGTGATTATGGATGGGCTTT CGGCGGAGGGACCGAGGTGGTGGTCAAA | 801 |

TABLE 7-continued

| Nucleotide sequences of LILRB1 mAb light chain variable region | | |
|---|---|---|
| mAb ID | Light chain nucleotide sequences | SEQ ID NO: |
| >B1-196-2-K | GAGCTCGATATGACCCAGACTCCATCTTCCACGTCTGCAGCTGTGGGAGGCACAGTCACCATCAAGTGCCAGGCCAGTCAAAGTGTTTACAATAACAACCAATTATCCTGGTTTCAGCAGAAACCAGGGCAGCCTCCCAAACGCCTGATCTATGGTGCATCCACTCTGGAATCTGGGGTCCCATCGCGGTTCAGCGGCAGTGGATCTGGGACACAGTTCACTCTCACCATTAGTGACCTGGAGTGTGACGATGCTGCCACTTACTACTGTCAAGGCGCTGTTAGTAGTGATTACTATCCTTTCGGCGGAGGGACCGAGGTGGAAATCAAA | 802 |
| >B1-198-K | GAGCTCGATATGACCCAGACACCAGCCTCCGTGTCTGAACCTGTGGGAGGCACAGTCACCATCAAGTGCCAGGCCAGTCAGAGTATTGGTAGCTATTTAGCCTGGTATCAGCAGAAACCAGGGCAGCCTCCCAAGCTCCTGGCCTTTTATGCTTCCACTCTGAAGTCTGGGGTCCCACCGCGGTTCAAAGGCAGTGGATCTGGGACAGAGTTCACTCTCACCATCAGCGACCTGGAGTGTGCCGATGCTGCCACTTATTACTGTCAAAGTAATCGTCTTAGTAGTAGTGACGTTAATGCTTTCGGCGGAGGGACCGAGGTGGAAATCAAA | 803 |
| >B1-202-2-K | GAGCTCGTGCTGACCCAGACTGCATCCCCCGTGTCTGGAGCTGTGGGAGGCACAGTCACCATCAAGTGCCAGGCCAGTCAGAACATTTACAGCAATTTAGCCTGGTATCAGCAGAAACCAGGGCAGCCTCCCAAGCTCCTGATCTATTCTGCATCCAAACTGGCATCTGGGGTCCCATCGCGGTTCAAAGGCAGTGGATCTGGGACAGAGTACACTCTCACCATCAGCGGCGTGCAGTGTGAAGATGCTGCCACTTACTACTGTCAAAGCTATTATTATACTGCTAGTGCTGATACTACTTTCGGCGGAGGGACCGAGGTGGAAATCAAA | 804 |
| >B1-203-1-K | GAGCTCGTGCTGACCCAGACTCCATCCTCCGTGGAGGCAGCTGTGGGAGGCACAGTCACCATCAAGTGCCAGGCCAGTCAGAGCATTGGTAGCTACTTAGCCTGGTATCAGCAGAAACCAGGGCAGCCTCCCAAGCTCCTGATCTACAAGGCATCCACTCTGTCATCTGGGGTCTCATCACGGTACAAAGGCAGTGGATCTGGGACAGAGTTCACTCTCACCATCAGCGACCTGGAGTGTGACGATGCTGCCACTTACTACTGTCAATATACTAGTTATAGTAGTGGTGGGGCTTTCGGCGGAGGGACCGAGGTGGTGGTCAAA | 805 |
| >B1-204-K | GAGCTCGATATGACCCAGACTCCATCCTCCGTGGAGGCAGCTGTGGGAGGCACAGTCACCATCAAGTGCCAGGCCAGTCAGACCATTTATACCAATTTAGCCTGGTATCAGCAGAAACCAGGGCAGCCTCCCAACCTCCTGATCTATGCTGCATCCACTCTGGCATCTGGGGTCTCATCGCGGTTCAAAGGCAGTGGATCCGGGACAGAGTTCACTCTCACCATCAGCGACCTGGAGTGTGCCGATGCTGCCACTTACTACTGTCAAAGCTATTATGGTAGTAGTACTACTGGTAATGGTTTCGGCGGAGGGACCGAGGTGGAAATCAAC | 806 |
| >B1-209-K | GAGCTCGTGATGACCCAGACTCCAGCCTCTGTGTCTGAACCTGTGGGAGGCACAGTCACCATCAAGTGCCAGGCCAGTCAGAGCATTAGTAGTTACTTATCCTGGTATCAGCAGAAACCAGGGCAGCCTCCCAAGCGCCTGATCTACAAGGCTTCCACTCTGGCATCTGGGGTCCCATCGCGGTTCAAAGGCAGTGGATCTGGGACAGAGTTCACTCTCACCATCAGCGGCGTGCAGTGTGCCGATGCTGCCACTTACTACTGTCAAAACAATTATCATAGTGGTAGTAGTAATGGTGGTGGTTTTGCTTTCGGCGGAGGGACCGAGGTGGAAATCAAA | 807 |
| >B1-210-K | GAGCTCGTGCTGACCCAGACTCCATCTTCCAAGTCTGTCGCTGTGGGAGACACAGTCACCATCAATTGCCAGGCCAGTGAGAGTGTTTATGGTAACAACCGTTGCTCCTGGTATCAGCAGAAACCAGGGCAGCCTCCCAAGCTCCTGATCTACCAGGCTTCCACTCTGGCCTCTGGGGTCCCATCGCGGTTCAGCGGCAGTGGATCTGGGACACAGTTCACTCTCACCATCAGCGATGTGGTGTGTGACGATGCTGCCACTTACTACTGTGCAGGACATAAAGGAACTACTAATGATGGGAATGATTTCGGCGGAGGGACCGAGGTGGAAATCAAA | 808 |
| >B1-220-K | GAGCTCGATATGACCCAGACTCCAGCCTCCGTGTCTGCAGCTGTGGGAGGCACAGTCACCATCAAGTGCCAGGCCAGTCAGAGCATTACCAATGCATTAGCCTGGTATCAACAGAAACCAGGGCAGCCTCCCAAGCTCCTGATCTACAGGGCATCCACTCTGGCATCTGGGGTCTCATCGCGGTTCAAAGGCAGCGGATCTGGGACAGAGTTCACTCTCACCATCAGTGACCTTGAGTGTGCCGATGCTGCCACTTACTATTGTCAATGTAGTTATTATGGTAGTACTTATTTTGGGAGTCCTTTCGGCGGAGGGACCGAGGTGGAAATCAAA | 809 |

TABLE 7-continued

| Nucleotide sequences of LILRB1 mAb light chain variable region | | |
|---|---|---|
| mAb ID | Light chain nucleotide sequences | SEQ ID NO: |
| >B1-224-K | GAGCTCGTGCTGACCCAGACTCCATCCTCCGTGTCTGAACCTGT GGGAGGCACAGTCACCATCAAGTGCCAGGCCAGTCAGAGCATTA GTAGTAGCTACTTAGCCTGGTATCAGCAGAAACCAGGGCAGCCT CCCAAGTTCCTGATCTATTCTGCATCCACTCTGGCATCTGGGGT CCCATCGCGGTTCAAAGGCAGTGGATCTGGGACAGAGTTCACTC TCACCATCAGCGACCTGGAGTGTGCCGATGCTGCCACTTACTAC TGTCAAAGCACTTATATTAGTAGTAGTAATTATGGTGCTGCTTT CGGCGGAGGGACCGAGGTGGAAATCAAA | 810 |
| >B1-221-K | GAGCTCGATCTGACCCAGACTCCATCCTCCGTGGAGGCAGCTGT GGGAGGCACAGTCACCATCAAGTGCCAGGCCAGTCAGAGCATTG GTAGTAATTTAGCCTGGTATCAGCAGAAACCAGGGCAGCCTCCC AAGGTCCTGATCTACAAGGCATCCACTCTGGCATCTGGGGTCCC ATCGCGGTTCAAAGGCAGTGGATCTGGGACACAGTTCACTCTCA CCATCAGCGACCTGGAGTGTGCCGATGCTGCCACTTATTACTGT CAAAACAATAATTATTGGAGTAATGGTAACCATTTCGGCGGAGG GACCGAGGTGGTGGTCAAA | 811 |
| >B1-226-K | GAGCTCGTGCTGACCCAGACTCCATCTTCCAAGTCTGTCGCTGT GGGAGACACAGTCACCATCAATTGCCAGGCCAGTGAGAATGTTT ATAGTAATAACTACACATCCTGGTTTCAGCAGAAACCAGGGCAG CCTCCCAAACAACTGCTCTATTATGCGGCCTATCGGGCATCTGG GGTCCCATCGCGGTTCAAAGGCAGTGGATCTGGGACAGAGTTCA CTCTCTCCATCAGCGATGTGGTGTGTGACGATGCTGCCACTTAC TATTGTTCAGGCCATAAAGATTATAGTGATGATGGTAGTACTTT CGGCGGAGGGACCGAGGTGGTGGTCAAA | 812 |
| >B1_227-k | GAGCTCGATCTGACCCAGACTGCATCCCCCGTGTCTGGAGCTGT GGGAGGCACAGTCACCATCAAGTGCCAGGCCAGTCAGAGCATTG CTAGCGACTTAGCCTGGTATCAGCAGAAACCAGGGCAGCCTCCC AACCTCCTGATCTATGCTGCATCCACTCTGGCATCTGGGGTCTC ATCGCGGTTCAAAGGCAGTGGATCCGGGACAGAGTTCACTCTCA CCATCAGCGACCTGGAGTGTGCCGATGCTGCCACTTACTACTGT CAAAGCTATTATGGTAGTAGTACTACTGGTAATGGTTTCGGCGG AGGGACCGAGGTGGTGGTCAAA | 813 |
| Hu176-k | GACATTCAGCTGACACAGAGCCCTAGCTTCCTGAGCGCTAGCGT GGGCGACAGAGTGACCATCACCTGCCAAGCCTCTCAGACCATCT ACACCAACCTGGCCTGGTATCAGCAGAAGCCCGGCAAAGCCCCC AAGCTGCTGATATACGCCGCTAGCACCCTGGCGAGCGGCGTGCC TAGCAGATTCAGCGGCAGCGGCAGCGGCACCGAGTTCACCCTGA CCATCAGCAGCCTGCAGCCCGAGGACTTCGCCACCTACTACTGT CAGAGCTACTACGGCAGCAGCACCACCGGCAACGGCTTCGGCGG CGGCACCAAGGTGGAGATCAAG | 875 |

TABLE 8

| Amino acid sequences of LILRB1 mAb light chain variable region | | |
|---|---|---|
| mAb ID | Light chain amino acid sequences | SEQ ID NO: |
| B1-3-K | ELDMTQTPASVEAAVGGTVTIKCQASQNIYSYLVWYQQKPGQPP KLLISKASTLASGVSSRFKGSGSGTEFTLTINDLECADAATYYC QTNYFSSTSHFGVFTFGGGTELEIK | 814 |
| B1-4-K | ELVLTQTPSPVSAVVGGSVTINCQSSQSLYNANDLSWYQQKPGQ PPKQLIYWASTLASGVPSRFKGSGSGTQFTLSISDVQCDDAATY YCLGEFSCSSFDCHVFGGGTEVVVK | 815 |
| B1-5-K | ELDMTQTPSSVSAAVGDTVTIKCQASQSIYRYLAWYQQKPGQRP SLLIYYGSDLASGVPSRFSGSGSGTEFTLTISDLECADAASYYC QTTYDDYHNGWAFGGGTNVEIN | 816 |
| B1-7-K | ELDLTQTPSSVSAAVGGTVTISCQASQSVYGNNRLAWYHQKPGQ PPKRLIYLASTLDSGVPSRFKGAGSGTQFTLTISDLECDDAATY YCAGGYAGNFNAFGGGTEVEIK | 817 |
| B1-10-K | ELDLTQTPASVSAAVGGTVTIKCQASQNIVSNLAWYQQKPGQRP KLLIYYASTLASGVPSRFKGSGSGTEYTLTISDLECADAATYYC QNNAGIYGNYGHGFGGGTELEIK | 818 |

TABLE 8-continued

| Amino acid sequences of LILRB1 mAb light chain variable region | | |
|---|---|---|
| mAb ID | Light chain amino acid sequences | SEQ ID NO: |
| B1-15-K | ELDLTQTPSSVEAAVGGTVTIKCQASQSIYNYLAWYQQKPGHSP KLLIYDVSKLASGVSSRFKGSGSGTEFTLTISDLECADAATYYC QSYYGNTVSFTFGGGTEVEIK | 819 |
| B1-18-K | ELVMTQTPSSVSAAVGGTVTISCQASQSVYNNNNLAWYQQKPGQ PPKRLIYSASTLDSGVPSRFSGSGSGTQFTLTISDLECDDAATY YCAGGYTYNINIFGGGTEVEIK | 820 |
| B1-19-K | ELDLTQTPASVSEPVGGTVTIKCQASQNIYNNLAWYQQKPGQPP KLLIYYASTLASGVPPRFSGSGSGTEYTLTISDLECDDAATYYC QNNAGIYGGYGHGFGGGTEVVVK | 821 |
| B1-22-K | ELDLTQTPASVEAAVGGTVTIKCQASQTIGSYLSWYQQKPGQRP KLLIYEASKLASGVPSWFKGSGSGTEFTLTISDLECADAATYYC QSNYYRAGGNYGGAFGGGTEVEIK | 822 |
| B1-25-K | ELDLTQTPFSVSAAVGGTVTIKCQASETISNRLAWYQQKPGQPP KLLIYSASTLESGVPSRFKGSGSGTEFTLTISDLECADAATYYC QSIRSSSGIVHPNTFGGGTEVEIK | 823 |
| B1-27-K | ELDLTQTPASVSEPVGGTVTITCQASQSISSYLSWYQQTPGQPP KLLIYKASTLASGVPSRFKGSGSGTEFTLTISDLECADAATYYC QSYYYISATVDNTFGGGTEVEIK | 824 |
| B1-28-K | ELDLTQTPTSVSAAVGGTVTIKCQASQSISDYLSWYQQKPGQPP KLLIYRASTLASGVPSRFKGSGSGTEFTLTISDLECADAATYYC QSNYYGSQGCTFGGGTEVEIK | 825 |
| B1-38-K | ELDMTQTPSSVEAAVGGTVTVKCQVSQSIGNAIAWYQQKPGQPP KLLIYKASTLASGVPSRFKGSGSGTEFTLTISDLECADAATYYC QNYYYSNTNSFGGGTEVVVK | 826 |
| B1-41-K | ELDMTQTASPVSGAVGGTVTIKCQASQNIYNNIGWYQQKPGQPP NLLIYGPSYLASGVPSRFKGSRSGTEYTLTISDLECADAATYYC QSDDWMSISPDIVFGGGTEVEIK | 827 |
| B1-56-K | ELVMTQTPSSSSAAVGGTVTIKCQASQSIGSRFAWYQQKPGQRP KLLIYEASKLPSGVPSRFKGSGSGTEFTLTISDLECADAAIYYC QCTYYESSSGGGFGGGTEVVVK | 828 |
| B1-58-1-K | ELVLTQTPSSVEVAVGGAVTIKCQASH11TNYLAWYQQRPGQPP KLLIYDASKLASGVPSRFKGSGSGTEFTLTISDLECADAATYYC QNYLYFSSGDWNVFGGGTEVVVK | 829 |
| B1-72-1-K | ELVMTQTPSSVSAAVGGTVTIKCQASPSISTYLSWYQQKPGQPP KRLINRASTLASGVPPRFKGSGAGTQFTLTISDLECADAATYYC QNNYHSGSSNGGGVAFGGGTEVEIK | 830 |
| B1-74-K | ELVLTQTPASVSAAVGGTVTINCQASQSIGSGNLAWYQQKPGQP PKLLIYLASTLASGVPPRFKGSGSGTEFTLTISDLECDDAATYY CQYTYYGTTYDNAFGGGTELEIK | 831 |
| B1-76-K | ELDLTQTPSPVSAAVGGTVTINCQASQIVANGRLAWYQQKPGQP PKLLIYATSTLASGVPSRFKGSGSGTQFTLTINGVQCDDAATYY CQGAYSSGDVRTFGGGTEVVVK | 832 |
| B1-79-K | ELVLTQTPSSVSAAVGGTVTINCQASEDIDRYLAWYQQKPGQRP KLLIVDASTLPSGVPSRFKGSGSGTEFTLTISDLECADGATYYC QSYDNSDNNGFGGGTEVVVK | 833 |
| B1-83-K | ELDLTQTPSSVEVAVGGAVTIKCQASHIITNYLAWYQQRPGQPP KLLIYDASKLASGVPSRFKGSGSGTEFTLTISDLECADAATYYC QNYLYFSSGDWNVFGGGTEVVVK | 834 |
| B1-93-K | ELDLTQTPASVSAAVGGTVTINCQASESIGSALAWYQQKPGQPP KLLIYSASALASGVPSRFKGSGSGTEYTLTISDLECADAATYYC QSYYGSGTTALDTFGGGTEVEIK | 835 |
| B1-98-K | ELDLTQTPGSVEAAVGGTVTIKCQAGQSIYNYLSWYQQKPGQPP KLLIYSASTLESGVPPRFSGSGSGTEFTLTISDLECADAATYSC QNNYGIGSNYGPGFGGGTEVEIK | 836 |

TABLE 8-continued

Amino acid sequences of LILRB1 mAb light chain variable region

| mAb ID | Light chain amino acid sequences | SEQ ID NO: |
|---|---|---|
| B1-110-K | ELDLTQTPASVEAAVGGTVTIKCQASLNINSWLAWYQQKPGQPP KLLISYTSSLASGVPSRFKGSGSGTEYTLTINDLECADAATYYC QTTYFGTNGGGFGGGTEVEIK | 837 |
| B1-115-K | ELVMTQTPSSVEAAVGGTVTNKCQASEDIYSNLAWYQQKPGQPP KLLIYGATTLASGVPSRFKGSGSGTEFTLTISDLECADAATYYC QAESNDVWAFGGGTEVVVK | 838 |
| B1-117-K | ELDLTQTPASVSAAVGGTVTIKCQASEDIYSNLAWYQQKPGQPP KLLIYKASTLASGVPPRFKGSGSGTEYTLTISGVQCDDAATYAC QTTYWTTTDDNPFGGGTEVEIK | 839 |
| B1-125-K | ELDLTQTPSSSSAAVGGTVTINCQASQSVYNKNYLSWFQQKPGQ PPKLLIYYASTLASGVPSRFKGSGSGTEFTLTISDVVCDDAATY YCAAYKGVSDDGISFGGGTEVEIK | 840 |
| B1-128-K | ELDMTQTPSSVSAAVGGTVTIKCQASQSISSYLSWYQQKPGQPP KRLIYKASTLPSGVPPRFKGSGSGTEFTLTISDLECADAATYYC QNNYHSGSSNGGGFAFGGGTQVEIK | 841 |
| B1-154-K | ELDLTQTPASVEAAVRGTVTIKCQASQSISYYLAWYQQKPGQPP KVLIYKASTLASGVPPRFKGSGFGTEFTLTISDLECADAATYYC QSTYGRDNNDLFFAFGGGTEVEIK | 842 |
| B1-160-K | ELDLTQTPASVSAAVGGTVTIKCQASQSISSSYLAWYQQKPGQP PKLLIYSASSTASGVPSRFKGSGSGTQFTLTISDLECADAATYY CQSTYISSSKYGAVFGGGTELEIK | 843 |
| B1-162-K | ELVMTQTASPVSAAVGGTVTISCQSSQSVYSNNWLSWYQQKPGQ PPKRLIYKASTLETGVPSRFKGSGSGKQFTLTISDLECDDAATY YCAGGYSGDLYAFGGGTEVVVK | 844 |
| B1-167-K | ELDMTQTPSPVSAAVGGSVTISCQASQTIYNNKNLAWYQQKPGQ PPKLLIYQASKLASGVSSRFSGSGSGTQFTLTISGVQCDDAATY YCQGEFSCSSGDCTTFGGGTEVVVK | 845 |
| B1-169-K | ELDMTQTPASVSEPVGGTVTIKCQASENIYSYLAWYQQKPGQPP KLLIYSASTLASGVPSRFKGSGSGTQFTLTISDLECADAATYYC QYSNFRVNDPSVFGGGTEVEIK | 846 |
| B1-170-K | ELDLTQTPASVSAAVGGTVTISCQSSQSVHHSQTVHNNQWLAWY QQKPGQPPKLLIYDASKLASGVPSRFTGSGSGTQFSLTISAVQC DDAATYYCQGGYSYGDVYGFGGGTELEIK | 847 |
| B1-173-2-K | ELVLTQTPSSTSAAVGGTVTINCQASQSVDNNKQLSWYQQKPGQ PPKQLIYSASKLASGVPSRFKGSGSGTQFTLTISDLECDDAATY YCAGYYYSGSATDAWAFGGATEVEIN | 848 |
| B1-175-K | ELVMTQTPSSVSAAVGDTLTINCQASETISNRLAWYQQKPGQPP KLLIYSASTLESGVPSRFRGSGSGTQFTLTISDLECADAATYYC QSIRSSSGVVHPNTFGGGTEVEIK | 849 |
| B1-176-K | ELDLTQTPSSVEAAVGGTVTIKCQASQTIYTNLAWYQQKPGQPP NLLIYAASTLASGVSSRFKGSGSGTEFTLTISDLECADAATYYC QSYYGSSTTGNGFGGGTEVEIK | 850 |
| B1-178-2-K | ELVLTQTPSSKSVAVGDTVTINCQASDNVYSNNYTSWFQQKPGQ PPKQLLYYAAYRASGVPSRFKGSGSGTEFTLSISDVVCDDAATY YCSGHKDYSDDGSTFGGGTEVEIK | 851 |
| B1-185-K | ELVLTQTPSSKSVAVGDTVTINCQASDNVYSNNYTSWFQQKPGQ PPKQLLYYAAYRASGVPSRFKGSGSGTEFTLSISDVVCDDAATY YCSGHKDYSDDGSTFGGGTEVEIK | 852 |
| B1-189-K | ELVMTQTPASVSAAVGGTVTINCQASEDISSNLAWYQQKPGQPP KLLISGASTLASGVPSRFKGSGSGTDFTLTMSDLECADAATYYC QGAYYGSSYGFGGGTEVVVK | 853 |
| B1-190-K | ELVLTQTPSPVSAAVGGTVTINCQASQSISNELSWYQQKPGQPP KLLIYLASTLDSGVPSRFKGSGSGTQFTLTISDLECADAATYYC QSHYYGGSSDYGWAFGGGTEVVVK | 854 |

TABLE 8-continued

Amino acid sequences of LILRB1 mAb light chain variable region

| mAb ID | Light chain amino acid sequences | SEQ ID NO: |
|---|---|---|
| B1-196-2-K | ELDMTQTPSSTSAAVGGTVTIKCQASQSVYNNNQLSWFQQKPGQ PPKRLIYGASTLESGVPSRFSGSGSGTQFTLTISDLECDDAATY YCQGAVSSDYYPFGGGTEVEIK | 855 |
| B1-198-K | ELDMTQTPASVSEPVGGTVTIKCQASQSIGSYLAWYQQKPGQPP KLLAFYASTLKSGVPPRFKGSGSGTEFTLTISDLECADAATYYC QSNRLSSSDVNAFGGGTEVEIK | 856 |
| B1-202-2-K | ELVLTQTASPVSGAVGGTVTIKCQASQNIYSNLAWYQQKPGQPP KLLIYSASKLASGVPSRFKGSGSGTEYTLTISGVQCEDAATYYC QSYYYTASADTTFGGGTEVEIK | 857 |
| B1-203-1-K | ELVLTQTPSSVEAAVGGTVTIKCQASQSIGSYLAWYQQKPGQPP KLLIYKASTLSSGVSSRYKGSGSGTEFTLTISDLECDDAATYYC QYTSYSSGGAFGGGTEVVVK | 858 |
| B1-209-K | ELVMTQTPASVSEPVGGTVTIKCQASQSISSYLSWYQQKPGQPP KRLIYKASTLASGVPSRFKGSGSGTEFTLTISGVQCADAATYYC QNNYHSGSSNGGGFAFGGGTEVEIK | 859 |
| B1-204-K | ELDMTQTPSSVEAAVGGTVTIKCQASQTIYTNLAWYQQKPGQPP NLLIYAASTLASGVSSRFKGSGSGTEFTLTISDLECADAATYYC QSYYGSSTTGNGFGGGTEVEIN | 860 |
| B1-210-K | ELVLTQTPSSKSVAVGDTVTINCQASESVYGNNRCSWYQQKPGQ PPKLLIYQASTLASGVPSRFSGSGSGTQFTLTISDVVCDDAATY YCAGHKGTTNDGNDFGGGTEVEIK | 861 |
| B1-220-K | ELDMTQTPASVSAAVGGTVTIKCQASQSITNALAWYQQKPGQPP KLLIYRASTLASGVSSRFKGSGSGTEFTLTISDLECADAATYYC QCSYYGSTYFGSPFGGGTEVEIK | 862 |
| B1-224-K | ELVLTQTPSSVSEPVGGTVTIKCQASQSISSSYLAWYQQKPGQP PKFLIYSASTLASGVPSRFKGSGSGTEFTLTISDLECADAATYY CQSTYISSSNYGAAFGGGTEVEIK | 863 |
| B1-221-K | ELDLTQTPSSVEAAVGGTVTIKCQASQSIGSNLAWYQQKPGQPP KVLIYKASTLASGVPSRFKGSGSGTQFTLTISDLECADAATYYC QNNNYWSNGNHFGGGTEVVVK | 864 |
| B1-226-K | ELVLTQTPSSKSVAVGDTVTINCQASENVYSNNYTSWFQQKPGQ PPKQLLYYAAYRASGVPSRFKGSGSGTEFTLSISDVVCDDAATY YCSGHKDYSDDGSTFGGGTEVVVK | 865 |
| B1-227-K | ELDLTQTASPVSGAVGGTVTIKCQASQSIASDLAWYQQKPGQPP NLLIYAASTLASGVSSRFKGSGSGTEFTLTISDLECADAATYYC QSYYGSSTTGNGFGGGTEVVVK | 866 |
| Hu176-K | DIQLTQSPSFLSASVGDRVTITCQASQTIYTNLAWYQQKPGKAP KLLIYAASTLASGVPSRFSGSGSGTEFTLTISSLQPEDFATYYC QSYYGSSTTGNGFGGGTKVEIK | 867 |

2. Exemplary Epitopes and Competing Antigen Binding Proteins

In another aspect, the present disclosure provides epitopes to which anti-LILRB1 antibodies bind. In some embodiments, epitopes that are bound by the antibodies described herein are useful. In certain embodiments, an epitope provided herein can be utilized to isolate antibodies or antigen binding proteins that bind to LILRB1. In certain embodiments, an epitope provided herein can be utilized to generate antibodies or antigen binding proteins which bind to LILRB1. In certain embodiments, an epitope or a sequence comprising an epitope provided herein can be utilized as an immunogen to generate antibodies or antigen binding proteins that bind to LILRB1. In certain embodiments, an epitope described herein or a sequence comprising an epitope described herein can be utilized to interfere with biological activity of LILRB1.

In some embodiments, antibodies or antigen-binding fragments thereof that bind to any of the epitopes are particularly useful. In some embodiments, an epitope provided herein, when bound by an antibody, modulates the biological activity of LILRB1. In some embodiments, an epitope provided herein, when bound by an antibody, activates LILRB1. In some embodiments, an epitope provided herein, when bound by an antibody, suppress the activation of LILRB1. In some embodiments, an epitope provided herein, when bound by an antibody, block the interaction between LILRB1 and its binding partners.

In some embodiments, the domain(s)/region(s) containing residues that are in contact with or are buried by an antibody can be identified by mutating specific residues in LILRB1 and determining whether the antibody can bind the mutated LILRB1 protein. By making a number of individual mutations, residues that play a direct role in binding or that are in sufficiently close proximity to the antibody such that a mutation can affect binding between the antibody and antigen can be identified. From knowledge of these amino acids, the domain(s) or region(s) of the antigen that contain residues in contact with the antigen binding protein or covered by the antibody can be elucidated. Such a domain can include the binding epitope of an antigen binding protein.

In another aspect, the present disclosure provides antigen-binding proteins that compete with one of the exemplified antibodies or antigen-binding fragment binding to the epitope described herein for specific binding to LILRB1. Such antigen binding proteins can also bind to the same epitope as one of the herein exemplified antibodies or the antigen-binding fragment, or an overlapping epitope. Antigen-binding proteins that compete with or bind to the same epitope as the exemplified antibodies are expected to show similar functional properties. The exemplified antibodies include those described above, including those with the heavy and light chain variable regions and CDRs included in Tables 1 and 3, heavy and light chains as shown in Tables 6 and 8, and heavy and light chain coding regions as shown in Tables 5 and 7.

C. Engineering of Antibody Sequences

In various embodiments, one may choose to engineer sequences of the identified antibodies for a variety of reasons, such as improved expression, improved cross-reactivity or diminished off-target binding. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns. Recombinant full-length IgG antibodies may be generated by subcloning heavy and light chain Fv DNAs from the cloning vector into an IgG plasmid vector, transfected into 293 Freestyle cells or CHO cells, and antibodies collected a purified from the 293 or CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), $F(ab')_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

1. Antigen Binding Modifications

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to $IgG_1$ can increase antibody dependent cell cytotoxicity, switching to class A can improve tissue distribution, and switching to class M can improve valency.

Modified antibodies may be made by any technique known to those of skill in the art, including expression through standard molecular biological techniques, or the chemical synthesis of polypeptides. Methods for recombinant expression are addressed elsewhere in this document.

2. Fc Region Modifications

The antibodies disclosed herein can also be engineered to include modifications within the Fc region, typically to alter one or more functional properties of the antibody, such as serum half-life, complement fixation, Fc receptor binding, and/or effector function (e.g., antigen-dependent cellular cytotoxicity). Furthermore, the antibodies disclosed herein can be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat. The antibodies disclosed herein also include antibodies with modified (or blocked) Fc regions to provide altered effector functions. See, e.g., U.S. Pat. No. 5,624,821; WO2003/086310; WO2005/120571; WO2006/0057702. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, enabling less frequent dosing and thus increased convenience and decreased use of material. This mutation has been reported to abolish the heterogeneity of inter-heavy chain disulfide bridges in the hinge region.

In one embodiment, the hinge region of CH1 is modified such that the number of cysteine residues in the hinge region is increased or decreased. This approach is described further in U.S. Pat. No. 5,677,425. The number of cysteine residues in the hinge region of CH1 is altered, for example, to facilitate assembly of the light and heavy chains or to increase or decrease the stability of the antibody. In another embodiment, the antibody is modified to increase its biological half-life. Various approaches are possible. For example, one or more of the following mutations can be introduced: T252L, T254S, T256F, as described in U.S. Pat. No. 6,277,375. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022. In yet other embodiments, the Fc region is altered by replacing at least one amino acid residue with a different amino acid residue to alter the effector function(s) of the antibodies. For example, one or more amino acids selected from amino acid residues 234, 235, 236, 237, 297, 318, 320 and 322 can be replaced with a different amino acid residue such that the antibody has an altered affinity for an effector ligand but retains the antigen binding ability of the parent antibody. The effector ligand to which affinity is altered can be, for example, an Fc receptor or the C1 component of complement. This approach is described in further detail in U.S. Pat. Nos. 5,624,821 and 5,648,260.

In another example, one or more amino acid residues within amino acid positions 231 and 239 are altered to thereby alter the ability of the antibody to fix complement. This approach is described further in PCT Publication WO 94/29351. In yet another example, the Fc region is modified to increase or decrease the ability of the antibodies to mediate antibody dependent cellular cytotoxicity (ADCC) and/or to increase or decrease the affinity of the antibodies for an Fcγ receptor by modifying one or more amino acids at the following positions: 238, 239, 243, 248, 249, 252, 254, 255, 256, 258, 264, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072. Moreover, the binding sites on human IgG1 for FcγR1, FcγRII, FcγRIII and FcRn have been mapped and variants with improved binding have been described. Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In one embodiment, the Fc region is modified to decrease the ability of the antibodies to mediate effector function and/or to increase anti-inflammatory properties by modifying residues 243 and 264. In one embodiment, the Fc region of the antibody is modified by changing the residues at positions 243 and 264 to alanine. In one embodiment, the Fc region is modified to decrease the ability of the antibody to mediate effector function and/or to increase anti-inflammatory properties by modifying residues 243, 264, 267 and 328.

In one embodiment, the Fc region is modified to abolish the ability of the antibodies to mediate effector function by modifying residues 234, 235 and 329 to alanine or glycine (L234A-L235A-P329G).

In one embodiment, the Fc region is modified to abolish the ability of the antibodies to mediate effector function by modifying residue 297 to alanine (N234A).

In still another embodiment, the antibody comprises a particular glycosylation pattern. For example, an aglycosylated antibody can be made (i.e., the antibody lacks glycosylation). The glycosylation pattern of an antibody may be altered to, for example, increase the affinity or avidity of the antibody for an antigen. Such modifications can be accomplished by, for example, altering one or more of the glycosylation sites within the antibody sequence. For example, one or more amino acid substitutions can be made that result removal of one or more of the variable region framework glycosylation sites to thereby eliminate glycosylation at that site. Such aglycosylation may increase the affinity or avidity of the antibody for antigen. See, e.g., U.S. Pat. Nos. 5,714,350 and 6,350,861.

An antibody may also be made in which the glycosylation pattern includes hypofucosylated or afucosylated glycans, such as a hypofucosylated antibodies or afucosylated antibodies have reduced amounts of fucosyl residues on the glycan. The antibodies may also include glycans having an increased amount of bisecting GlcNac structures. Such altered glycosylation patterns have been demonstrated to increase the ADCC ability of antibodies. Such modifications can be accomplished by, for example, expressing the antibodies in a host cell in which the glycosylation pathway was been genetically engineered to produce glycoproteins with particular glycosylation patterns. These cells have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (a (1,6)-fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see U.S. Patent Publication No. 20040110704). As another example, EP 1 176 195 describes a cell line with a functionally disrupted FUT8 gene, which encodes a fucosyl transferase, such that antibodies expressed in such a cell line exhibit hypofucosylation by reducing or eliminating the α-1,6 bond-related enzyme.

EP 1 176 195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell. Antibodies with a modified glycosylation profile can also be produced in chicken eggs, as described in PCT Publication WO 06/089231. Alternatively, antibodies with a modified glycosylation profile can be produced in plant cells, such as *Lemna* (U.S. Pat. No. 7,632,983). Methods for production of antibodies in a plant system are disclosed in the U.S. Pat. Nos. 6,998,267 and 7,388,081. PCT Publication WO 99/54342 describes cell lines engineered to express glycoprotein-modifying glycosyl transferases (e.g., β(1,4)-N-acetylglucosaminyltransferase III (GnTIII)) such that antibodies expressed in the engineered cell lines exhibit increased bisecting GlcNac structures which results in increased ADCC activity of the antibodies.

Alternatively, the fucose residues of the antibodies can be cleaved off using a fucosidase enzyme; e.g., the fucosidase α-L-fucosidase removes fucosyl residues from antibodies. Antibodies disclosed herein further include those produced in lower eukaryote host cells, in particular fungal host cells such as yeast and filamentous fungi have been genetically engineered to produce glycoproteins that have mammalian- or human-like glycosylation patterns. A particular advantage of these genetically modified host cells over currently used mammalian cell lines is the ability to control the glycosylation profile of glycoproteins that are produced in the cells such that compositions of glycoproteins can be produced wherein a particular N-glycan structure predominates (see, e.g., U.S. Pat. Nos. 7,029,872 and 7,449,308). These genetically modified host cells have been used to produce antibodies that have predominantly particular N-glycan structures.

In addition, since fungi such as yeast or filamentous fungi lack the ability to produce fucosylated glycoproteins, antibodies produced in such cells will lack fucose unless the cells are further modified to include the enzymatic pathway for producing fucosylated glycoproteins (see, for example, PCT Publication WO2008112092). In particular embodiments, the antibodies disclosed herein further include those produced in lower eukaryotic host cells and which comprise fucosylated and nonfucosylated hybrid and complex N-glycans, including bisected and multiantennary species, including but not limited to N-glycans such as GlcNAc(1-4) Man3GlcNAc2; Gal(1-4)GlcNAc(1-4)Man3GlcNAc2; NANA(1-4)Gal(1-4)GlcNAc(1-4)Man3GlcNAc2. In particular embodiments, the antibody compositions provided herein may comprise antibodies having at least one hybrid N-glycan selected from the group consisting of GlcNAcMan5GlcNAc2; GalGlcNAcMan5GlcNAc2; and NANAGalGlcNAcMan5GlcNAc2. In particular aspects, the hybrid N-glycan is the predominant N-glycan species in the composition. In further aspects, the hybrid N-glycan is a particular N-glycan species that comprises about 30%, 40%, 50%, 60%, 70%, 80%, 90%, 95%, 97%, 98%, 99%, or 100% of the hybrid N-glycans in the composition.

In particular embodiments, the antibody compositions provided herein comprise antibodies having at least one complex N-glycan selected from the group consisting of GlcNAcMan3GlcNAc2; GalGlcNAcMan3GlcNAc2; NANAGalGlcNAcMan3GlcNAc2; GlcNAc2Man3 GlcNAc2; GalGlcNAc2Man3GlcNAc2; Ga l2GlcNAc2Man3GlcNAc2; NANAGal2GlcNAc2Man 3GlcNAc2; and NANA2Gal2GlcNAc2Man3GlcNAc2. In particular aspects, the complex N-glycan is the predominant N-glycan species in the composition. In further aspects, the complex N-glycan is a particular N-glycan species that comprises about 30%, 40%, 50%, 60%, 70%, 80%, 90%, 95%, 97%, 98%, 99%, or 100% of the complex N-glycans in the composition. In particular embodiments, the N-glycan is fusosylated. In general, the fucose is in an α1,3-linkage with the GlcNAc at the reducing end of the N-glycan, an α1,6-linkage with the GlcNAc at the reducing end of the N-glycan, an α1,2-linkage with the Gal at the non-reducing end of the N-glycan, an α1,3-linkage with the GlcNac at the non-reducing end of the N-glycan, or an α1,4-linkage with a GlcNAc at the non-reducing end of the N-glycan.

Therefore, in particular aspects of the above the glycoprotein compositions, the glycoform is in an α1,3-linkage or α1,6-linkage fucose to produce a glycoform selected from the group consisting of Man5GlcNAc2(Fuc), GlcNAc Man5GlcNAc2(Fuc), Man3GlcNAc2(Fuc), GlcNAcMan3 GlcNAc2(Fuc), GlcNAc2Man3GlcNAc2(Fuc), GalGlcN Ac2 Man3GlcNAc2(Fuc), Gal2GlcNAc2Man3GlcNAc2 (Fuc), NANAGal2GlcNAc2Man3GlcNAc2(Fuc), and NANA2Gal2GlcNAc2Man3GlcNAc2(Fuc); in an α1,3-linkage or α1,4-linkage fucose to produce a glycoform selected from the group consisting of GlcNAc(Fuc) Man5GlcNAc2, GlcNAc(Fuc)Man3GlcNAc2, GlcNAc2 (Fuc1-2)Man3GlcNAc2, GalGlcNAc2(Fuc1-2)Man 3GlcNAc2, Gal2GlcNAc2(Fuc1-2)Man3GlcNAc2, NANA Gal2GlcNAc2(Fuc1-2)Man3GlcNAc2, and NANA2Gal2 GlcNAc2(Fuc1-2)Man3GlcNAc2; or in an α1,2-linkage fucose to produce a glycoform selected from the group consisting of Gal(Fuc)GlcNAc2Man3GlcNAc2, Gal2(Fuc1-2)GlcNAc2Man3GlcNAc2, NANAGal2(Fuc1-2)GlcN Ac2Man3GlcNAc2, and NANA2Gal2(Fuc1-2)GlcNA c2Man3GlcNAc2.

In further aspects, the antibodies comprise high mannose N-glycans, including but not limited to, Man8GlcNAc2, Man7GlcNAc2, Man6GlcNAc2, Man5GlcNAc2, Man4GlcNAc2, or N-glycans that consist of the Man3GlcNAc2 N-glycan structure. In further aspects of the above, the complex N-glycans further include fucosylated and non-fucosylated bisected and multiantennary species. As used herein, the terms "N-glycan" and "glycoform" are used interchangeably and refer to an N-linked oligosaccharide, for example, one that is attached by an asparagine-N-acetylglucosamine linkage to an asparagine residue of a polypeptide. N-linked glycoproteins contain an N-acetylglucosamine residue linked to the amide nitrogen of an asparagine residue in the protein.

D. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5\times10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the VH C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338 describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. LILRB1 Related Diseases

LILRB1, a member of the ITIM-containing LILR receptor family, plays critical roles in regulation of both innate and adaptive immunity. It is expressed on several types of immune cells, including NK cells, and acts as an immune checkpoint protein. LILRB expression in myeloid-derived suppressor cells (MDSCs) can promote tumor growth and result in a suppressive immune microenvironment for tumor progression and metastasis. On the other hand, activation of LILRB1 signaling using agonistic antibodies can reduce tissue inflammation and can be used for management of autoimmune diseases. Both agonistic and antagonistic human LILRB1 monoclonal antibodies are provided herein, with specific targeting properties for modulation of LILRB1 signaling. These LILRB1 antibodies can be used to treatment human diseases, including cancer, auto-immune disease, and inflammatory disorders.

While hyperproliferative diseases can be associated with any disease which causes a cell to begin to reproduce uncontrollably, the prototypical example is cancer.

Examples of cancer can be generally categorized into solid tumors and hematologic malignancies. Solid tumors include but are not limited to, adrenal cancer, bile duct carcinoma, bone cancer, brain cancer (e.g., astrocytoma, brain stem glioma, craniopharyngioma, ependymoma, hemangioblastoma, medulloblastoma, meningioma, oligodendroglioma, spinal axis tumor), breast cancer (including acoustic neuroma, basal breast carcinoma, ductal carcinoma and lobular breast carcinoma), cervical cancer, choriocarcinoma, colon cancer, colorectal cancer, esophageal cancer, eye cancer, gastric cancer, glioblastoma, head and neck cancer, kidney cancer (including Wilms tumor), liver cancer (including hepatocellular carcinoma (HCC)), lung cancer (including bronchogenic carcinoma, non-small cell lung cancer (squamous/non-squamous), bronchioloalveolar cell lung cancer, papillary adenocarcinomas), mesothelioma, melanoma, merkel cell cancer, nasopharyngeal carcinoma, neuroblastoma, oral cancer, ovarian cancer, pancreatic cancer, penile cancer, pinealoma, prostate cancer, renal cell cancer, retinoblastoma, sarcoma (including chondrosarcoma, Ewing's sarcoma, fibrosarcoma, leiomyosarcoma, liposarcoma, myxosarcoma, osteogenic sarcoma, rhabdomyosarcoma, synovial sarcoma), skin cancer (including basal cell carcinoma, sebaceous gland carcinoma, squamous cell carcinoma), testicular cancer (including seminoma), thymic carcinoma, thyroid cancer (e.g., medullary thyroid carcinoma, papillary thyroid carcinoma), uterine cancer, and vaginal cancer.

Hematologic malignancies include but are not limited to blastic plasmacytoid dendritic cell neoplasm (BPDCN), heavy chain disease, leukemias (including but not limited to acute lymphocytic leukemia (ALL), acute myeloid leukemia (AML) (including but not limited to acute promyelocytic leukemia (APL) or M3 AML, acute myelomonocytic leukemia or M4 AML, acute monocytic leukemia or M5 AML), B-cell leukemia, chronic lymphoblastic leukemia (CLL), chronic myelomonocytic leukemia (CMML), chronic myelocytic leukemia (CML), pre-B acute lymphocytic leukemia (Pre-B ALL), diffuse large B-cell lymphoma (DLBCL), extranodal NK/T-cell lymphoma, hairy cell leukemia, HHV8-associated primary effusion lymphoma, plasmablastic lymphoma, primary CNS lymphoma, primary mediastinal large B-cell lymphoma, T-cell/histiocyte-rich B-cell lymphoma), lymphomas (including but not limited to Hodgkin's lymphoma, non-Hodgkin's lymphoma, Waldenstrom's macroglobulinemia), multiple myeloma (MM), myelodysplastic syndromes (MDS), myeloproliferative neoplasms, and polycythemia vera.

Immunotherapy holds great promise to achieve long-lasting anti-tumor effects. Immune checkpoint PD-1 and CTLA-4 blockade therapies have been successful in treating some types of cancers but not others. These immunotherapies target inhibitory molecules on T cells to reactivate dysfunctional T cells within the tumor microenvironment (TME). Other populations of immune cells, including monocytic cells, are present in the TME in even larger numbers than T cells. In fact, monocyte-derived macrophages are the most abundant immune cell population in tumor tissues. While these innate cells possess the capacity to kill tumor cells and to prime or reactivate T cells, they become dysfunctional in TME and turn into MDSCs and tumor-associated macrophages (TAMs) that support tumor development and suppress immune surveillance and attack. MDSCs, including monocytic MDSCs (M-MDSCs) and polymorphonuclear MDSCs (PMN-MDSCs), represent a heterogeneous population of immature myeloid cells that fail to terminally differentiate. TAMs are a mixed macrophage population in TME. They are anti-inflammatory and correlated with a poor prognosis. Despite their phenotypic plasticity, MDSCs and TAMs are defined by their immunosuppressive function. Removing, reprogramming, or blocking trafficking of these immune-suppressive monocytic cells is becoming an attractive anti-cancer therapeutic strategy.

LILRB1 is expressed on MDSCs and TAMs in TME. Therapeutic blocking of LILRB1 has the potential to reactivate or enhance anti-tumor immune responses in patients presenting with disease unresponsive/relapsed to T cell checkpoint inhibitors.

LILRB1 expression on myeloid cells may regulate systems involved in autoimmune and inflammatory diseases. Therapeutics activating or agonizing LILRB1 have the potential to treat autoimmune or inflammatory diseases.

Autoimmune or inflammatory diseases include, but are not limited to, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pemacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma, systemic scleroderma, progressive systemic sclerosis (PSS), systemic sclerosis (SS), Sjogren's syndrome, stiff-man syndrome, systemic lupus erythematosus (SLE), Takayasu arteritis, temporal arteritis/giant cell arteritis, inflammatory bowel disease (IBD), ulcerative colitis, Cohn's disease, intestinal mucosal inflammation, wasting disease associated with colitis, uveitis, vitiligo and Wegener's granulomatosis, Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy, ventilator induced lung injury, viral infections, autoimmune diabetes and the like. Inflammatory disorders include, for example, chronic and acute inflammatory disorders.

IV. Treatment of Disease

A. Formulation and Administration

The present disclosure provides pharmaceutical compositions comprising anti-LILRB antibodies and antigens for generating the same. Such compositions comprise a prophylactically or therapeutically effective amount of an antibody or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Antibodies of the present disclosure, as described herein, can be formulated for parenteral administration, e.g., formulated for injection via the intradermal, intravenous, intraarterial, intramuscular, subcutaneous, intra-tumoral or even intraperitoneal routes. The antibodies could alternatively be administered by a topical route directly to the mucosa, for example by nasal drops, inhalation, or by nebulizer. Pharmaceutically acceptable salts include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

B. Cell Therapies

In another aspect, the present disclosure provides immune cells which express a chimeric antigen receptor (CAR). In some embodiment, The CAR comprises an antigen-binding fragment provided herein. In an embodiment, the CAR protein includes from the N-terminus to the C-terminus: a leader peptide, an anti-LILRB1 heavy chain variable domain, a linker domain, an anti-LILRB1 light chain variable domain, a human IgG1-CH2-CH3 domain, a spacer region, a CD28 transmembrane domain, a 4-1BB intracellular co-stimulatory signaling and a CD3 (intracellular T cell signaling domain.

Also provided are methods for immunotherapy comprising administering an effective amount of the immune cells of the present disclosure. In one embodiment, a medical disease or disorder is treated by transfer of an immune cell population that elicits an immune response. In certain embodiments of the present disclosure, cancer or infection is treated by transfer of an immune cell population that elicits an immune response. Provided herein are methods for treating or delaying progression of cancer in an individual comprising administering to the individual an effective amount of an antigen-specific cell therapy.

The immune cells may be T cells (e.g., regulatory T cells, CD4+ T cells, CD8+ T cells, or gamma-delta T cells), NK cells, invariant NK cells, NKT cells, or macrophages. Also provided herein are methods of producing and engineering the immune cells as well as methods of using and administering the cells for adoptive cell therapy, in which case the cells may be autologous or allogeneic. Thus, the immune cells may be used as immunotherapy, such as to target cancer cells.

The immune cells may be isolated from subjects, particularly human subjects. The immune cells can be obtained from healthy human subjects, healthy volunteers, or healthy donors. The immune cells can be obtained from a subject of interest, such as a subject suspected of having a particular disease or condition, a subject suspected of having a predisposition to a particular disease or condition, or a subject who is undergoing therapy for a particular disease or condition. Immune cells can be collected from any location in which they reside in the subject including, but not limited to, blood, cord blood, spleen, thymus, lymph nodes, and bone marrow. The isolated immune cells may be used directly, or they can be stored for a period of time, such as by freezing.

The immune cells may be enriched/purified from any tissue where they reside including, but not limited to, blood (including blood collected by blood banks or cord blood banks), spleen, bone marrow, tissues removed and/or exposed during surgical procedures, and tissues obtained via biopsy procedures. Tissues/organs from which the immune cells are enriched, isolated, and/or purified may be isolated from both living and non-living subjects, wherein the non-living subjects are organ donors. In particular embodiments, the immune cells are isolated from blood, such as peripheral blood or cord blood. In some aspects, immune cells isolated from cord blood have enhanced immunomodulation capacity, such as measured by CD4- or CD8-positive T cell suppression. In specific aspects, the immune cells are isolated from pooled blood, particularly pooled cord blood, for enhanced immunomodulation capacity. The pooled blood may be from 2 or more sources, such as 3, 4, 5, 6, 7, 8, 9, 10 or more sources (e.g., donor subjects).

The population of immune cells can be obtained from a subject in need of therapy or suffering from a disease associated with reduced immune cell activity. Thus, the cells will be autologous to the subject in need of therapy. Alternatively, the population of immune cells can be obtained from a donor, preferably a histocompatibility matched donor. The immune cell population can be harvested from the peripheral blood, cord blood, bone marrow, spleen, or any other organ/tissue in which immune cells reside in said subject or donor. The immune cells can be isolated from a pool of subjects and/or donors, such as from pooled cord blood.

When the population of immune cells is obtained from a donor distinct from the subject, the donor is preferably allogeneic, provided that the cells obtained are subject-compatible in that they can be introduced into the subject. Allogeneic donor cells may or may not be human-leukocyte-antigen (HLA)-compatible. To be rendered subject-compatible, allogeneic cells can be treated to reduce immunogenicity.

The immune cells can be genetically engineered to express antigen receptors such as engineered TCRs and/or chimeric antigen receptors (CARs). For example, the host cells (e.g., autologous or allogeneic T-cells) are modified to express a T cell receptor (TCR) having antigenic specificity for a cancer antigen. In particular embodiments, NK cells are engineered to express a TCR. The NK cells may be further engineered to express a CAR. Multiple CARs and/or TCRs, such as to different antigens, may be added to a single cell type, such as T cells or NK cells.

Suitable methods of modification are known in the art. See, for instance, Sambrook et al., supra; and Ausubel et al., Current Protocols in Molecular Biology, Greene Publishing Associates and John Wiley & Sons, N Y, 1994. For example, the cells may be transduced to express a T cell receptor (TCR) having antigenic specificity for a cancer antigen using transduction techniques described in Heemskerk et al. (2008) and Johnson et al. (2009).

In some embodiments, the cells comprise one or more nucleic acids introduced via genetic engineering that encode one or more antigen receptors, and genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature (e.g., chimeric).

C. Combination Therapies

It may also be desirable to provide combination treatments using antibodies of the present disclosure in conjunction with additional anti-cancer therapies. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the antibody and the other includes the other agent.

Alternatively, the antibody may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several 10 days (2, 3, 4, 5, 6 or 7) to several weeks (1, 2, 3, 4, 5, 6, 7 or 8) lapse between the respective administrations.

It also is conceivable that more than one administration of either the anti-LILRB1 antibody or the other therapy will be desired. Various combinations may be employed, where the antibody is "A," and the other therapy is "B," as exemplified below:

| | | | | | | | |
|---|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A | |
| A/A/A/B | B/A/A/A | A/B/A/A | A/A/B/A | A/B/B/B | B/A/B/B | B/B/A/B | |

Other combinations are contemplated. To kill cells, inhibit cell growth, inhibit metastasis, inhibit angiogenesis or otherwise reverse or reduce the malignant phenotype of tumor cells, using the methods and compositions of the present invention, one may contact a target cell or site with an antibody and at least one other therapy. These therapies would be provided in a combined amount effective to kill or inhibit proliferation of cancer cells. This process may involve contacting the cells/site/subject with the agents/therapies at the same time.

Particular agents contemplated for combination therapy with antibodies of the present disclosure include chemotherapy and hematopoietic stem cell transplantation. Chemotherapy may include cytarabine (ara-C) and an anthracycline (most often daunorubicin), high-dose cytarabine alone, all-trans-retinoic acid (ATRA) in addition to induction chemotherapy, usually an anthracycline, histamine dihydrochloride (Ceplene) and interleukin 2 (Proleukin) after the completion of consolidation therapy, gemtuzumab ozogamicin (Mylotarg) for patients aged more than 60 years with relapsed AML who are not candidates for high-dose chemotherapy, clofarabine, as well as targeted therapies, such as kinase inhibitors, farnesyl transferase inhibitors, decitabine, and inhibitors of MDR1 (multidrug-resistance protein), or arsenic trioxide or relapsed acute promyelocytic leukemia (APL).

In certain embodiments, the agents for combination therapy are one or more drugs selected from the group consisting of a topoisomerase inhibitor, an anthracycline topoisomerase inhibitor, an anthracycline, a daunorubicin, a nucleoside metabolic inhibitor, a cytarabine, a hypomethylating agent, a low dose cytarabine (LDAC), a combination of daunorubicin and cytarabine, a daunorubicin and cytarabine liposome for injection, Vyxeos®, an azacytidine, Vidaza®, a decitabine, an all-trans-retinoic acid (ATRA), an arsenic, an arsenic trioxide, a histamine dihydrochloride, Ceplene®, an interleukin-2, an aldesleukin, Proleukin®, a gemtuzumab ozogamicin, Mylotarg®, an FLT-3 inhibitor, a midostaurin, Rydapt®, a clofarabine, a farnesyl transferase inhibitor, a decitabine, an IDH1 inhibitor, an ivosidenib, Tibsovo®, an IDH2 inhibitor, an enasidenib, Idhifa®, a smoothened (SMO) inhibitor, a glasdegib, an arginase inhibitor, an IDO inhibitor, an epacadostat, a BCL-2 inhibitor, a venetoclax, Venclexta®, a platinum complex derivative, oxaliplatin, a kinase inhibitor, a tyrosine kinase inhibitor, a PI3 kinase inhibitor, a BTK inhibitor, an ibrutinib, IMBRUVICA®, an acalabrutinib, CALQUENCE®, a zanubrutinib, a PD-1 antibody, a PD-L1 antibody, a CTLA-4 antibody, a LAG3 antibody, an ICOS antibody, a TIGIT antibody, a TIM3 antibody, a CD40 antibody, a 4-1BB antibody, a CD47 antibody, a SIRP1α antibody or fusions protein, a CD70 antibody, and CLL1 antibody, a CD123 antibody, an antagonist of E-selectin, an antibody binding to a tumor antigen, an antibody binding to a T-cell surface marker, an antibody binding to a myeloid cell or NK cell surface marker, an alkylating agent, a nitrosourea agent, an antimetabolite, an antitumor antibiotic, an alkaloid derived from a plant, a hormone therapy medicine, a hormone antagonist, an aromatase inhibitor, and a P-glycoprotein inhibitor.

V. Antibody Conjugates

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody-drug conjugates have emerged as a breakthrough approach to the development of cancer therapeutics. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

Antibody conjugates are also preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugate contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

VI. Immunodetection Methods

In still further embodiments, the present disclosure concerns immunodetection methods for binding, purifying, removing, quantifying and otherwise generally detecting LILRB-related cancers. While such methods can be applied in a traditional sense, another use will be in quality control and monitoring of vaccine and other virus stocks, where antibodies according to the present disclosure can be used to assess the amount or integrity (i.e., long term stability) of H1 antigens in viruses. Alternatively, the methods may be used to screen various antibodies for appropriate/desired reactivity profiles.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of LILRBs also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing LILRB-related cancers and contacting the sample with a first antibody in accordance with the present disclosure, as the case may be, under conditions effective to allow the formation of immunocomplexes.

These methods include methods for detecting or purifying LILRBs or LILRB-related cancer cells from a sample. The antibody will preferably be linked to a solid support, such as in the form of a column matrix, and the sample suspected of containing the LILRB-related cancer cells will be applied to the immobilized antibody. The unwanted components will be washed from the column, leaving the LILRB-expressing cells immunocomplexed to the immobilized antibody, which is then collected by removing the organism or antigen from the column.

The immunobinding methods also include methods for detecting and quantifying the amount of LILRB-related cancer cells or related components in a sample and the detection and quantification of any immune complexes formed during the binding process. Here, one would obtain a sample suspected of containing LILRB-related cancer cells and contact the sample with an antibody that binds LILRBs or components thereof, followed by detecting and quantifying the amounts of immune complexes formed under the specific conditions. In terms of antigen detection, the biological sample analyzed may be any sample that is suspected of containing LILRB-related cancers, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to LILRBs. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the LILRB-related cancer cells is added to the wells. After binding and washing to remove non-specifically bound immune complexes, the bound antigen may be detected. Detection may be achieved by the addition of another anti-LILRB antibody that is linked to a detectable label. This type of ELISA is a simple "sandwich ELISA." Detection may also be achieved by the addition of a second anti-LILRB1 antibody, followed by the addition of a third antibody that has binding affinity for the second antibody, with the third antibody being linked to a detectable label.

In another exemplary ELISA, the samples suspected of containing the LILRB1-related cancer cells are immobilized onto the well surface and then contacted with the anti-LILRB1 antibodies of the disclosure. After binding and washing to remove non-specifically bound immune complexes, the bound anti-LILRB1 antibodies are detected. Where the initial anti-LILRB1 antibodies are linked to a detectable label, the immune complexes may be detected directly. Again, the immune complexes may be detected using a second antibody that has binding affinity for the first anti-LILRB1 antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C. or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

D. Immunodetection Kits

In still further embodiments, the present disclosure concerns immunodetection kits for use with the immunodetection methods described above. As the antibodies may be used to detect LILRB-related cancer cells, the antibodies may be included in the kit. The immunodetection kits will thus comprise, in suitable container means, a first antibody that binds to an LILRB, and optionally an immunodetection reagent.

In certain embodiments, the antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of LILRBs, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

E. Flow Cytometry and FACS

The antibodies of the present disclosure may also be used in flow cytometry or FACS. Flow cytometry is a laser- or impedance-based technology employed in many detection assays, including cell counting, cell sorting, biomarker detection and protein engineering. The technology suspends cells in a stream of fluid and passing them through an electronic detection apparatus, which allows simultaneous multiparametric analysis of the physical and chemical characteristics of up to thousands of particles per second. Flow cytometry is routinely used in the diagnosis disorders, especially blood cancers, but has many other applications in basic research, clinical practice and clinical trials.

Fluorescence-activated cell sorting (FACS) is a specialized type of cytometry. It provides a method for sorting a heterogenous mixture of biological cells into two or more containers, one cell at a time, based on the specific light scattering and fluorescent characteristics of each cell. In general, the technology involves a cell suspension entrained in the center of a narrow, rapidly flowing stream of liquid. The flow is arranged so that there is a large separation between cells relative to their diameter. A vibrating mechanism causes the stream of cells to break into individual droplets. Just before the stream breaks into droplets, the flow passes through a fluorescence measuring station where the fluorescence of each cell is measured. An electrical charging ring is placed just at the point where the stream breaks into droplets. A charge is placed on the ring based immediately prior to fluorescence intensity being measured, and the opposite charge is trapped on the droplet as it breaks form the stream. The charged droplets then fall through an electrostatic deflection system that diverts droplets into containers based upon their charge.

In certain embodiments, to be used in flow cytometry or FACS, the antibodies of the present disclosure are labeled with fluorophores and then allowed to bind to the cells of interest, which are analyzed in a flow cytometer or sorted by a FACS machine.

VII. Kits

In various aspects of the embodiments, a kit is envisioned containing therapeutic agents and/or other therapeutic and delivery agents. In some embodiments, a kit is provided for preparing and/or administering a therapy of the embodiments. The kit may comprise one or more sealed vials containing any of the pharmaceutical compositions of the present embodiments. The kit may include, for example, at least one LILRB1 antibody or LILRB1-specific CAR construct, as well as reagents to prepare, formulate, and/or administer the components of the embodiments or perform one or more steps of the inventive methods. In some embodiments, the kit may also comprise a suitable container, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods set forth herein, and will follow substantially the same procedures as described herein or are known to those of ordinary skill in the art. The instruction information may be in a computer readable media containing machine-readable instructions that, when executed using a computer, cause the display of a real or virtual procedure of delivering a pharmaceutically effective amount of a therapeutic agent.

VIII. Definitions

It is to be understood that both the foregoing general description and the following detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

As used herein, the singular forms "a", "an" and "the" include plural references unless the context clearly dictates otherwise.

The term "about" as used herein when referring to a measurable value such as an amount, a temporal duration, and the like, is meant to encompass variations of up to ±10% from the specified value. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the disclosed subject matter. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" is a species of an antigen binding protein. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies as described further below. The antigen binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the term also encompasses peptibodies.

Naturally occurring antibody structural units typically comprise a tetramer. Each such tetramer typically is composed of two identical pairs of polypeptide chains, each pair having one full-length "light" (in certain embodiments, about 25 kDa) and one full-length "heavy" chain (in certain embodiments, about 50-70 kDa). The amino-terminal portion of each chain typically includes a variable region of about 100 to 110 or more amino acids that typically is responsible for antigen recognition. The carboxy-terminal portion of each chain typically defines a constant region that can be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids. See, e.g., Fundamental Immunology, Ch. 7 (Paul, W., ed., 2nd ed. Raven Press, N.Y. (1989)) (incorporated by reference in its entirety for all purposes). The variable regions of each light/heavy chain pair typically form the antigen binding site.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain embodiments, variable regions of different antibodies differ extensively in amino acid sequence even among antibodies of the same species. The variable region of an antibody typically determines specificity of a particular antibody for its target.

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), Chothia & Lesk, J. Mol. Biol., 196:901-917 (1987) or Chothia et al., Nature, 342: 878-883 (1989).

In certain embodiments, an antibody heavy chain binds to an antigen in the absence of an antibody light chain. In certain embodiments, an antibody light chain binds to an antigen in the absence of an antibody heavy chain. In certain embodiments, an antibody binding region binds to an antigen in the absence of an antibody light chain. In certain embodiments, an antibody binding region binds to an antigen in the absence of an antibody heavy chain. In certain embodiments, an individual variable region specifically binds to an antigen in the absence of other variable regions.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the AbM definition and the contact definition.

The Kabat definition is a standard for numbering the residues in an antibody and is typically used to identify CDR regions. See, e.g., Johnson & Wu, Nucleic Acids Res., 28: 214-8 (2000). The Chothia definition is similar to the Kabat definition, but the Chothia definition takes into account positions of certain structural loop regions. See, e.g., Chothia et al., J. Mol. Biol., 196: 901-17 (1986); Chothia et al., Nature, 342: 877-83 (1989). The AbM definition uses an integrated suite of computer programs produced by Oxford Molecular Group that model antibody structure. See, e.g., Martin et al., Proc Natl Acad Sci (USA), 86:9268-9272 (1989); "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl., 3:194-198 (1999). The contact definition is based on an analysis of the available complex crystal structures. See, e.g., MacCallum et al., J. Mol. Biol., 5:732-45 (1996).

By convention, the CDR regions in the heavy chain are typically referred to as H1, H2, and H3 and are numbered sequentially in the direction from the amino terminus to the carboxy terminus. The CDR regions in the light chain are typically referred to as L1, L2, and L3 and are numbered sequentially in the direction from the amino terminus to the carboxy terminus.

The term "light chain" includes a full-length light chain and fragments thereof having sufficient variable region sequence to confer binding specificity. A full-length light chain includes a variable region domain, VL, and a constant region domain, CL. The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain, VH, and three constant region domains, CH1, CH2, and CH3. The VH domain is at the amino-terminus of the polypeptide, and the CH domains are at the carboxyl-terminus, with the CH3 being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE.

A "back mutation" is a mutation introduced in a nucleotide sequence which encodes a humanized antibody, the mutation results in an amino acid corresponding to an amino acid in the parent antibody (e.g., donor antibody, for example, a rabbit antibody). Certain framework residues from the parent antibody may be retained during the humanization of the antibodies of the invention in order to substantially retain the binding properties of the parent antibody, while at the same time minimizing the potential immunogenicity of the resultant antibody. In one embodiment of the invention, the parent antibody is of mouse origin. For example, the back mutation changes a human framework residue to a parent murine residue. Examples of framework residues that may be back mutated include, but are not limited to, canonical residues, interface packing residues, unusual parent residues which are close to the binding site, residues in the "Vernier Zone" (which forms a platform on which the CDRs rest) (Foote & Winter, 1992, *J. Mol. Biol.* 224, 487-499), and those close to CDR H3.

A bispecific or bifunctional antibody typically is an artificial hybrid antibody having two different heavy/light chain pairs and two different binding sites. Bispecific antibodies can be produced by a variety of methods including, but not limited to, fusion of hybridomas or linking of Fab' fragments. See, e.g., Songsivilai et al., Clin. Exp. Immunol., 79: 315-321 (1990); Kostelny et al., J. Immunol., 148:1547-1553 (1992).

The term "antigen" refers to a substance capable of inducing adaptive immune responses. Specifically, an antigen is a substance which serves as a target for the receptors of an adaptive immune response. Typically, an antigen is a molecule that binds to antigen-specific receptors but cannot induce an immune response in the body by itself. Antigens are usually proteins and polysaccharides, less frequently also lipids. Suitable antigens include without limitation parts of bacteria (coats, capsules, cell walls, flagella, fimbrai, and toxins), viruses, and other microorganisms. Antigens also include tumor antigens, e.g., antigens generated by mutations in tumors. As used herein, antigens also include immunogens and haptens.

An "antigen binding protein" ("ABP") as used herein means any protein that binds a specified target antigen. In the instant application, the specified target antigen is the LILRB protein or fragment thereof. "Antigen binding protein" includes but is not limited to antibodies and antigen-binding fragment thereof. Peptibodies are another example of antigen binding proteins.

The term "antigen-binding fragment" as used herein refers to a portion of a protein which is capable of binding specifically to an antigen. In certain embodiment, the antigen-binding fragment is derived from an antibody comprising one or more CDRs, or any other antibody fragment that binds to an antigen but does not comprise an intact native antibody structure. In certain embodiments, the antigen-binding fragment is not derived from an antibody but rather is derived from a receptor. Examples of antigen-binding fragment include, without limitation, a diabody, a Fab, a Fab', a $F(ab')_2$, an Fv fragment, a disulfide stabilized Fv fragment (dsFv), a $(dsFv)_2$, a bispecific dsFv (dsFv-dsFv'), a disulfide stabilized diabody (ds diabody), a single-chain antibody molecule (scFv), an scFv dimer (bivalent diabody), a multispecific antibody, a single domain antibody (sdAb), a camelid antibody or a nanobody, a domain antibody, and a bivalent domain antibody. In certain embodiments, an antigen-binding fragment is capable of binding to the same antigen to which the parent antibody binds. In certain embodiments, an antigen-binding fragment may comprise one or more CDRs from a particular human antibody grafted to a framework region from one or more different human antibodies. In certain embodiments, the antigen-binding fragment is derived from a receptor and contains one or more mutations. In certain embodiments, the antigen-binding fragment does not bind to the natural ligand of the receptor from which the antigen-binding fragment is derived.

A "Fab fragment" comprises one light chain and the CH1 and variable regions of one heavy chain. The heavy chain of a Fab molecule cannot form a disulfide bond with another heavy chain molecule.

A "Fab' fragment" comprises one light chain and a portion of one heavy chain that contains the VH domain and the CH1 domain and also the region between the CH1 and CH2 domains, such that an interchain disulfide bond can be formed between the two heavy chains of two Fab' fragments to form an $F(ab')_2$ molecule.

A "$F(ab')_2$ fragment" contains two light chains and two heavy chains containing a portion of the constant region between the CH1 and CH2 domains, such that an interchain disulfide bond is formed between the two heavy chains. A $F(ab')_2$ fragment thus is composed of two Fab' fragments that are held together by a disulfide bond between the two heavy chains.

An "Fc" region comprises two heavy chain fragments comprising the CH1 and CH2 domains of an antibody. The two heavy chain fragments are held together by two or more disulfide bonds and by hydrophobic interactions of the CH3 domains.

The "Fv region" comprises the variable regions from both the heavy and light chains but lacks the constant regions.

"Single-chain antibodies" are Fv molecules in which the heavy and light chain variable regions have been connected by a flexible linker to form a single polypeptide chain, which forms an antigen binding region. Single chain antibodies are discussed in detail in International Patent Application Publication No. WO 88/01649 and U.S. Pat. Nos. 4,946,778 and 5,260,203, the disclosures of which are incorporated by reference.

A "domain antibody" is an immunologically functional immunoglobulin fragment containing only the variable region of a heavy chain or the variable region of a light chain. In some instances, two or more VH regions are covalently joined with a peptide linker to create a bivalent domain antibody. The two VH regions of a bivalent domain antibody can target the same or different antigens.

A "bivalent antigen binding protein" or "bivalent antibody" comprises two antigen binding sites. In some instances, the two binding sites have the same antigen specificities. Bivalent antigen binding proteins and bivalent antibodies can be bispecific, see, infra. A bivalent antibody other than a "multispecific" or "multifunctional" antibody, in certain embodiments, typically is understood to have each of its binding sites identical.

A "multispecific antigen binding protein" or "multispecific antibody" is one that targets more than one antigen or epitope.

A "bispecific," "dual-specific" or "bifunctional" antigen binding protein or antibody is a hybrid antigen binding protein or antibody, respectively, having two different antigen binding sites. Bispecific antigen binding proteins and antibodies are a species of multispecific antigen binding protein antibody and can be produced by a variety of methods including, but not limited to, fusion of hybridomas or linking of Fab' fragments. See, e.g., Songsivilai and Lachmann, 1990, Clin. Exp. Immunol. 79:315-321; Kostelny et al., 1992, J. Immunol. 148:1547-1553. The two binding sites of a bispecific antigen binding protein or antibody will bind to two different epitopes, which can reside on the same or different protein targets.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity that reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity are described in the following.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope. For example, the LILRB1 specific antibodies of the present invention are specific to LILRB1. In some embodiments, the antibody that binds to LILRB1 has a dissociation constant (Kd) of ≤100 nM, ≤10 nM, ≤1 nM, ≤0.1 nM, ≤0.01 nM, or ≤0.001 nM (e.g., $10^{-8}$M or less, e.g., from $10^{-8}$M to $10^{-13}$M, e.g., from $10^{-9}$M to $10^{-13}$ M). The dissociation constant Kd used herein refers to the ratio of the dissociation rate to the association rate ($k_{off}/k_{on}$), which may be determined by using any conventional method known in the art, including but are not limited to surface plasmon resonance method, microscale thermophoresis method, HPLC-MS method and flow cytometry (such as FACS) method. In certain embodiments, the Kd value can be appropriately determined by using flow cytometry.

The term "compete" when used in the context of antigen binding proteins (e.g., antibody or antigen-binding fragment thereof) that compete for the same epitope means competition between antigen binding proteins as determined by an assay in which the antigen binding protein (e.g., antibody or antigen-binding fragment thereof) being tested prevents or inhibits (e.g., reduces) specific binding of a reference antigen binding protein (e.g., a ligand, or a reference antibody) to a common antigen (e.g., LILRB or a fragment thereof). Numerous types of competitive binding assays can be used to determine if one antigen binding protein competes with another, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabelled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Additional details regarding methods for determining competitive binding are provided in the examples herein. Usually, when a competing antigen binding protein is present in excess, it will inhibit (e.g., reduce) specific binding of a reference antigen binding protein to a common antigen by at least 40-45%, 45-50%, 50-55%, 55-60%, 60-65%, 65-70%, 70-75% or 75% or more. In some instances, binding is inhibited by at least 80-85%, 85-90%, 90-95%, 95-97%, or 97% or more.

The term "epitope" as used herein refers to the specific group of atoms or amino acids on an antigen to which an antibody binds. The epitope can be either linear epitope or a conformational epitope. A linear epitope is formed by a continuous sequence of amino acids from the antigen and interacts with an antibody based on their primary structure. A conformational epitope, on the other hand, is composed of discontinuous sections of the antigen's amino acid sequence and interacts with the antibody based on the 3D structure of the antigen. In general, an epitope is approximately five or six amino acid in length. Two antibodies may bind the same epitope within an antigen if they exhibit competitive binding for the antigen.

A "cell", as used herein, can be prokaryotic or eukaryotic. A prokaryotic cell includes, for example, bacteria. A eukaryotic cell includes, for example, a fungus, a plant cell, and an animal cell. The types of an animal cell (e.g., a mammalian cell or a human cell) includes, for example, a cell from circulatory/immune system or organ, e.g., a B cell, a T cell (cytotoxic T cell, natural killer T cell, regulatory T cell, T helper cell), a natural killer cell, a granulocyte (e.g., basophil granulocyte, an eosinophil granulocyte, a neutrophil granulocyte and a hypersegmented neutrophil), a monocyte or macrophage, a red blood cell (e.g., reticulocyte), a mast cell, a thrombocyte or megakaryocyte, and a dendritic cell; a cell from an endocrine system or organ, e.g., a thyroid cell (e.g., thyroid epithelial cell, parafollicular cell), a parathyroid cell (e.g., parathyroid chief cell, oxyphil cell), an adrenal cell (e.g., chromaffin cell), and a pineal cell (e.g., pinealocyte); a cell from a nervous system or organ, e.g., a glioblast (e.g., astrocyte and oligodendrocyte), a microglia, a magnocellular neurosecretory cell, a stellate cell, a boettcher cell, and a pituitary cell (e.g., gonadotrope, corticotrope, thyrotrope, somatotrope, and lactotroph); a cell from a respiratory system or organ, e.g., a pneumocyte (a type I pneumocyte and a type II pneumocyte), a clara cell, a goblet cell, and an alveolar macrophage; a cell from circular system or organ (e.g., myocardiocyte and pericyte); a cell from digestive system or organ, e.g., a gastric chief cell, a parietal cell, a goblet cell, a paneth cell, a G cell, a D cell, an ECL cell, an I cell, a K cell, an S cell, an enteroendocrine cell, an enterochromaffin cell, an APUD cell, and a liver cell (e.g., a hepatocyte and Kupffer cell); a cell from integumentary system or organ, e.g., a bone cell (e.g., an osteoblast, an osteocyte, and an osteoclast), a teeth cell (e.g., a cementoblast, and an ameloblast), a cartilage cell (e.g., a chondroblast and a chondrocyte), a skin/hair cell (e.g., a trichocyte, a keratinocyte, and a melanocyte (Nevus cell), a muscle cell (e.g., myocyte), an adipocyte, a fibroblast, and a tendon cell; a cell from urinary system or organ (e.g., a podocyte, a juxtaglomerular cell, an intraglomerular mesangial cell, an extraglomerular mesangial cell, a kidney proximal tubule brush border cell, and a macula densa cell); and a cell from reproductive system or organ (e.g., a spermatozoon, a Sertoli cell, a leydig cell, an ovum, an oocyte). A cell can be normal, healthy cell; or a diseased or unhealthy cell (e.g., a cancer cell). A cell further includes a mammalian zygote or a stem cell which include an embryonic stem cell, a fetal stem cell, an induced pluripotent stem cell, and an adult stem cell. A stem cell is a cell that is capable of undergoing cycles of cell division while maintaining an undifferentiated state and differentiating into specialized cell types. A stem cell can be an omnipotent stem cell, a pluripotent stem cell, a multipotent stem cell, an oligopotent stem cell and a unipotent stem cell, any of which may be induced from a somatic cell. A stem cell may also include a cancer stem cell. A mammalian cell can be a rodent cell, e.g., a mouse, rat, hamster cell. A mammalian cell can be a lagomorpha cell, e.g., a rabbit cell. A mammalian cell can also be a primate cell, e.g., a human cell.

The term "chimeric antigen receptor" or "CAR" as used herein refers to an artificially constructed hybrid protein or polypeptide containing an antigen binding domain of an antibody (e.g., a single chain variable fragment (scFv)) linked to a domain or signaling, e.g., T-cell signaling or T-cell activation domains, that activates an immune cell, e.g., a T cell or a NK cell (see, e.g., Kershaw et al., supra, Eshhar et al., Proc. Natl. Acad. Sci. USA, 90(2): 720-724 (1993), and Sadelain et al., Curr. Opin. Immunol. 21(2): 215-223 (2009)). CARs are capable of redirecting the immune cell specificity and reactivity toward a selected target in a non-MHC-restricted manner, taking advantage of the antigen-binding properties of monoclonal antibodies. The non-MHC-restricted antigen recognition confers immune cells expressing CARs on the ability to recognize an antigen independent of antigen processing, thus bypassing a major mechanism of tumor escape. In addition, when expressed in T-cells, CARs advantageously do not dimerize with endogenous T-cell receptor (TCR) alpha and beta chains.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073.

In calculating percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Examples of parameters that can be employed in determining percent identity for polypeptides or nucleotide sequences using the GAP program can be found in Needleman et al., 1970, J. Mol. Biol. 48:443-453.

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 or other number of contiguous amino acids of the target polypeptide.

The term "link" as used herein refers to the association via intramolecular interaction, e.g., covalent bonds, metallic bonds, and/or ionic bonding, or inter-molecular interaction, e.g., hydrogen bond or noncovalent bonds.

Leukocyte immunoglobulin-like receptor subfamily B member 2 (LILRB1) is a protein that in humans is encoded by the LILRB1 gene. This gene is a member of the leukocyte immunoglobulin-like receptor (LIR) family, which is found in a gene cluster at chromosomal region 19q13.4. The encoded protein belongs to the subfamily B class of LIR receptors which contain two or four extracellular immunoglobulin domains, a transmembrane domain, and two to four cytoplasmic immunoreceptor tyrosine-based inhibitory motifs (ITIMs). The receptor is expressed on immune cells where it binds to MHC class I molecules on antigen-presenting cells and transduces a negative signal that inhibits stimulation of an immune response. It is thought to control inflammatory responses and cytotoxicity to help focus the immune response and limit autoreactivity.

The term "operably linked" refers to an arrangement of elements wherein the components so described are configured so as to perform their usual function. Thus, a given signal peptide that is operably linked to a polypeptide directs the secretion of the polypeptide from a cell. In the case of a promoter, a promoter that is operably linked to a coding sequence will direct the expression of the coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The terms “polypeptide” or “protein” means a macromolecule having the amino acid sequence of a native protein, that is, a protein produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The term also includes amino acid polymers in which one or more amino acids are chemical analogs of a corresponding naturally-occurring amino acid and polymers. The terms “polypeptide” and “protein” specifically encompass LILRB antigen binding proteins, antibodies, or sequences that have deletions from, additions to, and/or substitutions of one or more amino acid of antigen-binding protein. The term “polypeptide fragment” refers to a polypeptide that has an amino-terminal deletion, a carboxyl-terminal deletion, and/or an internal deletion as compared with the full-length native protein. Such fragments can also contain modified amino acids as compared with the native protein. In certain embodiments, fragments are about five to 500 amino acids long. For example, fragments can be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains. In the case of a LILRB-binding antibody, useful fragments include but are not limited to a CDR region, a variable domain of a heavy and/or light chain, a portion of an antibody chain or just its variable region including two CDRs, and the like.

The pharmaceutically acceptable carriers useful in this invention are conventional. Remington’s Pharmaceutical Sciences, by E. W. Martin, Mack Publishing Co., Easton, PA, 15th Edition (1975), describes compositions and formulations suitable for pharmaceutical delivery of the fusion proteins herein disclosed. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As used herein, the term “subject” refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term “subject” is used herein interchangeably with “individual” or “patient.” A subject can be afflicted with or is susceptible to a disease or disorder but may or may not display symptoms of the disease or disorder.

The term “therapeutically effective amount” or “effective dosage” as used herein refers to the dosage or concentration of a drug effective to treat a disease or condition. For example, with regard to the use of the monoclonal antibodies or antigen-binding fragments thereof disclosed herein to treat cancer, a therapeutically effective amount is the dosage or concentration of the monoclonal antibody or antigen-binding fragment thereof capable of reducing the tumor volume, eradicating all or part of a tumor, inhibiting or slowing tumor growth or cancer cell infiltration into other organs, inhibiting growth or proliferation of cells mediating a cancerous condition, inhibiting or slowing tumor cell metastasis, ameliorating any symptom or marker associated with a tumor or cancerous condition, preventing or delaying the development of a tumor or cancerous condition, or some combination thereof.

“Treating” or “treatment” of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

As used herein, a “vector” refers to a nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

As used herein, “essentially free,” in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

The use of the term “or” in the claims is used to mean “and/or” unless explicitly indicated to refer to alternatives only or the alternatives are mutually exclusive, although the disclosure supports a definition that refers to only alternatives and “and/or.” As used herein “another” may mean at least a second or more.

IX. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Mice. Female NOD-SCID IL2Rγ-null (NSG) mice, aged 6-8 weeks (weight about 20 g) were purchased from the animal core facility of UT Southwestern. Mice were kept in a specific pathogen free (SPF) room with a 12-hour light/dark cycle, controlled room temperature, and ab libitum food and water. Mice were randomly allocated to each treatment group for experiments.

Cell lines and primary samples. Expi293F (Cat #A14528) was obtained from Life Technologies (Carlsbad). Hematological cancer cell lines 697, MHH-CALL-2, and OPM2 were purchased from DSMZ (Braunschweig, Germany). KMS27, KMS26, KMS12PE, and KMS20 were purchased from Health Sciences Research Resources Bank (HSRRB), Japan Health Sciences Foundation. LILRB1 reporter cells were described previously[18]. All other cell lines were purchased from ATCC except as noted. Hematological cancer cell lines were maintained in RPMI 1640 supplemented with 10% heat-inactivated FBS (Sigma Aldrich) (R10). Solid tumor cell lines were maintained in DMEM with 10% heat-inactivated FBS except for H460 and H1299 maintenance in R10. NKL cells were cultured as previously described[19]. All cell culture media were supplemented with +1% penicillin and streptomycin.

The peripheral blood mononuclear cells (PBMC) were separated from the buffy coats of healthy donors (Interstate Blood Bank) by gradient centrifugation using Ficoll media (GE Lifesciences). To isolate LILRB1 positive NK cells, PBMC were incubated with anti-human CD56 microbeads (Miltenyi Biotech) and separated using an AutoMACS Pro Separation System. Isolated $CD56^{+}$ cells were then stained with anti-CD3-PE (clone: HIT3a, BioLegend)), anti-CD56-FITC (clone: TULY56, eBioscience), and anti-LILRB1-APC (clone: HP-F1, eBioscience) or Mouse IgG1 kappa Isotype Control-APC (eBioscience). $LILRB1^{+}$ NK cells ($CD56^{+}CD3^{-}$) were sorted using a FACSAria I system. Sorted LILRB1+NK cells were maintained in the same medium as NKL cells for 2-3 days. Cancer patient samples were obtained from UT Southwestern Medical Center (UTSW) and Hematologic Malignancies Tissue Bank of UTSW. Patient NK cells were isolated using the same protocol except that AutoMACS-separated NK cells were cultured, activated, and used for cytotoxicity assays without FACS.

Generation of anti-LILRB1 monoclonal antibodies (mAbs). Two New Zealand white rabbits were immunized subcutaneously with 0.5 mg recombinant human LILRB1 protein (untagged ECD, Sino Biological). Four boosters were given after the initial immunization in a three-week interval. Serum anti-LILRB1 titers were evaluated by indirect enzyme-linked immunosorbent assay (ELISA). Single LILRB1 positive memory B cells enriched using antigen pull down were cultured in 96-well plates for 14 days and the culture supernatants were analyzed by ELISA for antibody binding to LILRB1. Antibody variable region genes were cloned from those positive B cells and sequences were determined.

Expression and purification of mAbs. Full-length IgG was produced in human embryonic kidney Expi293F cells using an ExpiFectamine™ 293 Transfection Kit (Catalog #: A14528, Gibco) by co-transfection HEK293 cells with both heavy and light chain expression constructs. After 7 days of fed-batch culture, the culture supernatants were harvested and antibodies were purified by affinity chromatography using protein A resin (Catalog #: 10-2001-XM, Repligen).

Epitope binning and affinity measurement with Bio-layer Interferometry. Classical sandwich epitope binning experiments were performed on an 8-channel Octet RED96 System. First, a baseline was established in kinetics buffer (Cat #18-1105, ForteBio) for 3 min. Then antibodies (30 μg/mL) were captured by protein A biosensors (Cat #18-5010, ForteBio) for 4 min. The remaining Fc-binding sites on the biosensors were then blocked with an irrelevant rabbit antibody (200 μg/ml) for 4 min, followed by soaking the biosensors in kinetics buffer for 10 sec. The biosensors were exposed to recombinant LILRB1 (25 μg/mL) for 4 min, and then incubated with the secondary antibodies (40 μg/mL). The surfaces were regenerated for 45 sec in 100 mM glycine (pH 2.6). The antibody pairs were assessed for competitive binding. Additional binding signal observed by the secondary antibody indicates an unoccupied epitope (non-competitor). A lack of binding by the secondary antibody (blocked by the first antibody binding) indicates that two antibodies compete for a similar epitope (competitor).

For antibody affinity measurement, antibodies (analyte, 30 μg/mL) were loaded onto the protein G biosensors (Cat #18-5082, ForteBio) for 4 min. Following a short baseline in kinetics buffer for 20 s, the loaded biosensors were exposed to solutions of recombinant LILRB1 in a range of concentrations (0-500 nM). After background was subtracted, data was fit to a 1:1 binding model to extract an association rate ($k_{on}$) and dissociation rate ($k_{off}$). The KD was calculated using the ratio $k_{off}/k_{on}$. Kinetic constant ranges for Octet RED96 systems is between 1 mM to 10 pM. Thus, affinity higher than 10 pM will be shown as KD<10 pM. All experiments were performed with shaking at 1,000 rpm. All raw data was processed using ForteBio Octet Data Analysis Software 9.0.

Generation of LILRB1-Fc, mutants-Fc and LILRBs-Fc fusion proteins. Ig-like C2-type domains (D), which including D1, D2, D3, D4 domains of LILRB1, were PCR cloned for expression. The motif between D4 and transmembrane domain is defined as the stalk region or attached region. Different mutants of LILRB1 were generated using QuikChange® Lightning Site-Directed Mutagenesis Kits (Agilent, Cat #210519) with LILRB1 wild type DNA construct as the template. LILRBs ECD, LILRB1 mutants and different domains were cloned with a Fc fusion in an expression vector and the Fc portion of human IgG1. Expression and purification of the LILRB Fc fusion proteins are conducted using the same procedures as those for the antibodies described above.

ELISA. LILRB1 recombinant proteins (50 ng/well, 100 μL per well) were coated on Corning 96-well ELISA plates at 37° C. for 4 hrs. Plates were blocked for 2 hrs at 37° C. with 5% non-fat milk. After washing with PBST, 100 μL of serial diluted anti-LILRB1 antibodies were added and incubated for 60 min at 37° C. Subsequently, the plates were washed with PBST for 5 times and incubated for 30 min with anti-rabbit or anti-human F(ab')2 HRP-conjugated antibody (Jackson ImmunoResearch Inc., Cat #111-036-003 and #109-036-003). Plates were washed again with PBST for another 5 times, then the immunoreactions were developed with TMB substrates (Sigma, Cat #T0440) and stopped by the addition of 2 M $H_2SO_4$ before the plate was read at 450 nm.

Humanization of rabbit mAb. Anti-LILRB1 rabbit antibodies were humanized by CDR-grafting into human germline matched framework. Briefly, CDRs in the heavy and light chains of the rabbit antibody were defined by a combination of three online programs: Kabat, IMGT, and Paratome. The parental rabbit mAb and the most homologous human germline sequences were aligned and residues that are known not to be structurally critical or subjected to change during the in vivo maturation process were identified in the mutational lineage guided analysis and humanized. DNA sequences encoding humanized VK and VH were synthesized (GENEWIZ) and a human IgG signal peptide and a Kozak sequence were engineered at the 5' ends of the VK and VH sequences. The humanized VK and VH fragments were then cloned in fusion with complete human constant regions.

Lentivirus/retrovirus infection. HLA-G-1 cDNA with a signal peptide mutant[23] was cloned into pLentiLox3.7-PuroR plasmid. Lentivirus plasmids pLentiLox3.7-luciferase-PuroR, pLentiLox3.7-HLA-G-PuroR, and pLVX-MICA-ZsGreen plasmids were utilized to overexpress target proteins in cell lines as described previously[24] The infected cells were enriched by selection with 1 μg/mL puromycin for luciferase or HLA-G overexpression. MICA-positive cells were enriched by FACS for three times (clone: 6D4, BioLegend). LILRB2-5 reporter cells and LILRA1-6 reporter cells were made by retrovirus infection, according to previous reports[18 25].

Flow cytometry-based in vitro killing assay. Carboxyfluorescein succinimidyl ester (CFSE, Thermo Fisher Scientific) labeling of target cells combined with propidium iodide (PI) staining of dead cells is a reliable method to measure in vitro cell killing by flow cytometry[26-28]. Briefly, NK cells were co-cultured with CFSE-labeled leukemia cells in U-bottom 96-well plates for 4 hours. Then, each sample was mixed with PI and analyzed by FACS Calibur. Cell lysis was calculated by the percentage of PI-positive leukemia cells among total leukemia cells. Spontaneous cell death, with no NK cells, was less than 5% and subtracted from total killing in the presence of NK cells.

Cytokine measurement. A total of $5\times10^4$ NKL cells were co-cultured with $5\times10^4$ cancer cells in U-bottom 96-well plates for 24 hrs. IFN-γ release was detected in culture supernatants by ELISA (BioLegend) following the manual provided by the vendor.

In vivo killing assay. A total of $5\times10^6$ (CFSE)-labeled 697 (NKL resistant) and 697-MICA (NKL sensitive) cells were mixed and injected in combination with $5\times10^7$ NKL into NSG mice intraperitoneally (IP). Anti-LILRB1 antibody (10 mg/kg) or control human IgG (hIgG) was administered retro-orbitally. After 24 hrs, cells from mice peritoneal cavities were harvested and stained with anti-MICA antibody and analyzed by FACS Calibur1 (BD Biosciences). In vivo cytotoxic activities of NKL were calculated as:

$$NK = \text{Ratio of 697-}MICA/697 \text{ in mice receiving 697, 697-}MICA \text{ cells and } NKL \text{ cells.}$$

$$CN = \text{Ratio of 697-}MICA/697 \text{ in mice receiving 697 and 697-}MICA \text{ cells \% in } vivo \text{ cytotoxic activity} = (1-\text{NK}/CN)*100.$$

In vivo cytotoxic activity of NKL cells against 697-MICA was also tested in NSG mice subcutaneously. A total of $1\times10^6$ luciferase-expressing 697-MICA (697 MICA-luci) cells were mixed with $5\times10^6$ NKL cells and injected into mice subcutaneously (sc). Anti-LILRB1 antibody (10 mg/kg) or control hIgG was administered to each mouse retro-orbitally. Bioluminescence imaging (BLI) was conducted 48 hrs later to monitor the remaining 697-MICA cells in mice.

Multiple myeloma xenograft. Age 6-8 week NSG mice were sublethally irradiated with 200 cGy X-ray on day −1. On day 0, each mouse was given $5\times10^5$ KMS27-luci together with $5\times10^6$ NKL cells via tail vein injection. Anti-LILRB1 antibody (10 mg/kg) or control hIgG was administered retro-orbitally on Day 0, Day 3, and Day 7, then once a week for one month. Another $5\times10^6$ NKL cells were injected on day 14. A total of 10,000 IU human IL2 was administrated to each mouse through IP injection every other day. BLI was assessed on Day 28 and Day 35.

Statistical analysis. Data are presented as mean±SE (standard error). Statistical significance between two groups is calculated by two-tailed unpaired t-test except as noted. Kaplan-Meier survival curves were analyzed using a log-rank test. Differences are considered statistically significant if $p<0.05$.

Antibody structure modeling. Antibody structure modeling of 176 Fv was generated using Discovery Studio® Software 2017 R2(DS). Homology template structures of the top hits predicted by the Identify Framework Templates protocol were selected. These structures were used as input structures, becoming the foundation on which the Model Antibody Framework protocol built a chimeric antibody Fab structure. The Model Antibody Loops protocol identifies templates and manufactures models for CDRs using Hidden Markov Models (HMM). This protocol was used to rebuild the CDR loops. Finally, the homology model of 176 Fv was subject to energy minimization using the CHARMM force field. In this way, a lowest energy structure was developed for docking and further analysis.

Antibody docking. The structure of the LILBR1 (PDB ID:5KNM) was retrieved from the Protein Data Bank (PDB) and subject to energy minimization by using CHARMm force field for the structure preparation. Rigid body docking of 176 and LILRB1 was performed using the ZDock algorithm as described (Chen & Weng, 2002). Next, hierarchical sets of clusters with different docked poses were generated according to antibody position. Rescoring of the poses was done using the ZRank scoring function based on the electrostatics, van der Waals, and desolvation energy terms.

Docked poses were filtered based on the ligand binding sites we identified, Arg-84 and Tyr-76. Next, 56 ranked poses with the ZRank scores lower than −55 were selected from the largest ten clusters. These were input into the RDock procedure. Input docked structures were refined by eliminating small clashes and optimizing polar and charge interactions, then re-ranked according to the electrostatics and solvation energy terms (Chen et al., 2003). All 56 docked poses were performed by RDock with default parameters.

Binding interaction analysis. The objective of using RDock was to identify the residues at the interface of antibody-antigen and calculate the binding energy between the 176 antibody and LILBR1. The interaction analysis was performed using DS and PyMOL. The nonpolar interaction energy was computed through the Calculate Interaction Energy protocol implemented in DS. Complexes with higher binding affinity between Tyr-76 and Arg-84 of LILBR1 and 176 Fv were considered to present favorable docking conformation.

The structure of h176 was predicted using DS. Docking of LILRB1-D1D2 with h176 Fab was performed using the ZDOCKpro module of the Insight II package. The general protocol for running ZDOCK includes two consecutive steps of calculation described as geometry search in ZDOCK and energy search in RDOCK. The crystal structure of LILRB1-D1D2 was obtained from the PDB database. RDOCK was used to refine the top ZDOCK poses. Poses with high scores in both ZDOCK and RDOCK were selected as candidate complexes.

Sequence alignment and phylogenetic analysis. D1 and D2 amino acid sequences of all LILRA and LILRB family members were analyzed. An exception was LILRB4, for which D1 domain was analyzed. The accession numbers of proteins in GenBank are as follows: LILRB1, Q8NHL6; LILRB2, Q8N423; LILRB3, 075022; LILRB4, Q8NHJ6; LILRB5, 075023; LILRA1, 075019; LILRA2, Q8N149; LILRA3, Q8N6C8; LILRA4, P59901; LILRA5, A6NI73; LILRA6, Q6PI73. The D1 region was defined as position 27 to position 115 and D2 as position 116 to position 221. Multiple alignments were performed using ClustalX (Version 2.1) with all the D1D2 sequences. MEGA (Version 7.0) was used to generate the phylogenetic tree.

Example 2—LILRB1 is Highly Expressed on NK Cells from the Peripheral Blood of Patients with MM and Prostate Cancer The function of immune inhibitory receptors of the LILRB family and immune activating receptor NKG2D in cancer development have been characterized[1-8]. To investigate if LILRB1 can be a molecular target for cancer immunotherapy, LILRB1 expression on NK cell from patients with cancer was determined and compared with that from health donors. LILRB1 is mainly expressed on $CD56^{dim}$ NK cells, rather than $CD56^{bright}$ NK cells, from both healthy donors and patients with cancer (FIG. 1A). The percentage of LILRB1 expressing NK cells among $CD56^{dim}$ NK cells from peripheral blood of patients with prostate cancer or multiple myeloma (MM) were evaluated. The percentages of LILRB1 NK cells (among $CD56^{dim}$ NK) were significantly higher in blood from patients with late-stage prostate cancer (3b and 3c) than in blood from healthy donors (FIG. 1B, Table 9). Moreover, NK cells in peripheral blood from patients with MM who had persistent disease while on treatment had a greater percentage of LILRB1V NK cells (among $CD56^{dim}$ NK) than that from health donors or patients with minimal disease to complete response (FIG. 1C, Table 10). These results suggest that the percentage of LILRB1 NK cells is significantly higher in patients with late-stage cancer or poor prognosis, and LILRB1 may be a molecular target for immunotherapy for these patients.

TABLE 9

Clinical characteristic of patients with prostate cancer before treatment

| Patient | Age (y) | Gender | TNM | Disease stage | LILRB1 + NK cell (%) |
|---|---|---|---|---|---|
| 1 | 65 | Male | pT2N0MX | 2B | 53 |
| 2 | 70 | Male | mpT2N0MX | 2B | 70 |
| 3 | 64 | Male | mpT2N0MX | 2B | 48 |
| 4 | 68 | Male | mpT2N0MX | 2B | 59 |
| 5 | 70 | Male | mpT2N0MX | 2B | 23.9 |
| 6 | 66 | Male | pT2N0MX | 2B | 34 |
| 7 | 66 | Male | mpT2NxMx | 2B | 20 |
| 8 | 62 | Male | mpT2N0MX | 2B | 40 |
| 9 | 66 | Male | unknown | 2b | 37 |
| 10 | 64 | Male | unknown | 2b | 26 |
| 11 | 57 | Male | unknown | 2b | 23 |
| 12 | 68 | Male | unknown | 2b | 39 |
| 13 | 67 | Male | mpT2N0MX | 2C | 20 |
| 14 | 72 | Male | pT2N0MX | 2C | 33 |
| 15 | 65 | Male | pT2N0MX | 2C | 21.1 |
| 16 | 70 | Male | unknown | 2C | 10 |
| 17 | 50 | Male | mpT3aN0MX | 3B | 74.2 |
| 18 | 52 | Male | pT3aN0MX | 3B | 47 |
| 19 | 71 | Male | mpT3aN0MX | 3B | 29.6 |
| 20 | 68 | Male | mpT3aN0MX | 3B | 27.5 |
| 21 | 73 | Male | mpT3bN0MX | 3B | 30 |
| 22 | 80 | Male | mpT3N0MX | 3B | 40 |
| 23 | 77 | Male | pT3bN1Mx | 3B | 15 |
| 24 | 65 | Male | mpT3aN0MX | 3B | 35 |
| 25 | 69 | Male | mpT3aN0MX | 3B | 20 |
| 26 | 57 | Male | unknown | 3B | 78.4 |
| 27 | 60 | Male | unknown | 3B | 44 |
| 28 | 52 | Male | unknown | 3b | 40 |
| 29 | 51 | Male | unknown | 3b | 52 |
| 30 | 72 | Male | unknown | 3b | 50.8 |
| 31 | 69 | Male | unknown | 3C | 27 |
| 32 | 67 | Male | unknown | 3C | 60 |
| 33 | 75 | Male | unknown | 3C | 45.5 |

TABLE 10

The response of multiple myelomas patients to treatment

| Patient | Disease burden at diagnosis Plasma cells (%) | Lenalidomide treatment | Induction Treatment | Duration | Disease control at time of specimen | LILRB1 + NK cell (%) |
|---|---|---|---|---|---|---|
| 1 | 40 | No | Untreated | No | Newly diagnosed | 20 |
| 2 | unknown | No | Untreated | No | Newly diagnosed | 56.8 |
| 3 | 30 | No | Untreated | No | Newly diagnosed | 8.08 |
| 4 | 5 | No | Untreated | No | Newly diagnosed | 43 |
| 5 | 2 | No | Untreated | No | Newly diagnosed | 54 |
| 6 | 20 | No | Untreated | No | Newly diagnosed | 67 |
| 7 | 70 | No | Untreated | No | Newly diagnosed | 49 |
| 8 | 20 | No | Untreated | No | Newly diagnosed | 62 |
| 9 | 10 to 20 | No | Untreated | No | Newly diagnosed | 37.6 |
| 10 | 2 to 3 | No | Untreated | No | Newly diagnosed | 26.1 |

TABLE 10-continued

The response of multiple myelomas patients to treatment

| Patient | Disease burden at diagnosis Plasma cells (%) | Lenalidomide treatment | Induction Treatment | Duration | Disease control at time of specimen | LILRB1 + NK cell (%) |
|---|---|---|---|---|---|---|
| 11 | 80 | Yes | Carfilzomib/ Lenalidomide/ Dexamethasone | 4 cycles | Partial Response | 77 |
| 12 | 90 | Yes | Bortezomib/ Lenalidomide/ Dexamethasone | 4 cycles | Partial Response | 33.3 |
| 13 | 70 | Yes | Bortezomib/ Lenalidomide/ Dexamethasone | 4 cycles | Partial Response | 72 |
| 14 | 10 | Yes | Ixazomib/ Lenalidomide/ Dexamethasone | 1 cycle | Partial Response | 63.6 |
| 15 | 40 | No | Cytoxan/ Bortezomib/ Dexamethsone | 3 cycles | Partial Response | 46 |
| 16 | 75 | Yes | Bortezomib/ Lenalidomide/ Dexamethasone | 5 cycles | Partial Response | 61 |
| 17 | 5 to 10 | No | Bortezomib/ Cyclophosphamide/ Dexamethasone | 6 cycles | Partial Response | 60 |
| 18 | 15 | Yes | Bortezomib/ Lenalidomide/ Dexamethasone | 4 cycles | Refractory | 53 |
| 19 | 40 | Yes | Daratumumab/ Lenalidomide/ Dexamethasone | 4 cycles | Very Good Partial Response | 34.7 |
| 20 | unknown | Yes | Carfilzomib/ Lenalidomide/ Dexamethasone | Many | Very Good Partial Response | 45 |
| 21 | 90 | Yes | Bortezomib/ Lenalidomide/ Dexamethasone | 5 cycles | Very Good Partial Response | 24 |
| 22 | 70 | Yes | Bortezomib/ Lenalidomide/ Dexamethasone | 4 cycles | Very Good Partial Response | 35.7 |
| 23 | 90 | No | Carfilzomib/ Dexamethasone | 4 cycles | Very Good Partial Response | 69.1 |
| 24 | 50 | Yes | Bortezomib/ Lenalidomide/ Dexamethasone | 5 cycles | Very Good Partial Response | 15 |
| 25 | 70 | Yes | Bortezomib/ Lenalidomide/ Dexamethasone | 10 cycles | Very Good Partial Response | 29.3 |
| 26 | unknown | Yes | Bortezomib/ Lenalidomide/ Dexamethasone | 3 cycles | Very Good Partial Response | 48 |
| 27 | 70 | Yes | Lenalidomide/ Dexamethasone | 2 yrs | Complete Response | 9.1 |

Example 3—Generation and Characterization of Antagonistic and Agonistic Monoclonal Antibodies for LILRB1

To evaluate therapeutic potential of anti-LILRB1 mAbs in activating NK cells, a panel of anti-LILRB1 mAbs was generated by screening single memory B clones, cloning antibody genes, and evaluating the blocking activity of recombinant mAbs (FIGS. 12A-B)[32-14]. In total, 229 anti-LILRB1 specific single B cell clones were generated from 384 LILRB1 B cell culture wells and assessed by ELISA (Table 11). Among them, 174 single B cell clones were identified that produce mAbs binding to LILRB1 expressed on cell surface of LILRB1 NFAT-GFP reporter cell (Table 12), which express GFP when the cell surface LILRB1 is cross-linked[18]. Sixty binders were selected for further cloning and expression, finding 44 antibodies of them with EC50 of low nanomolar range (0.05-3 nM) (FIG. 12C). Estimated EC50s based on antibody concentration titration binding curves are provided in Table 13. To group the 44 mAbs by their binding epitopes, classic sandwich epitope binning assay were performed by using Octet RED96, and twelve epitope bins were identified for these 44 high binders (FIG. 12D).

TABLE 11

Binding of mAbs in the supernatants of 229 B cell clones, determined by ELISA

| #clone | OD450 |
|---|---|
| 1 | 2.11 |
| 2 | 1.58 |
| 3 | 2.11 |

TABLE 11-continued

Binding of mAbs in the supernatants of 229 B cell clones, determined by ELISA

| #clone | OD450 |
|---|---|
| 4 | 2.47 |
| 5 | 2.27 |
| 6 | 1.6 |
| 7 | 2.4 |
| 8 | 1.23 |
| 9 | 2.36 |
| 10 | 2.17 |
| 11 | 1.77 |
| 12 | 2.36 |
| 13 | 1.03 |
| 14 | 2.54 |
| 15 | 2.5 |
| 16 | 1.85 |
| 17 | 1.78 |
| 18 | 2.41 |
| 19 | 2.32 |
| 20 | 1.97 |
| 21 | 1.3 |
| 22 | 1.84 |
| 23 | 1.67 |
| 24 | 1.08 |
| 25 | 2.3 |
| 26 | 2.48 |
| 27 | 2.56 |
| 28 | 2.27 |
| 29 | 1.79 |
| 30 | 2.28 |
| 31 | 1.75 |
| 32 | 2.04 |
| 33 | 2.2 |
| 34 | 1.98 |
| 35 | 2.01 |
| 36 | 2.15 |
| 37 | 2.13 |
| 38 | 2.32 |
| 39 | 1.02 |
| 40 | 2.19 |
| 41 | 2.26 |
| 42 | 1.73 |
| 43 | 2.04 |
| 44 | 2 |
| 45 | 1.08 |
| 46 | 1.4 |
| 47 | 2.36 |
| 48 | 2.01 |
| 49 | 2.34 |
| 50 | 2.16 |
| 51 | 1.9 |
| 52 | 2.27 |
| 53 | 2.09 |
| 54 | 1.36 |
| 55 | 1.3 |
| 56 | 2.09 |
| 57 | 2.02 |
| 58 | 2.26 |
| 59 | 1.9 |
| 60 | 1.23 |
| 61 | 2.38 |
| 62 | 1.96 |
| 63 | 2.1 |
| 64 | 1.97 |
| 65 | 1.12 |
| 66 | 1.78 |
| 67 | 1.34 |
| 68 | 2.03 |
| 69 | 1.39 |
| 70 | 1.36 |
| 71 | 1.39 |
| 72 | 2.25 |
| 73 | 1.7 |
| 74 | 2.4 |
| 75 | 2.06 |
| 76 | 2.14 |
| 77 | 2.26 |
| 78 | 1.87 |

TABLE 11-continued

Binding of mAbs in the supernatants of 229 B cell clones, determined by ELISA

| #clone | OD450 |
|---|---|
| 79 | 2.32 |
| 80 | 2.11 |
| 81 | 1.11 |
| 82 | 1.97 |
| 83 | 2.32 |
| 84 | 1.88 |
| 85 | 2.28 |
| 86 | 1.97 |
| 87 | 2.28 |
| 88 | 2.42 |
| 89 | 1.97 |
| 90 | 2.39 |
| 91 | 1.8 |
| 92 | 1.96 |
| 93 | 1.72 |
| 94 | 1.98 |
| 95 | 1.95 |
| 96 | 1.97 |
| 97 | 1.16 |
| 98 | 2.01 |
| 99 | 2.05 |
| 100 | 1.79 |
| 101 | 2.32 |
| 102 | 1.45 |
| 103 | 2.33 |
| 104 | 2.15 |
| 105 | 2.2 |
| 106 | 2.11 |
| 107 | 1.15 |
| 108 | 2.04 |
| 109 | 1.64 |
| 110 | 2.31 |
| 111 | 2.1 |
| 112 | 1.99 |
| 113 | 1.73 |
| 114 | 1.89 |
| 115 | 1.53 |
| 116 | 2.06 |
| 117 | 2.23 |
| 118 | 2.06 |
| 119 | 1.26 |
| 120 | 1.4 |
| 121 | 2.06 |
| 122 | 1.47 |
| 123 | 1.86 |
| 124 | 1.66 |
| 125 | 2.43 |
| 126 | 2.45 |
| 127 | 1.87 |
| 128 | 2.51 |
| 129 | 2.42 |
| 130 | 2.07 |
| 131 | 1.8 |
| 132 | 2.2 |
| 133 | 2.15 |
| 134 | 2.05 |
| 135 | 1.93 |
| 136 | 2.42 |
| 137 | 2.1 |
| 138 | 2.04 |
| 139 | 2.1 |
| 140 | 1.93 |
| 141 | 1.84 |
| 142 | 1.84 |
| 143 | 2.4 |
| 144 | 1.64 |
| 145 | 1.97 |
| 146 | 1.44 |
| 147 | 2.51 |
| 148 | 1.96 |
| 149 | 1.95 |
| 150 | 1.97 |
| 151 | 2.03 |
| 152 | 0.11 |
| 153 | 0.1 |

TABLE 11-continued

Binding of mAbs in the supernatants of 229 B cell clones, determined by ELISA

| #clone | OD450 |
|---|---|
| 154 | 1.98 |
| 155 | 2.06 |
| 156 | 2.21 |
| 157 | 0.12 |
| 158 | 0.13 |
| 159 | 1.89 |
| 160 | 1.87 |
| 161 | 1.85 |
| 162 | 2.02 |
| 163 | 1.49 |
| 164 | 2.26 |
| 165 | 2.1 |
| 166 | 2.22 |
| 167 | 1.12 |
| 168 | 1.77 |
| 169 | 2.01 |
| 170 | 2.26 |
| 171 | 1.79 |
| 172 | 1.97 |
| 173 | 2.14 |
| 174 | 2.02 |
| 175 | 2.02 |
| 176 | 2.06 |
| 177 | 2.04 |
| 178 | 1.81 |
| 179 | 2.3 |
| 180 | 1.27 |
| 181 | 1.97 |
| 182 | 0.09 |
| 183 | 2.1 |
| 184 | 2.07 |
| 185 | 1.67 |
| 186 | 2.01 |
| 187 | 1.98 |
| 188 | 2.02 |
| 189 | 2012 |
| 190 | 1.9 |
| 191 | 1.99 |
| 192 | 1.84 |
| 193 | 2.19 |
| 194 | 1.87 |
| 195 | 1.8 |
| 196 | 2.27 |
| 197 | 1.87 |
| 198 | 2.28 |
| 199 | 2.01 |
| 200 | 2.27 |
| 201 | 1.78 |
| 202 | 1.95 |
| 203 | 1.75 |
| 204 | 2.03 |
| 205 | 1.82 |
| 206 | 1.87 |
| 207 | 1.93 |
| 208 | 1.31 |
| 209 | 2.18 |
| 210 | 1.75 |
| 211 | 2.29 |
| 212 | 2.24 |
| 213 | 0.08 |
| 214 | 0.09 |
| 215 | 1.26 |
| 216 | 1.97 |
| 217 | 1.55 |
| 218 | 1.92 |
| 219 | 2.22 |
| 220 | 2.24 |
| 221 | 1.64 |
| 222 | 1.87 |
| 223 | 1.79 |
| 224 | 2.09 |
| 225 | 2.07 |
| 226 | 2.38 |
| 227 | 2.08 |
| 228 | 0.13 |
| 229 | 1.07 |
| Ctrl | 0.1 |

TABLE 12

Binding of mAbs in the supernatants of 229 B cell clones to the LILRB1 on cell surface of reporter cells. Anti-mAbs in supernatants were immobilized by protein A coated cell culture plate. 96-well cell culture plates were coated with 5 μg/mL protein A in phosphate buffered saline (PBS) at 37° C. for 2 hours. After washed with PBS 3 times, the plates were incubated with the supernatants of 229 B cell clones at 4° C. overnight. LILRB1 reporter cells were cultured in the plate for 24 hrs. The percentage of GFP reporter cells were analyzed by flow cytometry.

| #clone | % GFP |
|---|---|
| 1 | 20.9 |
| 2 | 1.74 |
| 3 | 14.6 |
| 4 | 2.02 |
| 5 | 12.1 |
| 6 | 1.26 |
| 7 | 73.9 |
| 8 | 1.38 |
| 9 | 18 |
| 10 | 15.8 |
| 11 | 1.48 |
| 12 | 1.43 |
| 13 | 1.32 |
| 14 | 1.49 |
| 15 | 37.1 |
| 16 | 1.1 |
| 17 | 2.49 |
| 18 | 63.7 |
| 19 | 31 |
| 20 | 24.7 |
| 21 | 1.99 |
| 22 | 41.3 |
| 23 | 1.13 |
| 24 | 1.11 |
| 25 | 54.7 |
| 26 | 1.06 |
| 27 | 64.2 |
| 28 | 65.4 |
| 29 | 1.56 |
| 30 | 32.2 |
| 31 | 0.902 |
| 32 | 15 |
| 33 | 20.2 |
| 34 | 28.8 |
| 35 | 31.7 |
| 36 | 44.6 |
| 37 | 15.2 |
| 38 | 62.7 |
| 39 | 0.941 |
| 40 | 47.9 |
| 41 | 63.7 |
| 42 | 0.889 |
| 43 | 34 |
| 44 | 24.4 |
| 45 | 0.893 |
| 46 | 5.74 |
| 47 | 70.9 |
| 48 | 21.6 |
| 49 | 1 |
| 50 | 20.3 |
| 51 | 31.6 |
| 52 | 44.8 |
| 53 | 38.7 |

TABLE 12-continued

Binding of mAbs in the supernatants of 229 B cell clones to the LILRB1 on cell surface of reporter cells. Anti-mAbs in supernatants were immobilized by protein A coated cell culture plate. 96-well cell culture plates were coated with 5 μg/mL protein A in phosphate buffered saline (PBS) at 37° C. for 2 hours. After washed with PBS 3 times, the plates were incubated with the supernatants of 229 B cell clones at 4° C. overnight. LILRB1 reporter cells were cultured in the plate for 24 hrs. The percentage of GFP reporter cells were analyzed by flow cytometry.

| #clone | % GFP |
|---|---|
| 54 | 2.63 |
| 55 | 0.897 |
| 56 | 55.4 |
| 57 | 60.5 |
| 58 | 70.7 |
| 59 | 20.5 |
| 60 | 1.29 |
| 61 | 37.8 |
| 62 | 23.5 |
| 63 | 31 |
| 64 | 26.2 |
| 65 | 0.905 |
| 66 | 18.7 |
| 67 | 0.874 |
| 68 | 35.9 |
| 69 | 1.28 |
| 70 | 12.2 |
| 71 | 7.92 |
| 72 | 65.3 |
| 73 | 27.2 |
| 74 | 57.1 |
| 75 | 27.6 |
| 76 | 60.9 |
| 77 | 38.3 |
| 78 | 40.8 |
| 79 | 54.6 |
| 80 | 32.7 |
| 81 | 0.879 |
| 82 | 24.4 |
| 83 | 61.6 |
| 84 | 30 |
| 85 | 44.1 |
| 86 | 12.6 |
| 87 | 1.35 |
| 88 | 32.5 |
| 89 | 31.2 |
| 90 | 31.1 |
| 91 | 10.4 |
| 92 | 28.3 |
| 93 | 59 |
| 94 | 21.2 |
| 95 | 42.2 |
| 96 | 19.3 |
| 97 | 1.11 |
| 98 | 54.7 |
| 99 | 33.8 |
| 100 | 1.06 |
| 101 | 28.6 |
| 102 | 0.883 |
| 103 | 0.912 |
| 104 | 28.4 |
| 105 | 32.5 |
| 106 | 11.5 |
| 107 | 0.796 |
| 108 | 27.4 |
| 109 | 14.8 |
| 110 | 60.2 |
| 111 | 32.7 |
| 112 | 25.8 |
| 113 | 34.1 |
| 114 | 45.3 |
| 115 | 61.7 |
| 116 | 15.2 |
| 117 | 15.8 |
| 118 | 24.8 |
| 119 | 0.872 |

TABLE 12-continued

Binding of mAbs in the supernatants of 229 B cell clones to the LILRB1 on cell surface of reporter cells. Anti-mAbs in supernatants were immobilized by protein A coated cell culture plate. 96-well cell culture plates were coated with 5 μg/mL protein A in phosphate buffered saline (PBS) at 37° C. for 2 hours. After washed with PBS 3 times, the plates were incubated with the supernatants of 229 B cell clones at 4° C. overnight. LILRB1 reporter cells were cultured in the plate for 24 hrs. The percentage of GFP reporter cells were analyzed by flow cytometry.

| #clone | % GFP |
|---|---|
| 120 | 3.68 |
| 121 | 24.5 |
| 122 | 2.6 |
| 123 | 43.2 |
| 124 | 5 |
| 125 | 76.2 |
| 126 | 0.848 |
| 127 | 28.9 |
| 128 | 63.5 |
| 129 | 69 |
| 130 | 40.6 |
| 131 | 22.1 |
| 132 | 52.3 |
| 133 | 39.3 |
| 134 | 25.5 |
| 135 | 18 |
| 136 | 0.762 |
| 137 | 22.3 |
| 138 | 28.9 |
| 139 | 16.1 |
| 140 | 25.7 |
| 141 | 26.7 |
| 142 | 20.5 |
| 143 | 37 |
| 144 | 1.01 |
| 145 | 19.3 |
| 146 | 0.864 |
| 147 | 54 |
| 148 | 4931 |
| 149 | 62.7 |
| 150 | 65.8 |
| 151 | 62.6 |
| 152 | 2.7 |
| 153 | 2.16 |
| 154 | 77.3 |
| 155 | 68.9 |
| 156 | 2.78 |
| 157 | 2.39 |
| 158 | 2.46 |
| 159 | 8.98 |
| 160 | 51.9 |
| 161 | 60.9 |
| 162 | 76.2 |
| 163 | 41.2 |
| 164 | 73.9 |
| 165 | 72.4 |
| 166 | 94.4 |
| 167 | 25 |
| 168 | 49.2 |
| 169 | 90.8 |
| 170 | 72.8 |
| 171 | 55.4 |
| 172 | 36.1 |
| 173 | 66.6 |
| 174 | 38.8 |
| 175 | 76.2 |
| 176 | 23 |
| 177 | 66.1 |
| 178 | 83.7 |
| 179 | 95.9 |
| 180 | 2.5 |
| 181 | 6.33 |
| 182 | 2.23 |
| 183 | 64.4 |
| 184 | 62.6 |
| 185 | 49.4 |

TABLE 12-continued

Binding of mAbs in the supernatants of 229 B cell clones to the LILRB1 on cell surface of reporter cells. Anti-mAbs in supernatants were immobilized by protein A coated cell culture plate. 96-well cell culture plates were coated with 5 μg/mL protein A in phosphate buffered saline (PBS) at 37° C. for 2 hours. After washed with PBS 3 times, the plates were incubated with the supernatants of 229 B cell clones at 4° C. overnight. LILRB1 reporter cells were cultured in the plate for 24 hrs. The percentage of GFP reporter cells were analyzed by flow cytometry.

| #clone | % GFP |
|---|---|
| 186 | 59.2 |
| 187 | 18.2 |
| 188 | 40 |
| 189 | 83.2 |
| 190 | 48.1 |
| 191 | 44.1 |
| 192 | 52.8 |
| 193 | 95.1 |
| 194 | 11.7 |
| 195 | 79.7 |
| 196 | 78.8 |
| 197 | 49.9 |
| 198 | 38.2 |
| 199 | 2.65 |
| 200 | 93.5 |
| 201 | 72.5 |
| 202 | 39.4 |
| 203 | 80.7 |
| 204 | 8.31 |
| 205 | 2.44 |
| 206 | 26.8 |
| 207 | 32.6 |
| 208 | 68.4 |
| 209 | 79.8 |
| 210 | 87.2 |
| 211 | 93.9 |
| 212 | 67.3 |
| 213 | 2.28 |
| 214 | 2.34 |
| 215 | 45.7 |
| 216 | 38.8 |
| 217 | 28.8 |
| 218 | 57.8 |
| 219 | 90.2 |
| 220 | 78.1 |
| 221 | 14 |
| 222 | 56.8 |
| 223 | 44.4 |
| 224 | 62.5 |
| 225 | 58.8 |
| 226 | 95.3 |
| 227 | 11.8 |
| 228 | 2.33 |
| 229 | 24 |

TABLE 13

Estimated $EC_{50}$ based on antibody concentration titration binding curves

| mAb | $EC_{50}$ (ng/mL) | mAb | $EC_{50}$ (ng/mL) |
|---|---|---|---|
| B1-#202-2 | 59.39 | B1-#79 | 15.36 |
| B1-#204 | 7.366 | B1-#15 | 9.303 |
| B1-#176 | 2.237 | B1-#173-2 | 6.565 |
| B1#56 | 43.8 | B1-#28 | 24.24 |
| B1#3 | 11.92 | B1-#41-1 | 94.38 |
| B1#5 | 6.024 | B1-#72-1 | 10.97 |
| B1-#190 | 6.777 | B1-#74 | 130.1 |
| B1-#220 | 10.62 | B1-#22 | 29.19 |
| B1-#175 | 5.296 | B1-#93 | 482.5 |
| B1#58-1 | 17.1 | B1-#160 | 28.52 |
| B1#27 | 7.941 | B1-#189 | 14.46 |

TABLE 13-continued

Estimated $EC_{50}$ based on antibody concentration titration binding curves

| mAb | $EC_{50}$ (ng/mL) | mAb | $EC_{50}$ (ng/mL) |
|---|---|---|---|
| B1#38 | 181.2 | B1-#224 | 10.95 |
| B1#83 | 15.55 | B1-#198 | 9.422 |
| B1#76 | 28.41 | B1-#115 | 52.03 |
| B1#25 | 13.24 | B1-#98 | 38.03 |
| B1-#166 | 8.614 | B1-#19 | 19.58 |
| B1-#226 | 8.261 | B1-#10 | 20.94 |
| B1-#179 | 6.467 | B1-#128 | 40.02 |
| B1-#125 | 7.603 | B1-#205 | 98.6 |
| B1-#7 | 15.93 | B1-#209 | 11 |
| B1-#18 | 18.19 | B1-#196-2 | 151.5 |
| B1-#178-2 | 14.25 | B1-#14-2 | 21.45 |
| B1-#110 | 17.77 | | |

Figure 2I:
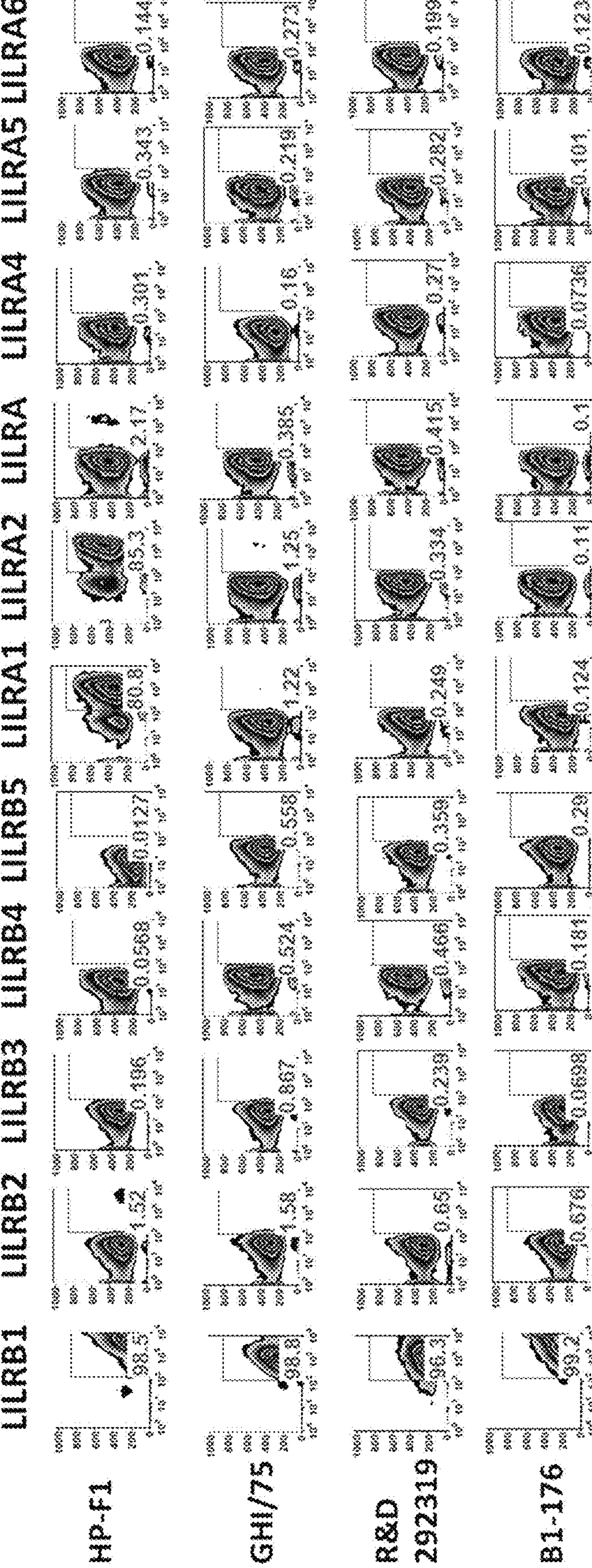

To screen antagonistic anti-LILRB1 mAbs, LILRB1 receptor cells were co-cultured with K562 cells overexpressing HLA-G1 (K562-HLA-G), the MHC class I molecule with the highest affinity for LILRB1 (FIG. 2A). The LILRB1 reporter cells were activated by K562-HLA-G cells, but not by parental K562 cells (MHC class I negative) (FIG. 2A). All antibodies were screened using this reporter assay. Antibodies in bin 1, bin 7, bin 8, and bind 9 showed antagonistic effects (FIG. 12E). Antibodies in bin2, bin3, bin4, bin5, bin6, bin10, bin11, and bin12 showed agonistic effects (FIGS. 12D-E). The cross binding of B1-176 and other commercial anti-LILRB1 were analyzed by flow cytometry (FIG. 2I).

Among the agonistic antibodies, antibodies from bin 1 showed the strongest blocking efficacy (FIG. 2B). B1-176 in bin 1 showed specific binding to LILRB1 as assessed by flow cytometry (FIG. 2C), ELISA (FIG. 2D), and Octet RED96 (FIG. 12F; Table 14). B1-176 showed high affinity to LILRB1 with a KD value of about 10 pM (FIG. 2E), significantly higher than that of two commercial anti-LILRB1 monoclonal antibodies HP-F1 and GHI/75 (FIG. 12G). Therefore, B1-176 was chosen to further evaluation of its binding epitope and function in modulation of NK cell activation.

TABLE 14

Binding affinities of LILRB1 monoclonal antibodies measured using Octet 96Red instrument

| mAb | KD (M) | kon(1/Ms) | kdis(1/s) | Full R^2 |
|---|---|---|---|---|
| B1-#3 | 5.05E−10 | 1.12E+05 | 5.63E−05 | 0.9974 |
| B1-#176 | 6.19E−10 | 9.03E+04 | 5.59E−05 | 0.996 |
| B1-#27 | 1.27E−09 | 1.27E+05 | 1.61E−04 | 0.9993 |
| B1-#178-2 | 1.59E−09 | 1.72E+05 | 2.73E−04 | 0.9992 |
| B1-#41-1 | 1.58E−08 | 3.20E+05 | 5.06E−03 | 0.8535 |
| B1-#173-2 | 1.37E−09 | 1.92E+05 | 2.62E−04 | 0.9983 |
| B1-#72-1 | 3.14E−09 | 7.57E+04 | 2.37E−04 | 0.9982 |
| B1-#22 | 6.11E−10 | 1.41E+05 | 8.62E−05 | 0.9971 |
| B1-#74 | 1.61E−08 | 8.99E+04 | 1.45E−03 | 0.948 |
| B1-#93 | 8.54E−09 | 3.96E+04 | 3.38E−04 | 0.9772 |
| B1-#198 | 2.72E−11 | 2.18E+05 | 5.92E−06 | 0.999 |
| B1-#209 | 3.03E−09 | 6.89E+04 | 2.09E−04 | 0.9993 |

To understand the mechanism of B1-176 in blocking LILRB1 activation, its binding epitope was determined. B1-176 showed specific binding to the D1D2 region of LILRB1 (FIG. 13A) not to the other domains, as assessed by ELISA (FIG. 2F). A series of amino acid mutations were made in the D1D2 region of LILRB1 to determine key amino acids for B1-176 binding (FIG. 13B). Two amino acids (R84 and Y76; which correspond to positions 107 and 99, respectively, of SEQ ID NO: 1) were found to contribute to LILRB1 interacting with B1-176 (FIG. 2G). Molecular docking of B1-176 was performed using Discovery Studio 2017. Based on the PDB structure of LILRB1 D1D2 region (PDBID:1UFU) and the modeling structure of B1-176 using the two key amino acids R84 and Y76, the most possible binding model was identified. In this model, the long HCDR3 of B1-176 inserts into the narrow ligand-binding pocket on LILRB1 D1 domain. Arg-84 of LILRB1 may interact with Tyr-102, Glu-103, and Asp-109 from HCDR3 loop by hydrogen bonds and electrostatic interactions. Tyr-76 of LILRB1 may be involved in hydrogen bonds with Asp-104 from HCDR3 (FIG. 2H).

Example 4—Humanization of Rabbit Anti-LILRB1 mAb

Figure 3B:
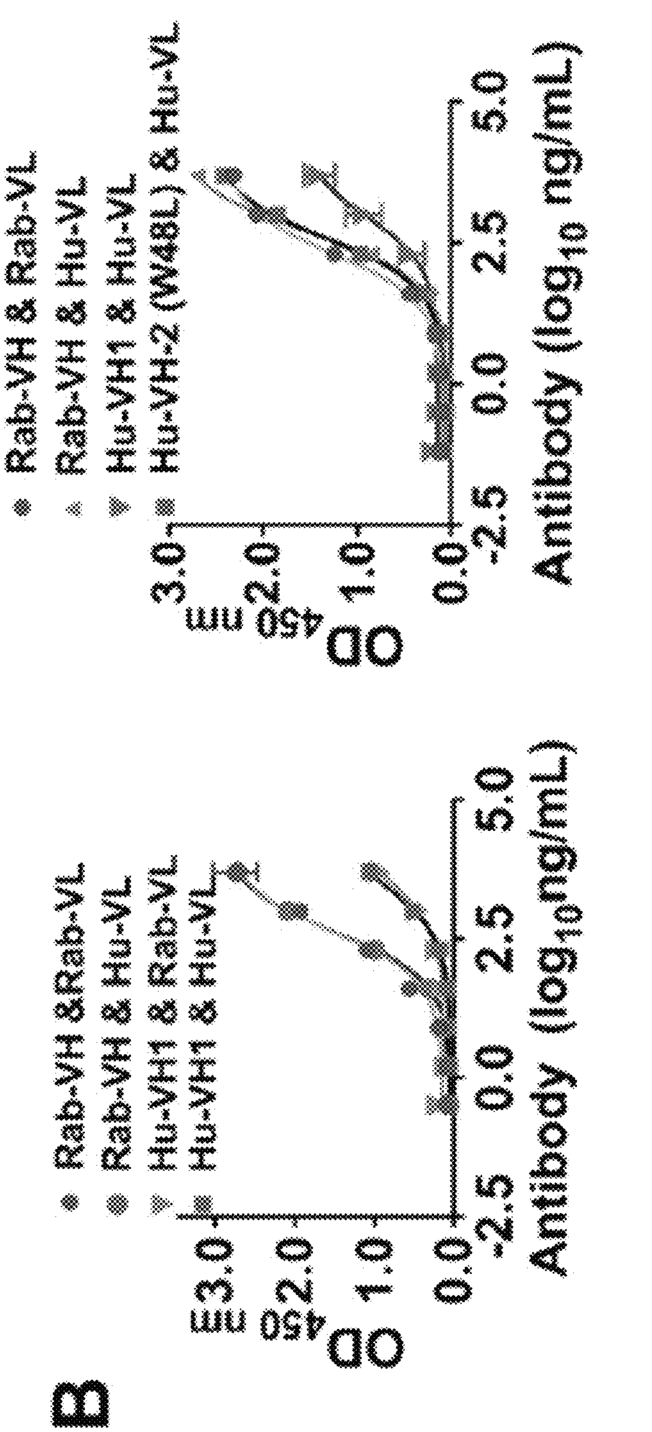
Figure 3C:
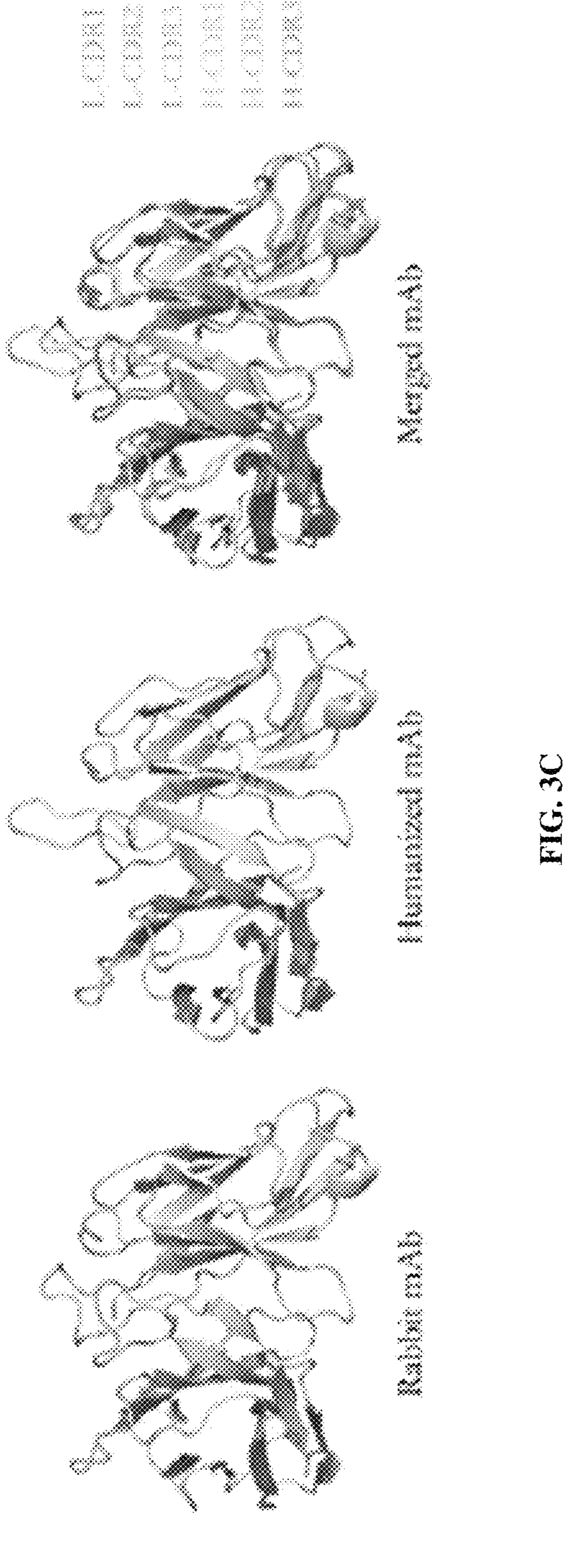

To minimize the immunogenicity of B1-176 for clinical applications, B1-176 was humanized and molecular engineering was conducted for optimization of the antibody sequences. The Kabat/IMGR/Paratome combined-CDRs in the heavy and light chain of B1-176 were identified as described previously[20]. The CDR sequences here were showed as short as HCDR and LCDR. Human germline IGHV3-53*04 and IGKV1-9*01 were selected as the backbones. Heavy chain Hu-176 VH-1 and light chain Hu-176 VL were generated from the CDR grafting. However, antibodies with humanized heavy chain sequence VH-1 showed reduced binding to LILRB1 (FIG. 3B). After rounds of single back-mutations in VH-1, mutation evaluation showed that amino acid L48 in FR2 was important to restore the binding activity (FIG. 3A and FIG. 3B). Molecular docking showed that Fabs of humanized and rabbit B1-176 shared similar superposition structures (FIG. 3C).

Figure 3D:
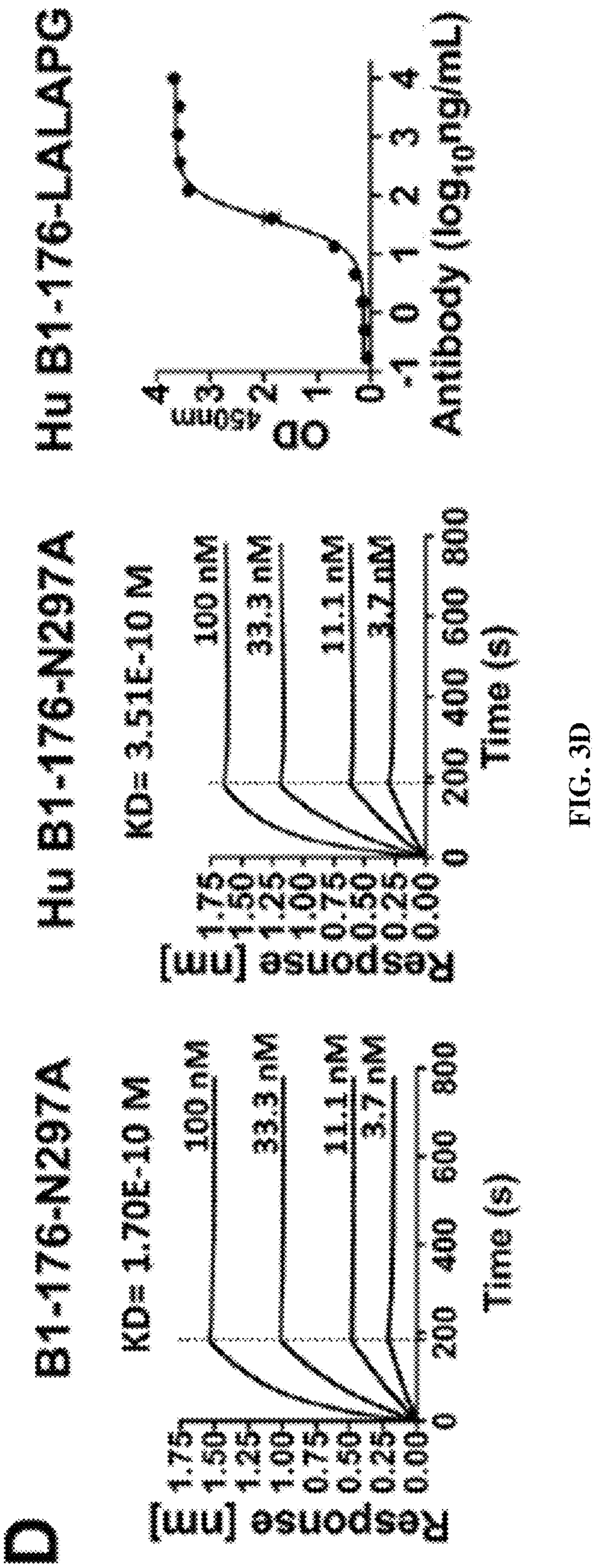

Considering the wide expression of LILRB1 on normal immune cells, rabbit B1-176 was expressed as human IgG1 with N297A mutation (B1-176-N297A), and humanized B1-176 was expressed as human IgG1 with N297A mutation (Hu B1-176-N297A) or with L234A, L235A, and P329G mutations (Hu B1-176-LALAPG) to abolish Fc mediated immune effector function[35 36]. All B1-176 with Fc mutants maintained strong affinity to LILRB1 (FIG. 3D).

Example 5—Antagonistic Anti-LILRB1 mAbs Block Activation of LILRB1 Reporter Cells by Cancer Cells Cancer cell lines that could activate LILRB1 were identified by co-culturing cancer cells with LILRB1 reporter cells (FIG. 4A). Flow cytometry was used to assess the expression of MHC class I molecules (antibody clone:HP-1F7, Santa Cruz), the ligands of LILRB1, on the cell surface of hematologic and solid cancer cell lines (FIG. 4A). The majority of cancer cell lines expressed MHC class I molecules and stimulated the activation of LILRB1 reporter cells. Exceptions were K562, DLD1, and Daudi cells, which did not express MHC class I molecules on their cell surface. Thus, the ability of cancer cells to activate the LILRB1 reporter cells is positively correlated with their MHC class I expression levels. B1-176 and Hu B1-176-N297A blocked the activation of LILRB1 reporter cells stimulated by hematologic cancer cell lines (FIG. 4B) or solid tumor cell lines (FIG. 4C). These results suggest that rabbit and humanized versions of B1-176 can block LILRB1 activation induced by HLA-G and other MHC class I molecules. It is noteworthy that LILRB1 binds to the conserved alpha3 domain of MHC class I[37]. This may explain why the antagonistic anti-LILRB1 antibody screened from K562-HLA-G cells can block LILRB1 activation by other cancer cell lines.

Example 6—In Vitro Function of Antagonistic Anti-LILRB1 mAb on NK Cells

Figure 14D:
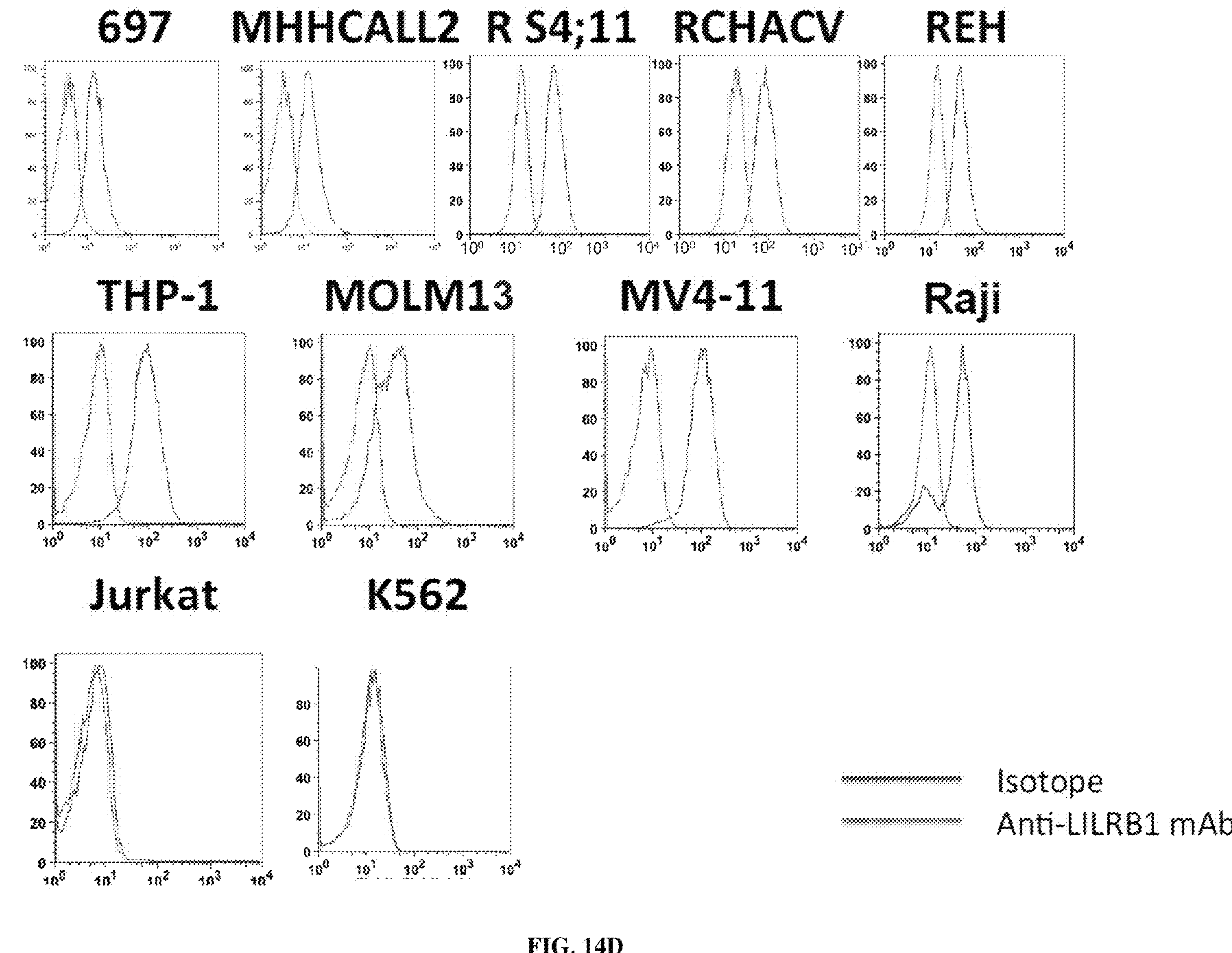

The in vitro efficacy of anti-LILRB1 mAbs was assessed using the NK cell line NKL. NKL cells express high levels of LILRB1 on surface (FIG. 14A). Treatment with different versions of anti-LILRB1 mAb: B1-176-N297A, Hu B1-176-N297A, and Hu B1-176-LALAPG, increased the cytotoxic activities of NKL cells against the MM cell line KMS27 at similar levels (FIG. 5A). Anti-LILRB1 antibody also increased the cytotoxic activity of NKL against other MM cell lines OPM2 and RPMI8226, and the T cell leukemia line Jurkat (FIG. 5B). By flow cytometry, it was found that LILRB1 was expressed on the cell surface of certain leukemia and lymphoma cell lines, such as 697 and Raji cells, but not on MM cell lines, Jurkat cells, or the majority of malignant plasma cells from a patient with MM (FIGS. 14B-D). Since the N297A mutation or LALAPG on Fc would abolish ADCC function of the antibody, these results indicate that the antagonistic anti-LILRB1 antibodies increased the natural cytotoxic activity of NKL cells against MM cell lines. Interestingly, pre-B leukemia cell line 697 and Burkitt lymphoma cell line Raji were resistant to NKL cytotoxicity even when treated with anti-LILRB1 antibody (FIG. 5C). A previous study reported that MHC class I chain-related gene AB (MICA/B), a ligand for the NK cell activating receptor NKG2D, was expressed on NK-sensitive acute lymphoblastic leukemia (ALL) cells but was absent on NK-resistant ALL cells[38]. To sensitize the 697 cells and Raji, MICA was overexpressed on 697 and Raji cells. As expected, MICA on the cancer cell surface stimulated the cytotoxic activities of NKL cells against these cells and anti-LILRB1 antibody further increased the cytotoxic activities of NKL cells (FIGS. 5C-D). These results suggest that LILRB1 blockade and NKG2D activation on NKL cells synergistically increase their cytotoxic activity. Besides hematologic cancer cells, anti-LILRB1 antibody stimulated NKL cells to kill solid tumor cancer cell lines, such as breast cancer cell line MDA-MB-231 and melanoma cell line MALME-3M (FIG. 5E).

NK cells can also improve the response of other immune cells against cancer cells by secreting cytokines. Anti-LILRB1 antibody increased IFN-γ secretion from NKL cells stimulated by T cell leukemia Jurkat cells, and MM cell lines RPMI8226, OPM2 cells and KMS27 (FIG. 5F). Anti-LILRB1 antibody increased the IFN-γ secretion from NKL cells induced by 697-MICA but not 697. This result suggests that LILRB1 blockade and NKG2D activation synergistically stimulated IFN-γ from NKL cells (FIG. 5F). The functions of antagonistic anti-LILRB1 antibodies were also confirmed by using another NK cell line, NK92m. The antagonistic anti-LILRB1 antibodies improved the cytotoxic activities of NK92mi against leukemia cell lines (FIG. 8A-B), solid tumor cell lines (FIG. 8B), multiple myeloma cell line (FIG. 8C), and primary leukemia cells (FIG. 8D).

Moreover, the function of anti-LILRB1 antibodies was confirmed using primary NK cells. Primary NK cells from healthy donors' buffy coats were isolated and LILRB1$^+$ NK cells were enriched by FACS. Anti-LILRB1 antibody increased the cytotoxic activities of primary LILRB1$^+$ NK cells from healthy donor against multiple myeloma cell lines (KMS27 and OPM2), 697 cells or Raji cells, but not against Daudi cells, which do not express the LILRB1 ligand MHC class I (FIG. 6A). Since NK cells also express MHC class I, this result suggests that MHC class I on neighboring NK cells or cis-MHC class I does not inhibit the cytotoxic activity of NK cells against cancer cells. Here, 697 and Raji cells were sensitive to the cytotoxic activity of primary NK cells, likely due to the more potent cytotoxic activity of primary NK cells than that of NKL cells. One previous publication also reported that activated primary NK cells showed stronger cytotoxic activity than NKL cells, possibly due to the relative higher level of cytotoxicity receptors and NK94 on primary NK cells 39. NK cells were also isolated in the peripheral blood from one patient with MM whose NK cells were about 80% LILRB1 positive, and the patient's NK cells were used for cytotoxic assay. Anti-LILRB1 mAb increased cytotoxic activity of the patient's NK cells against MM cell line KMS27 (FIG. 6B).

Example 7—In Vivo Function of Antagonistic Anti-LILRB1 mAb on NK Cells

The in vivo function of anti-LILRB1 antibody was tested using NSG mice. NKL-resistant 697 cell and NKL-sensitive 697 MICA mixtures were injected together with NKL cells into the peritoneal cavity of NSG mice. After 24 hours, the ratio of 697-MICA/697 was analyzed and calculated as the cytotoxic activity of NKL cells in vivo (FIG. 7A). These results showed that anti-LILRB1 antibody increased the in vivo cytotoxic activity of NKL cells against 697-MICA cells. The cytotoxic activity of NKL cells was also tested in vivo by injecting the NKL and luciferase-overexpressed 697-MICA cell mixtures into NSG mice subcutaneously. After 48 hrs, bioluminescence imaging (BLI) showed that mice receiving anti-LILRB1 antibody had significantly lower tumor burdens compared to control hIgG-treated mice (FIG. 7B). Together, the anti-LILRB1 antibody can improve the in vivo cytotoxic function of NKL cells.

The efficacy of anti-LILRB1 antibody to prevent multiple myeloma development was further assessed in a xenograft mouse model. NSG mice were engrafted with KMS27 cells and NKL cells through their tail vein and were administrated with control IgG or anti-LILRB1 antibody, with cancer development monitored by BLI. The mice that received NKL cells and anti-LILRB1 antibody had significantly lower disease burden and longer survival than did mice that received NKL cells and control IgG or mice that received only phosphate buffered saline (PBS) (FIG. 7C). Taken together, these results suggest the antagonistic anti-LILRB1 antibody can improve the function of NKL cells against multiple myeloma development in vivo.

Example 8—In Vitro Function of Agonistic Anti-LILRB1 mAb

B1-7 and B1-41 were selected to determine the function of agonistic LILRB1. B1-7 and B1-41 showed agonistic function on LILRB1 reporter cells, cocultured with K562 cells (FIG. 9). B1-7 and B1-41 did not activate LILRB1 reporter cells without K562 cells. Considering K562 cells have Fc receptors, this result indicated that agonistic LILRB1 mAbs only played roles when the Fc was binding to Fc receptors in the environments. To confirm this, N297A or S267E was introduced into Fc of agonistic LILRB1 mAbs to abolish or enhance the binding of Fc to Fc receptor, respectively. Results showed that N297A abolished, while S267E enhanced the activation of LILRB1 reporter cells, induced by B1-7 and B1-41 (FIG. 9). These results suggested the agonistic effects of anti-LILRB1 are Fc dependent. Agonistic LILRB1 mAbs inhibited cytotoxic activities of NK92mi (FIG. 10A-B) and NKL (FIG. 10C) cells against cancer cells in vitro. The activity of agonistic B1-7 was abolished by N297A mutation in Fc (FIG. 10D). Agonistic LILRB1 mAbs also inhibited IFN-γ secretion from of NKL cells (FIG. 11).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Chen R, Weng Z P. Docking unbound proteins using shape complementarity, desolvation, and electrostatics. *Proteins* 2002; 47:281-94.

Chen R, Li L, Weng Z P. ZDOCK: An initial-stage protein-docking algorithm. *Proteins* 2003; 52:80-87.

1. Guillerey C, Huntington N D, Smyth M J. Targeting natural killer cells in cancer immunotherapy. *Nat Immunol* 2016; 17:1025-36. doi: 10.1038/ni.3518
2. Weiner L M, Surana R, Wang S. Monoclonal antibodies: versatile platforms for cancer immunotherapy. *Nat Rev Immunol* 2010; 10:317-27. doi: 10.1038/nri2744
3. de Weers M, Tai Y T, van der Veer M S, et al. Daratumumab, a novel therapeutic human CD38 monoclonal antibody, induces killing of multiple myeloma and other hematological tumors. *J Immunol* 2011; 186:1840-48. doi: 10.4049/jimmunol.1003032
4. Ferrari de Andrade L, Tay R E, Pan D, et al. Antibody-mediated inhibition of MICA and MICB shedding promotes NK cell-driven tumor immunity. *Science* 2018; 359:1537-42. doi: 10.1126/science.aao0505
5. Gauthier L, Morel A, Anceriz N, et al. Multifunctional Natural Killer Cell Engagers Targeting NKp46 Trigger Protective Tumor Immunity. *Cell* 2019; 177:1701-13 e16. doi: 10.1016/j.cell.2019.04.041
6. Romagne F, Andre P, Spee P, et al. Preclinical characterization of 1-7F9, a novel human anti-KIR receptor therapeutic antibody that augments natural killer-mediated killing of tumor cells. *Blood* 2009; 114:2667-77. doi: 10.1182/blood-2009-02-206532
7. Andre P, Denis C, Soulas C, et al. Anti-NKG2A mAb Is a Checkpoint Inhibitor that Promotes Anti-tumor Immunity by Unleashing Both T and NK Cells. *Cell* 2018; 175:1731-43. doi: 10.1016/j.cell.2018.10.014
8. Kang X, Kim J, Deng M, et al. Inhibitory leukocyte immunoglobulin-like receptors: immune checkpoint proteins and tumor sustaining factors. *Cell Cycle* 2016; 15:25-40. doi: 10.1080/15384101.2015.1121324
9. Pasero C, Gravis G, Guerin M, et al. Inherent and Tumor-Driven Immune Tolerance in the Prostate Microenvironment Impairs Natural Killer Cell Antitumor Activity. *Cancer Res* 2016; 76:2153-65. doi: 10.1158/0008-5472.CAN-15-1965

10. Roberti M P, Juliá E P, Rocca Y S, et al. Overexpression of CD85j in TNBC patients inhibits Cetuximab-mediated NK-cell ADCC but can be restored with CD85j functional blockade. *European journal of immunology* 2015; 45:1560-69. doi: 10.1002/eji.201445353
11. Mamessier E, Sylvain A, Thibult M L, et al. Human breast cancer cells enhance self tolerance by promoting evasion from NK cell antitumor immunity. *The Journal of clinical investigation* 2011; 121:3609-22. doi: 10.1172/JCI45816
12. Godal R, Bachanova V, Gleason M, et al. Natural killer cell killing of acute myelogenous leukemia and acute lymphoblastic leukemia blasts by killer cell immunoglobulin-like receptor-negative natural killer cells after NKG2A and LIR-1 blockade. *Biology of blood and marrow transplantation: journal of the American Society for Blood and Marrow Transplantation* 2010; 16:612-21. doi: 10.1016/j.bbmt.2010.01.019
13. Lesport E, Baudhuin J, Sousa S, et al. Inhibition of human V gamma 9V delta 2 T-cell antitumoral activity through HLA-G: implications for immunotherapy of cancer. *Cell Mol Life Sci* 2011; 68:3385-99. doi: 10.1007/s00018-011-0632-7
14. Kim A, Han C J, Driver I, et al. LILRB1 Blockade Enhances Bispecific T Cell Engager Antibody-Induced Tumor Cell Killing by Effector CD8(+) T Cells. *J Immunol* 2019; 4:1076-87. doi: 10.4049/jimmunol.1801472
15. Barkal A A, Weiskopf K, Kao K S, et al. Engagement of MHC class I by the inhibitory receptor LILRB1 suppresses macrophages and is a target of cancer immunotherapy. *Nature Immunology* 2018; 19:76-84. doi: 10.1038/s41590-017-0004-z
16. Harly C, Peyrat M-A, Netzer S, et al. Up-regulation of cytolytic functions of human Vδ2-γδ T lymphocytes through engagement of ILT2 expressed by tumor target cells. *Blood* 2011; 117:2864-73. doi: 10.1182/blood-2010-09-309781
17. Lozano E, Diaz T, Mena M P, et al. Loss of the Immune Checkpoint CD85j/LILRB1 on Malignant Plasma Cells Contributes to Immune Escape in Multiple Myeloma. *J Immunol* 2018; 200:2581-91. doi: 10.4049/jimmunol.1701622
18. Shiroishi M, Kuroki K, Ose T, et al. Efficient leukocyte Ig-like receptor signaling and crystal structure of disulfide-linked HLA-G dimer. *The Journal of biological chemistry* 2006; 281:10439-47. doi: 10.1074/jbc.M512305200
19. Zou Y Z, Luo W G, Guo J, et al. NK cell-mediated anti-leukemia cytotoxicity is enhanced using a NKG2D ligand MICA and anti-CD20 scfv chimeric protein. *European Journal of Immunology* 2018; 48:1750-63. doi: 10.1002/eji.201847550
20. Gui X, Deng M, Song H, et al. Disrupting LILRB4/APOE Interaction by an Efficacious Humanized Antibody Reverses T-cell Suppression and Blocks AML Development. *Cancer Immunol Res* 2019; 7:1244-57. doi: 10.1158/2326-6066.CIR-19-0036
21. Chapman T L, Heikema A P, West A P, Jr., et al. Crystal structure and ligand binding properties of the D1D2 region of the inhibitory receptor LIR-1 (ILT2). *Immunity* 2000; 13:727-36. doi: 10.1016/s1074-7613(00)00071-6
22. Meng W, Li L, Xiong W, et al. Efficient generation of monoclonal antibodies from single rhesus macaque antibody secreting cells. *MAbs* 2015; 7:707-18. doi: 10.1080/19420862.2015.1051440
23. Navarro F, Llano M, Bellon T, et al. The ILT2(LIR1) and CD94/NKG2A NK cell receptors respectively recognize HLA-G1 and HLA-E molecules co-expressed on target cells. *Eur J Immunol* 1999; 29:277-83. doi: 10.1002/(SICI)1521-4141(199901)29:01<277::AID-IMMU277>3.0.CO;2-4
24. Kang X, Lu Z, Cui C, et al. The ITIM-containing receptor LAIR1 is essential for acute myeloid leukaemia development. *Nature cell biology* 2015; 17:665-77. doi: 10.1038/ncb3158
25. Deng M, Lu Z G, Zheng J K, et al. A motif in LILRB2 critical for Angptl2 binding and activation. *Blood* 2014; 124:924-35. doi: 10.1182/blood-2014-01-549162
26. Dumitriu I E, Mohr W, Kolowos W, et al. 5, 6-carboxyfluorescein diacetate succinimidyl ester-labeled apoptotic and necrotic as well as detergent-treated cells can be traced in composite cell samples. *Analytical biochemistry* 2001; 299:247-52. doi: 10.1006/abio.2001.5415
27. Aktas E, Kucuksezer U C, Bilgic S, et al. Relationship between CD107a expression and cytotoxic activity. *Cellular immunology* 2009; 254:149-54. doi: 10.1016/j.cellimm.2008.08.007
28. Schonberg K, Hejazi M, Uhrberg M. Protocol for the clonal analysis of NK cell effector functions by multi-parameter flow cytometry. *Methods Mol Biol* 2012; 903:381-92. doi: 10.1007/978-1-61779-937-2_26
29. Zheng J, Umikawa M, Cui C, et al. Inhibitory receptors bind ANGPTLs and support blood stem cells and leukaemia development. *Nature* 2012; 485:656-60. doi: 10.1038/nature11095
30. Deng M, Gui X, Kim J, et al. LILRB4 signalling in leukaemia cells mediates T cell suppression and tumour infiltration. *Nature* 2018; 562:605-09. doi: 10.1038/s41586-018-0615-z
31. John S, Chen H, Deng M, et al. A Novel Anti-LILRB4 CAR-T Cell for the Treatment of Monocytic AML. *Mol Ther* 2018; 26:2487-95. doi: 10.1016/j.ymthe.2018.08.001
32. Freed D C, Tang Q, Tang A M, et al. Pentameric complex of viral glycoprotein H is the primary target for potent neutralization by a human cytomegalovirus vaccine. *P Natl Acad Sci USA* 2013; 110:E4997-05. doi: 10.1073/pnas.1316517110
33. Seeber S, Ros F, Thorey I, et al. A Robust High Throughput Platform to Generate Functional Recombinant Monoclonal Antibodies Using Rabbit B Cells from Peripheral Blood. *Plos One* 2014; 9:e86184. doi: ARTN e8618410.1371/journal.pone.0086184
34. Yu Y, Lee P, Ke Y, et al. A humanized anti-VEGF rabbit monoclonal antibody inhibits angiogenesis and blocks tumor growth in xenograft models. *Plos One* 2010; 5:e9072. doi: 10.1371/journal.pone.0009072
35. Ha S, Ou Y, Vlasak J, et al. Isolation and characterization of IgG1 with asymmetrical Fc glycosylation. *Glycobiology* 2011; 21:1087-96. doi: 10.1093/glycob/cwr047
36. Lo M, Kim H S, Tong R K, et al. Effector-attenuating Substitutions That Maintain Antibody Stability and Reduce Toxicity in Mice. *Journal of Biological Chemistry* 2017; 292:3900-08. doi: 10.1074/jbc.M116.767749
37. Chapman T L, Heikeman A P, Bjorkman P J. The inhibitory receptor LIR-1 uses a common binding interaction to recognize class I MHC molecules and the viral homolog UL18. *Immunity* 1999; 11:603-13. doi: 10.1016/s1074-7613(00)80135-1

38. Romanski A, Bug G, Becker S, et al. Mechanisms of resistance to natural killer cell-mediated cytotoxicity in acute lymphoblastic leukemia. *Exp Hematol* 2005; 33:344-52. doi: 10.1016/j.exphem.2004.11.006
39. Gross C, Schmidt-Wolf I G H, Nagaraj S, et al. Heat shock protein 70-reactivity is associated with increased cell surface density of CD94/CD56 on primary natural killer cells. *Cell Stress Chaperon* 2003; 8:348-60. doi: 10.1379/1466-1268(2003)008<0348:Hspria>2.0.Co;2
40. Morandi F, Ferretti E, Castriconi R, et al. Soluble HLA-G dampens CD94/NKG2A expression and function and differentially modulates chemotaxis and cytokine and chemokine secretion in CD56bright and CD56dim NK cells. *Blood* 2011; 118:5840-50. doi: 10.1182/blood-2011-05-352393
41. Desgrandchamps F, LeMaoult J, Goujon A, et al. Prediction of non-muscle-invasive bladder cancer recurrence by measurement of checkpoint HLAG's receptor ILT2 on peripheral CD8(+) T cells. *Oncotarget* 2018; 9:33160-69. doi: 10.18632/oncotarget.26036
42. Yu K, Davidson C E, Burshtyn D N. LILRB1 Intron 1 Has a Polymorphic Regulatory Region That Enhances Transcription in NK Cells and Recruits YY1. *J Immunol* 2020; 204:3030-41. doi: 10.4049/jimmunol.2000164
43. LeMaoult J, Zafaranloo K, Le Danff C, et al. HLA-G up-regulates ILT2, ILT3, ILT4, and KIR2DL4 in antigen presenting cells, NK cells, and T cells. *FASEB journal: official publication of the Federation of American Societies for Experimental Biology* 2005; 19:662-4. doi: 10.1096/fj.04-1617fje
44. Bjorkstrom N K, Riese P, Heuts F, et al. Expression patterns of NKG2A, KIR, and CD57 define a process of CD56dim NK-cell differentiation uncoupled from NK-cell education. *Blood* 2010; 116:3853-64. doi: 10.1182/blood-2010-04-281675
45. Muntasell A, Servitja S, Cabo M, et al. High Numbers of Circulating CD57(+) NK Cells Associate with Resistance to HER2-Specific Therapeutic Antibodies in HER2 (+) Primary Breast Cancer. *Cancer Immunol Res* 2019; 7:1280-92. doi: 10.1158/2326-6066.CIR-18-0896
46. Heidenreich S, Zu Eulenburg C, Hildebrandt Y, et al. Impact of the NK cell receptor LIR-1 (ILT-2/CD85j/LILRB1) on cytotoxicity against multiple myeloma. *Clinical & developmental immunology* 2012; 2012: 652130. doi: 10.1155/2012/652130
47. Suck G, Odendahl M, Nowakowska P, et al. NK-92: an 'off-the-shelf therapeutic' for adoptive natural killer cell-based cancer immunotherapy. *Cancer Immunol Immun* 2016; 65:485-92. doi: 10.1007/s00262-015-1761-x
48. Carbone E, Neri P, Mesuraca M, et al. HLA class I, NKG2D, and natural cytotoxicity receptors regulate multiple myeloma cell recognition by natural killer cells. *Blood* 2005; 105:251-58. doi: 10.1182/blood-2004-04-1422
49. Menier C, Riteau B, Carosella E D, et al. MICA triggering signal for NK cell tumor lysis is counteracted by HLA-G1-mediated inhibitory signal. *Int J Cancer* 2002; 100:63-70. doi: 10.1002/ijc.10460
50. Miller J S, Soignier Y, Panoskaltsis-Mortari A, et al. Successful adoptive transfer and in vivo expansion of human haploidentical NK cells in patients with cancer. *Blood* 2005; 105:3051-57. doi: 10.1182/blood-2004-07-2974

What is claimed is:

1. An isolated monoclonal antibody or an antigen-binding fragment thereof which specifically binds to LILRB1, comprising a heavy chain (HC) variable region (VH) and a light chain (LC) variable region (VL), wherein the VH comprises HC-CDR1 of SEQ ID NO: 113, HC-CDR2 of SEQ ID NO: 114 and HC-CDR3 of SEQ ID NO: 115, and wherein the VL comprises LC-CDR1 of SEQ ID NO: 434, LC-CDR2 of SEQ ID NO: 435 and LC-CDR3 of SEQ ID NO: 436.

2. The isolated monoclonal antibody or an antigen binding fragment thereof of claim 1, wherein the isolated monoclonal antibody is a rabbit antibody.

3. The isolated monoclonal antibody or an antigen-binding fragment thereof of claim 1, wherein the antigen-binding fragment is a recombinant ScFv (single chain fragment variable) antibody, a Fab fragment, a F(ab') 2 fragment, or a Fv fragment.

4. The isolated monoclonal antibody or an antigen binding fragment thereof of claim 1, wherein the isolated monoclonal antibody is a humanized antibody.

5. The isolated monoclonal antibody or an antigen-binding fragment thereof of claim 1, wherein the VH and VL chains have amino acid sequences at least 90% or 95% identical to SEQ ID NOs: 741 and 850, respectively.

6. The isolated monoclonal antibody or an antigen-binding fragment thereof of claim 5, wherein the VH and VL chains have amino acid sequences identical to SEQ ID NOs: 741 and 850, respectively.

7. The isolated monoclonal antibody or an antigen-binding fragment thereof of claim 1, wherein the VH and VL chains are encoded by nucleic acid sequences at least 80% or 90% identical to SEQ ID NOs: 687 and 797, respectively.

8. The isolated monoclonal antibody or an antigen binding fragment thereof of claim 7, wherein the VH and VL chains are encoded by nucleic acid sequences identical to SEQ ID NOs: 687 and 797, respectively.

9. The isolated monoclonal antibody or an antigen binding fragment thereof of claim 1, wherein the isolated monoclonal antibody is a humanized antibody.

10. The isolated monoclonal antibody or an antigen binding fragment thereof of claim 9, wherein the humanized antibody has VH and VL chains having amino acid sequences at least 90% or 95% identical to SEQ ID NOs: 758 and 867, respectively.

11. The isolated monoclonal antibody or an antigen-binding fragment thereof of claim 10, wherein the VH and VL chains have amino acid sequences identical SEQ ID NOs: 758 and 867, respectively.

12. The isolated monoclonal antibody or an antigen binding fragment thereof of claim 9, wherein the humanized antibody has VH and VL chains having amino acid sequences at least 90% or 95% identical to SEQ ID NOs: 759 and 867, respectively.

13. The isolated monoclonal antibody or an antigen-binding fragment thereof of claim 10, wherein the VH and VL chains have amino acid sequences identical to SEQ ID NOs: 759 and 867, respectively.

14. The isolated monoclonal antibody or an antigen-binding fragment thereof of claim 1, comprising an IgG Fc region comprising an amino acid modification in one or more of amino acid positions 234, 235, 297, and 329.

15. The isolated monoclonal antibody or an antigen-binding fragment thereof of claim 14, wherein the IgG Fc region comprises an amino acid substitution N to A at amino acid position 297.

16. The isolated monoclonal antibody or an antigen-binding fragment thereof of claim 14, wherein the IgG Fc region comprises the amino acid substitutions L to A at amino acid position 234, L to A at amino acid position 235, and P to G at amino acid position 329.

17. The isolated monoclonal antibody or an antigen binding fragment thereof of claim 1, wherein the antibody is a chimeric antibody.

18. The isolated monoclonal antibody or an antigen binding fragment thereof of claim 1, wherein the antibody or fragment thereof is conjugated or fused to an imaging agent or a cytotoxic agent.

19. The isolated monoclonal antibody or an antigen binding fragment thereof of claim 1, wherein the antibody or fragment thereof is labeled.

20. The isolated monoclonal antibody or an antigen binding fragment thereof of claim 19, wherein the label is a fluorescent label, an enzymatic label, or a radioactive label.

21. A pharmaceutical composition comprising the isolated monoclonal antibody or an antigen-binding fragment thereof according to claim 1, and a pharmaceutically acceptable carrier.

22. An isolated nucleic acid that encodes the isolated monoclonal antibody according to claim 1.

23. A vector comprising the isolated nucleic acid of claim 22.

24. A host cell comprising the vector of claim 23.

25. The host cell of claim 24, wherein the host cell is a mammalian cell.

26. The host cell of claim 24, wherein the host cell is a CHO cell.

27. A hybridoma or engineered cell comprising a nucleic acid encoding the isolated monoclonal antibody according to claim 1.

28. A process of producing an antibody, comprising culturing the host cell of claim 24 under conditions suitable for expressing the antibody, and recovering the antibody.

29. A chimeric antigen receptor (CAR) protein comprising an antigen-binding fragment according to claim 1.

30. An isolated nucleic acid that encodes a CAR protein of claim 29.

31. A vector comprising the isolated nucleic acid of claim 30.

32. An engineered cell comprising the isolated nucleic acid of claim 30.

33. The engineered cell of claim 32, wherein the cell is a T cell, NK cell, or macrophage.

34. A method of treating or ameliorating the effect of a cancer in a subject, the method comprising administering to the subject a therapeutically effective amount of the antibody or an antigen-binding fragment thereof according to claim 1.

35. A method of detecting a cancer cell or cancer stem cell in a sample or subject comprising:

(a) contacting a subject or a sample from the subject with the antibody or an antigen-binding fragment thereof according to claim 1; and (b) detecting binding of said antibody to a cancer cell or cancer stem cell in said subject or sample.

36. A method of treating or ameliorating the effect of an autoimmune disease in a subject, the method comprising administering to the subject a therapeutically effective amount of the antibody or an antigen-binding fragment thereof according to claim 1.

* * * * *